US012435336B2

(12) United States Patent
Brown et al.

(10) Patent No.: US 12,435,336 B2
(45) Date of Patent: Oct. 7, 2025

(54) COMPOSITIONS AND METHODS FOR INHIBITING LPA EXPRESSION

(71) Applicant: Dicerna Pharmaceuticals, Inc., Lexington, MA (US)

(72) Inventors: Bob Dale Brown, Littleton, MA (US); Henryk T. Dudek, Belmont, MA (US); Marc Abrams, Natick, MA (US); Wen Han, Boston, MA (US); Anton Turanov, Revere, MA (US)

(73) Assignee: Dicerna Pharmaceuticals, Inc., Lexington, MA (US)

( * ) Notice: Subject to any disclaimer, the term of this patent is extended or adjusted under 35 U.S.C. 154(b) by 0 days.

(21) Appl. No.: 18/040,302

(22) PCT Filed: Aug. 5, 2021

(86) PCT No.: PCT/US2021/071109

§ 371 (c)(1),
(2) Date: Feb. 2, 2023

(87) PCT Pub. No.: WO2022/032288

PCT Pub. Date: Feb. 10, 2022

(65) Prior Publication Data

US 2024/0344063 A1 Oct. 17, 2024

Related U.S. Application Data

(60) Provisional application No. 63/074,779, filed on Sep. 4, 2020, provisional application No. 63/061,676, filed on Aug. 5, 2020.

(51) Int. Cl.
*C12N 15/113* (2010.01)

(52) U.S. Cl.
CPC ........ *C12N 15/113* (2013.01); *C12N 2310/14* (2013.01); *C12N 2310/315* (2013.01); *C12N 2310/321* (2013.01); *C12N 2310/322* (2013.01); *C12N 2310/351* (2013.01); *C12N 2310/531* (2013.01)

(58) Field of Classification Search
CPC .............. C12N 15/113; C12N 2310/14; C12N 2310/315; C12N 2310/321; C12N 2310/322; C12N 2310/351; C12N 2310/531; C12N 2310/312; C12N 2310/3521; C12N 2310/3525; C12N 2310/3533; C12N 15/1137; C12Y 304/21007

See application file for complete search history.

(56) References Cited

U.S. PATENT DOCUMENTS 8,372,968 B2 2/2013 Tuschl et al.
8,513,207 B2 8/2013 Brown
8,883,996 B2 11/2014 Rossi et al.
8,927,513 B2 1/2015 Manoharan et al.
8,927,705 B2 1/2015 Brown
9,012,138 B2 4/2015 Tuschl et al.
9,012,621 B2 4/2015 Tuschl et al.
9,193,753 B2 11/2015 Tuschl et al.
11,414,659 B2 8/2022 Wang et al.
2009/0099115 A1 4/2009 McSwiggen et al.

FOREIGN PATENT DOCUMENTS

WO 2010033225 A2 3/2010
WO 2011133871 A2 10/2011
WO 2016100401 A1 6/2016
WO 2017059223 A2 4/2017
WO 2018045317 A1 3/2018
WO 2019092283 A1 5/2019
WO 2019118638 A2 6/2019
WO 2021119034 A1 6/2021
WO 2022032288 A1 2/2022

OTHER PUBLICATIONS

NCBI Reference Sequence: NM_005577.4: *Homo sapiens* lipoprotein(a) (LPA), mRNA. PRI Aug. 27, 2019. (Year: 2019).*
Tsimikas et al. "Antisense therapy targeting apolipoprotein(a): a randomised, double-blind, placebo-controlled phase 1 study". The Lancet. vol. 386, Issue 10002, p. 1472-1483, Oct. 10, 2015. (Year: 2015).*
Ndisang and Rastogi. "Cardiometabolic Diseases and Related Complications: Current Status and Future Perspective". Biomed Res Int. Oct. 9, 2013;2013:467682. (Year: 2013).*
Yang et al. "LPA signaling is required for dopaminergic neuron development and is reduced through low expression of the LPA1 receptor in a 6-OHDA lesion model of Parkinson's disease". Neurol Sci 36, 2027-2033 (2015).; see attached PTO-892 (Year: 2015).*
Vaverkova et al. "Inverse Association of Lipoprotein (a) With Markers of Insulin Resistance in Dyslipidemic Subjects". Physiol. Res. 66 (Suppl. 1): S113-S120, 2017. (Year: 2017).*
Brunzell et al. "Lipoprotein Management in Patients With Cardiometabolic Risk: Consensus Conference Report From the American Diabetes Association and the American College of Cardiology Foundation." Journal of the American College of Cardiology, vol. 51, Issue 15, Apr. 15, 2008, pp. 1512-1524 (Year: 2008).*
Foster et al., "Advanced siRNA Designs Further Improve In Vivo Performance of GalINAc-siRNA Conjugates," Molecular Therapy. 2018;26(3):708-717.
Hu et al., "Therapeutic siRNA: state of the art," Signal Transduction and Targeted Therapy. 2020;5(101):1-25.
Yu, et al., "Disposition and Pharmacokinetics of a GalNAc3-Conjugated Antisense Oligonucleotide Targeting Human Lipoprotein (a) in Monkeys," Nucleic Acid Therapeutics. 2016;26(6):372-384.

(Continued)

*Primary Examiner* — Richard A Schnizer
*Assistant Examiner* — Amanda M Zahorik
(74) *Attorney, Agent, or Firm* — Dechert LLP; Andrea L.C. Reid; Gang Wang

(57) ABSTRACT

Oligonucleotides are provided herein that inhibit apolipoprotein(a) (LPA) expression. Also provided are compositions including the same and uses thereof, particularly uses relating to treating diseases, disorders and/or conditions associated with LPA expression.

22 Claims, 12 Drawing Sheets

Specification includes a Sequence Listing.

(56) References Cited

OTHER PUBLICATIONS

PCT International Search Report from PCT/US2021/071109 dated Nov. 18, 2021.
Prakash, et al., "Identification of metabolically stable 5'-phosphate analogs that support single-stranded siRNA activity," Nucleic Acids Research. 2015;43(6):2993-3011.
Woese, et al., "Architecture of ribosomal RNA: Constraints of the sequence of "tetra-loops"," Proc. Natl. Acad. Sci. 1990;87:8467-8471.
Antao, et al., "A thermodynamic study of unusually stable RNA and DNA hairpins," Nucleic Acids Research. 1991;19(21):5901-5905.
Nakano, et al., "Selection for Thermodynamically Stable DNA Tetraloops Using Temperature Gradient Gel Electrophoresis Reveals Four Motifs: d(cGNNAg), d(cGNABg), d(cCNNGg), and d(gCNNGc)," Biochemistry. 2002;41:14281-14292.
Moore, et al., "Short Hairpin RNA (shRNA): Design, Delivery, and Assessment of Gene Knockdown," Methods Mol. Biol. 2010;619:141-158.
Kraynack and Baker, "Small interfering RNAs containing full 2'-O-methylribonucleotide-modified sense strands display Argonaute2/elF2C2-dependent activity," RNA. 2006;12:163-176.
Sun et al., "Asymmetric RNA duplexes mediate RNA interference in mammalian cells," Nature Biotechnology. 2008;26:1379-1382.
Chang, et al., "Asymmetric Shorter-duplex siRNA Structures Triggers Efficient Gene Silencing with Reduced Nonspecific Effects," Molecular Therapy. 2009;4:725-732.
Hamilton, et al., "Two classes of short interfering RNA in RNA silencing," EMBO J. 2002;21(17):4671-4679.

* cited by examiner

COMPOSITIONS AND METHODS FOR INHIBITING LPA EXPRESSION

This application is a National Stage of International Application No. PCT/US2021/071109, filed Aug. 5, 2021, which claims the benefit under 35 U.S.C. § 119 (e) of U.S. Provisional Patent Application No. 63/061,676, filed Aug. 5, 2020, and claims the benefit under 35 U.S.C. § 119 (e) of U.S. Provisional Patent Application No. 63/074,779, filed Sep. 4, 2020, the contents of each of which are incorporated herein by reference in their entirety.

TECHNICAL FIELD

The disclosure relates to oligonucleotides that inhibit apolipoprotein(a) ("LPA") expression and uses thereof, particularly uses relating to treating diseases, disorders and/or conditions associated with LPA expression.

REFERENCE TO SEQUENCE LISTING

A Sequence Listing is submitted concurrently with the specification as an ASCII formatted text file, with a file name of DRNA_C002WO_ST25.txt, a creation date of Aug. 5, 2021, and a size of 238 kilobytes. The information in the electronic format of the Sequence Listing is part of the specification and is hereby incorporated herein by reference in its entirety.

BACKGROUND

Lipoprotein(a) (Lp(a)) is a heterogeneous low density lipoprotein (LDL)-like particle containing a lipid core and apolipoprotein B (apoB-100) with a unique constituent, apolipoprotein(a) (apo(a)), that is attached to apoB-100 through a disulfide bond. The apo(a) gene (LPA) is expressed predominantly in the liver and expression is restricted to human and non-human primates. Lp(a) levels in humans are genetically defined and do not change significantly with diet, exercise, or other lifestyle changes. LPA varies in length depending upon the number of Kringle KIV2 domains present and its expression is inversely correlated with the number of domains present. Normal Lp(a) levels range from 0.1-25 mg/dl, with about 25% of the population in the United States of America having Lp(a) levels of 30 mg/dl or higher. Analysis of Lp(a) levels in multiple studies have implicated high Lp(a) levels as an independent risk factor for cardiovascular disease, stroke, and other related disorders including atherosclerotic stenosis. In addition, genome-wide association analyses have also implicated LPA as a genetic risk factor for diseases such as atherosclerotic stenosis. When therapeutic lipoprotein apheresis is used to lower both Lp(a) and LDL levels in hyperlipidemic patients, significant reductions of cardiovascular events have been observed.

Therefore, there exists a need for therapeutics and treatments related to these and other LPA-related diseases.

BRIEF SUMMARY OF THE INVENTION

Embodiments of the disclosure relate to compositions and methods for treating a disease, disorder and/or condition related to LPA expression. The disclosure is based, in part, on the discovery and development of oligonucleotides that selectively inhibit and/or reduce LPA expression in the liver. Accordingly, target sequences within LPA mRNA were identified and RNAi oligonucleotides that bind to these target sequences and inhibit LPA mRNA expression were generated. As demonstrated herein, the RNAi oligonucleotides inhibited monkey and human LPA expression in the liver. Without being bound by theory, the RNAi oligonucleotides described herein are useful for treating a disease, disorder or condition associated with LPA expression (e.g., cardiometabolic diseases, atherosclerosis, dyslipidemia, NAFLD and NASH).

Accordingly, in some embodiments, the present disclosure provides an RNAi oligonucleotide for reducing LPA expression, the oligonucleotide comprising a sense strand and an antisense strand, wherein the sense strand and the antisense strand form a duplex region, wherein the antisense strand comprises a region of complementarity to a LPA mRNA target sequence of any one of SEQ ID NOs: 4-387, and wherein the region of complementarity is at least 15 contiguous nucleotides in length.

In any of the foregoing or related embodiments, the sense strand is 15 to 50 nucleotides in length. In some embodiments, the sense strand is 18 to 36 nucleotides in length.

In any of the foregoing or related aspects, the antisense strand is 15 to 30 nucleotides in length.

In any of the foregoing or related aspects, the antisense strand is 22 nucleotides in length and wherein antisense strand and the sense strand form a duplex region of at least 19 nucleotides in length, optionally at least 20 nucleotides in length.

In any of the foregoing or related aspects, the region of complementarity is at least 19 contiguous nucleotides in length, optionally at least 20 nucleotides in length.

In any of the foregoing or related aspects, the 3' end of the sense strand comprises a stem-loop set forth as S1-L-S2, wherein S1 is complementary to S2, and wherein L forms a loop between S1 and S2 of 3-5 nucleotides in length.

In some aspects, the disclosure provides an RNAi oligonucleotide for reducing LPA expression, the oligonucleotide comprising a sense strand of 15 to 50 nucleotides in length and an antisense strand, wherein the sense strand and the antisense strand form a duplex region, wherein the wherein the antisense strand comprises a region of complementarity to a LPA mRNA target sequence of any one of SEQ ID NOs: 4-387, and wherein the region of complementarity is at least 15 contiguous nucleotides in length.

In other aspects, the disclosure provides an RNAi oligonucleotide for reducing LPA expression, the oligonucleotide comprising a sense strand of 15 to 50 nucleotides in length and an antisense strand of 15 to 30 nucleotides in length, wherein the sense strand and the antisense strand form a duplex region, wherein the antisense strand comprises a region of complementarity to a LPA mRNA target sequence of any one of SEQ ID NOs: 4-387, and wherein the region of complementarity is at least 15 contiguous nucleotides in length.

In yet other aspects, the disclosure provides an RNAi oligonucleotide for reducing LPA expression, the oligonucleotide comprising a sense strand of 15 to 50 nucleotides in length and an antisense strand, wherein the sense strand and the antisense strand form a duplex region, wherein the antisense strand comprises a region of complementarity to a LPA mRNA target sequence of any one of SEQ ID NOs: 4-387, and wherein the region of complementarity is 19 contiguous nucleotides in length, optionally 20 nucleotides in length.

In further aspects, the disclosure provides an RNAi oligonucleotide for reducing LPA expression, the oligonucleotide comprising a sense strand of 18 to 36 nucleotides in length and an antisense strand, wherein the sense strand and the antisense strand form a duplex region, wherein the antisense strand comprises a region of complementarity to a LPA mRNA target sequence of any one of SEQ ID NOs: 4-387, and wherein the region of complementarity is 19 contiguous nucleotides in length, optionally 20 nucleotides in length.

In other aspects, the disclosure provides an RNAi oligonucleotide for reducing LPA expression, the oligonucleotide comprising a sense strand of 18 to 36 nucleotides in length and an antisense strand of 22 nucleotides in length, wherein the sense strand and the antisense strand form a duplex region, wherein the antisense strand comprises a region of complementarity to a LPA mRNA target sequence of any one of SEQ ID NOs: 4-387, and wherein the region of complementarity is 19 contiguous nucleotides in length, optionally 20 nucleotides in length.

In some aspects, the disclosure provides an RNAi oligonucleotide for reducing LPA expression, the oligonucleotide comprising a sense strand of 18 to 36 nucleotides in length and an antisense strand of 22 nucleotides in length, wherein the sense strand and the antisense strand form a duplex region, wherein the 3' end of the sense strand comprises a stem-loop set forth as S1-L-S2, wherein S1 is complementary to S2, and wherein L forms a loop between S1 and S2 of 3-5 nucleotides in length, wherein the antisense strand comprises a region of complementarity to a LPA mRNA target sequence of any one of SEQ ID NOs: 4-387, and wherein the region of complementarity is 19 contiguous nucleotides in length, optionally 20 nucleotides in length.

In other aspects, the disclosure provides an RNAi oligonucleotide for reducing LPA expression, the oligonucleotide comprising a sense strand of 36 nucleotides in length and an antisense strand of 22 nucleotides in length, wherein the sense strand and the antisense strand form a duplex region, wherein the 3' end of the sense strand comprises a stem-loop set forth as S1-L-S2, wherein S1 is complementary to S2, and wherein L forms a loop between S1 and S2 of 3-5 nucleotides in length, wherein the antisense strand comprises a region of complementarity to a LPA mRNA target sequence of any one of SEQ ID NOs: 4-387, and wherein the region of complementarity is 19 contiguous nucleotides in length, optionally 20 nucleotides in length.

In yet other aspects, the disclosure provides an RNAi oligonucleotide for reducing LPA expression, the oligonucleotide comprising a sense strand of 36 nucleotides in length and an antisense strand of 22 nucleotides in length, wherein the sense strand and the antisense strand form a duplex region of at least 19 nucleotides in length, optionally 20 nucleotides in length, wherein the 3' end of the sense strand comprises a stem-loop set forth as S1-L-S2, wherein S1 is complementary to S2, and wherein L forms a loop between S1 and S2 of 3-5 nucleotides in length, wherein the antisense strand comprises a region of complementarity to a LPA mRNA target sequence of any one of SEQ ID NOs: 4-387, and wherein the region of complementarity is 19 contiguous nucleotides in length, optionally 20 nucleotides in length.

In any of the foregoing or related aspects, L is a triloop or a tetraloop. In some embodiments, L is a tetraloop. In some embodiments, the tetraloop comprises the sequence 5'-GAAA-3'.

In any of the foregoing or related embodiments, the S1 and S2 are 1-10 nucleotides in length and have the same length. In some embodiments, S1 and S2 are 1 nucleotide, 2 nucleotides, 3 nucleotides, 4 nucleotides, 5 nucleotides, 6 nucleotides, 7 nucleotides, 8 nucleotides, 9 nucleotides, or 10 nucleotides in length. In some embodiments, S1 and S2 are 6 nucleotides in length. In some embodiments, the stem-loop comprises the sequence 5'-GCAGCCGAAAGGCUGC-3' (SEQ ID NO: 1197).

In any of the foregoing or related embodiments, the antisense strand comprises a 3' overhang sequence of one or more nucleotides in length. In some embodiments, the 3' overhang sequence is 2 nucleotides in length, optionally wherein the 3' overhang sequence is GG.

In any of the foregoing or related embodiments, the oligonucleotide comprises at least one modified nucleotide. In some embodiments, the modified nucleotide comprises a 2'-modification. In some embodiments, the 2'-modification is a modification selected from 2'-aminoethyl, 2'-fluoro, 2'-O-methyl, 2'-O-methoxyethyl, and 2'-deoxy-2'-fluoro-β-d-arabinonucleic acid. In some embodiments, all nucleotides comprising the oligonucleotide are modified, optionally wherein the modification is a 2'-modification selected from 2'-fluoro and 2'-O-methyl.

In any of the foregoing or related embodiments, the oligonucleotide comprises at least one modified internucleotide linkage. In some embodiments, the at least one modified internucleotide linkage is a phosphorothioate linkage.

In any of the foregoing or related embodiments, the 4'-carbon of the sugar of the 5'-nucleotide of the antisense strand comprises a phosphate analog. In some embodiments, the phosphate analog is oxymethylphosphonate, vinylphosphonate or malonyl phosphonate, optionally wherein the phosphate analog is a 4'-phosphate analog comprising 5'-methoxyphosphonate-4'-oxy.

In any of the foregoing or related embodiments, at least one nucleotide of the oligonucleotide is conjugated to one or more targeting ligands. In some embodiments, each targeting ligand comprises a carbohydrate, amino sugar, cholesterol, polypeptide, or lipid. In some embodiments, each targeting ligand comprises a N-acetylgalactosamine (GalNAc) moiety. In some embodiments, the GalNAc moiety is a monovalent GalNAc moiety, a bivalent GalNAc moiety, a trivalent GalNAc moiety or a tetravalent GalNAc moiety. In some embodiments, up to 4 nucleotides of L of the stem-loop are each conjugated to a monovalent GalNAc moiety.

In any of the foregoing or related embodiments, the sense strand comprises a nucleotide sequence of any one of SEQ ID NOs: 388, 389, 390, 391, 392, 393, 394, 395, 396, 397, 398, 399, 400, 401, 402, and 403.

In any of the foregoing or related embodiments, the antisense strand comprises a nucleotide sequence of any one of SEQ ID NOs: 788, 789, 790, 791, 792, 793, 794, 795, 796, 797, 798, 799, 800, 801, 802, and 803.

In any of the foregoing or related embodiments, the sense strand and antisense strands comprise nucleotide sequences selected from the group consisting of:

(a) SEQ ID NOs: 393 and 793, respectively;
(b) SEQ ID NOs: 388 and 788, respectively;
(c) SEQ ID NOs: 389 and 789, respectively;
(d) SEQ ID NOs: 390 and 790, respectively;
(e) SEQ ID NOs: 391 and 791, respectively;
(f) SEQ ID NOs: 392 and 792, respectively;
(g) SEQ ID NOs: 394 and 794, respectively;
(h) SEQ ID NOs: 395 and 795, respectively;
(i) SEQ ID NOs: 396 and 796, respectively;
(j) SEQ ID NOs: 397 and 797, respectively;
(k) SEQ ID NOs: 398 and 798, respectively;
(l) SEQ ID NOs: 399 and 799, respectively;
(m) SEQ ID NOs: 400 and 800, respectively;
(n) SEQ ID NOs: 401 and 801, respectively;
(o) SEQ ID NOs: 402 and 802, respectively; and
(p) SEQ ID NOs: 403 and 803, respectively.

In some embodiments, the sense strand comprises a nucleotide sequence as set forth in SEQ ID NO: 393, wherein the antisense strand comprises a nucleotide sequence as set forth in SEQ ID NO: 793. In some embodiments, the sense strand comprises a nucleotide sequence as set forth in SEQ ID NO: 388, wherein the antisense strand comprises a nucleotide sequence as set forth in SEQ ID NO: 788. In some embodiments, the sense strand comprises a nucleotide sequence as set forth in SEQ ID NO: 389, wherein the antisense strand comprises a nucleotide sequence as set forth in SEQ ID NO: 789. In some embodiments, the sense strand comprises a nucleotide sequence as set forth in SEQ ID NO: 390, wherein the antisense strand comprises a nucleotide sequence as set forth in SEQ ID NO: 790. In some embodiments, the sense strand comprises a nucleotide sequence as set forth in SEQ ID NO: 391, wherein the antisense strand comprises a nucleotide sequence as set forth in SEQ ID NO: 791. In some embodiments, the sense strand comprises a nucleotide sequence as set forth in SEQ ID NO: 392, wherein the antisense strand comprises a nucleotide sequence as set forth in SEQ ID NO: 792. In some embodiments, the sense strand comprises a nucleotide sequence as set forth in SEQ ID NO: 394, wherein the antisense strand comprises a nucleotide sequence as set forth in SEQ ID NO: 794. In some embodiments, the sense strand comprises a nucleotide sequence as set forth in SEQ ID NO: 395, wherein the antisense strand comprises a nucleotide sequence as set forth in SEQ ID NO: 795. In some embodiments, the sense strand comprises a nucleotide sequence as set forth in SEQ ID NO: 396, wherein the antisense strand comprises a nucleotide sequence as set forth in SEQ ID NO: 796. In some embodiments, the sense strand comprises a nucleotide sequence as set forth in SEQ ID NO: 397, wherein the antisense strand comprises a nucleotide sequence as set forth in SEQ ID NO: 797. In some embodiments, the sense strand comprises a nucleotide sequence as set forth in SEQ ID NO: 398, wherein the antisense strand comprises a nucleotide sequence as set forth in SEQ ID NO: 798. In some embodiments, the sense strand comprises a nucleotide sequence as set forth in SEQ ID NO: 399, wherein the antisense strand comprises a nucleotide sequence as set forth in SEQ ID NO: 799. In some embodiments, the sense strand comprises a nucleotide sequence as set forth in SEQ ID NO: 400, wherein the antisense strand comprises a nucleotide sequence as set forth in SEQ ID NO: 800. In some embodiments, the sense strand comprises a nucleotide sequence as set forth in SEQ ID NO: 401, wherein the antisense strand comprises a nucleotide sequence as set forth in SEQ ID NO: 801. In some embodiments, the sense strand comprises a nucleotide sequence as set forth in SEQ ID NO: 402, wherein the antisense strand comprises a nucleotide sequence as set forth in SEQ ID NO: 802. In some embodiments, the sense strand comprises a nucleotide sequence as set forth in SEQ ID NO: 403, wherein the antisense strand comprises a nucleotide sequence as set forth in SEQ ID NO: 803.

In some embodiments, the disclosure provides an RNAi oligonucleotide for reducing LPA expression, the oligonucleotide comprising a sense strand and an antisense strand, wherein the sense strand and the antisense strand form a duplex region, wherein all nucleotides comprising the sense strand and antisense strand are modified, wherein the antisense strand comprises a region of complementarity to a LPA mRNA target sequence of any one of SEQ ID NOs: 4-387, and wherein the region of complementarity is at least 15 contiguous nucleotides in length.

In further embodiments, the disclosure provides an RNAi oligonucleotide for reducing LPA expression, the oligonucleotide comprising a sense strand and an antisense strand, wherein the sense strand and the antisense strand form a duplex region, wherein all nucleotides comprising the sense strand and antisense strand are modified, wherein the 4'-carbon of the sugar of the 5'-nucleotide of the antisense strand comprises a phosphate analog, wherein the antisense strand comprises a region of complementarity to a LPA mRNA target sequence of any one of SEQ ID NOs: 4-387, and wherein the region of complementarity is at least 15 contiguous nucleotides in length.

In other embodiments, the disclosure provides an RNAi oligonucleotide for reducing LPA expression, the oligonucleotide comprising a sense strand and an antisense strand, wherein the sense strand and the antisense strand form a duplex region, wherein all nucleotides comprising the sense strand and antisense strand are modified, wherein the 4'-carbon of the sugar of the 5'-nucleotide of the antisense strand comprises a phosphate analog, wherein the antisense strand comprises a region of complementarity to a LPA mRNA target sequence of any one of SEQ ID NOs: 4-387, and wherein the region of complementarity is at least 15 contiguous nucleotides in length.

In some embodiments, the disclosure provides an RNAi oligonucleotide for reducing LPA expression, the oligonucleotide comprising a sense strand and an antisense strand, wherein the sense strand and the antisense strand form a duplex region, wherein all nucleotides comprising the sense strand and the antisense strand are modified, wherein the antisense strand and the sense strand comprise one or more 2'-fluoro and 2'-O-methyl modified nucleotides and at least one phosphorothioate linkage, wherein the 4'-carbon of the sugar of the 5'-nucleotide of the antisense strand comprises a phosphate analog, wherein the antisense strand comprises a region of complementarity to a LPA mRNA target sequence of any one of SEQ ID NOs: 4-387, and wherein the region of complementarity is at least 15 contiguous nucleotides in length.

In some embodiments, the disclosure provides a method for treating a subject having a disease, disorder or condition associated with LPA expression, the method comprising administering to the subject a therapeutically effective amount of the RNAi oligonucleotide of any one of the preceding claims, or pharmaceutical composition thereof, thereby treating the subject.

In other embodiments, the disclosure provides a pharmaceutical composition comprising a RNAi oligonucleotide described herein, and a pharmaceutically acceptable carrier, delivery agent or excipient.

In other embodiments, the disclosure provides a method of delivering an oligonucleotide to a subject, the method comprising administering a pharmaceutical composition described herein to the subject.

In another embodiments, the disclosure provides a method for reducing LPA expression in a cell, a population of cells or a subject, the method comprising the step of:

i. contacting the cell or the population of cells with a RNAi oligonucleotide or pharmaceutical composition described herein; or
ii. administering to the subject a RNAi oligonucleotide or pharmaceutical composition described herein. In some embodiments, reducing LPA expression comprises reducing an amount or level of LPA mRNA, an amount or level of LPA protein, or both. In some embodiments, the subject has a disease, disorder or condition associated with LPA expression. In some embodiments, the disease, disorder, or condition associated with LPA expression is a cardiometabolic disease, optionally atherosclerosis, dyslipidemia, NAFLD and NASH. In some embodiments, the RNAi oligonucleotide, or pharmaceutical composition, is administered in combination with a second composition or therapeutic agent.

In another aspect, the disclosure provides a method for treating a subject having a disease, disorder or condition associated with LPA expression, the method comprising administering to the subject a therapeutically effective amount of an RNAi oligonucleotide comprising a sense strand and an antisense strand, wherein the sense strand and the antisense strand form a duplex region, wherein the antisense strand comprises a region of complementarity to a LPA mRNA target sequence of any one of SEQ ID NOs: 4-387, and wherein the region of complementarity is at least 15 contiguous nucleotides in length.

In another aspect, the disclosure provides a method for treating a subject having a disease, disorder or condition associated with LPA expression, the method comprising administering to the subject a therapeutically effective amount of an RNAi oligonucleotide comprising a sense strand and an antisense strand selected from a row set forth in Table 5, or pharmaceutical composition thereof, thereby treating the subject.

In other embodiments, the disclosure provides a method for treating a subject having a disease, disorder or condition associated with LPA expression, the method comprising administering to the subject a therapeutically effective amount of an RNAi oligonucleotide comprising a sense strand and an antisense strand, wherein the sense strand and antisense strands comprise nucleotide sequences selected from the group consisting of:

(a) SEQ ID NOs: 393 and 793, respectively;
(b) SEQ ID NOs: 388 and 788, respectively;
(c) SEQ ID NOs: 389 and 789, respectively;
(d) SEQ ID NOs: 390 and 790, respectively;
(e) SEQ ID NOs: 391 and 791, respectively;
(f) SEQ ID NOs: 392 and 792, respectively;
(g) SEQ ID NOs: 394 and 794, respectively;
(h) SEQ ID NOs: 395 and 795, respectively;
(i) SEQ ID NOs: 396 and 796, respectively;
(j) SEQ ID NOs: 397 and 797, respectively;
(k) SEQ ID NOs: 398 and 798, respectively;
(l) SEQ ID NOs: 399 and 799, respectively;
(m) SEQ ID NOs: 400 and 800, respectively;
(n) SEQ ID NOs: 401 and 801, respectively;
(o) SEQ ID NOs: 402 and 802, respectively; and
(p) SEQ ID NOs: 403 and 803, respectively.

In some embodiments, the sense strand comprises a nucleotide sequence as set forth in SEQ ID NO: 393, wherein the antisense strand comprises a nucleotide sequence as set forth in SEQ ID NO: 793. In some embodiments, the sense strand comprises a nucleotide sequence as set forth in SEQ ID NO: 388, wherein the antisense strand comprises a nucleotide sequence as set forth in SEQ ID NO: 788. In some embodiments, the sense strand comprises a nucleotide sequence as set forth in SEQ ID NO: 389, wherein the antisense strand comprises a nucleotide sequence as set forth in SEQ ID NO: 789. In some embodiments, the sense strand comprises a nucleotide sequence as set forth in SEQ ID NO: 390, wherein the antisense strand comprises a nucleotide sequence as set forth in SEQ ID NO: 790. In some embodiments, the sense strand comprises a nucleotide sequence as set forth in SEQ ID NO: 391, wherein the antisense strand comprises a nucleotide sequence as set forth in SEQ ID NO: 791. In some embodiments, the sense strand comprises a nucleotide sequence as set forth in SEQ ID NO: 392, wherein the antisense strand comprises a nucleotide sequence as set forth in SEQ ID NO: 792. In some embodiments, the sense strand comprises a nucleotide sequence as set forth in SEQ ID NO: 394, wherein the antisense strand comprises a nucleotide sequence as set forth in SEQ ID NO: 794. In some embodiments, the sense strand comprises a nucleotide sequence as set forth in SEQ ID NO: 395, wherein the antisense strand comprises a nucleotide sequence as set forth in SEQ ID NO: 795. In some embodiments, the sense strand comprises a nucleotide sequence as set forth in SEQ ID NO: 396, wherein the antisense strand comprises a nucleotide sequence as set forth in SEQ ID NO: 796. In some embodiments, the sense strand comprises a nucleotide sequence as set forth in SEQ ID NO: 397, wherein the antisense strand comprises a nucleotide sequence as set forth in SEQ ID NO: 797. In some embodiments, the sense strand comprises a nucleotide sequence as set forth in SEQ ID NO: 398, wherein the antisense strand comprises a nucleotide sequence as set forth in SEQ ID NO: 798. In some embodiments, the sense strand comprises a nucleotide sequence as set forth in SEQ ID NO: 399, wherein the antisense strand comprises a nucleotide sequence as set forth in SEQ ID NO: 799. In some embodiments, the sense strand comprises a nucleotide sequence as set forth in SEQ ID NO: 400, wherein the antisense strand comprises a nucleotide sequence as set forth in SEQ ID NO: 800. In some embodiments, the sense strand comprises a nucleotide sequence as set forth in SEQ ID NO: 401, wherein the antisense strand comprises a nucleotide sequence as set forth in SEQ ID NO: 801. In some embodiments, the sense strand comprises a nucleotide sequence as set forth in SEQ ID NO: 402, wherein the antisense strand comprises a nucleotide sequence as set forth in SEQ ID NO: 802. In some embodiments, the sense strand comprises a nucleotide sequence as set forth in SEQ ID NO: 403, wherein the antisense strand comprises a nucleotide sequence as set forth in SEQ ID NO: 803.

In some embodiments, the disease, disorder, or condition associated with LPA expression is a cardiometabolic disease, optionally atherosclerosis, dyslipidemia, NAFLD and NASH.

In some embodiments, the disclosure provides use of an RNAi oligonucleotide or pharmaceutical composition described herein, in the manufacture of a medicament for the treatment of a disease, disorder or condition associated with LPA expression, optionally for the treatment of a cardiometabolic disease, optionally atherosclerosis, dyslipidemia, NAFLD and NASH.

In some embodiments, the disclosure provides use of an RNAi oligonucleotide or pharmaceutical composition described herein, for use, or adaptable for use, in the treatment of a disease, disorder or condition associated with LPA expression, optionally for the treatment of a cardiometabolic disease, optionally atherosclerosis, dyslipidemia, NAFLD and NASH.

In other embodiments, the disclosure provides a kit comprising an RNAi oligonucleotide described herein, an optional pharmaceutically acceptable carrier, and a package insert comprising instructions for administration to a subject having a disease, disorder or condition associated with LPA expression.

In any of the foregoing or related embodiments, the disease, disorder, or condition associated with LPA expression is a cardiometabolic disease, optionally atherosclerosis, dyslipidemia, NAFLD and NASH.

DETAILED DESCRIPTION

I. Definitions

Figure 1:
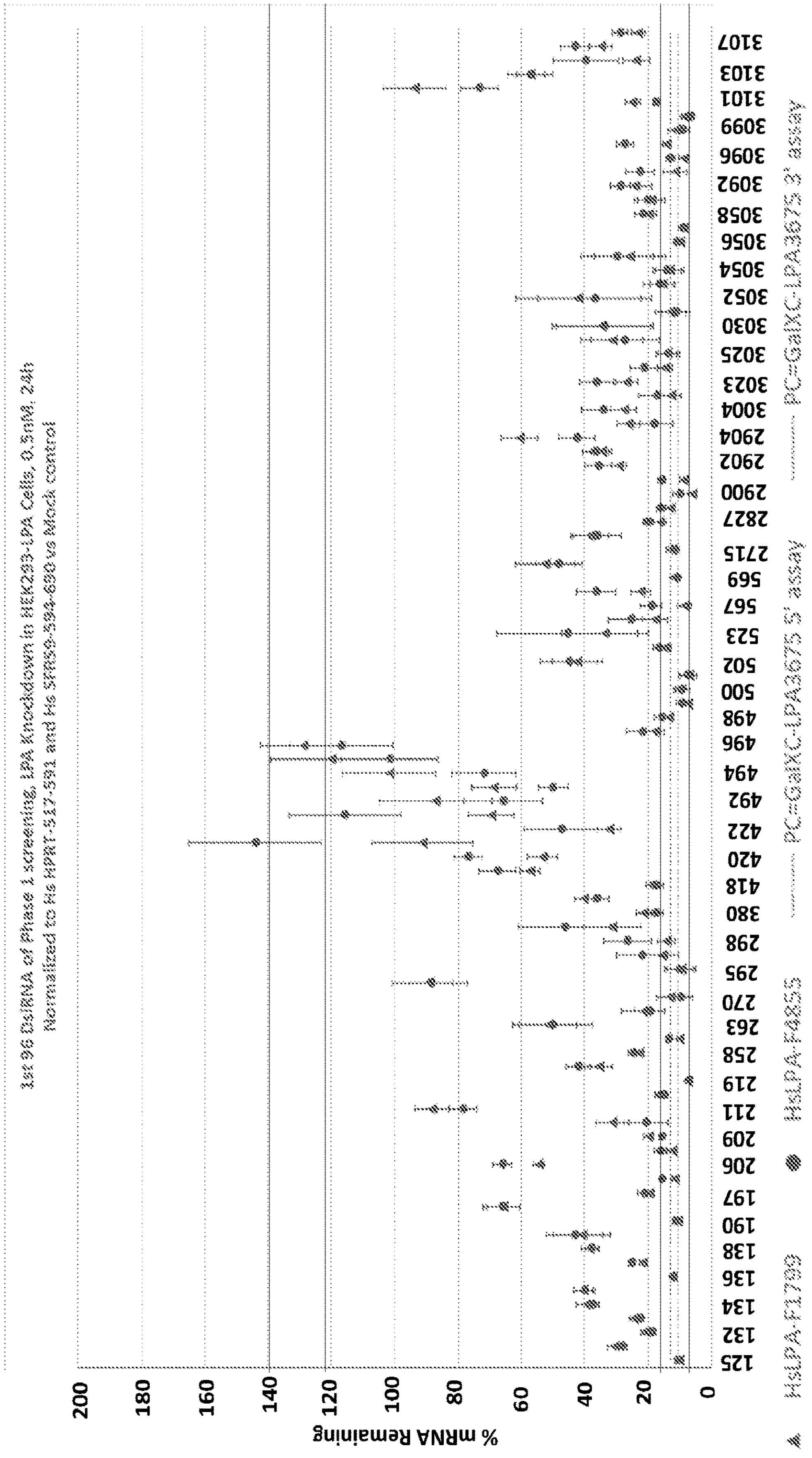
FIGS. 1-4 provide graphs depicting the percent (%) of LPA mRNA in HEK293-LPA cells transfected with the indicated DsiRNAs relative to the % of LPA mRNA control mock-treated cells.
Figure 2:
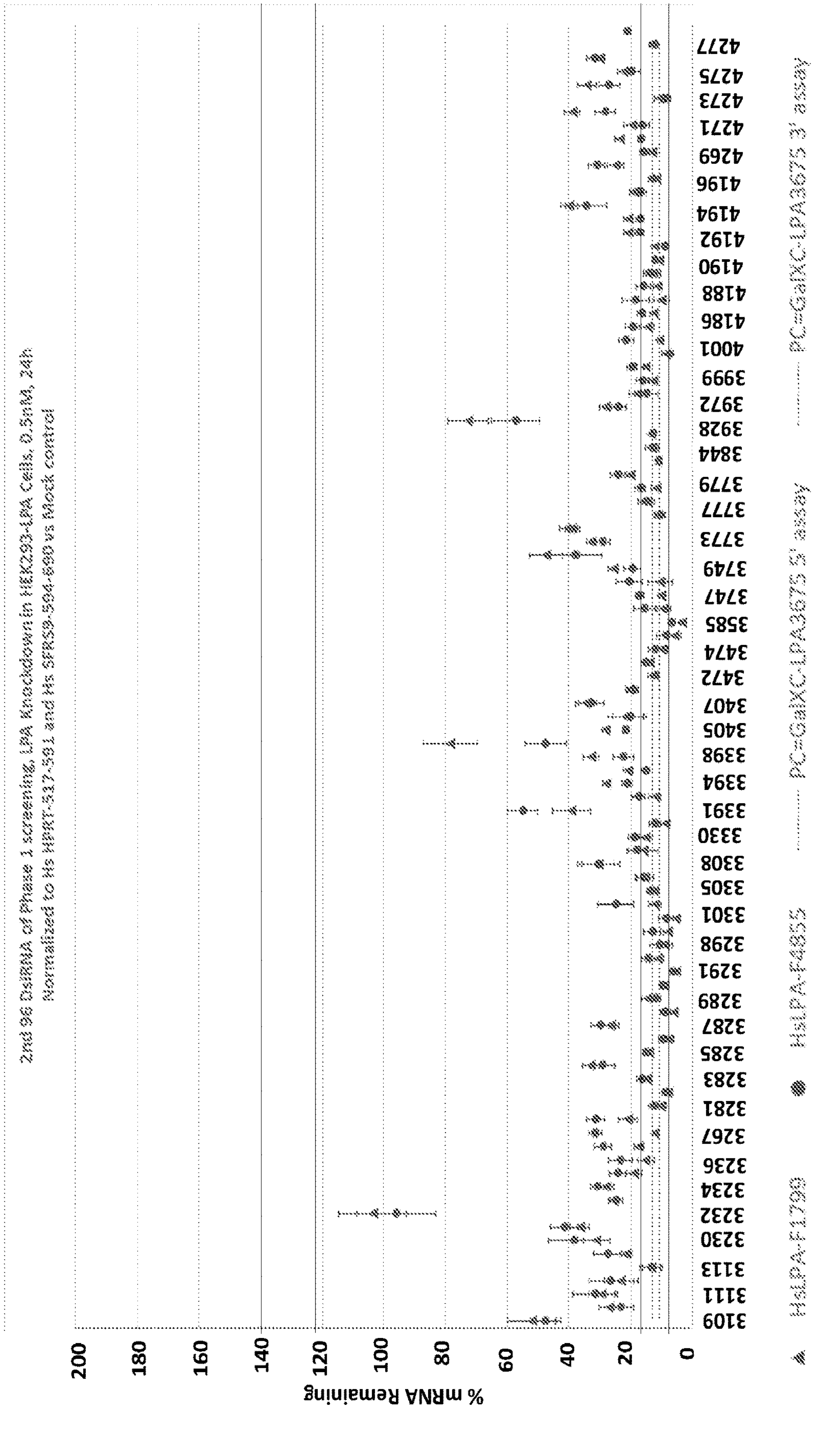

As used herein, "about," as applied to one or more values of interest, refers to a value that is similar to a stated reference value. In certain embodiments, "about" refers to a range of values that fall within 25%, 20%, 19%, 18%1, 17%, 16%, 15%, 14%, 13%, 12%, 11%, 10%, 9%, 8%, 7%, 6%, 5%, 4%, 3%, 2%, 1% or less in either direction (greater than or less than) of the stated reference value unless otherwise stated or otherwise evident from the context (except where such number would exceed 100% of a possible value).

As used herein, "administer," "administering," "administration" and the like refers to providing a substance (e.g., an oligonucleotide) to a subject in a manner that is pharmacologically useful (e.g., to treat a condition in the subject).

As used herein, the term "apolipoprotein(a)" and abbreviated as "apo(a)", refers to the apolipoprotein(a) polypeptide, which is a member of the apolipoprotein class of polypeptides that bind lipids to form lipoproteins. Apo(a) is a polymorphic glycoprotein encoded by the LPA gene in humans. LPA mRNA and apo(a) polypeptide are expressed predominantly in the liver. Lipoprotein(a) (abbreviated as Lp(a)) is a class of lipoprotein formed in the liver and comprises a single copy of apolipoprotein(apo) B-100 (Apo-B100) covalently tethered to apo(a). In humans, apo(a) includes at least 10 subtypes of KIV repeats, composed of 1 copy each of $KIV_1$, multiple copies of $KIV_2$, and 1 copy each of $KIV_3$-$KIV_{10}$, KV, and an inactive protease-like domain. The presence of apo(a) distinguishes Lp(a) from all other lipoprotein classes (Marcovina et al., (1995) Clin Chem. 41(2):246-55). For the purposes of the disclosure, "apolipoprotein(a)" or "apo(a)" refers to the apo(a) polypeptide from any vertebrate or mammal including, but not limited to, human, mouse, primate, monkey, bovine, chicken, rodent, rat, porcine, ovine and guinea pig. "Apo(a)" also refers to fragments and variants of native apo(a) that maintain at least one in vivo or in vitro activity of a native apo(a). Apo(a) encompasses full-length, unprocessed precursor forms of Apo(a), as well as mature forms resulting from post-translational processing. An exemplary sequence of a human LPA mRNA transcript is publicly available (GenBank Accession No. NM_005577.3) and disclosed herein (SEQ ID NO: 1). An exemplary sequence of cynomolgus monkey LPA mRNA is publicly available (GenBank Accession No. XM_015448517.1) and disclosed herein (SEQ ID NO: 2).

As used herein, "asialoglycoprotein receptor" or "ASGPR" refers to a bipartite C-type lectin formed by a major 48 kDa subunit (ASGPR-1) and minor 40 kDa subunit (ASGPR-2). ASGPR is primarily expressed on the sinusoidal surface of hepatocyte cells and has a major role in binding, internalizing and subsequent clearing of circulating glycoproteins that contain terminal galactose or GalNAc residues (asialoglycoproteins).

As used herein, "attenuate," "attenuating," "attenuation" and the like refers to reducing or effectively halting. As a non-limiting example, one or more of the treatments herein may reduce or effectively halt the onset or progression of cardiometabolic diseases including atherosclerosis, dyslipidemia, NAFLD and NASH in a subject. This attenuation may be exemplified by, for example, a decrease in one or more aspects (e.g., symptoms, tissue characteristics, and cellular, inflammatory or immunological activity, etc.) of cardiometabolic diseases including atherosclerosis, dyslipidemia, NAFLD and NASH, no detectable progression (worsening) of one or more aspects of cardiometabolic diseases including atherosclerosis, dyslipidemia, NAFLD and NASH, or no detectable aspects of cardiometabolic diseases including atherosclerosis, dyslipidemia, NAFLD and NASH in a subject when they might otherwise be expected.

As used herein, "complementary" refers to a structural relationship between two nucleotides (e.g., on two opposing nucleic acids or on opposing regions of a single nucleic acid strand) that permits the two nucleotides to form base pairs with one another. For example, a purine nucleotide of one nucleic acid that is complementary to a pyrimidine nucleotide of an opposing nucleic acid may base pair together by forming hydrogen bonds with one another. In some embodiments, complementary nucleotides can base pair in the Watson-Crick manner or in any other manner that allows for the formation of stable duplexes. In some embodiments, two nucleic acids may have regions of multiple nucleotides that are complementary with each other to form regions of complementarity, as described herein.

As used herein, "deoxyribonucleotide" refers to a nucleotide having a hydrogen in place of a hydroxyl at the 2' position of its pentose sugar when compared with a ribonucleotide. A modified deoxyribonucleotide is a deoxyribonucleotide having one or more modifications or substitutions of atoms other than at the 2' position, including modifications or substitutions in or of the sugar, phosphate group or base.

As used herein, "double-stranded oligonucleotide" or "ds oligonucleotide" refers to an oligonucleotide that is substantially in a duplex form. In some embodiments, the complementary base-pairing of duplex region(s) of a ds oligonucleotide is formed between antiparallel sequences of nucleotides of covalently separate nucleic acid strands. In some embodiments, complementary base-pairing of duplex region(s) of a ds oligonucleotide is formed between antiparallel sequences of nucleotides of nucleic acid strands that are covalently linked. In some embodiments, complementary base-pairing of duplex region(s) of a ds oligonucleotide is formed from single nucleic acid strand that is folded (e.g., via a hairpin) to provide complementary antiparallel sequences of nucleotides that base pair together. In some embodiments, a ds oligonucleotide comprises two covalently separate nucleic acid strands that are fully duplexed with one another. However, in some embodiments, a ds oligonucleotide comprises two covalently separate nucleic acid strands that are partially duplexed (e.g., having overhangs at one or both ends). In some embodiments, a ds oligonucleotide comprises antiparallel sequence of nucleotides that are partially complementary, and thus, may have one or more mismatches, which may include internal mismatches or end mismatches.

As used herein, "duplex," in reference to nucleic acids (e.g., oligonucleotides), refers to a structure formed through complementary base pairing of two antiparallel sequences of nucleotides.

As used herein, "excipient" refers to a non-therapeutic agent that may be included in a composition, for example, to provide or contribute to a desired consistency or stabilizing effect.

As used herein, "hepatocyte" or "hepatocytes" refers to cells of the parenchymal tissues of the liver. These cells make up about 70%-85% of the liver's mass and manufacture serum albumin, FBN and the prothrombin group of clotting factors (except for Factors 3 and 4). Markers for hepatocyte lineage cells include, but are not limited to, transthyretin (Ttr), glutamine synthetase (Glul), hepatocyte nuclear factor 1a (Hnf1a) and hepatocyte nuclear factor 4a (Hnf4a). Markers for mature hepatocytes may include, but are not limited to, cytochrome P450 (Cyp3a11), fumarylacetoacetate hydrolase (Fah), glucose 6-phosphate (G6p), albumin (Alb) and OC2-2F8. See, e.g., Huch et al. (2013) *Nature* 494:247-250.

As used herein, a "hepatotoxic agent" refers to a chemical compound, virus or other substance that is itself toxic to the liver or can be processed to form a metabolite that is toxic to the liver. Hepatotoxic agents may include, but are not limited to, carbon tetrachloride ($CCl_4$), acetaminophen (paracetamol), vinyl chloride, arsenic, chloroform, nonsteroidal anti-inflammatory drugs (such as aspirin and phenylbutazone).

As used herein, "labile linker" refers to a linker that can be cleaved (e.g., by acidic pH). A "fairly stable linker" refers to a linker that cannot be cleaved.

As used herein, "liver inflammation" or "hepatitis" refers to a physical condition in which the liver becomes swollen, dysfunctional and/or painful, especially as a result of injury or infection, as may be caused by exposure to a hepatotoxic agent. Symptoms may include jaundice (yellowing of the skin or eyes), fatigue, weakness, nausea, vomiting, appetite reduction and weight loss. Liver inflammation, if left untreated, may progress to fibrosis, cirrhosis, liver failure or liver cancer.

As used herein, "liver fibrosis" or "fibrosis of the liver" refers to an excessive accumulation in the liver of extracellular matrix proteins, which could include collagens (I, III, and IV), FBN, undulin, elastin, laminin, hyaluronan and proteoglycans resulting from inflammation and liver cell death. Liver fibrosis, if left untreated, may progress to cirrhosis, liver failure or liver cancer.

As used herein, "loop" refers to a unpaired region of a nucleic acid (e.g., oligonucleotide) that is flanked by two antiparallel regions of the nucleic acid that are sufficiently complementary to one another, such that under appropriate hybridization conditions (e.g., in a phosphate buffer, in a cells), the two antiparallel regions, which flank the unpaired region, hybridize to form a duplex (referred to as a "stem").

As used herein, "modified internucleotide linkage" refers to an internucleotide linkage having one or more chemical modifications when compared with a reference internucleotide linkage comprising a phosphodiester bond. In some embodiments, a modified nucleotide is a non-naturally occurring linkage. Typically, a modified internucleotide linkage confers one or more desirable properties to a nucleic acid in which the modified internucleotide linkage is present. For example, a modified nucleotide may improve thermal stability, resistance to degradation, nuclease resistance, solubility, bioavailability, bioactivity, reduced immunogenicity, etc.

As used herein, "modified nucleotide" refers to a nucleotide having one or more chemical modifications when compared with a corresponding reference nucleotide selected from: adenine ribonucleotide, guanine ribonucleotide, cytosine ribonucleotide, uracil ribonucleotide, adenine deoxyribonucleotide, guanine deoxyribonucleotide, cytosine deoxyribonucleotide and thymidine deoxyribonucleotide. In some embodiments, a modified nucleotide is a non-naturally occurring nucleotide. In some embodiments, a modified nucleotide has one or more chemical modification in its sugar, nucleobase and/or phosphate group. In some embodiments, a modified nucleotide has one or more chemical moieties conjugated to a corresponding reference nucleotide. Typically, a modified nucleotide confers one or more desirable properties to a nucleic acid in which the modified nucleotide is present. For example, a modified nucleotide may improve thermal stability, resistance to degradation, nuclease resistance, solubility, bioavailability, bioactivity, reduced immunogenicity, etc.

As used herein, "nicked tetraloop structure" refers to a structure of a RNAi oligonucleotide that is characterized by separate sense (passenger) and antisense (guide) strands, in which the sense strand has a region of complementarity with the antisense strand, and in which at least one of the strands, generally the sense strand, has a tetraloop configured to stabilize an adjacent stem region formed within the at least one strand.

As used herein, "oligonucleotide" refers to a short nucleic acid (e.g., less than about 100 nucleotides in length). An oligonucleotide may be single-stranded (ss) or ds. An oligonucleotide may or may not have duplex regions. As a set of non-limiting examples, an oligonucleotide may be, but is not limited to, a small interfering RNA (siRNA), microRNA (miRNA), short hairpin RNA (shRNA), dicer substrate interfering RNA (dsiRNA), antisense oligonucleotide, short siRNA or ss siRNA. In some embodiments, a ds oligonucleotide is an RNAi oligonucleotide.

As used herein, "overhang" refers to terminal non-base pairing nucleotide(s) resulting from one strand or region extending beyond the terminus of a complementary strand with which the one strand or region forms a duplex. In some embodiments, an overhang comprises one or more unpaired nucleotides extending from a duplex region at the 5' terminus or 3' terminus of a ds oligonucleotide. In certain embodiments, the overhang is a 3' or 5' overhang on the antisense strand or sense strand of a ds oligonucleotides.

As used herein, "phosphate analog" refers to a chemical moiety that mimics the electrostatic and/or steric properties of a phosphate group. In some embodiments, a phosphate analog is positioned at the 5' terminal nucleotide of an oligonucleotide in place of a 5'-phosphate, which is often susceptible to enzymatic removal. In some embodiments, a 5' phosphate analog contains a phosphatase-resistant linkage. Examples of phosphate analogs include, but are not limited to, 5' phosphonates, such as 5' methylenephosphonate (5'-MP) and 5'-(E)-vinylphosphonate (5'-VP). In some embodiments, an oligonucleotide has a phosphate analog at a 4'-carbon position of the sugar (referred to as a "4'-phosphate analog") at a 5'-terminal nucleotide. An example of a 4'-phosphate analog is oxymethylphosphonate, in which the oxygen atom of the oxymethyl group is bound to the sugar moiety (e.g., at its 4'-carbon) or analog thereof. See, e.g., US Provisional Patent Application Nos. 62/383,207 (filed on 2 Sep. 2016) and 62/393,401 (filed on 12 Sep. 2016). Other modifications have been developed for the 5' end of oligonucleotides (see, e.g., Intl. Patent Application No. WO 2011/133871; U.S. Pat. No. 8,927,513; and Prakash et al. (2015) *Nucleic Acids Res.* 43:2993-3011).

As used herein, "reduced expression" of a gene (e.g., LPA) refers to a decrease in the amount or level of RNA transcript (e.g., LPA mRNA) or protein encoded by the gene and/or a decrease in the amount or level of activity of the gene in a cell, a population of cells, a sample or a subject, when compared to an appropriate reference (e.g., a reference cell, population of cells, sample or subject). For example, the act of contacting a cell with an oligonucleotide herein (e.g., an oligonucleotide comprising an antisense strand having a nucleotide sequence that is complementary to a nucleotide sequence comprising LPA mRNA) may result in a decrease in the amount or level of LPA mRNA, apo(a) protein and/or apo(a) activity (e.g., via inactivation and/or degradation of LPA mRNA by the RNAi pathway) when compared to a cell that is not treated with the ds oligonucleotide. Similarly, and as used herein, "reducing expression" refers to an act that results in reduced expression of a gene (e.g., LPA). As used herein, "reduction of LPA expression" refers to a decrease in the amount or level of LPA mRNA, apo(a) protein and/or apo(a) activity in a cell, a population of cells, a sample or a subject when compared to an appropriate reference (e.g., a reference cell, population of cells, sample, or subject).

As used herein, "region of complementarity" refers to a sequence of nucleotides of a nucleic acid (e.g., a ds oligonucleotide) that is sufficiently complementary to an antiparallel sequence of nucleotides to permit hybridization between the two sequences of nucleotides under appropriate hybridization conditions (e.g., in a phosphate buffer, in a cell, etc.). In some embodiments, an oligonucleotide herein comprises a targeting sequence having a region of complementary to a mRNA target sequence.

As used herein, "ribonucleotide" refers to a nucleotide having a ribose as its pentose sugar, which contains a hydroxyl group at its 2' position. A modified ribonucleotide is a ribonucleotide having one or more modifications or substitutions of atoms other than at the 2' position, including modifications or substitutions in or of the ribose, phosphate group or base.

As used herein, "RNAi oligonucleotide" refers to either (a) a ds oligonucleotide having a sense strand (passenger) and antisense strand (guide), in which the antisense strand or part of the antisense strand is used by the Argonaute 2 (Ago2) endonuclease in the cleavage of a target mRNA (e.g., LPA mRNA) or (b) a ss oligonucleotide having a single antisense strand, where that antisense strand (or part of that antisense strand) is used by the Ago2 endonuclease in the cleavage of a target mRNA (e.g., LPA mRNA).

As used herein, "strand" refers to a single, contiguous sequence of nucleotides linked together through internucleotide linkages (e.g., phosphodiester linkages or phosphorothioate linkages). In some embodiments, a strand has two free ends (e.g., a 5' end and a 3' end).

As used herein, "subject" means any mammal, including mice, rabbits and humans. In one embodiment, the subject is a human or NHP. Moreover, "individual" or "patient" may be used interchangeably with "subject."

As used herein, "synthetic" refers to a nucleic acid or other molecule that is artificially synthesized (e.g., using a machine (e.g., a solid-state nucleic acid synthesizer)) or that is otherwise not derived from a natural source (e.g., a cell or organism) that normally produces the molecule.

As used herein, "targeting ligand" refers to a molecule (e.g., a carbohydrate, amino sugar, cholesterol, polypeptide or lipid) that selectively binds to a cognate molecule (e.g., a receptor) of a tissue or cell of interest and that is conjugatable to another substance for purposes of targeting the other substance to the tissue or cell of interest. For example, in some embodiments, a targeting ligand may be conjugated to an oligonucleotide for purposes of targeting the oligonucleotide to a specific tissue or cell of interest. In some embodiments, a targeting ligand selectively binds to a cell surface receptor. Accordingly, in some embodiments, a targeting ligand when conjugated to an oligonucleotide facilitates delivery of the oligonucleotide into a particular cell through selective binding to a receptor expressed on the surface of the cell and endosomal internalization by the cell of the complex comprising the oligonucleotide, targeting ligand and receptor. In some embodiments, a targeting ligand is conjugated to an oligonucleotide via a linker that is cleaved following or during cellular internalization such that the oligonucleotide is released from the targeting ligand in the cell.

As used herein, "tetraloop" refers to a loop that increases stability of an adjacent duplex formed by hybridization of flanking sequences of nucleotides. The increase in stability is detectable as an increase in melting temperature ($T_m$) of an adjacent stem duplex that is higher than the $T_m$ of the adjacent stem duplex expected, on average, from a set of loops of comparable length consisting of randomly selected sequences of nucleotides. For example, a tetraloop can confer a $T_m$ of at least about 50° C., at least about 55° C., at least about 56° C., at least about 58° C., at least about 60° C., at least about 65° C. or at least about 75° C. in 10 mM $NaHPO_4$ to a hairpin comprising a duplex of at least 2 base pairs (bp) in length. In some embodiments, a tetraloop may stabilize a bp in an adjacent stem duplex by stacking interactions. In addition, interactions among the nucleotides in a tetraloop include, but are not limited to, non-Watson-Crick base pairing, stacking interactions, hydrogen bonding and contact interactions (Cheong et al. (1990) Nature 346: 680-82; Heus & Pardi (1991) Science 253:191-94). In some embodiments, a tetraloop comprises or consists of 3 to 6 nucleotides and is typically 4 to 5 nucleotides. In certain embodiments, a tetraloop comprises or consists of 3, 4, 5 or 6 nucleotides, which may or may not be modified (e.g., which may or may not be conjugated to a targeting moiety). In one embodiment, a tetraloop consists of 4 nucleotides.

Any nucleotide may be used in the tetraloop and standard IUPAC-IUB symbols for such nucleotides may be used as described in Cornish-Bowden (1985) *Nucleic Acids Res.* 13:3021-3030. For example, the letter "N" may be used to mean that any base may be in that position, the letter "R" may be used to show that A (adenine) or G (guanine) may be in that position, and "B" may be used to show that C (cytosine), G (guanine), T (thymine) or U (uracil) may be in that position. Examples of tetraloops include the UNCG family of tetraloops (e.g., UUCG), the GNRA family of tetraloops (e.g., GAAA), and the CUUG tetraloop (Woese et al. (1990) *Proc. Natl. Acad. Sci. USA* 87:8467-8471; Antao et al. (1991) *Nucleic Acids Res.* 19:5901-5905). Examples of DNA tetraloops include the d(GNNA) family of tetraloops (e.g., d(GTTA), the d(GNRA)) family of tetraloops, the d(GNAB) family of tetraloops, the d(CNNG) family of tetraloops, and the d(TNCG) family of tetraloops (e.g., d(TTCG)). See, e.g., Nakano et al. (2002) *Biochem.* 41:4281-14292; Shinji et al. (2000) *Nippon Kagakkai Koen Yokoshu* 78:731. In some embodiments, the tetraloop is contained within a nicked tetraloop structure.

As used herein, "treat" or "treating" refers to the act of providing care to a subject in need thereof, for example, by administering a therapeutic agent (e.g., an oligonucleotide herein) to the subject, for purposes of improving the health and/or well-being of the subject with respect to an existing condition (e.g., a disease, disorder) or to prevent or decrease the likelihood of the occurrence of a condition. In some embodiments, treatment involves reducing the frequency or severity of at least one sign, symptom or contributing factor of a condition (e.g., disease, disorder) experienced by a subject.

II. Oligonucleotide Inhibitors of LPA Expression

The disclosure provides, inter alia, oligonucleotides that inhibit LPA expression. In some embodiments, an oligonucleotide that inhibits LPA expression herein is targeted to an LPA mRNA.

i. LPA Target Sequences

In some embodiments, the oligonucleotide is targeted to a target sequence comprising an LPA mRNA. In some embodiments, the oligonucleotide, or a portion, fragment or strand thereof (e.g., an antisense strand or a guide strand of a ds oligonucleotide) binds or anneals to a target sequence comprising an LPA mRNA, thereby inhibiting LPA expression. In some embodiments, the oligonucleotide is targeted to an LPA target sequence for the purpose of inhibiting LPA expression in vivo. In some embodiments, the amount or extent of inhibition of LPA expression by an oligonucleotide targeted to an LPA target sequence correlates with the potency of the oligonucleotide. In some embodiments, the amount or extent of inhibition of LPA expression by an oligonucleotide targeted to an LPA target sequence correlates with the amount or extent of therapeutic benefit in a subject or patient having a disease, disorder or condition associated with the expression of LPA treated with the oligonucleotide.

Through examination and analysis of the nucleotide sequence of LPA mRNAs encoding apo(a), including mRNAs of multiple different species (e.g., human, cynomolgus monkey, and rhesus monkey; see, e.g., Example 1) and as a result of in vitro and in vivo testing (see, e.g., Example 2 and Example 3), it has been discovered that certain nucleotide sequences of LPA mRNA are more amenable than others to oligonucleotide-based inhibition of LPA expression and are thus useful as target sequences for the oligonucleotides herein. In some embodiments, a sense strand of an oligonucleotide (e.g., a ds oligonucleotide) described herein (e.g., in Table 5) comprises an LPA target sequence. In some embodiments, a portion or region of the sense strand of a ds oligonucleotide described herein (e.g., in Table 5) comprises an LPA target sequence. In some embodiments, an LPA target sequence comprises, or consists of, a sequence of any one of SEQ ID Nos: 4-387.

ii. LPA Targeting Sequences

In some embodiments, the oligonucleotides herein have regions of complementarity to LPA mRNA (e.g., within a target sequence of LPA mRNA) for purposes of targeting the LPA mRNA in cells and inhibiting LPA expression. In some embodiments, the oligonucleotides herein comprise an LPA targeting sequence (e.g., an antisense strand or a guide strand of a ds oligonucleotide) having a region of complementarity that binds or anneals to an LPA target sequence by complementary (Watson-Crick) base pairing. The targeting sequence or region of complementarity is generally of a suitable length and base content to enable binding or annealing of the oligonucleotide (or a strand thereof) to an LPA mRNA for purposes of inhibiting its expression. In some embodiments, the targeting sequence or region of complementarity is at least about 12, at least about 13, at least about 14, at least about 15, at least about 16, at least about 17, at least about 18, at least about 19, at least about 20, at least about 21, at least about 22, at least about 23, at least about 24, at least about 25, at least about 26, at least about 27, at least about 28, at least about 29 or at least about 30 nucleotides in length. In some embodiments, the targeting sequence or region of complementarity is about 12 to about 30 (e.g., 12 to 30, 12 to 22, 15 to 25, 17 to 21, 18 to 27, 19 to 27, or 15 to 30) nucleotides in length. In some embodiments, the targeting sequence or region of complementarity is about 12, 13, 14, 15, 16, 17, 18, 19, 20, 21, 22, 23, 24, 25, 26, 27, 28, 29 or 30 nucleotides in length. In some embodiments, the targeting sequence or region of complementarity is 18 nucleotides in length. In some embodiments, the targeting sequence or region of complementarity is 19 nucleotides in length. In some embodiments, the targeting sequence or region of complementarity is 20 nucleotides in length. In some embodiments, the targeting sequence or region of complementarity is 21 nucleotides in length. In some embodiments, the targeting sequence or region of complementarity is 22 nucleotides in length. In some embodiments, the targeting sequence or region of complementarity is 23 nucleotides in length. In some embodiments, the targeting sequence or region of complementarity is 24 nucleotides in length.

In some embodiments, an oligonucleotide herein comprises a targeting sequence or a region of complementarity (e.g., an antisense strand or a guide strand of a double-stranded oligonucleotide) that is fully complementary to an LPA target sequence. In some embodiments, the targeting sequence or region of complementarity is partially complementary to an LPA target sequence. In some embodiments, the oligonucleotide comprises a targeting sequence or region of complementarity that is fully complementary to a sequence of any one of SEQ ID NOs: 4-387. In some embodiments, the oligonucleotide comprises a targeting sequence or region of complementarity that is partially complementary to a sequence of any one of SEQ ID NOs: 4-387.

In some embodiments, the oligonucleotide herein comprises a targeting sequence or region of complementarity that is complementary to a contiguous sequence of nucleotides comprising an LPA mRNA, wherein the contiguous sequence of nucleotides is about 12 to about 30 nucleotides in length (e.g., 12 to 30, 12 to 28, 12 to 26, 12 to 24, 12 to 20, 12 to 18, 12 to 16, 14 to 22, 16 to 20, 18 to 20 or 18 to 19 nucleotides in length). In some embodiments, the oligonucleotide comprises a targeting sequence or region of complementarity that is complementary to a contiguous sequence of nucleotides comprising an LPA mRNA, wherein the contiguous sequence of nucleotides is 10, 11, 12, 13, 14, 15, 16, 17, 18, 19 or 20 nucleotides in length. In some embodiments, the oligonucleotide comprises a targeting sequence or region of complementarity that is complementary to a contiguous sequence of nucleotides comprising an LPA mRNA, wherein the contiguous sequence of nucleotides is 19 nucleotides in length. In some embodiments, the oligonucleotide comprises a targeting sequence or region of complementarity that is complementary to a contiguous sequence of nucleotides comprising an LPA mRNA, wherein the contiguous sequence of nucleotides is 20 nucleotides in length. In some embodiments, the oligonucleotide comprises a targeting sequence or a region of complementarity that is complementary to a contiguous sequence of nucleotides of any one of SEQ ID NOs: 4-387, optionally wherein the contiguous sequence of nucleotides is 19 nucleotides in length.

In some embodiments, a targeting sequence or region of complementarity of an oligonucleotide that is complementary to contiguous nucleotides of a sequence as set forth in any one of SEQ ID NOs: 4-387 and spans the entire length of an antisense strand. In some embodiments, a region of complementarity of an oligonucleotide that is complementary to contiguous nucleotides of a sequence as set forth in any one of SEQ ID NOs: 4-387 and spans a portion of the entire length of an antisense strand. In some embodiments, an oligonucleotide herein comprises a region of complementarity (e.g., on an antisense strand of a ds oligonucleotide) that is at least partially (e.g., fully) complementary to a contiguous stretch of nucleotides spanning nucleotides 1-20 of a sequence as set forth in any one of SEQ ID NOs: 4-387.

In some embodiments, an oligonucleotide herein comprises a targeting sequence or region of complementarity having one or more base pair (bp) mismatches with the corresponding LPA target sequence. In some embodiments, the targeting sequence or region of complementarity may have up to about 1, up to about 2, up to about 3, up to about 4, up to about 5, etc. mismatches with the corresponding LPA target sequence provided that the ability of the targeting sequence or region of complementarity to bind or anneal to the LPA mRNA under appropriate hybridization conditions and/or the ability of the oligonucleotide to reduce or inhibit LPA expression is maintained. Alternatively, in some embodiments, the targeting sequence or region of complementarity comprises no more than 1, no more than 2, no more than 3, no more than 4, or no more than 5 mismatches with the corresponding LPA target sequence provided that the ability of the targeting sequence or region of complementarity to bind or anneal to the LPA mRNA under appropriate hybridization conditions and/or the ability of the oligonucleotide to reduce or inhibit LPA expression is maintained. In some embodiments, the oligonucleotide comprises a targeting sequence or region of complementarity having 1 mismatch with the corresponding target sequence. In some embodiments, the oligonucleotide comprises a targeting sequence or region of complementarity having 2 mismatches with the corresponding target sequence. In some embodiments, the oligonucleotide comprises a targeting sequence or region of complementarity having 3 mismatches with the corresponding target sequence. In some embodiments, the oligonucleotide comprises a targeting sequence or region of complementarity having 4 mismatches with the corresponding target sequence. In some embodiments, the oligonucleotide comprises a targeting sequence or region of complementarity having 5 mismatches with the corresponding target sequence. In some embodiments, the oligonucleotide comprises a targeting sequence or region of complementarity more than one mismatch (e.g., 2, 3, 4, 5 or more mismatches) with the corresponding target sequence, wherein at least 2 (e.g., all) of the mismatches are positioned consecutively (e.g., 2, 3, 4, 5 or more mismatches in a row), or wherein the mismatches are interspersed in any position throughout the targeting sequence or region of complementarity. In some embodiments, the oligonucleotide comprises a targeting sequence or region of complementarity more than one mismatch (e.g., 2, 3, 4, 5 or more mismatches) with the corresponding target sequence, wherein at least 2 (e.g., all) of the mismatches are positioned consecutively (e.g., 2, 3, 4, 5 or more mismatches in a row), or wherein at least one or more non-mismatched base pair is located between the mismatches, or a combination thereof.

iii. Types of Oligonucleotides

A variety of oligonucleotide types and/or structures are useful for targeting LPA mRNA in the methods herein including, but not limited to, RNAi oligonucleotides, antisense oligonucleotides, miRNAs, etc. Any of the oligonucleotide types described herein or elsewhere are contemplated for use as a framework to incorporate an LPA mRNA targeting sequence herein for the purposes of inhibiting LPA expression.

In some embodiments, the oligonucleotides herein inhibit LPA expression by engaging with RNA interference (RNAi) pathways upstream or downstream of Dicer involvement. For example, RNAi oligonucleotides have been developed with each strand having sizes of about 19-25 nucleotides with at least one 3' overhang of 1 to 5 nucleotides (see, e.g., U.S. Pat. No. 8,372,968). Longer oligonucleotides also have been developed that are processed by Dicer to generate active RNAi products (see, e.g., U.S. Pat. No. 8,883,996). Further work produced extended ds oligonucleotides where at least one end of at least one strand is extended beyond a duplex targeting region, including structures where one of the strands includes a thermodynamically-stabilizing tetraloop structure (see, e.g., U.S. Pat. Nos. 8,513,207 and 8,927,705, as well as Intl. Patent Application Publication No. WO 2010/033225). Such structures may include ss extensions (on one or both sides of the molecule) as well as ds extensions.

In some embodiments, the oligonucleotides herein engage with the RNAi pathway downstream of the involvement of Dicer (e.g., Dicer cleavage). In some embodiments, the oligonucleotide has an overhang (e.g., of 1, 2, or 3 nucleotides in length) in the 3' end of the sense strand. In some embodiments, the oligonucleotide (e.g., siRNA) comprises a 21-nucleotide guide strand that is antisense to a target mRNA (e.g., LPA mRNA) and a complementary passenger strand, in which both strands anneal to form a 19-bp duplex and 2 nucleotide overhangs at either or both 3' ends. Longer oligonucleotide designs also are contemplated including oligonucleotides having a guide strand of 23 nucleotides and a passenger strand of 21 nucleotides, where there is a blunt end on the right side of the molecule (3' end of passenger strand/5' end of guide strand) and a two nucleotide 3'-guide strand overhang on the left side of the molecule (5' end of the passenger strand/3' end of the guide strand). In such molecules, there is a21 bp duplex region. See, e.g., U.S. Pat. Nos. 9,012,138; 9,012,621 and 9,193,753.

In some embodiments, the oligonucleotides herein comprise sense and antisense strands that are both in the range of about 17 to 26 (e.g., 17 to 26, 20 to 25 or 21-23)

nucleotides in length. In some embodiments, an oligonucleotide herein comprises a sense and antisense strand that are both in the range of about 19-22 nucleotides in length. In some embodiments, the sense and antisense strands are of equal length. In some embodiments, an oligonucleotide comprises sense and antisense strands, such that there is a 3'-overhang on either the sense strand or the antisense strand, or both the sense and antisense strand. In some embodiments, for oligonucleotides that have sense and antisense strands that are both in the range of about 21-23 nucleotides in length, a 3' overhang on the sense, antisense, or both sense and antisense strands is 1 or 2 nucleotides in length. In some embodiments, the oligonucleotide has a guide strand of 22 nucleotides and a passenger strand of 20 nucleotides, where there is a blunt end on the right side of the molecule (3' end of passenger strand/5' end of guide strand) and a 2 nucleotide 3'-guide strand overhang on the left side of the molecule (5' end of the passenger strand/3' end of the guide strand). In such molecules, there is a 20 bp duplex region.

Other oligonucleotide designs for use with the compositions and methods herein include: 16-mer siRNAs (see, e.g., NUCLEIC ACIDS IN CHEMISTRY AND BIOLOGY, Blackburn (ed.), Royal Society of Chemistry, 2006), shRNAs (e.g., having 19 bp or shorter stems; see, e.g., Moore et al. (2010) Methods Mol. Biol. 629:141-58), blunt siRNAs (e.g., of 19 bps in length; see, e.g., Kraynack & Baker (2006) *RNA* 12:163-76), asymmetrical siRNAs (aiRNA; see, e.g., Sun et al. (2008) Nat. Biotechnol. 26:1379-82), asymmetric shorter-duplex siRNA (see, e.g., Chang et al. (2009) Mol. Ther. 17:725-32), fork siRNAs (see, e.g., Hohjoh (2004) FEBS Lett. 557:193-198), ss siRNAs (Elsner (2012) Nat. Biotechnol. 30:1063), dumbbell-shaped circular siRNAs (see, e.g., Abe et al. (2007) J. Am. Chem. Soc. 129:15108-09), and small internally segmented interfering RNA (siRNA; see, e.g., Bramsen et al. (2007) Nucleic Acids Res. 35:5886-97). Further non-limiting examples of an oligonucleotide structures that may be used in some embodiments to reduce or inhibit the expression of LPA are microRNA (miRNA), short hairpin RNA (shRNA) and short siRNA (see, e.g., Hamilton et al. (2002) EMBO J. 21:4671-79; see also, US Patent Application Publication No. 2009/0099115).

Still, in some embodiments, an oligonucleotide for reducing or inhibiting LPA expression herein is single-stranded (ss). Such structures may include but are not limited to ss RNAi molecules. Recent efforts have demonstrated the activity of ss RNAi molecules (see, e.g., Matsui et al. (2016) *Mol. Ther.* 24:946-955). However, in some embodiments, oligonucleotides herein are antisense oligonucleotides (ASOs). An antisense oligonucleotide is a ss oligonucleotide that has a nucleobase sequence which, when written or depicted in the 5' to 3' direction, comprises the reverse complement of a targeted segment of a particular nucleic acid and is suitably modified (e.g., as a gapmer) so as to induce RNaseH-mediated cleavage of its target RNA in cells or (e.g., as a mixmer) so as to inhibit translation of the target mRNA in cells. ASOs for use herein may be modified in any suitable manner known in the art including, for example, as shown in U.S. Pat. No. 9,567,587 (including, e.g., length, sugar moieties of the nucleobase (pyrimidine, purine), and alterations of the heterocyclic portion of the nucleobase). Further, ASOs have been used for decades to reduce expression of specific target genes (see, e.g., Bennett et al. (2017) *Annu. Rev. Pharmacol.* 57:81-105).

iv. Double-Stranded Oligonucleotides

The disclosure provides double-stranded (ds) oligonucleotides for targeting LPA mRNA and inhibiting LPA expression (e.g., via the RNAi pathway) comprising a sense strand (also referred to herein as a passenger strand) and an antisense strand (also referred to herein as a guide strand). In some embodiments, the sense strand and antisense strand are separate strands and are not covalently linked. In some embodiments, the sense strand and antisense strand are covalently linked.

In some embodiments, the sense strand has a first region (R1) and a second region (R2), wherein R2 comprises a first subregion (S1), a tetraloop (L) or triloop (triL), and a second subregion (S2), wherein L or triL is located between S1 and S2, and wherein S1 and S2 form a second duplex (D2). D2 may have various lengths. In some embodiments, D2 is about 1-6 bp in length. In some embodiments, D2 is 2-6, 3-6, 4-6, 5-6, 1-5, 2-5, 3-5 or 4-5 bp in length. In some embodiments, D2 is 1, 2, 3, 4, 5 or 6 bp in length. In some embodiments, D2 is 6 bp in length.

In some embodiments, R1 of the sense strand and the antisense strand form a first duplex (D1). In some embodiments, D1 is at least about 15 (e.g., at least 15, at least 16, at least 17, at least 18, at least 19, at least 20 or at least 21) nucleotides in length. In some embodiments, D1 is in the range of about 12 to 30 nucleotides in length (e.g., 12 to 30, 12 to 27, 15 to 22, 18 to 22, 18 to 25, 18 to 27, 18 to 30 or 21 to 30 nucleotides in length). In some embodiments, D1 is at least 12 nucleotides in length (e.g., at least 12, at least 15, at least 20, at least 25, or at least 30 nucleotides in length). In some embodiments, D1 is 12, 13, 14, 15, 16, 17, 18, 19, 20, 21, 22, 23, 24, 25, 26, 27, 28, 29 or 30 nucleotides in length. In some embodiments, D1 is 20 nucleotides in length. In some embodiments, D1 comprising sense strand and antisense strand does not span the entire length of the sense strand and/or antisense strand. In some embodiments, D1 comprising the sense strand and antisense strand spans the entire length of either the sense strand or antisense strand or both. In certain embodiments, D1 comprising the sense strand and antisense strand spans the entire length of both the sense strand and the antisense strand.

In some embodiments, a ds oligonucleotide herein comprises a sense strand having a sequence of any one of SEQ ID NOs: 388-403 and an antisense strand comprising a complementary sequence selected from SEQ ID NOs: 788-803, as is arranged Table 3. In some embodiments, the sense strand comprises the sequence of SEQ ID NO: 393 and the antisense strand comprises the sequence of SEQ ID NO: 793.

It should be appreciated that, in some embodiments, sequences presented in the Sequence Listing may be referred to in describing the structure of an oligonucleotide (e.g., a ds oligonucleotide) or other nucleic acid. In such embodiments, the actual oligonucleotide or other nucleic acid may have one or more alternative nucleotides (e.g., an RNA counterpart of a DNA nucleotide or a DNA counterpart of an RNA nucleotide) and/or one or more modified nucleotides and/or one or more modified internucleotide linkages and/or one or more other modification when compared with the specified sequence while retaining essentially same or similar complementary properties as the specified sequence.

In some embodiments, a ds oligonucleotide herein comprises a 25-nucleotide sense strand and a 27-nucleotide antisense strand that when acted upon by a Dicer enzyme results in an antisense strand that is incorporated into the mature RISC. In some embodiments, the sense strand of the ds oligonucleotide is longer than 27 nucleotides (e.g., 28, 29, 30, 31, 32, 33, 34, 35, 36, 37, 38, 39 or 40 nucleotides). In some embodiments, the sense strand of the ds oligonucleotide is longer than 25 nucleotides (e.g., 26, 27, 28, 29 or 30 nucleotides).

In some embodiments, the ds oligonucleotides herein have one 5' end that is thermodynamically less stable when compared to the other 5' end. In some embodiments, an asymmetric ds oligonucleotide is provided that comprises a blunt end at the 3' end of a sense strand and a 3'-overhang at the 3' end of an antisense strand. In some embodiments, the 3'-overhang on the antisense strand is about 1-8 nucleotides in length (e.g., 1, 2, 3, 4, 5, 6, 7 or 8 nucleotides in length). Typically, a ds oligonucleotide for RNAi has a two-nucleotide overhang on the 3' end of the antisense (guide) strand. However, other overhangs are possible. In some embodiments, an overhang is a 3'-overhang comprising a length of between 1 and 6 nucleotides, optionally 1 to 5, 1 to 4, 1 to 3, 1 to 2, 2 to 6, 2 to 5, 2 to 4, 2 to 3, 3 to 6, 3 to 5, 3 to 4, 4 to 6, 4 to 5, 5 to 6 nucleotides, or 1, 2, 3, 4, 5 or 6 nucleotides. However, in some embodiments, the overhang is a 5'-overhang comprising a length of between 1 and 6 nucleotides, optionally 1 to 5, 1 to 4, 1 to 3, 1 to 2, 2 to 6, 2 to 5, 2 to 4, 2 to 3, 3 to 6, 3 to 5, 3 to 4, 4 to 6, 4 to 5, 5 to 6 nucleotides, or 1, 2, 3, 4, 5 or 6 nucleotides.

In some embodiments, two terminal nucleotides on the 3' end of an antisense strand are modified. In some embodiments, the two terminal nucleotides on the 3' end of the antisense strand are complementary with the target mRNA (e.g., LPA mRNA). In some embodiments, the two terminal nucleotides on the 3' end of the antisense strand are not complementary with the target mRNA. In some embodiments, two terminal nucleotides on each 3' end of an oligonucleotide in the nicked tetraloop structure are GG. Typically, one or both of the two terminal GG nucleotides on each 3' end of a ds oligonucleotide is not complementary with the target mRNA.

In some embodiments, there is one or more (e.g., 1, 2, 3, 4 or 5) mismatch(s) between a sense and antisense strand. If there is more than one mismatch between a sense and antisense strand, they may be positioned consecutively (e.g., 2, 3 or more in a row), or interspersed throughout the region of complementarity. In some embodiments, the 3' end of the sense strand contains one or more mismatches. In one embodiment, two mismatches are incorporated at the 3' end of the sense strand. In some embodiments, base mismatches, or destabilization of segments at the 3' end of the sense strand of the oligonucleotide improves or increases the potency of the ds oligonucleotide.

a. Antisense Strands

In some embodiments, an oligonucleotide (e.g., ads oligonucleotide) disclosed herein for targeting LPA mRNA and inhibiting LPA expression comprises an antisense strand comprising or consisting of a sequence as set forth in any one of SEQ ID NOs: 404-803. In some embodiments, an oligonucleotide herein comprises an antisense strand comprising or consisting of at least about 12 (e.g., at least 12, at least 13, at least 14, at least 15, at least 16, at least 17, at least 18, at least 19, at least 20, at least 21, at least 22 or at least 23) contiguous nucleotides of a sequence as set forth in any one of SEQ ID NOs: 404-803.

In some embodiments, an oligonucleotide (e.g., a ds oligonucleotide) herein comprises an antisense strand of up to about 40 nucleotides in length (e.g., up to 40, up to 35, up to 30, up to 27, up to 25, up to 21, up to 19, up to 17 or up to 12 nucleotides in length). In some embodiments, an oligonucleotide may have an antisense strand of at least about 12 nucleotides in length (e.g., at least 12, at least 15, at least 19, at least 21, at least 22, at least 25, at least 27, at least 30, at least 35 or at least 38 nucleotides in length). In some embodiments, an oligonucleotide may have an antisense strand in a range of about 12 to about 40 (e.g., 12 to 40, 12 to 36, 12 to 32, 12 to 28, 15 to 40, 15 to 36, 15 to 32, 15 to 28, 17 to 22, 17 to 25, 19 to 27, 19 to 30, 20 to 40, 22 to 40, 25 to 40 or 32 to 40) nucleotides in length. In some embodiments, an oligonucleotide may have an antisense strand of 12, 13, 14, 15, 16, 17, 18, 19, 20, 21, 22, 23, 24, 25, 26, 27, 28, 29, 30, 31, 32, 33, 34, 35, 36, 37, 38, 39 or 40 nucleotides in length.

In some embodiments, an antisense strand of an oligonucleotide is referred to as a "guide strand." For example, an antisense strand that engages with RNA-induced silencing complex (RISC) and binds to an Argonaute protein such as Ago2, or engages with or binds to one or more similar factors, and directs silencing of a target gene, the antisense strand is referred to as a guide strand. In some embodiments, a sense strand complementary to a guide strand is referred to as a "passenger strand."

b. Sense Strands

In some embodiments, an oligonucleotide (e.g., a ds oligonucleotide) herein for targeting LPA mRNA and inhibiting LPA expression comprises or consists of a sense strand sequence as set forth in in any one of SEQ ID NOs: 4-403. In some embodiments, an oligonucleotide has a sense strand that comprises or consists of at least about 12 (e.g., at least 13, at least 14, at least 15, at least 16, at least 17, at least 18, at least 19, at least 20, at least 21, at least 22 or at least 23) contiguous nucleotides of a sequence as set forth in in any one of SEQ ID NOs: 4-403.

In some embodiments, an oligonucleotide (e.g., a ds oligonucleotide) herein comprises a sense strand (or passenger strand) of up to about 40 nucleotides in length (e.g., up to 40, up to 36, up to 30, up to 27, up to 25, up to 21, up to 19, up to 17 or up to 12 nucleotides in length). In some embodiments, an oligonucleotide may have a sense strand of at least about 12 nucleotides in length (e.g., at least 12, at least 15, at least 19, at least 21, at least 25, at least 27, at least 30, at least 36 or at least 38 nucleotides in length). In some embodiments, an oligonucleotide may have a sense strand in a range of about 12 to about 40 (e.g., 12 to 40, 12 to 36, 12 to 32, 12 to 28, 15 to 40, 15 to 36, 15 to 32, 15 to 28, 17 to 21, 17 to 25, 19 to 27, 19 to 30, 20 to 40, 22 to 40, 25 to 40 or 32 to 40) nucleotides in length. In some embodiments, an oligonucleotide may have a sense strand of 12, 13, 14, 15, 16, 17, 18, 19, 20, 21, 22, 23, 24, 25, 26, 27, 28, 29, 30, 31, 32, 33, 34, 35, 36, 37, 38, 39 or 40 nucleotides in length.

Figure 10:
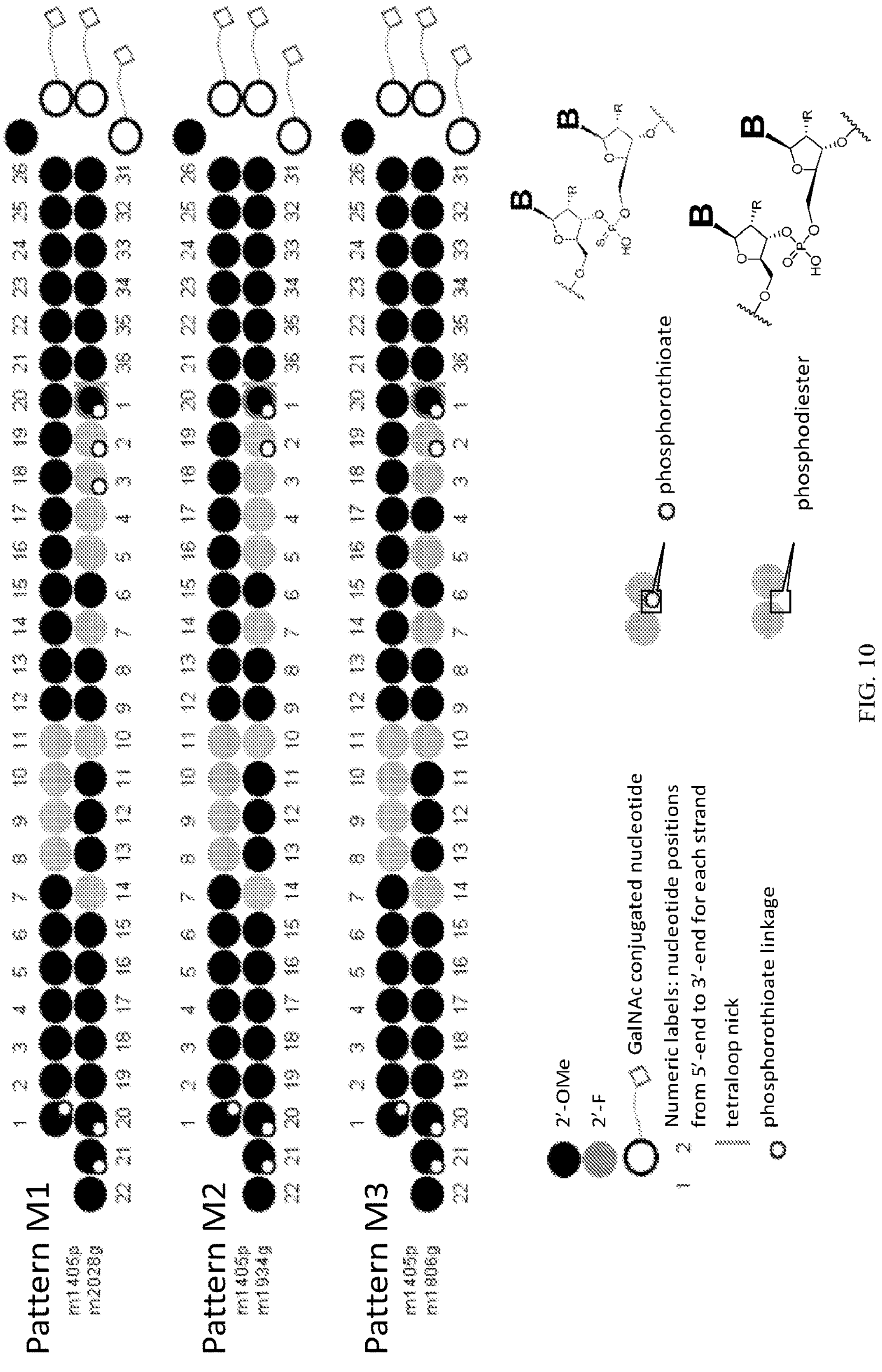
FIG. 10 provides a schematic depicting the structure and chemical modification patterns of generic N-Acetylgalactosamine (GalNAc)-conjugated LPA oligonucleotides.

In some embodiments, a sense strand comprises a stem-loop structure at its 3' end. In some embodiments, a sense strand comprises a stem-loop structure at its 5' end. In some embodiments, a stem is a duplex of 2, 3, 4, 5, 6, 7, 8, 9, 10, 11, 12, 13 or 14 bp in length. In some embodiments, a stem-loop provides the oligonucleotide protection against degradation (e.g., enzymatic degradation) and facilitates or improves targeting and/or delivery to a target cell, tissue, or organ (e.g, the liver), or both. For example, in some embodiments, the loop of a stem-loop provides nucleotides comprising one or more modifications that facilitate, improve, or increase targeting to a target mRNA (e.g., an LPA mRNA), inhibition of target gene expression (e.g., LPA expression), and/or delivery to a target cell, tissue, or organ (e.g., the liver), or both. In some embodiments, the stem-loop itself or modification(s) to the stem-loop do not substantially affect the inherent gene expression inhibition activity of the oligonucleotide, but facilitates, improves, or increases stability (e.g., provides protection against degradation) and/or delivery of the oligonucleotide to a target cell, tissue, or organ (e.g., the liver). In certain embodiments, an oligonucleotide comprises a sense strand comprising (e.g., at its 3' end) a stem-loop set forth as: S1-L-S2, in which S1 is complementary to S2, and in which L forms a single-stranded loop between S1 and S2 of up to about 10 nucleotides in length (e.g., 3, 4, 5, 6, 7, 8, 9 or 10 nucleotides in length). In some embodiments, the loop (L) is 4 nucleotides in length. FIG. 10 depicts a non-limiting example of such an oligonucleotide. In some embodiments, a loop (L) of a stem-loop having the structure S1-L-S2 as described above is a tetraloop (e.g., within a nicked tetraloop structure). In some embodiments, the tetraloop comprises ribonucleotides, deoxyribonucleotides, modified nucleotides, delivery ligands, and combinations thereof.

v. Oligonucleotide Modifications a. Sugar Modifications

In some embodiments, a modified sugar (also referred herein to a sugar analog) includes a modified deoxyribose or ribose moiety in which, for example, one or more modifications occur at the 2', 3', 4' and/or 5' carbon position of the sugar. In some embodiments, a modified sugar may also include non-natural alternative carbon structures such as those present in locked nucleic acids ("LNA"; see, e.g., Koshkin et al. (1998) Tetrahedon 54:3607-30), unlocked nucleic acids ("UNA"; see, e.g., Snead et al. (2013) Mol. Ther-Nucl. Acids 2:e103) and bridged nucleic acids ("BNA"; see, e.g., Imanishi & Obika (2002) Chem Commun. (Camb) 21:1653-59).

In some embodiments, a nucleotide modification in a sugar comprises a 2'-modification. In some embodiments, a 2'-modification may be 2'-O-propargyl, 2'-O-propylamin, 2'-amino, 2'-ethyl, 2'-fluoro (2'-F), 2'-aminoethyl (EA), 2'-O-methyl (2'-OMe), 2'-O-methoxyethyl (2'-MOE), 2'-O-[2-(methylamino)-2-oxoethyl](2'-O-NMA) or 2'-deoxy-2'-fluoro-β-d-arabinonucleic acid (2'-FANA). In some embodiments, the modification is 2'-F, 2'-OMe or 2'-MOE. In some embodiments, a modification in a sugar comprises a modification of the sugar ring, which may comprise modification of one or more carbons of the sugar ring. For example, a modification of a sugar of a nucleotide may comprise a 2'-oxygen of a sugar is linked to a 1'-carbon or 4'-carbon of the sugar, or a 2'-oxygen is linked to the 1'-carbon or 4'-carbon via an ethylene or methylene bridge. In some embodiments, a modified nucleotide has an acyclic sugar that lacks a 2'-carbon to 3'-carbon bond. In some embodiments, a modified nucleotide has a thiol group, e.g., in the 4' position of the sugar.

In some embodiments, the oligonucleotide described herein comprises at least about 1 modified nucleotide (e.g., at least 1, at least 5, at least 10, at least 15, at least 20, at least 25, at least 30, at least 35, at least 40, at least 45, at least 50, at least 55, at least 60, or more). In some embodiments, the sense strand of the oligonucleotide comprises at least about 1 modified nucleotide (e.g., at least 1, at least 5, at least 10, at least 15, at least 20, at least 25, at least 30, at least 35, or more). In some embodiments, the antisense strand of the oligonucleotide comprises at least about 1 modified nucleotide (e.g., at least 1, at least 5, at least 10, at least 15, at least 20, or more).

In some embodiments, all the nucleotides of the sense strand of the oligonucleotide are modified. In some embodiments, all the nucleotides of the antisense strand of the oligonucleotide are modified. In some embodiments, all the nucleotides of the oligonucleotide (i.e., both the sense strand and the antisense strand) are modified. In some embodiments, the modified nucleotide comprises a 2'-modification (e.g., a 2'-F or 2'-OMe, 2'-MOE, and 2'-deoxy-2'-fluoro-β-d-arabinonucleic acid). In some embodiments, the modified nucleotide comprises a 2'-modification (e.g., a 2'-F or 2'-OMe)

The disclosure provides oligonucleotides having different modification patterns. In some embodiments, the modified oligonucleotides comprise a sense strand sequence having a modification pattern as set forth in any one of Tables 3 and 4 (as well as FIG. 10) and an antisense strand having a modification pattern as set forth in any one of Tables 3 and 4 (as well as FIG. 10). In some embodiments, for these oligonucleotides, one or more of positions 8, 9, 10 or 11 of the sense strand is modified with a 2'—F group. In other embodiments, for these oligonucleotides, the sugar moiety at each of nucleotides at positions 1-7 and 12-20 in the sense strand is modified with a 2'-OMe.

In some embodiments, the antisense strand has 3 nucleotides that are modified at the 2'-position of the sugar moiety with a 2'-F. In some embodiments, the sugar moiety at positions 2, 5 and 14 and optionally up to 3 of the nucleotides at positions 1, 3, 7 and 10 of the antisense strand are modified with a 2'-F. In other embodiments, the sugar moiety at each of the positions at positions 2, 5 and 14 of the antisense strand is modified with the 2'-F. In other embodiments, the sugar moiety at each of the positions at positions 1, 2, 5 and 14 of the antisense strand is modified with the 2'-F. In still other embodiments, the sugar moiety at each of the positions at positions 1, 2, 3, 5, 7 and 14 of the antisense strand is modified with the 2'-F. In yet another embodiment, the sugar moiety at each of the positions at positions 1, 2, 3, 5, 10 and 14 of the antisense strand is modified with the 2'-F. In another embodiment, the sugar moiety at each of the positions at positions 2, 3, 5, 7, 10 and 14 of the antisense strand is modified with the 2'-F.

b. 5' Terminal Phosphates

In some embodiments, 5'-terminal phosphate groups of an RNAi oligonucleotide enhance the interaction with Ago2. However, oligonucleotides comprising a 5'-phosphate group may be susceptible to degradation via phosphatases or other enzymes, which can limit their bioavailability in vivo. In some embodiments, an oligonucleotide (e.g., a ds oligonucleotide) herein includes analogs of 5' phosphates that are resistant to such degradation. In some embodiments, the phosphate analog is oxymethylphosphonate, vinylphosphonate or malonyl phosphonate, or a combination thereof. In certain embodiments, the 3' end of an oligonucleotide strand is attached to chemical moiety that mimics the electrostatic and steric properties of a natural 5'-phosphate group ("phosphate mimic").

In some embodiments, an oligonucleotide has a phosphate analog at a 4'-carbon position of the sugar (referred to as a "4'-phosphate analog"). See, e.g., Intl. Patent Application Publication No. WO 2018/045317. In some embodiments, an oligonucleotide herein comprises a 4'-phosphate analog at a 5'-terminal nucleotide. In some embodiments, a phosphate analog is an oxymethylphosphonate, in which the oxygen atom of the oxymethyl group is bound to the sugar moiety (e.g., at its 4'-carbon) or analog thereof. In other embodiments, a4'-phosphate analog is a thiomethylphosphonate or an aminomethylphosphonate, in which the sulfur atom of the thiomethyl group or the nitrogen atom of the amino methyl group is bound to the 4'-carbon of the sugar moiety or analog thereof. In certain embodiments, a 4'-phosphate analog is an oxymethylphosphonate. In some embodiments, an oxymethylphosphonate is represented by the formula $—O—CH_2—PO(OH)_2$ or $—O—CH_2—PO(OR)_2$, in which R is independently selected from H, $CH_3$, an alkyl group, $CH_2CH_2CN$, $CH_2OCOC(CH_3)_3$, $CH_2OCH_2CH_2Si$ $(CH_3)_3$ or a protecting group. In certain embodiments, the alkyl group is $CH_2CH_3$. More typically, R is independently selected from H, $CH_3$ or $CH_2CH_3$.

c. Modified Intranucleoside Linkages

In some embodiments, an oligonucleotide comprises a modified internucleoside linkage. In some embodiments, phosphate modifications or substitutions result in an oligonucleotide that comprises at least about 1 (e.g., at least 1, at least 2, at least 3 or at least 5) modified internucleotide linkage. In some embodiments, any one of the oligonucleotides disclosed herein comprises about 1 to about 10 (e.g., 1 to 10, 2 to 8, 4 to 6, 3 to 10, 5 to 10, 1 to 5, 1 to 3 or 1 to 2) modified internucleotide linkages. In some embodiments, any one of the oligonucleotides disclosed herein comprises 1, 2, 3, 4, 5, 6, 7, 8, 9 or 10 modified internucleotide linkages.

A modified internucleotide linkage may be a phosphorodithioate linkage, a phosphorothioate linkage, a phosphotriester linkage, a thionoalkylphosphonate linkage, a thionalkylphosphotriester linkage, a phosphoramidite linkage, a phosphonate linkage or a boranophosphate linkage. In some embodiments, at least one modified internucleotide linkage of any one of the oligonucleotides as disclosed herein is a phosphorothioate linkage.

In some embodiments, the oligonucleotide described herein has a phosphorothioate linkage between one or more of positions 1 and 2 of the sense strand, positions 1 and 2 of the antisense strand, positions 2 and 3 of the antisense strand, positions 3 and 4 of the antisense strand, positions 20 and 21 of the antisense strand, and positions 21 and 22 of the antisense strand. In some embodiments, the oligonucleotide described herein has a phosphorothioate linkage between each of positions 1 and 2 of the sense strand, positions 1 and 2 of the antisense strand, positions 2 and 3 of the antisense strand, positions 20 and 21 of the antisense strand, and positions 21 and 22 of the antisense strand.

d. Base Modifications

In some embodiments, oligonucleotides herein have one or more modified nucleobases. In some embodiments, modified nucleobases (also referred to herein as base analogs) are linked at the 1' position of a nucleotide sugar moiety. In certain embodiments, a modified nucleobase is a nitrogenous base. In certain embodiments, a modified nucleobase does not contain nitrogen atom. See, e.g., US Patent Application Publication No. 2008/0274462. In some embodiments, a modified nucleotide comprises a universal base. However, in certain embodiments, a modified nucleotide does not contain a nucleobase (abasic).

In some embodiments, a universal base is a heterocyclic moiety located at the 1' position of a nucleotide sugar moiety in a modified nucleotide, or the equivalent position in a nucleotide sugar moiety substitution, that, when present in a duplex, can be positioned opposite more than one type of base without substantially altering structure of the duplex. In some embodiments, compared to a reference single-stranded nucleic acid (e.g., oligonucleotide) that is fully complementary to a target nucleic acid, a single-stranded nucleic acid containing a universal base forms a duplex with the target nucleic acid that has a lower $T_m$ than a duplex formed with the complementary nucleic acid. However, in some embodiments, when compared to a reference single-stranded nucleic acid in which the universal base has been replaced with a base to generate a single mismatch, the single-stranded nucleic acid containing the universal base forms a duplex with the target nucleic acid that has a higher $T_m$ than a duplex formed with the nucleic acid comprising the mismatched base.

Non-limiting examples of universal-binding nucleotides include, but are not limited to, inosine, 1-β-D-ribofuranosyl-5-nitroindole and/or 1-β-D-ribofuranosyl-3-nitropyrrole (see, US Patent Application Publication No. 2007/0254362; Van Aerschot et al. (1995) Nucleic Acids Res. 23:4363-70; Loakes et al. (1995) Nucleic Acids Res. 23:2361-66; and Loakes & Brown (1994) Nucleic Acids Res. 22:4039-43).

e. Reversible Modifications

While certain modifications to protect an oligonucleotide from the in vivo environment before reaching target cells can be made, they can reduce the potency or activity of the oligonucleotide once it reaches the cytosol of the target cell. Reversible modifications can be made such that the molecule retains desirable properties outside of the cell, which are then removed upon entering the cytosolic environment of the cell. Reversible modification can be removed, for example, by the action of an intracellular enzyme or by the chemical conditions inside of a cell (e.g., through reduction by intracellular glutathione).

In some embodiments, a reversibly modified nucleotide comprises a glutathione-sensitive moiety. Typically, nucleic acid molecules have been chemically modified with cyclic disulfide moieties to mask the negative charge created by the internucleotide diphosphate linkages and improve cellular uptake and nuclease resistance. See US Patent Application Publication No. 2011/0294869, Intl. Patent Application Publication Nos. WO 2014/088920 and WO 2015/188197, and Meade et al. (2014) Nat. Biotechnol. 32:1256-63. This reversible modification of the internucleotide diphosphate linkages is designed to be cleaved intracellularly by the reducing environment of the cytosol (e.g. glutathione). Earlier examples include neutralizing phosphotriester modifications that were reported to be cleavable inside cells (see, Dellinger et al. (2003) J. Am. Chem. Soc. 125:940-50).

In some embodiments, such a reversible modification allows protection during in vivo administration (e.g., transit through the blood and/or lysosomal/endosomal compartments of a cell) where the oligonucleotide will be exposed to nucleases and other harsh environmental conditions (e.g., pH). When released into the cytosol of a cell where the levels of glutathione are higher compared to extracellular space, the modification is reversed, and the result is a cleaved oligonucleotide. Using reversible, glutathione-sensitive moieties, it is possible to introduce sterically larger chemical groups into the oligonucleotide of interest when compared to the options available using irreversible chemical modifications. This is because these larger chemical groups will be removed in the cytosol and, therefore, should not interfere with the biological activity of the oligonucleotides inside the cytosol of a cell. As a result, these larger chemical groups can be engineered to confer various advantages to the nucleotide or oligonucleotide, such as nuclease resistance, lipophilicity, charge, thermal stability, specificity and reduced immunogenicity. In some embodiments, the structure of the glutathione-sensitive moiety can be engineered to modify the kinetics of its release.

In some embodiments, a glutathione-sensitive moiety is attached to the sugar of the nucleotide. In some embodiments, a glutathione-sensitive moiety is attached to the 2'-carbon of the sugar of a modified nucleotide. In some embodiments, the glutathione-sensitive moiety is located at the 5'-carbon of a sugar, particularly when the modified nucleotide is the 5'-terminal nucleotide of the oligonucleotide. In some embodiments, the glutathione-sensitive moiety is located at the 3'-carbon of sugar, particularly when the modified nucleotide is the 3'-terminal nucleotide of the oligonucleotide. In some embodiments, the glutathione-sensitive moiety comprises a sulfonyl group. See, e.g., U.S. Provisional Patent Application No. 62/378,635, entitled Compositions Comprising Reversibly Modified Oligonucleotides and Uses Thereof, which was filed on Aug. 23, 2016.

vi. Targeting Ligands

In some embodiments, it is desirable to target the oligonucleotides of the disclosure to one or more cells or one or more organs. Such a strategy can help to avoid undesirable effects in other organs or avoid undue loss of the oligonucleotide to cells, tissue or organs that would not benefit from the oligonucleotide. Accordingly, in some embodiments, oligonucleotides disclosed herein are modified to facilitate targeting and/or delivery to a tissue, cell or organ (e.g., to facilitate delivery of the oligonucleotide to the liver). In certain embodiments, oligonucleotides disclosed herein are modified to facilitate delivery of the oligonucleotide to the hepatocytes of the liver. In some embodiments, an oligonucleotide comprises at least one nucleotide (e.g., 1, 2, 3, 4, 5, 6 or more nucleotides) conjugated to one or more targeting ligand(s).

In some embodiments, the targeting ligand comprises a carbohydrate, amino sugar, cholesterol, peptide, polypeptide, protein or part of a protein (e.g., an antibody or antibody fragment), or lipid. In some embodiments, the targeting ligand is an aptamer. For example, a targeting ligand may be an RGD peptide that is used to target tumor vasculature or glioma cells, CREKA peptide to target tumor vasculature or stoma, transferring, lactoferrin, or an aptamer to target transferrin receptors expressed on CNS vasculature, or an anti-EGFR antibody to target EGFR on glioma cells. In certain embodiments, the targeting ligand is one or more GalNAc moieties.

In some embodiments, 1 or more (e.g., 1, 2, 3, 4, 5 or 6) nucleotides of an oligonucleotide are each conjugated to a separate targeting ligand. In some embodiments, 2 to 4 nucleotides of an oligonucleotide are each conjugated to a separate targeting ligand. In some embodiments, targeting ligands are conjugated to 2 to 4 nucleotides at either ends of the sense or antisense strand (e.g., targeting ligands are conjugated to a 2 to 4 nucleotide overhang or extension on the 5' or 3' end of the sense or antisense strand) such that the targeting ligands resemble bristles of a toothbrush and the oligonucleotide resembles a toothbrush. For example, an oligonucleotide may comprise a stem-loop at either the 5' or 3' end of the sense strand and 1, 2, 3 or 4 nucleotides of the loop of the stem may be individually conjugated to a targeting ligand. In some embodiments, an oligonucleotide (e.g., a ds oligonucleotide) provided by the disclosure comprises a stem-loop at the 3' end of the sense strand, wherein the loop of the stem-loop comprises a triloop or a tetraloop, and wherein the 3 or 4 nucleotides comprising the triloop or tetraloop, respectfully, are individually conjugated to a targeting ligand.

GalNAc is a high affinity ligand for the ASGPR, which is primarily expressed on the sinusoidal surface of hepatocyte cells and has a major role in binding, internalizing and subsequent clearing circulating glycoproteins that contain terminal galactose or GalNAc residues (asialoglycoproteins). Conjugation (either indirect or direct) of GalNAc moieties to oligonucleotides of the instant disclosure can be used to target these oligonucleotides to the ASGPR expressed on cells. In some embodiments, an oligonucleotide of the instant disclosure is conjugated to at least one or more GalNAc moieties, wherein the GalNAc moieties target the oligonucleotide to an ASGPR expressed on human liver cells (e.g. human hepatocytes). In some embodiments, the GalNAc moiety target the oligonucleotide to the liver.

In some embodiments, an oligonucleotide of the instant disclosure is conjugated directly or indirectly to a monovalent GalNAc. In some embodiments, the oligonucleotide is conjugated directly or indirectly to more than one monovalent GalNAc (i.e., is conjugated to 2, 3 or 4 monovalent GalNAc moieties, and is typically conjugated to 3 or 4 monovalent GalNAc moieties). In some embodiments, an oligonucleotide is conjugated to one or more bivalent GalNAc, trivalent GalNAc or tetravalent GalNAc moieties.

In some embodiments, 1 or more (e.g., 1, 2, 3, 4, 5 or 6) nucleotides of an oligonucleotide are each conjugated to a GalNAc moiety. In some embodiments, 2 to 4 nucleotides of a tetraloop are each conjugated to a separate GalNAc. In some embodiments, 1 to 3 nucleotides of a triloop are each conjugated to a separate GalNAc. In some embodiments, targeting ligands are conjugated to 2 to 4 nucleotides at either ends of the sense or antisense strand (e.g., ligands are conjugated to a 2 to 4 nucleotide overhang or extension on the 5' or 3' end of the sense or antisense strand) such that the GalNAc moieties resemble bristles of a toothbrush and the oligonucleotide resembles a toothbrush. In some embodiments, GalNAc moieties are conjugated to a nucleotide of the sense strand. For example, 4 GalNAc moieties can be conjugated to nucleotides in the tetraloop of the sense strand where each GalNAc moiety is conjugated to 1 nucleotide.

In some embodiments, an oligonucleotide herein comprises a monovalent GalNAc attached to a guanine nucleotide referred to as [ademG-GalNAc] or 2'-aminodiethoxymethanol-Guanine-GalNAc, as depicted below:

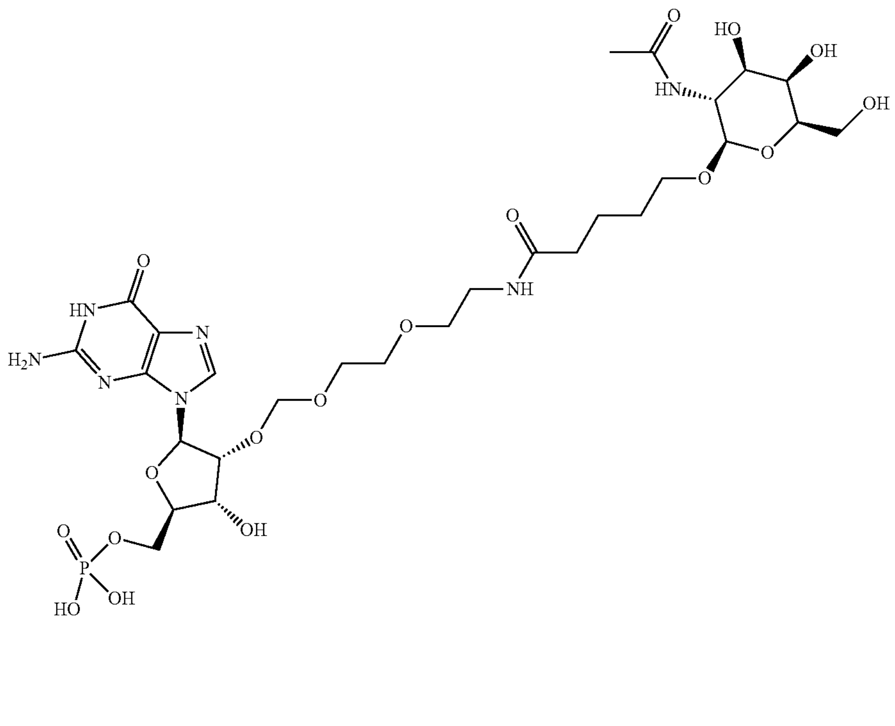 [SMILES: CC(=O)N[C@H]1[C@H](OCCCCC(=O)NCCOCCOCO[C@@H]2[C@H](O)[C@@H](COP(=O)(O)O)O[C@H]2n2cnc3c(=O)[nH]c(N)nc32)O[C@H](CO)[C@H](O)[C@@H]1O]

In some embodiments, an oligonucleotide herein comprises a monovalent GalNAc attached to an adenine nucleotide, referred to as [ademA-GalNAc] or 2'-aminodiethoxymethanol-Adenine-GalNAc, as depicted below:

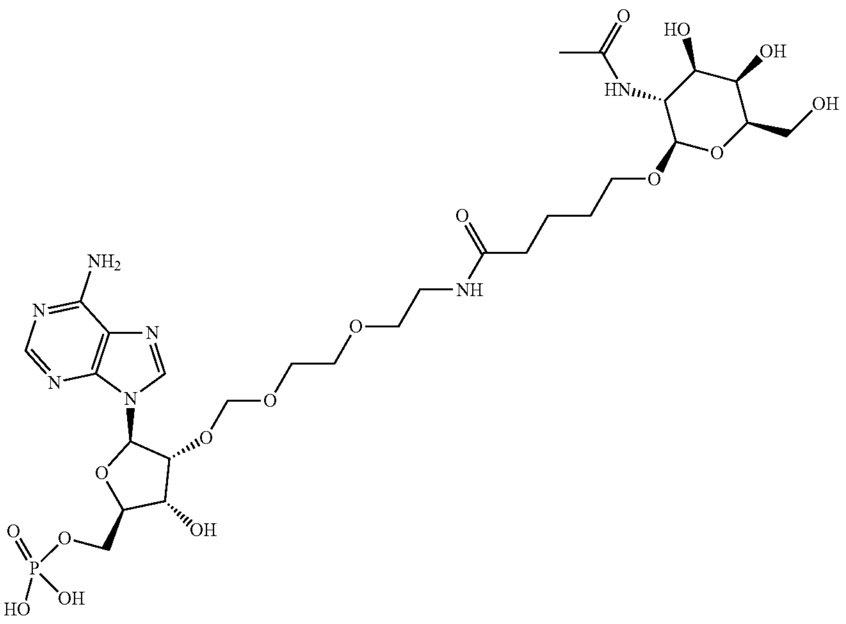 [SMILES: CC(=O)N[C@H]1[C@H](OCCCCC(=O)NCCOCCOCO[C@@H]2[C@H](O)[C@@H](COP(=O)(O)O)O[C@H]2n2cnc3c(N)ncnc32)O[C@H](CO)[C@H](O)[C@@H]1O]

Figure 3:
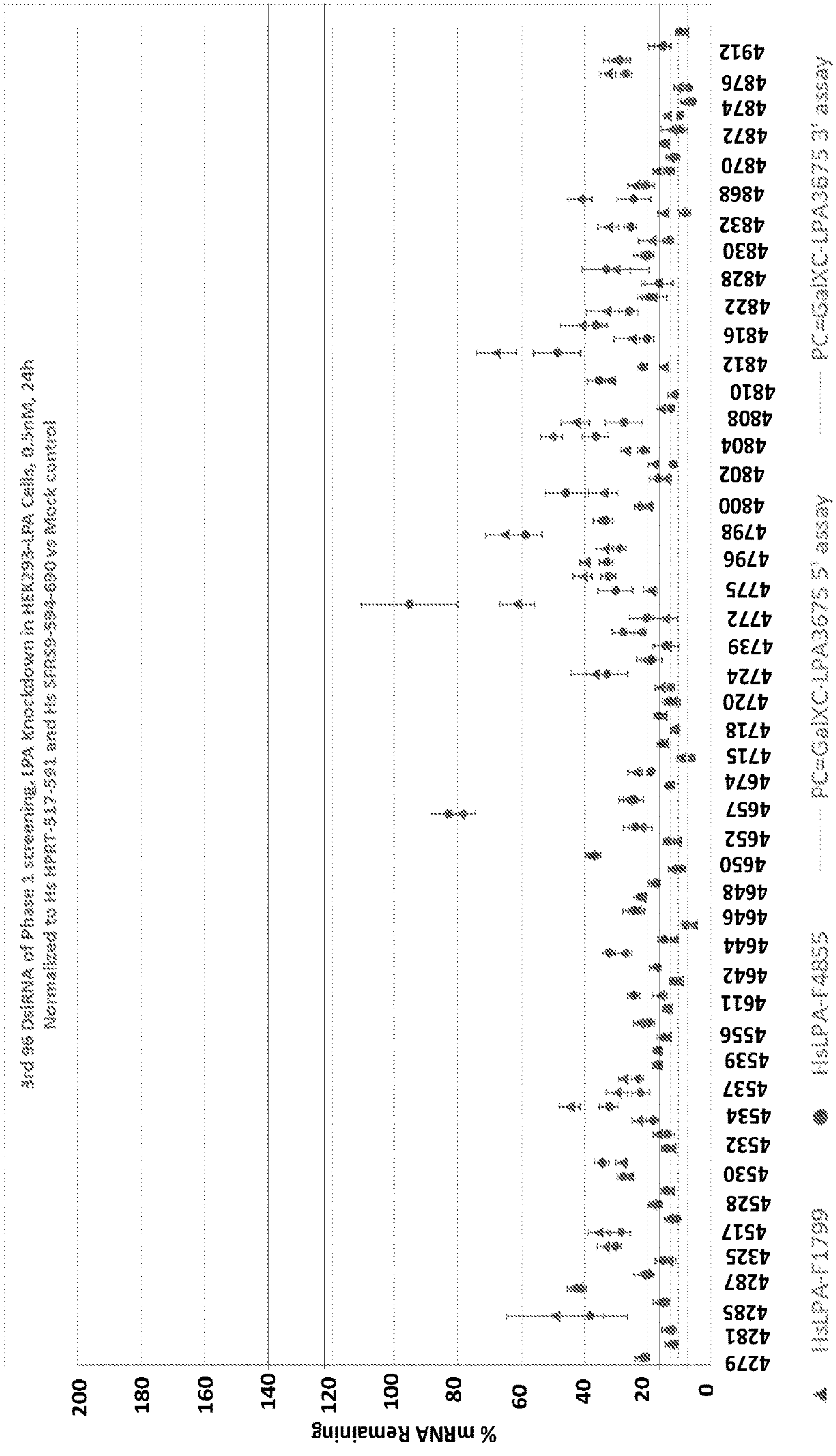
Figure 4:
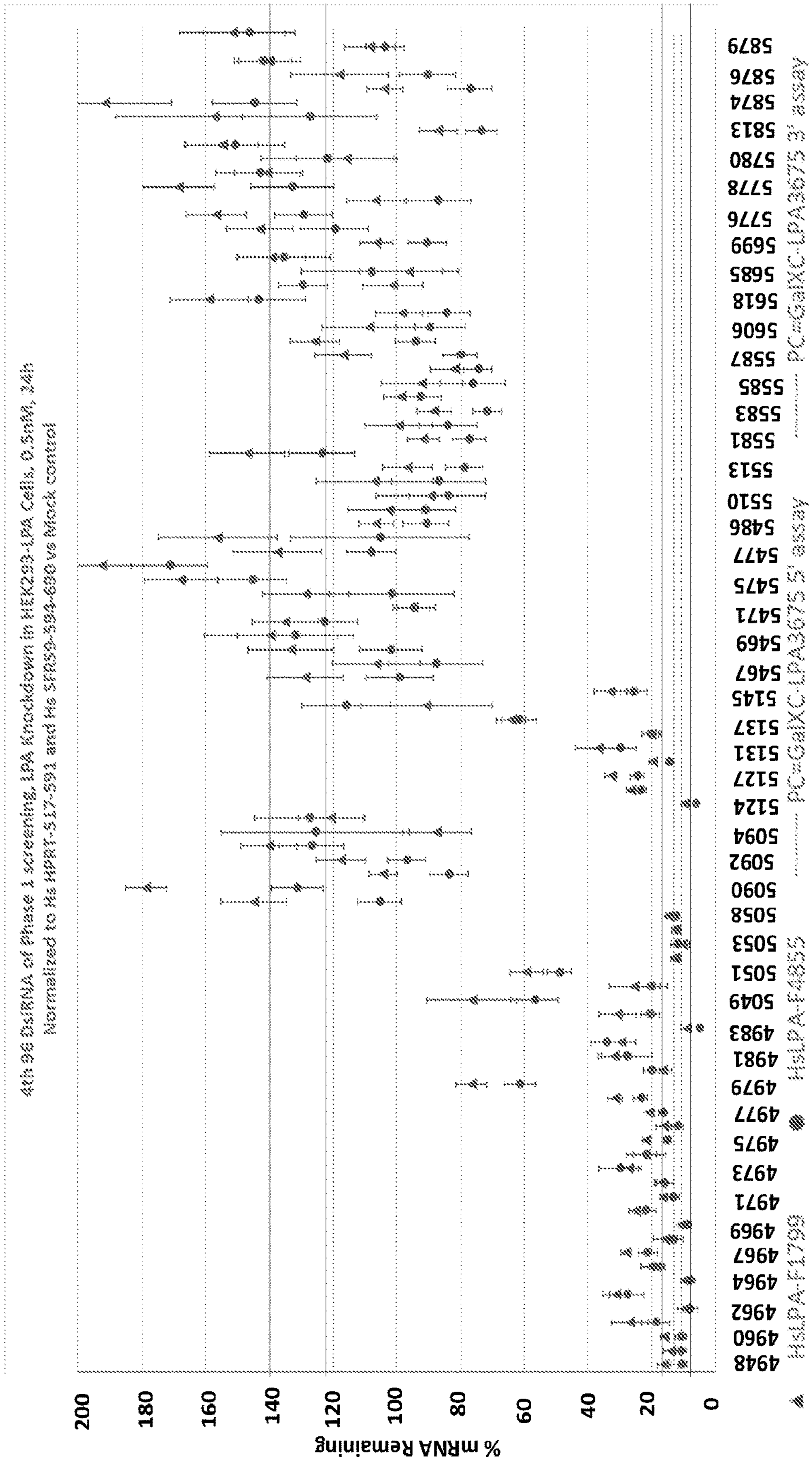
Figure 5:
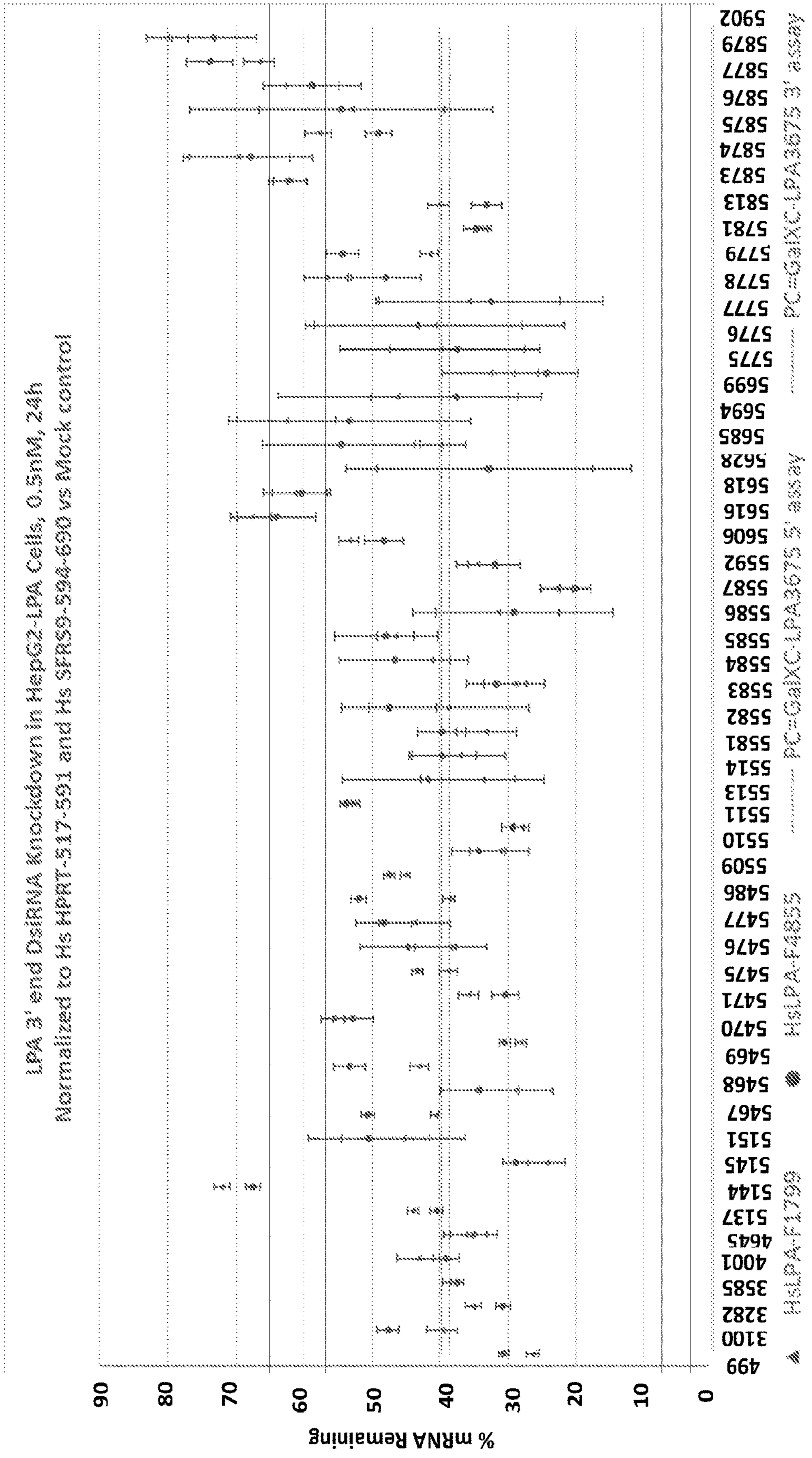
FIG. 5 provides a graph depicting the percent (%) of LPA mRNA in HepG2-LPA cells transfected with the indicated DsiRNAs relative to the % of LPA mRNA control mock-treated cells.

An example of such conjugation is shown below for a loop comprising from 5' to 3' the nucleotide sequence GAAA (L=linker, X=heteroatom) stem attachment points are shown. Such a loop may be present, for example, at positions 27-30 of the sense strand listed in Table 5 and as shown in FIG. 3. In the chemical formula,

is used to describe an attachment point to the oligonucleotide strand.

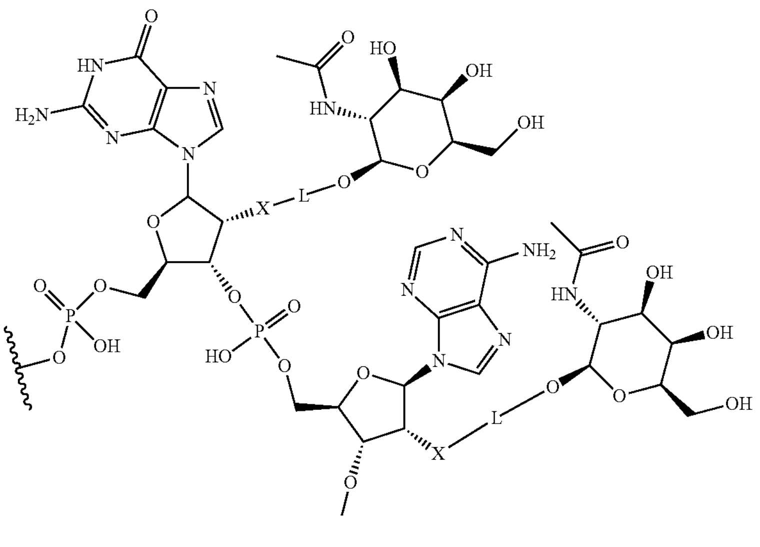

-continued

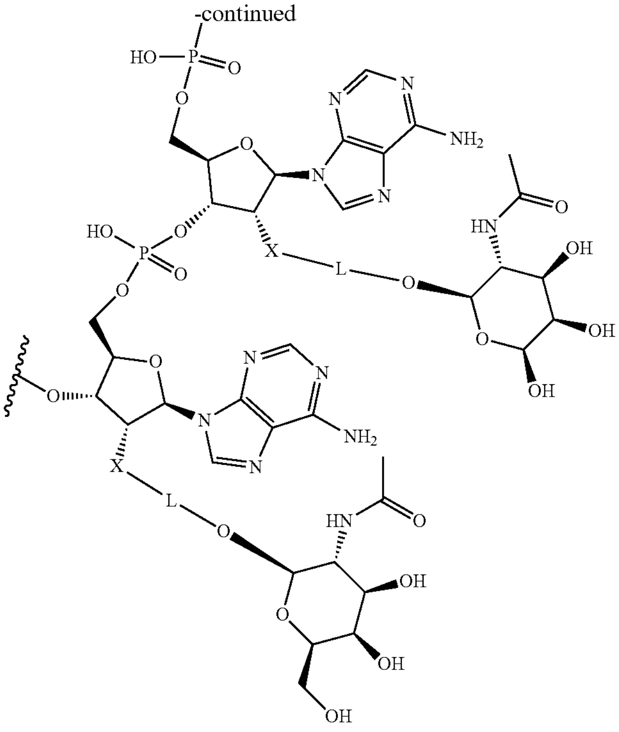

Appropriate methods or chemistry (e.g., click chemistry) can be used to link a targeting ligand to a nucleotide. In some embodiments, a targeting ligand is conjugated to a nucleotide using a click linker. In some embodiments, an acetal-based linker is used to conjugate a targeting ligand to a nucleotide of any one of the oligonucleotides described herein. Acetal-based linkers are disclosed, for example, in Intl. Patent Application Publication No. WO 2016/100401. In some embodiments, the linker is a labile linker. However, in other embodiments, the linker is stable. An example is shown below for a loop comprising from 5' to 3' the nucleotides GAAA, in which GalNAc moieties are attached to nucleotides of the loop using an acetal linker. Such a loop may be present, for example, at positions 27-30 of the any one of the sense strand listed in Tables 3 or 4 and as shown in FIG. 10. In the chemical formula,

is an attachment point to the oligonucleotide strand.

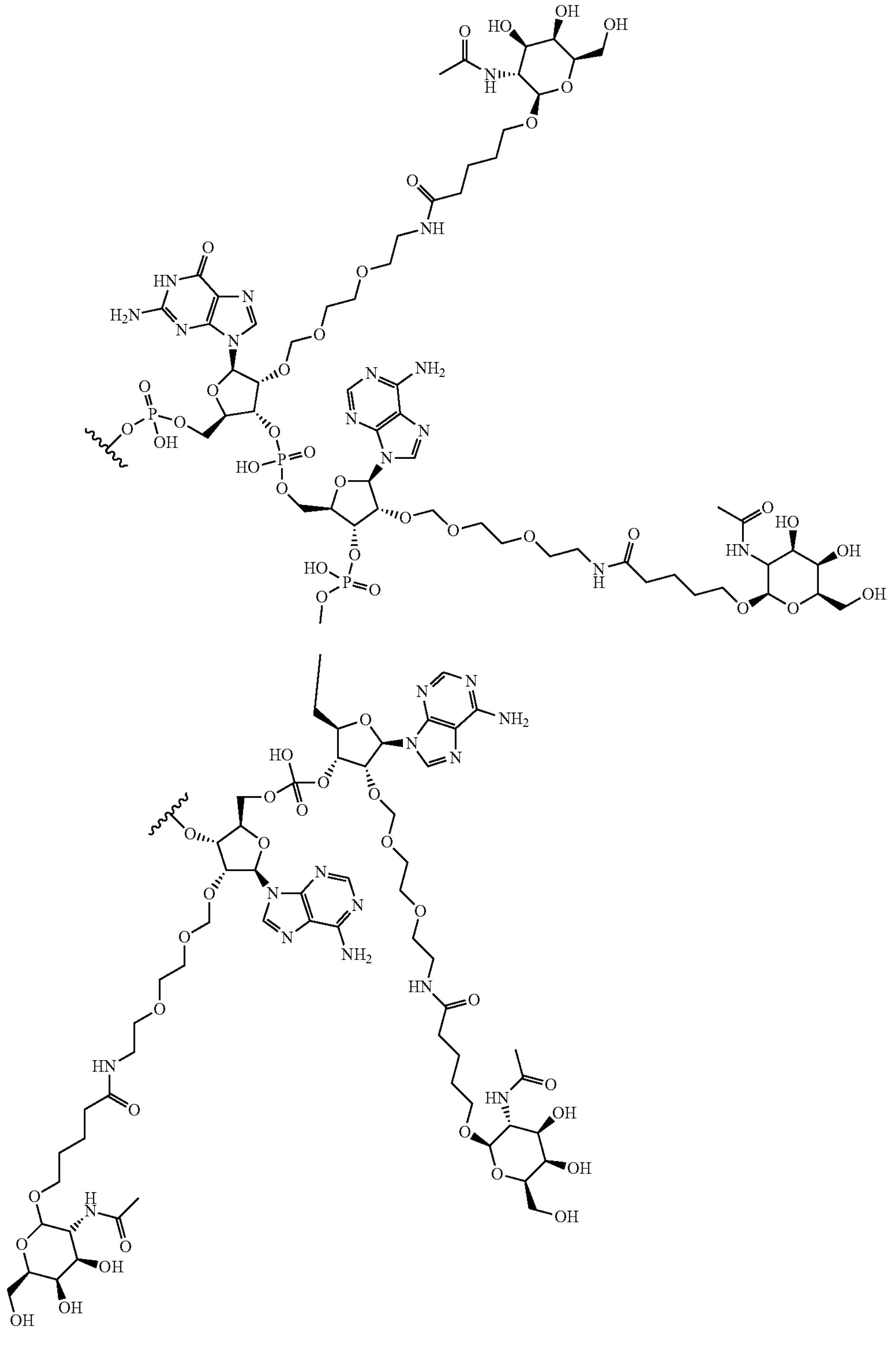

As mentioned, various appropriate methods or chemistry synthetic techniques (e.g., click chemistry) can be used to link a targeting ligand to a nucleotide. In some embodiments, a targeting ligand is conjugated to a nucleotide using a click linker. In some embodiments, an acetal-based linker is used to conjugate a targeting ligand to a nucleotide of any one of the oligonucleotides described herein. Acetal-based linkers are disclosed, for example, in Intl. Patent Application Publication No. WO 2016/100401. In some embodiments, the linker is a labile linker. However, in other embodiments, the linker is a stable linker.

In some embodiments, a duplex extension (e.g., of up to 3, 4, 5 or 6 bp in length) is provided between a targeting ligand (e.g., a GalNAc moiety) and a ds oligonucleotide. In some embodiments, the oligonucleotides herein do not have a GalNAc conjugated thereto.

III. Formulations

Various formulations have been developed to facilitate oligonucleotide use. For example, oligonucleotides can be delivered to a subject or a cellular environment using a formulation that minimizes degradation, facilitates delivery and/or uptake, or provides another beneficial property to the oligonucleotides in the formulation. In some embodiments, an oligonucleotide is formulated in buffer solutions such as phosphate buffered saline solutions, liposomes, micellar structures and capsids.

Formulations of oligonucleotides with cationic lipids can be used to facilitate transfection of the oligonucleotides into cells. For example, cationic lipids, such as lipofectin, cationic glycerol derivatives, and polycationic molecules (e.g., polylysine, can be used. Suitable lipids include Oligofectamine, Lipofectamine (Life Technologies), NC388 (Ribozyme Pharmaceuticals, Inc., Boulder, Colo.), or FuGene 6 (Roche) all of which can be used according to the manufacturer's instructions.

Accordingly, in some embodiments, a formulation comprises a lipid nanoparticle. In some embodiments, an excipient comprises a liposome, a lipid, a lipid complex, a microsphere, a microparticle, a nanosphere or a nanoparticle, or may be otherwise formulated for administration to the cells, tissues, organs, or body of a subject in need thereof (see, e.g., Remington: THE SCIENCE AND PRACTICE OF PHARMACY, 22nd edition, Pharmaceutical Press, 2013).

In some embodiments, the formulations herein comprise an excipient. In some embodiments, an excipient confers to a composition improved stability, improved absorption, improved solubility and/or therapeutic enhancement of the active ingredient. In some embodiments, an excipient is a buffering agent (e.g., sodium citrate, sodium phosphate, a tris base, or sodium hydroxide) or a vehicle (e.g., a buffered solution, petrolatum, dimethyl sulfoxide or mineral oil). In some embodiments, an oligonucleotide is lyophilized for extending its shelf-life and then made into a solution before use (e.g., administration to a subject). Accordingly, an excipient in a composition comprising any one of the oligonucleotides described herein may be a lyoprotectant (e.g., mannitol, lactose, polyethylene glycol or polyvinylpyrrolidone) or a collapse temperature modifier (e.g., dextran, Ficoll™ or gelatin).

In some embodiments, a pharmaceutical composition is formulated to be compatible with its intended route of administration. Examples of routes of administration include parenteral (e.g., intravenous, intramuscular, intraperitoneal, intradermal, subcutaneous), oral (e.g., inhalation), transdermal (e.g., topical), transmucosal and rectal administration.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). The carrier can be a solvent or dispersion medium containing, for example, water, ethanol, polyol (e.g., glycerol, propylene glycol, and liquid polyethylene glycol, and the like), and suitable mixtures thereof. In many cases, it will be preferable to include isotonic agents, for example, sugars, polyalcohols such as mannitol, sorbitol, sodium chloride in the composition. Sterile injectable solutions can be prepared by incorporating the oligonucleotides in a required amount in a selected solvent with one or a combination of ingredients enumerated above, as required, followed by filtered sterilization.

In some embodiments, a composition may contain at least about 0.1% of the therapeutic agent or more, although the percentage of the active ingredient(s) may be between about 1% to about 80% or more of the weight or volume of the total composition. Factors such as solubility, bioavailability, biological half-life, route of administration, product shelf life, as well as other pharmacological considerations will be contemplated by one skilled in the art of preparing such pharmaceutical formulations, and as such, a variety of dosages and treatment regimens may be desirable.

Even though several embodiments are directed to liver-targeted delivery of any of the oligonucleotides herein, targeting of other tissues is also contemplated.

IV. Methods of Use i. Reducing LPA Expression in Cells

The disclosure provides methods for contacting or delivering to a cell or population of cells an effective amount any of the oligonucleotides (e.g., a ds oligonucleotide) herein for purposes of reducing LPA expression. In some embodiments, a reduction of LPA expression is determined by measuring a reduction in the amount or level of LPA mRNA, apo(a) protein, or apo(a) activity in a cell. The methods can include the steps described herein, and these maybe be, but not necessarily, carried out in the sequence as described. Other sequences, however, also are conceivable. Moreover, individual or multiple steps bay be carried out either in parallel and/or overlapping in time and/or individually or in multiply repeated steps. Furthermore, the methods may include additional, unspecified steps.

Methods herein are useful in any appropriate cell type. In some embodiments, a cell is any cell that expresses mRNA (e.g., hepatocytes, macrophages, monocyte-derived cells, prostate cancer cells, cells of the brain, endocrine tissue, bone marrow, lymph nodes, lung, gall bladder, liver, duodenum, small intestine, pancreas, kidney, gastrointestinal tract, bladder, adipose and soft tissue and skin). In some embodiments, the cell is a primary cell obtained from a subject. In some embodiments, the primary cell has undergone a limited number of passages such that the cell substantially maintains is natural phenotypic properties. In some embodiments, a cell to which the oligonucleotide is delivered is ex vivo or in vitro (i.e., can be delivered to a cell in culture or to an organism in which the cell resides).

In some embodiments, the oligonucleotides herein are delivered to a cell or population of cells using a nucleic acid delivery method known in the art including, but not limited to, injection of a solution containing the oligonucleotide, bombardment by particles covered by the oligonucleotide, exposing the cell or population of cells to a solution containing the oligonucleotide, or electroporation of cell membranes in the presence of the oligonucleotide. Other methods known in the art for delivering oligonucleotides to cells may be used, such as lipid-mediated carrier transport, chemical-mediated transport, and cationic liposome transfection such as calcium phosphate, and others.

In some embodiments, reduction of LPA expression is determined by an assay or technique that evaluates one or more molecules, properties or characteristics of a cell or population of cells associated with LPA expression (e.g., using an LPA expression biomarker) or by an assay or technique that evaluates molecules that are directly indicative of LPA expression in a cell or population of cells (e.g., LPA mRNA or apo(a) protein). In some embodiments, the extent to which an oligonucleotide herein reduces LPA expression is evaluated by comparing LPA expression in a cell or population of cells contacted with the oligonucleotide to a control cell or population of cells (e.g., a cell or population of cells not contacted with the oligonucleotide or contacted with a control oligonucleotide). In some embodiments, a control amount or level of LPA expression in a control cell or population of cells is predetermined, such that the control amount or level need not be measured in every instance the assay or technique is performed. The predetermined level or value can take a variety of forms. In some embodiments, a predetermined level or value can be single cut-off value, such as a median or mean.

In some embodiments, contacting or delivering an oligonucleotide (e.g., a ds oligonucleotide) herein to a cell or a population of cells results in a reduction in LPA expression. In some embodiments, the reduction in LPA expression is relative to a control amount or level of LPA expression in cell or population of cells not contacted with the oligonucleotide or contacted with a control oligonucleotide. In some embodiments, the reduction in LPA expression is about 1% or lower, about 5% or lower, about 10% or lower, about 15% or lower, about 20% or lower, about 25% or lower, about 30% or lower, about 35% or lower, about 40% or lower, about 45% or lower, about 50% or lower, about 55% or lower, about 60% or lower, about 70% or lower, about 80% or lower, or about 90% or lower relative to a control amount or level of LPA expression. In some embodiments, the control amount or level of LPA expression is an amount or level of LPA mRNA and/or apo(a) protein in a cell or population of cells that has not been contacted with an oligonucleotide herein. In some embodiments, the effect of delivery of an oligonucleotide to a cell or population of cells according to a method herein is assessed after any finite period or amount of time (e.g., minutes, hours, days, weeks, months). For example, in some embodiments, LPA expression is determined in a cell or population of cells at least about 4 hours, about 8 hours, about 12 hours, about 18 hours, about 24 hours; or at least about 1 day, about 2 days, about 3 days, about 4 days, about 5 days, about 6 days, about 7 days, about 8 days, about 9 days, about 10 days, about 11 days, about 12 days, about 13 days, about 14 days, about 21 days, about 28 days, about 35 days, about 42 days, about 49 days, about 56 days, about 63 days, about 70 days, about 77 days, or about 84 days or more after contacting or delivering the oligonucleotide to the cell or population of cells. In some embodiments, LPA expression is determined in a cell or population of cells at least about 1 month, about 2 months, about 3 months, about 4 months, about 5 months, or about 6 months or more after contacting or delivering the oligonucleotide to the cell or population of cells.

In some embodiments, an oligonucleotide is delivered in the form of a transgene that is engineered to express in a cell the oligonucleotide or strands comprising the oligonucleotide (e.g., its sense and antisense strands). In some embodiments, an oligonucleotide is delivered using a transgene engineered to express any oligonucleotide disclosed herein. Transgenes may be delivered using viral vectors (e.g., adenovirus, retrovirus, vaccinia virus, poxvirus, adeno-associated virus or herpes simplex virus) or non-viral vectors (e.g., plasmids or synthetic mRNAs). In some embodiments, transgenes can be injected directly to a subject.

ii. Medical Use

The disclosure also provides oligonucleotides for use, or adaptable for use, to treat a subject (e.g., a human having a disease, disorder or condition associated with LPA expression) that would benefit from reducing LPA expression. In some embodiments, the disclosure provides oligonucleotides for use, or adapted for use, to treat a subject having a disease, disorder or condition associated with expression of LPA. The disclosure also provides oligonucleotides for use, or adaptable for use, in the manufacture of a medicament or pharmaceutical composition for treating a disease, disorder or condition associated with LPA expression. In some embodiments, the oligonucleotides for use, or adaptable for use, target LPA mRNA and reduce LPA expression (e.g., via the RNAi pathway). In some embodiments, the oligonucleotides for use, or adaptable for use, target LPA mRNA and reduce the amount or level of LPA mRNA, apo(a) protein and/or apo(a) activity.

In addition, in some embodiments of the methods herein, a subject having a disease, disorder or condition associated with LPA expression or is predisposed to the same is selected for treatment with an oligonucleotide (e.g., a ds oligonucleotide) herein. In some embodiments, the method comprises selecting an individual having a marker (e.g., a biomarker) for a disease, disorder or condition associated with LPA expression, or predisposed to the same, such as, but not limited to, LPA mRNA, apo(a) protein, lipoprotein (a), or a combination thereof. Likewise, and as detailed below, some embodiments of the methods provided by the disclosure include steps such as measuring or obtaining a baseline value for a marker of LPA expression (e.g., lipoprotein(a)), and then comparing such obtained value to one or more other baseline values or values obtained after the subject is administered the oligonucleotide to assess the effectiveness of treatment.

iii. Methods of Treatment

The disclosure also provides methods of treating a subject having, suspected of having, or at risk of developing a disease, disorder or condition associated with LPA expression with an oligonucleotide herein. In some embodiments, the disclosure provides methods of treating or attenuating the onset or progression of a disease, disorder or condition associated with LPA expression using the oligonucleotides herein. In other embodiments, the disclosure provides methods to achieve one or more therapeutic benefits in a subject having a disease, disorder or condition associated with LPA expression using the oligonucleotides herein. In some embodiments of the methods herein, the subject is treated by administering a therapeutically effective amount of any one or more of the oligonucleotides herein. In some embodiments, treatment comprises reducing LPA expression. In some embodiments, the subject is treated therapeutically. In some embodiments, the subject is treated prophylactically.

In some embodiments of the methods herein, an oligonucleotide herein, or a pharmaceutical composition comprising the oligonucleotide, is administered to a subject having a disease, disorder or condition associated with LPA expression such that LPA expression is reduced in the subject, thereby treating the subject. In some embodiments, an amount or level of LPA mRNA is reduced in the subject. In some embodiments, an amount or level of apo(a) protein is reduced in the subject. In some embodiments, an amount or level of lipoprotein(a) is reduced in the subject. In some embodiments, an amount or level of apo(a) activity is reduced in the subject. In some embodiments, an amount or level of triglyceride (TG) (e.g., one or more TG(s) or total TGs) is reduced in the subject. In some embodiments, an amount or level of cholesterol (e.g., total cholesterol, LDL cholesterol, and/or HDL cholesterol) is reduced in the subject. In some embodiments, an amount or level of low-density lipoprotein (LDL) cholesterol is reduced in the subject. In some embodiments, an amount or activity of OxPL is reduced or altered in the subject. In some embodiments, an amount or activity of LDL-C is reduced or altered in the subject. In some embodiments, an amount or activity of apoB-100 is reduced or altered in the subject. In some embodiments, any combination of the following is reduced or altered in the subject: LPA expression, an amount or level of LPA mRNA, an amount or level of apo(a) protein, an amount or level of apo(a) activity, an amount or level of TG, an amount or level of cholesterol, an amount or activity of OxPL, an amount or activity of LDL-C, and/or an amount or activity of apoB-100.

In some embodiments of the methods herein, an oligonucleotide herein, or a pharmaceutical composition comprising the oligonucleotide, is administered to a subject having a disease, disorder or condition associated with LPA expression such that LPA expression is reduced in the subject by at least about 30%, about 35%, about 40%, about 45%, about 50%, about 55%, about 60%, about 65%, about 70%, about 75%, about 80%, about 85%, about 90%, about 95%, about 99% or greater than 99% when compared to LPA expression prior to administration of the oligonucleotide or pharmaceutical composition. In some embodiments, LPA expression is reduced in the subject by at least about 30%, about 35%, about 40%, about 45%, about 50%, about 55%, about 60%, about 65%, about 70%, about 75%, about 80%, about 85%, about 90%, about 95%, about 99% or greater than 99% when compared to LPA expression in a subject (e.g., a reference or control subject) not receiving the oligonucleotide or pharmaceutical composition or receiving a control oligonucleotide, pharmaceutical composition or treatment.

In some embodiments of the methods herein, an oligonucleotide herein, or a pharmaceutical composition comprising the oligonucleotide, is administered to a subject having a disease, disorder or condition associated with LPA expression such that an amount or level of LPA mRNA is reduced in the subject by at least about 30%, about 35%, about 40%, about 45%, about 50%, about 55%, about 60%, about 65%, about 70%, about 75%, about 80%, about 85%, about 90%, about 95%, about 99% or greater than 99% when compared to the amount or level of LPA mRNA prior to administration of the oligonucleotide or pharmaceutical composition. In some embodiments, an amount or level of LPA mRNA is reduced in the subject by at least about 30%, about 35%, about 40%, about 45%, about 50%, about 55%, about 60%, about 65%, about 70%, about 75%, about 80%, about 85%, about 90%, about 95%, about 99% or greater than 99% when compared to an amount or level of LPA mRNA in a subject (e.g., a reference or control subject) not receiving the oligonucleotide or pharmaceutical composition or receiving a control oligonucleotide, pharmaceutical composition or treatment.

In some embodiments of the methods herein, an oligonucleotide herein, or a pharmaceutical composition comprising the oligonucleotide, is administered to a subject having a disease, disorder or condition associated with LPA expression such that an amount or level of apo(a) protein is reduced in the subject by at least about 30%, about 35%, about 40%, about 45%, about 50%, about 55%, about 60%, about 65%, about 70%, about 75%, about 80%, about 85%, about 90%, about 95%, about 99% or greater than 99% when compared to the amount or level of apo(a) protein prior to administration of the oligonucleotide or pharmaceutical composition. In some embodiments, an amount or level of apo(a) protein is reduced in the subject by at least about 30%, about 35%, about 40%, about 45%, about 50%, about 55%, about 60%, about 65%, about 70%, about 75%, about 80%, about 85%, about 90%, about 95%, about 99% or greater than 99% when compared to an amount or level of apo(a) protein in a subject (e.g., a reference or control subject) not receiving the oligonucleotide or pharmaceutical composition or receiving a control oligonucleotide, pharmaceutical composition or treatment.

In some embodiments of the methods herein, an oligonucleotide herein, or a pharmaceutical composition comprising the oligonucleotide, is administered to a subject having a disease, disorder or condition associated with LPA expression such that an amount or level of apo(a) activity is reduced in the subject by at least about 30%, about 35%, about 40%, about 45%, about 50%, about 55%, about 60%, about 65%, about 70%, about 75%, about 80%, about 85%, about 90%, about 95%, about 99% or greater than 99% when compared to the amount or level of apo(a) activity prior to administration of the oligonucleotide or pharmaceutical composition. In some embodiments, an amount or level of apo(a) activity is reduced in the subject by at least about 30%, about 35%, about 40%, about 45%, about 50%, about 55%, about 60%, about 65%, about 70%, about 75%, about 80%, about 85%, about 90%, about 95%, about 99% or greater than 99% when compared to an amount or level of apo(a) activity in a subject (e.g., a reference or control subject) not receiving the oligonucleotide or pharmaceutical composition or receiving a control oligonucleotide, pharmaceutical composition or treatment.

In some embodiments of the methods herein, an oligonucleotide herein, or a pharmaceutical composition comprising the oligonucleotide, is administered to a subject having a disease, disorder or condition associated with LPA expression such that an amount or level of lipoprotein(a) is reduced in the subject by at least about 30%, about 35%, about 40%, about 45%, about 50%, about 55%, about 60%, about 65%, about 70%, about 75%, about 80%, about 85%, about 90%, about 95%, about 99% or greater than 99% when compared to the amount or level of lipoprotein(a) prior to administration of the oligonucleotide or pharmaceutical composition. In some embodiments, an amount or level of lipoprotein(a) is reduced in the subject by at least about 30%, about 35%, about 40%, about 45%, about 50%, about 55%, about 60%, about 65%, about 70%, about 75%, about 80%, about 85%, about 90%, about 95%, about 99% or greater than 99% when compared to an amount or level of lipoprotein(a) in a subject (e.g., a reference or control subject) not receiving the oligonucleotide or pharmaceutical composition or receiving a control oligonucleotide, pharmaceutical composition or treatment.

Lipoprotein(a) levels range widely in human adults with plasma levels ranging from <0.1 mg/dL to >200 mg/dL, thus exhibiting up to three orders of magnitude difference among individuals (Schmidt et al., (2016) J Lipid Res. 57(8):1339-1359). Lipoprotein(a) levels <30 mg/dl are considered optimal in the United States and Canada (Anderson et al., (2016) CAN J CARDIOL 32:1263-82). The European Atherosclerosis Society (EAS) has proposed <50 mg/dL as optimal, and lipoprotein(a) levels >60 mg/dl are used as a cutoff for the reimbursement of apheresis in Germany and the United Kingdom (Tsimikas (2017) J AM COLL CARDIOL. 69(6):692-711). In some embodiments, a subject selected for treatment or treated with an oligonucleotide herein is identified or determined to have an amount or level of lipoprotein(a) of about 30 mg/dL or greater. In some embodiments, a subject selected for treatment or treated with an oligonucleotide herein is identified or determined to have an amount or level of lipoprotein(a) of >30 mg/dL. In some embodiments, a subject selected for treatment or treated with an oligonucleotide herein is identified or determined to have an amount or level of lipoprotein(a) of about 50 mg/dL or greater. In some embodiments, a subject selected for treatment or treated with an oligonucleotide herein is identified or determined to have an amount or level of lipoprotein(a) of about 60 mg/dL or greater. In some embodiments, a subject selected for treatment or treated with an oligonucleotide herein is identified or determined to have an amount or level of lipoprotein(a) in the range of 30 mg/dL to 300 mg/dL.

Generally, a normal or desirable TG range for a human patient is <150 mg/dL of blood, with <100 being considered ideal. In some embodiments, the patient selected for treatment or treated is identified or determined to have an amount or level of TG of ≥150 mg/dL. In some embodiments, the patient selected for treatment or treated is identified or determined to have an amount or level of TG in the range of 150 to 199 mg/dL, which is considered borderline high TG levels. In some embodiments, the patient selected for treatment or treated is identified or determined to have an amount or level of TG in the range of 200 to 499 mg/dL, which is considered high TG levels. In some embodiments, the patient selected for treatment or treated is identified or determined to have an amount or level of TG in the range of 500 mg/dL or higher (i.e., ≥500 mg/dL), which is considered very high TG levels. In some embodiments, the patient selected for treatment or treated is identified or determined to have an amount or level of TG which is ≥150 mg/dL, ≥200 mg/dL or ≥500 mg/dL. In some embodiments, the patient selected for treatment or treated is identified or determined to have an amount of level of TG of 200 to 499 mg/dL, or 500 mg/dL or higher. In some embodiments, the patient selected for treatment or treated is identified or determined to have an amount or level of TG which is ≥200 mg/dL.

In some embodiments of the methods herein, an oligonucleotide herein, or a pharmaceutical composition comprising the oligonucleotide, is administered to a subject having a disease, disorder or condition associated with LPA expression such that an amount or level of cholesterol (e.g., total cholesterol, LDL cholesterol, and/or HDL cholesterol) is reduced in the subject by at least about 30%, about 35%, about 40%, about 45%, about 50%, about 55%, about 60%, about 65%, about 70%, about 75%, about 80%, about 85%, about 90%, about 95%, about 99% or greater than 99% when compared to the amount or level of cholesterol prior to administration of the oligonucleotide or pharmaceutical composition. In some embodiments, an amount or level of cholesterol is reduced in the subject by at least about 30%, about 35%, about 40%, about 45%, about 50%, about 55%, about 60%, about 65%, about 70%, about 75%, about 80%, about 85%, about 90%, about 95%, about 99% or greater than 99% when compared to an amount or level of cholesterol in a subject (e.g., a reference or control subject) not receiving the oligonucleotide or pharmaceutical composition or receiving a control oligonucleotide, pharmaceutical composition or treatment.

Generally, a normal or desirable cholesterol range (total cholesterol) for an adult human patient is <200 mg/dL of blood. In some embodiments, the patient selected for treatment or treated is identified or determined to have an amount or level of cholesterol of ≥200 mg/dL. In some embodiments, the patient selected for treatment or treated is identified or determined to have an amount or level of cholesterol in the range of 200 to 239 mg/dL, which is considered borderline high cholesterol levels. In some embodiments, the patient selected for treatment or treated is identified or determined to have an amount or level of cholesterol in the range of 240 mg/dL and higher (i.e., ≥240 mg/dL), which is considered high cholesterol levels. In some embodiments, the patient selected from treatment or treated is identified or determined to have an amount or level of cholesterol of 200 to 239 mg/dL, or 240 mg/dL or higher. In some embodiments, the patient selected for treatment or treated is identified or determined to have an amount or level of cholesterol which is ≥200 mg/dL or ≥240 mg/dL or higher.

In some embodiments of the methods herein, an oligonucleotide herein, or a pharmaceutical composition comprising the oligonucleotide, is administered to a subject having a disease, disorder, or condition associated with LPA expression such that an amount or level of LDL cholesterol is reduced in the subject by at least about 30%, about 35%, about 40%, about 45%, about 50%, about 55%, about 60%, about 65%, about 70%, about 75%, about 80%, about 85%, about 90%, about 95%, about 99% or greater than 99% when compared to the amount or level of LDL cholesterol prior to administration of the oligonucleotide or pharmaceutical composition. In some embodiments, an amount or level of LDL cholesterol is reduced in the subject by at least about 30%, about 35%, about 40%, about 45%, about 50%, about 55%, about 60%, about 65%, about 70%, about 75%, about 80%, about 85%, about 90%, about 95%, about 99% or greater than 99% when compared to an amount or level of LDL cholesterol in a subject (e.g., a reference or control subject) not receiving the oligonucleotide or pharmaceutical composition or receiving a control oligonucleotide, pharmaceutical composition or treatment.

Generally, a normal or desirable LDL cholesterol range for an adult human patient is <100 mg/dL of blood. In some embodiments, the patient selected for treatment or treated is identified or determined to have an amount or level of cholesterol of ≥100 mg/dL. In some embodiments, the patient selected for treatment or treated is identified or determined to have an amount or level of LDL cholesterol in the range of 100 to 129 mg/dL, which is considered above optimal. In some embodiments, the patient selected for treatment or treated is identified or determined to have an amount or level of LDL cholesterol in the range of 130 to 159 mg/dL, which is considered borderline high levels. In some embodiments, the patient selected for treatment or treated is identified or determined to have an amount or level of LDL cholesterol in the range of 160 to 189 mg/dL, which is considered high LDL cholesterol levels. In some embodiments, the patient selected for treatment or treated is identified or determined to have an amount or level of LDL cholesterol in the range of 190 mg/dL and higher (i.e., ≥190 mg/dL), which is considered very high LDL cholesterol levels. In some embodiments, the patient selected for treatment or treated is identified or determined to have an amount or level of LDL cholesterol which is ≥100 mg/dL, ≥130 mg/dL, ≥160 mg/dL, or ≥190 mg/dL or higher, preferably ≥160 mg/dL, or ≥190 mg/dL or higher. In some embodiments, the patient selected for treatment or treated is identified or determined to have an amount or level of LDL cholesterol of 100 to 129 mg/dL, 130 to 159 mg/dL, 160 to 189 mg/dL, or 190 mg/dL and higher.

Suitable methods for determining LPA expression, an amount or level of LPA mRNA, an amount or level of apo(a) protein, an amount or level of apo(a) activity, an amount or level of lipoprotein(a), and/or an amount or level of OxPL, LDL-C, apoB-100, TG and/or LDL cholesterol in the subject, or in a sample from the subject, are known in the art. Further, the Examples set forth herein illustrate exemplary methods for determining LPA expression.

In some embodiments, LPA expression, the amount or level of LPA mRNA, apo(a) protein, apo(a) activity, OxPL, LDL-C, apoB-100, TG, LDL cholesterol, or any combination thereof, is reduced in a cell (e.g., a hepatocyte), a population or a group of cells (e.g., an organoid), an organ (e.g., liver), blood or a fraction thereof (e.g., plasma), a tissue (e.g., liver tissue), a sample (e.g., a liver biopsy sample), or any other biological material obtained or isolated from the subject. In some embodiments, LPA expression, the amount or level of LPA mRNA, apo(a) protein, apo(a) activity, OxPL, LDL-C, apoB-100, TG, LDL cholesterol, or any combination thereof, is reduced in more than one type of cell (e.g., a hepatocyte and one or more other type(s) of cell), more than one groups of cells, more than one organ (e.g., liver and one or more other organ(s)), more than one fraction of blood (e.g., plasma and one or more other blood fraction(s)), more than one type of tissue (e.g., liver tissue and one or more other type(s) of tissue), more than one type of sample (e.g., a liver biopsy sample and one or more other type(s) of biopsy sample) obtained or isolated from the subject.

Examples of a disease, disorder or condition associated with LPA expression include, but are not limited to, Berger's disease, peripheral artery disease, coronary artery disease, metabolic syndrome, acute coronary syndrome, aortic valve stenosis, aortic valve regurgitation, aortic dissection, retinal artery occlusion, cerebrovascular disease, mesenteric ischemia, superior mesenteric artery occlusion, renal artery stenosis, stable/unstable angina, acute coronary syndrome, heterozygous or homozygous familial hypercholesterolemia, hyperapobetalipoproteinemia, cerebrovascular atherosclerosis, cerebrovascular disease, and venous thrombosis, or a combination thereof.

Because of their high specificity, the oligonucleotides herein specifically target mRNAs of target genes of cells, tissues, or organs (e.g., liver). In preventing disease, the target gene may be one which is required for initiation or maintenance of the disease or which has been identified as being associated with a higher risk of contracting the disease. In treating disease, the oligonucleotide can be brought into contact with the cells or tissue exhibiting or responsible for mediating the disease. For example, an oligonucleotide substantially identical to all or part of a wild-type (i.e., native) or mutated gene associated with a disorder or condition associated with LPA expression may be brought into contact with or introduced into a cell or tissue type of interest such as a hepatocyte or other liver cell.

In some embodiments, the target gene may be a target gene from any mammal, such as a human. Any gene may be silenced according to the method described herein.

Methods described herein are typically involve administering to a subject a therapeutically effective amount of an oligonucleotide herein, that is, an amount capable of producing a desirable therapeutic result. A therapeutically acceptable amount may be an amount that can therapeutically treat a disease or disorder. The appropriate dosage for any one subject will depend on certain factors, including the subject's size, body surface area, age, the particular composition to be administered, the active ingredient(s) in the composition, time and route of administration, general health, and other drugs being administered concurrently.

In some embodiments, a subject is administered any one of the compositions herein either enterally (e.g., orally, by gastric feeding tube, by duodenal feeding tube, via gastrostomy or rectally), parenterally (e.g., subcutaneous injection, intravenous injection or infusion, intra-arterial injection or infusion, intraosseous infusion, intramuscular injection, intracerebral injection, intracerebroventricular injection, intrathecal), topically (e.g., epicutaneous, inhalational, via eye drops, or through a mucous membrane), or by direct injection into a target organ (e.g., the liver of a subject). Typically, oligonucleotides herein are administered intravenously or subcutaneously.

As a non-limiting set of examples, the oligonucleotides herein would typically be administered quarterly (once every three months), bi-monthly (once every two months), monthly or weekly. For example, the oligonucleotides may be administered every week or at intervals of two, or three weeks. Alternatively, the oligonucleotides may be administered daily. In some embodiments, a subject is administered one or more loading doses of the oligonucleotide followed by one or more maintenance doses of the oligonucleotide.

In some embodiments, the subject to be treated is a human or non-human primate or other mammalian subject. Other exemplary subjects include domesticated animals such as dogs and cats; livestock such as horses, cattle, pigs, sheep, goats, and chickens; and animals such as mice, rats, guinea pigs, and hamsters.

V. Kits

In some embodiments, the disclosure provides a kit comprising an oligonucleotide herein, and instructions for use. In some embodiments, the kit comprises an oligonucleotide herein, and a package insert containing instructions for use of the kit and/or any component thereof. In some embodiments, the kit comprises, in a suitable container, an oligonucleotide herein, one or more controls, and various buffers, reagents, enzymes and other standard ingredients well known in the art. In some embodiments, the container comprises at least one vial, well, test tube, flask, bottle, syringe or other container means, into which the oligonucleotide is placed, and in some instances, suitably aliquoted. In some embodiments where an additional component is provided, the kit contains additional containers into which this component is placed. The kits can also include a means for containing the oligonucleotide and any other reagent in close confinement for commercial sale. Such containers may include injection or blow-molded plastic containers into which the desired vials are retained. Containers and/or kits can include labeling with instructions for use and/or warnings.

In some embodiments, a kit comprises an oligonucleotide herein, and a pharmaceutically acceptable carrier, or a pharmaceutical composition comprising the oligonucleotide and instructions for treating or delaying progression of a disease, disorder or condition associated with LPA expression in a subject in need thereof.

EXAMPLES

While the disclosure has been described with reference to the specific embodiments set forth in the following Examples, it should be understood by those skilled in the art that various changes may be made, and equivalents may be substituted without departing from the true spirit and scope of the disclosure. Further, the following Examples are offered by way of illustration and are not intended to limit the scope of the disclosure in any manner. In addition, modifications may be made to adapt to a situation, material, composition of matter, process, process step or steps, to the objective, spirit and scope of the disclosure. All such modifications are intended to be within the scope of the disclosure. Standard techniques well known in the art or the techniques specifically described below are utilized.

Example 1: Preparation of Double-Stranded RNAi Oligonucleotides

Oligonucleotide Synthesis and Purification

The ds RNAi oligonucleotides described in the foregoing Examples are chemically synthesized using methods described herein. Generally, ds RNAi oligonucleotides are synthesized using solid phase oligonucleotide synthesis methods as described for 19-23mer siRNAs (see, e.g., Scaringe et al. (1990) Nucleic Acids Res. 18:5433-41 and Usman et al. (1987) J. Am. Chem. Soc. 109:7845-45; see also, U.S. Pat. Nos. 5,804,683; 5,831,071; 5,998,203; 6,008,400; 6,111,086; 6,117,657; 6,353,098; 6,362,323; 6,437,117 and 6,469,158).

Individual RNA strands are synthesized and HPLC purified according to standard methods (Integrated DNA Technologies; Coralville, IA). For example, RNA oligonucleotides are synthesized using solid phase phosphoramidite chemistry, deprotected and desalted on NAP-5 columns (Amersham Pharmacia Biotech; Piscataway, NJ) using standard techniques (Damha & Olgivie (1993) Methods Mol. Biol. 20:81-114; Wincott et al. (1995) Nucleic Acids Res. 23:2677-84). The oligomers are purified using ion-exchange high performance liquid chromatography (IE-HPLC) on an Amersham Source 15Q column (1.0 cm×25 cm; Amersham Pharmacia Biotech) using a 15 min step-linear gradient. The gradient varies from 90:10 Buffers A:B to 52:48 Buffers A:B, where Buffer A is 100 mM Tris pH 8.5 and Buffer B is 100 mM Tris pH 8.5, 1 M NaCl. Samples are monitored at 260 nm and peaks corresponding to the full-length oligonucleotide species are collected, pooled, desalted on NAP-5 columns, and lyophilized.

The purity of each oligomer is determined by capillary electrophoresis (CE) on a Beckman PACE 5000 (Beckman Coulter, Inc.; Fullerton, CA). The CE capillaries have a 100 μm inner diameter and contain ssDNA 100R Gel (Beckman-Coulter). Typically, about 0.6 nmole of oligonucleotide is injected into a capillary, is run in an electric field of 444 V/cm and is detected by UV absorbance at 260 nm. Denaturing Tris-Borate-7 M-urea running buffer is purchased from Beckman-Coulter. Oligoribonucleotides are obtained that are at least 90% pure as assessed by CE for use in experiments described below. Compound identity is verified by matrix-assisted laser desorption ionization time-of-flight (MALDI-TOF) mass spectroscopy on a Voyager DE™ Biospectometry Work Station (Applied Biosystems; Foster City, CA) following the manufacturer's recommended protocol. Relative molecular masses of all oligomers are obtained, often within 0.2% of expected molecular mass.

Preparation of Duplexes ssRNA oligomers are resuspended (e.g., at 100 μM concentration) in duplex buffer consisting of 100 mM potassium acetate, 30 mM HEPES, pH 7.5. Complementary sense and antisense strands are mixed in equal molar amounts to yield a final solution of, for example, 50 μM duplex. Samples are heated to 100° C. for 5' in RNA buffer (IDT) and are allowed to cool to room temperature before use. The ds RNA oligonucleotides are stored at −20° C. ss RNA oligomers are stored lyophilized or in nuclease-free water at −80° C.

Example 2: RNAi Oligonucleotide Inhibition of LPA Expression In Vitro

LPA mRNA Target Sequence Identification

To identify RNAi oligonucleotide inhibitors of LPA expression, a computer-based algorithm was used to computationally identify LPA mRNA target sequences suitable for assaying inhibition of LPA expression by the RNAi pathway. The algorithm provides RNAi oligonucleotide guide (antisense) strand sequences each having a region of complementarity to a suitable LPA target sequence of human LPA mRNA (e.g., SEQ ID NO: 1; Table 1). Some of the guide strand sequences identified by the algorithm are also complementary to the corresponding LPA target sequence of monkey LPA mRNA (SEQ ID NO: 2; Table 1). RNAi oligonucleotides (formatted as DsiRNA oligonucleotides) were generated (Table 2), each with a unique guide strand having a region of complementarity to an LPA target sequence identified by the algorithm. The passenger (sense) strands of the DsiRNAs provided in Table 2 comprise a unique human LPA mRNA target sequence identified by the algorithm.

TABLE 1

Sequences of Human and NHP (Monkey) mRNA

| Species | GenBank Ref Seq # | SEQ ID NO: |
|---|---|---|
| Human (Hs) | NM_005577.3 | 1 |
| Cynomolgus monkey (Mf) | XM_015448517.1 | 2 |
| Rhesus monkey | XM_028847001.1 | 3 |

TABLE 2

DsiRNAs Targeting Human LPA mRNA and Controls Evaluated in Cells

| DsiRNA | Passenger (Sense) | SEQ ID NO: | Guide (Antisense) | SEQ ID NO: | Target Sequence | SEQ ID NO: |
|---|---|---|---|---|---|---|
| LPA-125 | CUGAGCAAAGCCAUGUGGUACAGGA | 4 | UCCUGUACCACAUGGCUUUGCUCAGGU | 404 | CUGAGCAAAGCCAUGUGGU | 804 |
| LPA-128 | AGCAAAGCCAUGUGGUCCAAGAUTG | 5 | CAAUCUUGGACCACAUGGCUUUGCUCA | 405 | AGCAAAGCCAUGUGGUCCA | 805 |
| LPA-132 | AAGCCAUGUGGUCCAGGAUAGCUAC | 6 | GUAGCUAUCCUGGACCACAUGGCUUUG | 406 | AAGCCAUGUGGUCCAGGAU | 806 |

TABLE 2-continued

DsiRNAs Targeting Human LPA mRNA and Controls Evaluated in Cells

| | Passenger (Sense) | SEQ ID NO: | Guide (Antisense) | SEQ ID NO: | Target Sequence | SEQ ID NO: |
|---|---|---|---|---|---|---|
| LPA-133 | AGCCAUGUGGUCCAGGAUUACUACC | 7 | GGUAGUAAUCCUGGACCACAUGGCUUU | 407 | AGCCAUGUGGUCCAGGAUU | 807 |
| LPA-134 | GCCAUGUGGUCCAGGAUUGAUACCA | 8 | UGGUAUCAAUCCUGGACCACAUGGCUU | 408 | GCCAUGUGGUCCAGGAUUG | 808 |
| LPA-135 | CCAUGUGGUCCAGGAUUGCAACCAT | 9 | AUGGUUGCAAUCCUGGACCACAUGGCU | 409 | CCAUGUGGUCCAGGAUUGC | 809 |
| LPA-136 | CAUGUGGUCCAGGAUUGCUACCATG | 10 | CAUGGUAGCAAUCCUGGACCACAUGGC | 410 | CAUGUGGUCCAGGAUUGCU | 810 |
| LPA-137 | AUGUGGUCCAGGAUUGCUAACAUGG | 11 | CCAUGUUAGCAAUCCUGGACCACAUGG | 411 | AUGUGGUCCAGGAUUGCUA | 811 |
| LPA-138 | UGUGGUCCAGGAUUGCUACAAUGGT | 12 | ACCAUUGUAGCAAUCCUGGACCACAUG | 412 | UGUGGUCCAGGAUUGCUAC | 812 |
| LPA-160 | GGUGAUGGACAGAGUUAUCAAGGCA | 13 | UGCCUUGAUAACUCUGUCCAUCACCAU | 413 | GGUGAUGGACAGAGUUAUC | 813 |
| LPA-190 | UCCACCACUGUCACAGGAAAGACCT | 14 | AGGUCUUUCCUGUGACAGUGGUGGAGU | 414 | UCCACCACUGUCACAGGAA | 814 |
| LPA-191 | CCACCACUGUCACAGGAAGAACCTG | 15 | CAGGUUCUUCCUGUGACAGUGGUGGAG | 415 | CCACCACUGUCACAGGAAG | 815 |
| LPA-197 | CUGUCACAGGAAGGACCUGACAAGC | 16 | GCUUGUCAGGUCCUUCCUGUGACAGUG | 416 | CUGUCACAGGAAGGACCUG | 816 |
| LPA-205 | GGAAGGACCUGCCAAGCUUAGUCAT | 17 | AUGACUAAGCUUGGCAGGUCCUUCCUG | 417 | GGAAGGACCUGCCAAGCUU | 817 |
| LPA-206 | GAAGGACCUGCCAAGCUUGAUCATC | 18 | GAUGAUCAAGCUUGGCAGGUCCUUCCU | 418 | GAAGGACCUGCCAAGCUUG | 818 |
| LPA-208 | AGGACCUGCCAAGCUUGGUAAUCTA | 19 | UAGAUUACCAAGCUUGGCAGGUCCUUC | 419 | AGGACCUGCCAAGCUUGGU | 819 |
| LPA-209 | GGACCUGCCAAGCUUGGUCAUCUAT | 20 | AUAGAUGACCAAGCUUGGCAGGUCCUU | 420 | GGACCUGCCAAGCUUGGUC | 820 |
| LPA-210 | GACCUGCCAAGCUUGGUCAACUATG | 21 | CAUAGUUGACCAAGCUUGGCAGGUCCU | 421 | GACCUGCCAAGCUUGGUCA | 821 |
| LPA-211 | ACCUGCCAAGCUUGGUCAUAUAUGA | 22 | UCAUAUAUGACCAAGCUUGGCAGGUCC | 422 | ACCUGCCAAGCUUGGUCAU | 822 |
| LPA-212 | CCUGCCAAGCUUGGUCAUCAAUGAC | 23 | GUCAUUGAUGACCAAGCUUGGCAGGUC | 423 | CCUGCCAAGCUUGGUCAUC | 823 |
| LPA-219 | AGCUUGGUCAUCUAUGACAACACAT | 24 | AUGUGUUGUCAUAGAUGACCAAGCUUG | 424 | AGCUUGGUCAUCUAUGACA | 824 |
| LPA-225 | GUCAUCUAUGACACCACAUAAACAT | 25 | AUGUUUAUGUGGUGUCAUAGAUGACCA | 425 | GUCAUCUAUGACACCACAU | 825 |
| LPA-258 | CACAGAAAACUACCCAAAUACUGGC | 26 | GCCAGUAUUUGGGUAGUUUUCUGUGGU | 426 | CACAGAAAACUACCCAAAU | 826 |
| LPA-261 | AGAAAACUACCCAAAUGCUAGCUTG | 27 | CAAGCUAGCAUUUGGGUAGUUUUCUGU | 427 | AGAAAACUACCCAAAUGCU | 827 |
| LPA-263 | AAAACUACCCAAAUGCUGGAUUGAT | 28 | AUCAAUCCAGCAUUUGGGUAGUUUUCU | 428 | AAAACUACCCAAAUGCUGG | 828 |
| LPA-269 | ACCCAAAUGCUGGCUUGAUAAUGAA | 29 | UUCAUUAUCAAGCCAGCAUUUGGGUAG | 429 | ACCCAAAUGCUGGCUUGAU | 829 |
| LPA-270 | CCCAAAUGCUGGCUUGAUCAUGAAC | 30 | GUUCAUGAUCAAGCCAGCAUUUGGGUA | 430 | CCCAAAUGCUGGCUUGAUC | 830 |

TABLE 2-continued

DsiRNAs Targeting Human LPA mRNA and Controls Evaluated in Cells

| | Passenger (Sense) | SEQ ID NO: | Guide (Antisense) | SEQ ID NO: | Target Sequence | SEQ ID NO: |
|---|---|---|---|---|---|---|
| LPA-291 | GAACUACUGCAGGAAUCCAAAUGCT | 31 | AGCAUUUGGAUUCCUGCAGUAGUUCAU | 431 | GAACUACUGCAGGAAUCCA | 831 |
| LPA-295 | UACUGCAGGAAUCCAGAUGAUGUGG | 32 | CCACAUCAUCUGGAUUCCUGCAGUAGU | 432 | UACUGCAGGAAUCCAGAUG | 832 |
| LPA-296 | ACUGCAGGAAUCCAGAUGCAGUGGC | 33 | GCCACUGCAUCUGGAUUCCUGCAGUAG | 433 | ACUGCAGGAAUCCAGAUGC | 833 |
| LPA-298 | UGCAGGAAUCCAGAUGCUGAGGCAG | 34 | CUGCCUCAGCAUCUGGAUUCCUGCAGU | 434 | UGCAGGAAUCCAGAUGCUG | 834 |
| LPA-355 | AGGUGGGAGUACUGCAACCAGACGC | 35 | GCGUCUGGUUGCAGUACUCCCACCUGA | 435 | AGGUGGGAGUACUGCAACC | 835 |
| LPA-380 | AAUGCUCAGACGCAGAAGGAACUGC | 36 | GCAGUUCCUUCUGCGUCUGAGCAUUGC | 436 | AAUGCUCAGACGCAGAAGG | 836 |
| LPA-417 | GACUGUUACCCCGGUUCCAAGCCTA | 37 | UAGGCUUGGAACCGGGGUAACAGUCGG | 437 | GACUGUUACCCCGGUUCCA | 837 |
| LPA-418 | ACUGUUACCCCGGUUCCAAACCUAG | 38 | CUAGGUUUGGAACCGGGGUAACAGUCG | 438 | ACUGUUACCCCGGUUCCAA | 838 |
| LPA-419 | CUGUUACCCCGGUUCCAAGACUAGA | 39 | UCUAGUCUUGGAACCGGGGUAACAGUC | 439 | CUGUUACCCCGGUUCCAAG | 839 |
| LPA-420 | UGUUACCCCGGUUCCAAGCAUAGAG | 40 | CUCUAUGCUUGGAACCGGGGUAACAGU | 440 | UGUUACCCCGGUUCCAAGC | 840 |
| LPA-421 | GUUACCCCGGUUCCAAGCCAAGAGG | 41 | CCUCUUGGCUUGGAACCGGGGUAACAG | 441 | GUUACCCCGGUUCCAAGCC | 841 |
| LPA-422 | UUACCCCGGUUCCAAGCCUAGAGGC | 42 | GCCUCUAGGCUUGGAACCGGGGUAACA | 442 | UUACCCCGGUUCCAAGCCU | 842 |
| LPA-423 | UACCCCGGUUCCAAGCCUAAAGGCT | 43 | AGCCUUUAGGCUUGGAACCGGGGUAAC | 443 | UACCCCGGUUCCAAGCCUA | 843 |
| LPA-492 | GUGCUACCAUGGUAAUGGAAAGAGT | 44 | ACUCUUUCCAUUACCAUGGUAGCACUC | 444 | GUGCUACCAUGGUAAUGGA | 844 |
| LPA-493 | UGCUACCAUGGUAAUGGACAGAGTT | 45 | AACUCUGUCCAUUACCAUGGUAGCACU | 445 | UGCUACCAUGGUAAUGGAC | 845 |
| LPA-494 | GCUACCAUGGUAAUGGACAAAGUTA | 46 | UAACUUUGUCCAUUACCAUGGUAGCAC | 446 | GCUACCAUGGUAAUGGACA | 846 |
| LPA-495 | CUACCAUGGUAAUGGACAGAGUUAT | 47 | AUAACUCUGUCCAUUACCAUGGUAGCA | 447 | CUACCAUGGUAAUGGACAG | 847 |
| LPA-496 | UACCAUGGUAAUGGACAGAAUUATC | 48 | GAUAAUUCUGUCCAUUACCAUGGUAGC | 448 | UACCAUGGUAAUGGACAGA | 848 |
| LPA-497 | ACCAUGGUAAUGGACAGAGAUAUCG | 49 | CGAUAUCUCUGUCCAUUACCAUGGUAG | 449 | ACCAUGGUAAUGGACAGAG | 849 |
| LPA-498 | CCAUGGUAAUGGACAGAGUAAUCGA | 50 | UCGAUUACUCUGUCCAUUACCAUGGUA | 450 | CCAUGGUAAUGGACAGAGU | 850 |
| LPA-499 | CAUGGUAAUGGACAGAGUUAUCGAG | 51 | CUCGAUAACUCUGUCCAUUACCAUGGU | 451 | CAUGGUAAUGGACAGAGUU | 851 |
| LPA-500 | AUGGUAAUGGACAGAGUUAACGAGG | 52 | CCUCGUUAACUCUGUCCAUUACCAUGG | 452 | AUGGUAAUGGACAGAGUUA | 852 |
| LPA-501 | UGGUAAUGGACAGAGUUAUAGAGGC | 53 | GCCUCUAUAACUCUGUCCAUUACCAUG | 453 | UGGUAAUGGACAGAGUUAU | 853 |
| LPA-502 | GGUAAUGGACAGAGUUAUCAAGGCA | 54 | UGCCUUGAUAACUCUGUCCAUUACCAU | 454 | GGUAAUGGACAGAGUUAUC | 854 |

TABLE 2-continued

DsiRNAs Targeting Human LPA mRNA and Controls Evaluated in Cells

| | Passenger (Sense) | SEQ ID NO: | Guide (Antisense) | SEQ ID NO: | Target Sequence | SEQ ID NO: |
|---|---|---|---|---|---|---|
| LPA-503 | GUAAUGGACAGAGUUAUCGAGGCAC | 55 | GUGCCUCGAUAACUCUGUCCAUUACCA | 455 | GUAAUGGACAGAGUUAUCG | 855 |
| LPA-523 | GGCACAUACUCCACCACUGACACAG | 56 | CUGUGUCAGUGGUGGAGUAUGUGCCUC | 456 | GGCACAUACUCCACCACUG | 856 |
| LPA-563 | CUUGGUCAUCUAUGACACCACACUC | 57 | GAGUGUGGUGUCAUAGAUGACCAAGCU | 457 | CUUGGUCAUCUAUGACACC | 857 |
| LPA-567 | GUCAUCUAUGACACCACACACGCAT | 58 | AUGCGUGUGUGGUGUCAUAGAUGACCA | 458 | GUCAUCUAUGACACCACAC | 858 |
| LPA-568 | UCAUCUAUGACACCACACUAGCATA | 59 | UAUGCUAGUGUGGUGUCAUAGAUGACC | 459 | UCAUCUAUGACACCACACU | 859 |
| LPA-569 | CAUCUAUGACACCACACUCACAUAG | 60 | CUAUGUGAGUGUGGUGUCAUAGAUGAC | 460 | CAUCUAUGACACCACACUC | 860 |
| LPA-1208 | GCACAUACUCCACCACUGUAACUGG | 61 | CCAGUUACAGUGGUGGAGUAUGUGCCU | 461 | GCACAUACUCCACCACUGU | 861 |
| LPA-2715 | AGCCCCUUAUUGUUAUACGAGGGAT | 62 | AUCCCUCGUAUAACAAUAAGGGGCUGC | 462 | AGCCCCUUAUUGUUAUACG | 862 |
| LPA-2716 | GCCCCUUAUUGUUAUACGAAGGATC | 63 | GAUCCUUCGUAUAACAAUAAGGGGCUG | 463 | GCCCCUUAUUGUUAUACGA | 863 |
| LPA-2827 | CCAAGCCUAGAGGCUCCUUAUGAAC | 64 | GUUCAUAAGGAGCCUCUAGGCUUGGAA | 464 | CCAAGCCUAGAGGCUCCUU | 864 |
| LPA-2837 | AGGCUCCUUCUGAACAAGCACCAAC | 65 | GUUGGUGCUUGUUCAGAAGGAGCCUCU | 465 | AGGCUCCUUCUGAACAAGC | 865 |
| LPA-2900 | AUGGACAGAGUUAUCAAGGAACATA | 66 | UAUGUUCCUUGAUAACUCUGUCCAUUU | 466 | AUGGACAGAGUUAUCAAGG | 866 |
| LPA-2901 | UGGACAGAGUUAUCAAGGCACAUAC | 67 | GUAUGUGCCUUGAUAACUCUGUCCAUU | 467 | UGGACAGAGUUAUCAAGGC | 867 |
| LPA-2902 | GGACAGAGUUAUCAAGGCAAAUACT | 68 | AGUAUUUGCCUUGAUAACUCUGUCCAU | 468 | GGACAGAGUUAUCAAGGCA | 868 |
| LPA-2903 | GACAGAGUUAUCAAGGCACAUACTT | 69 | AAGUAUGUGCCUUGAUAACUCUGUCCA | 469 | GACAGAGUUAUCAAGGCAC | 869 |
| LPA-2904 | ACAGAGUUAUCAAGGCACAAACUTC | 70 | GAAGUUUGUGCCUUGAUAACUCUGUCC | 470 | ACAGAGUUAUCAAGGCACA | 870 |
| LPA-2905 | CAGAGUUAUCAAGGCACAUACUUCA | 71 | UGAAGUAUGUGCCUUGAUAACUCUGUC | 471 | CAGAGUUAUCAAGGCACAU | 871 |
| LPA-3004 | UACCCAAAUGCUGGCUUGAACAAGA | 72 | UCUUGUUCAAGCCAGCAUUUGGGUAGU | 472 | UACCCAAAUGCUGGCUUGA | 872 |
| LPA-3007 | CCAAAUGCUGGCUUGAUCAAGAACT | 73 | AGUUCUUGAUCAAGCCAGCAUUUGGGU | 473 | CCAAAUGCUGGCUUGAUCA | 873 |
| LPA-3023 | UCAAGAACUACUGCCGAAAACCAGA | 74 | UCUGGUUUUCGGCAGUAGUUCUUGAUC | 474 | UCAAGAACUACUGCCGAAA | 874 |
| LPA-3024 | CAAGAACUACUGCCGAAAUACAGAT | 75 | AUCUGUAUUUCGGCAGUAGUUCUUGAU | 475 | CAAGAACUACUGCCGAAAU | 875 |
| LPA-3025 | AAGAACUACUGCCGAAAUCAAGATC | 76 | GAUCUUGAUUUCGGCAGUAGUUCUUGA | 476 | AAGAACUACUGCCGAAAUC | 876 |
| LPA-3027 | GAACUACUGCCGAAAUCCAAAUCCT | 77 | AGGAUUUGGAUUUCGGCAGUAGUUCUU | 477 | GAACUACUGCCGAAAUCCA | 877 |
| LPA-3030 | CUACUGCCGAAAUCCAGAUACUGTG | 78 | CACAGUAUCUGGAUUUCGGCAGUAGUU | 478 | CUACUGCCGAAAUCCAGAU | 878 |

TABLE 2-continued

DsiRNAs Targeting Human LPA mRNA and Controls Evaluated in Cells

| | Passenger (Sense) | SEQ ID NO: | Guide (Antisense) | SEQ ID NO: | Target Sequence | SEQ ID NO: |
|---|---|---|---|---|---|---|
| LPA-3051 | UGUGGCAGCCCCUUGGUGUAAUACA | 79 | UGUAUUACACCAAGGGCUGCCACAGG | 479 | UGUGGCAGCCCCUUGGUGU | 879 |
| LPA-3052 | GUGGCAGCCCCUUGGUGUUAUACAA | 80 | UUGUAUAACACCAAGGGGCUGCCACAG | 480 | GUGGCAGCCCCUUGGUGUU | 880 |
| LPA-3053 | UGGCAGCCCCUUGGUGUUAAACAAC | 81 | GUUGUUUAACACCAAGGGGCUGCCACA | 481 | UGGCAGCCCCUUGGUGUUA | 881 |
| LPA-3054 | GGCAGCCCCUUGGUGUUAUACAACA | 82 | UGUUGUAUAACACCAAGGGGCUGCCAC | 482 | GGCAGCCCCUUGGUGUUAU | 882 |
| LPA-3055 | GCAGCCCCUUGGUGUUAUAAAACAG | 83 | CUGUUUUAUAACACCAAGGGGCUGCCA | 483 | GCAGCCCCUUGGUGUUAUA | 883 |
| LPA-3056 | CAGCCCCUUGGUGUUAUACAACAGA | 84 | UCUGUUGUAUAACACCAAGGGGCUGCC | 484 | CAGCCCCUUGGUGUUAUAC | 884 |
| LPA-3057 | AGCCCCUUGGUGUUAUACAACAGAT | 85 | AUCUGUUGUAUAACACCAAGGGGCUGC | 485 | AGCCCCUUGGUGUUAUACA | 885 |
| LPA-3058 | GCCCCUUGGUGUUAUACAAAAGATC | 86 | GAUCUUUUGUAUAACACCAAGGGGCUG | 486 | GCCCCUUGGUGUUAUACAA | 886 |
| LPA-3059 | CCCCUUGGUGUUAUACAACAGAUCC | 87 | GGAUCUGUUGUAUAACACCAAGGGGCU | 487 | CCCCUUGGUGUUAUACAAC | 887 |
| LPA-3092 | GGUGGGAGUACUGCAACCUAACACG | 88 | CGUGUUAGGUUGCAGUACUCCCACCUG | 488 | GGUGGGAGUACUGCAACCU | 888 |
| LPA-3093 | GUGGGAGUACUGCAACCUGACACGA | 89 | UCGUGUCAGGUUGCAGUACUCCCACCU | 489 | GUGGGAGUACUGCAACCUG | 889 |
| LPA-3096 | GGAGUACUGCAACCUGACAAGAUGC | 90 | GCAUCUUGUCAGGUUGCAGUACUCCCA | 490 | GGAGUACUGCAACCUGACA | 890 |
| LPA-3097 | GAGUACUGCAACCUGACACAAUGCT | 91 | AGCAUUGUGUCAGGUUGCAGUACUCCC | 491 | GAGUACUGCAACCUGACAC | 891 |
| LPA-3099 | GUACUGCAACCUGACACGAAGCUCA | 92 | UGAGCUUCGUGUCAGGUUGCAGUACUC | 492 | GUACUGCAACCUGACACGA | 892 |
| LPA-3100 | UACUGCAACCUGACACGAUACUCAG | 93 | CUGAGUAUCGUGUCAGGUUGCAGUACU | 493 | UACUGCAACCUGACACGAU | 893 |
| LPA-3101 | ACUGCAACCUGACACGAUGAUCAGA | 94 | UCUGAUCAUCGUGUCAGGUUGCAGUAC | 494 | ACUGCAACCUGACACGAUG | 894 |
| LPA-3102 | CUGCAACCUGACACGAUGCACAGAT | 95 | AUCUGUGCAUCGUGUCAGGUUGCAGUA | 495 | CUGCAACCUGACACGAUGC | 895 |
| LPA-3103 | UGCAACCUGACACGAUGCUAAGATG | 96 | CAUCUUAGCAUCGUGUCAGGUUGCAGU | 496 | UGCAACCUGACACGAUGCU | 896 |
| LPA-3105 | CAACCUGACACGAUGCUCAAAUGCA | 97 | UGCAUUUGAGCAUCGUGUCAGGUUGCA | 497 | CAACCUGACACGAUGCUCA | 897 |
| LPA-3107 | ACCUGACACGAUGCUCAGAAGCAGA | 98 | UCUGCUUCUGAGCAUCGUGUCAGGUUG | 498 | ACCUGACACGAUGCUCAGA | 898 |
| LPA-3108 | CCUGACACGAUGCUCAGAUACAGAA | 99 | UUCUGUAUCUGAGCAUCGUGUCAGGUU | 499 | CCUGACACGAUGCUCAGAU | 899 |
| LPA-3109 | CUGACACGAUGCUCAGAUGAAGAAT | 100 | AUUCUUCAUCUGAGCAUCGUGUCAGGU | 500 | CUGACACGAUGCUCAGAUG | 900 |
| LPA-3110 | UGACACGAUGCUCAGAUGCAGAATG | 101 | CAUUCUGCAUCUGAGCAUCGUGUCAGG | 501 | UGACACGAUGCUCAGAUGC | 901 |
| LPA-3111 | GACACGAUGCUCAGAUGCAAAAUGG | 102 | CCAUUUUGCAUCUGAGCAUCGUGUCAG | 502 | GACACGAUGCUCAGAUGCA | 902 |

TABLE 2-continued

DsiRNAs Targeting Human LPA mRNA and Controls Evaluated in Cells

| | Passenger (Sense) | SEQ ID NO: | Guide (Antisense) | SEQ ID NO: | Target Sequence | SEQ ID NO: |
|---|---|---|---|---|---|---|
| LPA-3112 | ACACGAUGCUCAGAUGCAGAAUGGA | 103 | UCCAUUCUGCAUCUGAGCAUCGUGUCA | 503 | ACACGAUGCUCAGAUGCAG | 903 |
| LPA-3113 | CACGAUGCUCAGAUGCAGAAUGGAC | 104 | GUCCAUUCUGCAUCUGAGCAUCGUGUC | 504 | CACGAUGCUCAGAUGCAGA | 904 |
| LPA-3229 | UGCUACUACCAUUAUGGACAGAGTT | 105 | AACUCUGUCCAUAAUGGUAGUAGCAGU | 505 | UGCUACUACCAUUAUGGAC | 905 |
| LPA-3230 | GCUACUACCAUUAUGGACAAAGUTA | 106 | UAACUUUGUCCAUAAUGGUAGUAGCAG | 506 | GCUACUACCAUUAUGGACA | 906 |
| LPA-3231 | CUACUACCAUUAUGGACAGAGUUAC | 107 | GUAACUCUGUCCAUAAUGGUAGUAGCA | 507 | CUACUACCAUUAUGGACAG | 907 |
| LPA-3232 | UACUACCAUUAUGGACAGAAUUACC | 108 | GGUAAUUCUGUCCAUAAUGGUAGUAGC | 508 | UACUACCAUUAUGGACAGA | 908 |
| LPA-3233 | ACUACCAUUAUGGACAGAGAUACCG | 109 | CGGUAUCUCUGUCCAUAAUGGUAGUAG | 509 | ACUACCAUUAUGGACAGAG | 909 |
| LPA-3234 | CUACCAUUAUGGACAGAGUAACCGA | 110 | UCGGUUACUCUGUCCAUAAUGGUAGUA | 510 | CUACCAUUAUGGACAGAGU | 910 |
| LPA-3235 | UACCAUUAUGGACAGAGUUACCGAG | 111 | CUCGGUAACUCUGUCCAUAAUGGUAGU | 511 | UACCAUUAUGGACAGAGUU | 911 |
| LPA-3236 | ACCAUUAUGGACAGAGUUAACGAGG | 112 | CCUCGUUAACUCUGUCCAUAAUGGUAG | 512 | ACCAUUAUGGACAGAGUUA | 912 |
| LPA-3257 | GAGGCACAUACUCCACCACAGUCAC | 113 | GUGACUGUGGUGGAGUAUGUGCCUCGG | 513 | GAGGCACAUACUCCACCAC | 913 |
| LPA-3267 | CUCCACCACUGUCACAGGAAGAACT | 114 | AGUUCUUCCUGUGACAGUGGUGGAGUA | 514 | CUCCACCACUGUCACAGGA | 914 |
| LPA-3280 | ACAGGAAGAACUUGCCAAGAUUGGT | 115 | ACCAAUCUUGGCAAGUUCUUCCUGUGA | 515 | ACAGGAAGAACUUGCCAAG | 915 |
| LPA-3281 | CAGGAAGAACUUGCCAAGCAUGGTC | 116 | GACCAUGCUUGGCAAGUUCUUCCUGUG | 516 | CAGGAAGAACUUGCCAAGC | 916 |
| LPA-3282 | AGGAAGAACUUGCCAAGCUAGGUCA | 117 | UGACCUAGCUUGGCAAGUUCUUCCUGU | 517 | AGGAAGAACUUGCCAAGCU | 917 |
| LPA-3283 | GGAAGAACUUGCCAAGCUUAGUCAT | 118 | AUGACUAAGCUUGGCAAGUUCUUCCUG | 518 | GGAAGAACUUGCCAAGCUU | 918 |
| LPA-3284 | GAAGAACUUGCCAAGCUUGAUCATC | 119 | GAUGAUCAAGCUUGGCAAGUUCUUCCU | 519 | GAAGAACUUGCCAAGCUUG | 919 |
| LPA-3285 | AAGAACUUGCCAAGCUUGGACAUCT | 120 | AGAUGUCCAAGCUUGGCAAGUUCUUCC | 520 | AAGAACUUGCCAAGCUUGG | 920 |
| LPA-3286 | AGAACUUGCCAAGCUUGGUAAUCTA | 121 | UAGAUUACCAAGCUUGGCAAGUUCUUC | 521 | AGAACUUGCCAAGCUUGGU | 921 |
| LPA-3287 | GAACUUGCCAAGCUUGGUCAUCUAT | 122 | AUAGAUGACCAAGCUUGGCAAGUUCUU | 522 | GAACUUGCCAAGCUUGGUC | 922 |
| LPA-3288 | AACUUGCCAAGCUUGGUCAACUATG | 123 | CAUAGUUGACCAAGCUUGGCAAGUUCU | 523 | AACUUGCCAAGCUUGGUCA | 923 |
| LPA-3289 | ACUUGCCAAGCUUGGUCAUAUAUGA | 124 | UCAUAUAUGACCAAGCUUGGCAAGUUC | 524 | ACUUGCCAAGCUUGGUCAU | 924 |
| LPA-3290 | CUUGCCAAGCUUGGUCAUCAAUGAC | 125 | GUCAUUGAUGACCAAGCUUGGCAAGUU | 525 | CUUGCCAAGCUUGGUCAUC | 925 |
| LPA-3291 | UUGCCAAGCUUGGUCAUCUAUGACA | 126 | UGUCAUAGAUGACCAAGCUUGGCAAGU | 526 | UUGCCAAGCUUGGUCAUCU | 926 |

TABLE 2-continued

DsiRNAs Targeting Human LPA mRNA and Controls Evaluated in Cells

| | Passenger (Sense) | SEQ ID NO: | Guide (Antisense) | SEQ ID NO: | Target Sequence | SEQ ID NO: |
|---|---|---|---|---|---|---|
| LPA-3292 | UGCCAAGCUUGGUCAUCUAAGACAC | 127 | GUGUCUUAGAUGACCAAGCUUGGCAAG | 527 | UGCCAAGCUUGGUCAUCUA | 927 |
| LPA-3298 | GCUUGGUCAUCUAUGACACAACACC | 128 | GGUGUUGUGUCAUAGAUGACCAAGCUU | 528 | GCUUGGUCAUCUAUGACAC | 928 |
| LPA-3300 | UUGGUCAUCUAUGACACCAAACCAG | 129 | CUGGUUUGGUGUCAUAGAUGACCAAGC | 529 | UUGGUCAUCUAUGACACCA | 929 |
| LPA-3301 | UGGUCAUCUAUGACACCACACCAGC | 130 | GCUGGUGUGGUGUCAUAGAUGACCAAG | 530 | UGGUCAUCUAUGACACCAC | 930 |
| LPA-3303 | GUCAUCUAUGACACCACACAAGCAT | 131 | AUGCUUGUGUGGUGUCAUAGAUGACCA | 531 | GUCAUCUAUGACACCACAC | 931 |
| LPA-3305 | CAUCUAUGACACCACACCAACAUAG | 132 | CUAUGUUGGUGUGGUGUCAUAGAUGAC | 532 | CAUCUAUGACACCACACCA | 932 |
| LPA-3306 | AUCUAUGACACCACACCAGAAUAGT | 133 | ACUAUUCUGGUGUGGUGUCAUAGAUGA | 533 | AUCUAUGACACCACACCAG | 933 |
| LPA-3308 | CUAUGACACCACACCAGCAAAGUCG | 134 | CGACUUUGCUGGUGUGGUGUCAUAGAU | 534 | CUAUGACACCACACCAGCA | 934 |
| LPA-3329 | GUCGGACCCCAGAAAACUAACCAAA | 135 | UUUGGUUAGUUUUCUGGGGUCCGACUA | 535 | GUCGGACCCCAGAAAACUA | 935 |
| LPA-3330 | UCGGACCCCAGAAAACUACACAAAT | 136 | AUUUGUGUAGUUUUCUGGGGUCCGACU | 536 | UCGGACCCCAGAAAACUAC | 936 |
| LPA-3340 | GAAAACUACCCAAAUGCUGACCUGA | 137 | UCAGGUCAGCAUUUGGGUAGUUUUCUG | 537 | GAAAACUACCCAAAUGCUG | 937 |
| LPA-3391 | GCUGAGAUUCGCCCUUGGUAUUACA | 138 | UGUAAUACCAAGGGCGAAUCUCAGCAU | 538 | GCUGAGAUUCGCCCUUGGU | 938 |
| LPA-3392 | CUGAGAUUCGCCCUUGGUGAUACAC | 139 | GUGUAUCACCAAGGGCGAAUCUCAGCA | 539 | CUGAGAUUCGCCCUUGGUG | 939 |
| LPA-3394 | GAGAUUCGCCCUUGGUGUUACACCA | 140 | UGGUGUAACACCAAGGGCGAAUCUCAG | 540 | GAGAUUCGCCCUUGGUGUU | 940 |
| LPA-3395 | AGAUUCGCCCUUGGUGUUAAACCAT | 141 | AUGGUUUAACACCAAGGGCGAAUCUCA | 541 | AGAUUCGCCCUUGGUGUUA | 941 |
| LPA-3398 | UUCGCCCUUGGUGUUACACAAUGGA | 142 | UCCAUUGUGUAACACCAAGGGCGAAUC | 542 | UUCGCCCUUGGUGUUACAC | 942 |
| LPA-3404 | CUUGGUGUUACACCAUGGAACCCAG | 143 | CUGGGUUCCAUGGUGUAACACCAAGGG | 543 | CUUGGUGUUACACCAUGGA | 943 |
| LPA-3405 | UUGGUGUUACACCAUGGAUACCAGT | 144 | ACUGGUAUCCAUGGUGUAACACCAAGG | 544 | UUGGUGUUACACCAUGGAU | 944 |
| LPA-3406 | UGGUGUUACACCAUGGAUCACAGTG | 145 | CACUGUGAUCCAUGGUGUAACACCAAG | 545 | UGGUGUUACACCAUGGAUC | 945 |
| LPA-3407 | GGUGUUACACCAUGGAUCCAAGUGT | 146 | ACACUUGGAUCCAUGGUGUAACACCAA | 546 | GGUGUUACACCAUGGAUCC | 946 |
| LPA-3409 | UGUUACACCAUGGAUCCCAAUGUCA | 147 | UGACAUUGGGAUCCAUGGUGUAACACC | 547 | UGUUACACCAUGGAUCCCA | 947 |
| LPA-3472 | GAAUCAAGUGUCCUUGCAAAUCUCA | 148 | UGAGAUUUGCAAGGACACUUGAUUCUG | 548 | GAAUCAAGUGUCCUUGCAA | 948 |
| LPA-3473 | AAUCAAGUGUCCUUGCAACACUCAC | 149 | GUGAGUGUUGCAAGGACACUUGAUUCU | 549 | AAUCAAGUGUCCUUGCAAC | 949 |
| LPA-3474 | AUCAAGUGUCCUUGCAACUAUCACG | 150 | CGUGAUAGUUGCAAGGACACUUGAUUC | 550 | AUCAAGUGUCCUUGCAACU | 950 |

TABLE 2-continued

DsiRNAs Targeting Human LPA mRNA and Controls Evaluated in Cells

| | Passenger (Sense) | SEQ ID NO: | Guide (Antisense) | SEQ ID NO: | Target Sequence | SEQ ID NO: |
|---|---|---|---|---|---|---|
| LPA-3584 | AUGGACAGAGUUAUCGAGGAUCATT | 151 | AAUGAUCCUCGAUAACUCUGUCCAUCA | 551 | AUGGACAGAGUUAUCGAGG | 951 |
| LPA-3585 | UGGACAGAGUUAUCGAGGCACAUTC | 152 | GAAUGUGCCUCGAUAACUCUGUCCAUC | 552 | UGGACAGAGUUAUCGAGGC | 952 |
| LPA-3655 | ACACCACACUGGCAUCAGAAGACAA | 153 | UUGUCUUCUGAUGCCAGUGUGGUGUCA | 553 | ACACCACACUGGCAUCAGA | 953 |
| LPA-3747 | UUGGUGUUAUACCAUGGAUACCAAT | 154 | AUUGGUAUCCAUGGUAUAACACCAAGG | 554 | UUGGUGUUAUACCAUGGAU | 954 |
| LPA-3748 | UGGUGUUAUACCAUGGAUCACAATG | 155 | CAUUGUGAUCCAUGGUAUAACACCAAG | 555 | UGGUGUUAUACCAUGGAUC | 955 |
| LPA-3749 | GGUGUUAUACCAUGGAUCCAAAUGT | 156 | ACAUUUGGAUCCAUGGUAUAACACCAA | 556 | GGUGUUAUACCAUGGAUCC | 956 |
| LPA-3750 | GUGUUAUACCAUGGAUCCCAAUGTC | 157 | GACAUUGGGAUCCAUGGUAUAACACCA | 557 | GUGUUAUACCAUGGAUCCC | 957 |
| LPA-3773 | UCAGAUGGGAGUACUGCAAACUGAC | 158 | GUCAGUUUGCAGUACUCCCAUCUGACA | 558 | UCAGAUGGGAGUACUGCAA | 958 |
| LPA-3776 | GAUGGGAGUACUGCAACCUAACACA | 159 | UGUGUUAGGUUGCAGUACUCCCAUCUG | 559 | GAUGGGAGUACUGCAACCU | 959 |
| LPA-3777 | AUGGGAGUACUGCAACCUGACACAA | 160 | UUGUGUCAGGUUGCAGUACUCCCAUCU | 560 | AUGGGAGUACUGCAACCUG | 960 |
| LPA-3778 | UGGGAGUACUGCAACCUGAAACAAT | 161 | AUUGUUUCAGGUUGCAGUACUCCCAUC | 561 | UGGGAGUACUGCAACCUGA | 961 |
| LPA-3779 | GGGAGUACUGCAACCUGACACAATG | 162 | CAUUGUGUCAGGUUGCAGUACUCCCAU | 562 | GGGAGUACUGCAACCUGAC | 962 |
| LPA-3840 | GGCUGUUUCUGAACAAGCAACAACG | 163 | CGUUGUUGCUUGUUCAGAAACAGCCGU | 563 | GGCUGUUUCUGAACAAGCA | 963 |
| LPA-3844 | GUUUCUGAACAAGCACCAAAGGAGC | 164 | GCUCCUUUGGUGCUUGUUCAGAAACAG | 564 | GUUUCUGAACAAGCACCAA | 964 |
| LPA-3927 | CUCCACCACUGUUACAGGAAGGACA | 165 | UGUCCUUCCUGUAACAGUGGUGGAGAA | 565 | CUCCACCACUGUUACAGGA | 965 |
| LPA-3928 | UCCACCACUGUUACAGGAAAGACAT | 166 | AUGUCUUUCCUGUAACAGUGGUGGAGA | 566 | UCCACCACUGUUACAGGAA | 966 |
| LPA-3929 | CCACCACUGUUACAGGAAGAACATG | 167 | CAUGUUCUUCCUGUAACAGUGGUGGAG | 567 | CCACCACUGUUACAGGAAG | 967 |
| LPA-3972 | GACACCACACUGGCAUCAGAGAACC | 168 | GGUUCUCUGAUGCCAGUGUGGUGUCAU | 568 | GACACCACACUGGCAUCAG | 968 |
| LPA-3973 | ACACCACACUGGCAUCAGAAAACCA | 169 | UGGUUUUCUGAUGCCAGUGUGGUGUCA | 569 | ACACCACACUGGCAUCAGA | 969 |
| LPA-3999 | AGAAUACUACCCAAAUGGUAGCCTG | 170 | CAGGCUACCAUUUGGGUAGUAUUCUGU | 570 | AGAAUACUACCCAAAUGGU | 970 |
| LPA-4000 | GAAUACUACCCAAAUGGUGACCUGA | 171 | UCAGGUCACCAUUUGGGUAGUAUUCUG | 571 | GAAUACUACCCAAAUGGUG | 971 |
| LPA-4001 | AAUACUACCCAAAUGGUGGACUGAC | 172 | GUCAGUCCACCAUUUGGGUAGUAUUCU | 572 | AAUACUACCCAAAUGGUGG | 972 |
| LPA-4185 | UCCUUCUGAAGAAGCACCAACUGAA | 173 | UUCAGUUGGUGCUUCUUCAGAAGGAAG | 573 | UCCUUCUGAAGAAGCACCA | 973 |
| LPA-4186 | CCUUCUGAAGAAGCACCAAAUGAAA | 174 | UUUCAUUUGGUGCUUCUUCAGAAGGAA | 574 | CCUUCUGAAGAAGCACCAA | 974 |

TABLE 2-continued

DsiRNAs Targeting Human LPA mRNA and Controls Evaluated in Cells

| | Passenger (Sense) | SEQ ID NO: | Guide (Antisense) | SEQ ID NO: | Target Sequence | SEQ ID NO: |
|---|---|---|---|---|---|---|
| LPA-4187 | CUUCUGAAGAAGCACCAACAGAAAA | 175 | UUUUCUGUUGGUGCUUCUUCAGAAGGA | 575 | CUUCUGAAGAAGCACCAAC | 975 |
| LPA-4188 | UUCUGAAGAAGCACCAACUAAAAAC | 176 | GUUUUUAGUUGGUGCUUCUUCAGAAGG | 576 | UUCUGAAGAAGCACCAACU | 976 |
| LPA-4189 | UCUGAAGAAGCACCAACUGAAAACA | 177 | UGUUUUCAGUUGGUGCUUCUUCAGAAG | 577 | UCUGAAGAAGCACCAACUG | 977 |
| LPA-4190 | CUGAAGAAGCACCAACUGAAAACAG | 178 | CUGUUUUCAGUUGGUGCUUCUUCAGAA | 578 | CUGAAGAAGCACCAACUGA | 978 |
| LPA-4191 | UGAAGAAGCACCAACUGAAAACAGC | 179 | GCUGUUUUCAGUUGGUGCUUCUUCAGA | 579 | UGAAGAAGCACCAACUGAA | 979 |
| LPA-4192 | GAAGAAGCACCAACUGAAAACAGCA | 180 | UGCUGUUUUCAGUUGGUGCUUCUUCAG | 580 | GAAGAAGCACCAACUGAAA | 980 |
| LPA-4193 | AAGAAGCACCAACUGAAAAAAGCAC | 181 | GUGCUUUUUUCAGUUGGUGCUUCUUCA | 581 | AAGAAGCACCAACUGAAAA | 981 |
| LPA-4194 | AGAAGCACCAACUGAAAACAGCACT | 182 | AGUGCUGUUUUCAGUUGGUGCUUCUUC | 582 | AGAAGCACCAACUGAAAAC | 982 |
| LPA-4195 | GAAGCACCAACUGAAAACAACACTG | 183 | CAGUGUUGUUUUCAGUUGGUGCUUCUU | 583 | GAAGCACCAACUGAAAACA | 983 |
| LPA-4196 | AAGCACCAACUGAAAACAGAACUGG | 184 | CCAGUUCUGUUUUCAGUUGGUGCUUCU | 584 | AAGCACCAACUGAAAACAG | 984 |
| LPA-4239 | AGGUGAUGGACAGAGUUAUAGAGGC | 185 | GCCUCUAUAACUCUGUCCAUCACCUCG | 585 | AGGUGAUGGACAGAGUUAU | 985 |
| LPA-4269 | CUCCACCACUAUCACAGGAAGAACA | 186 | UGUUCUUCCUGUGAUAGUGGUGGAGAG | 586 | CUCCACCACUAUCACAGGA | 986 |
| LPA-4270 | UCCACCACUAUCACAGGAAAAACAT | 187 | AUGUUUUUCCUGUGAUAGUGGUGGAGA | 587 | UCCACCACUAUCACAGGAA | 987 |
| LPA-4271 | CCACCACUAUCACAGGAAGAACATG | 188 | CAUGUUCUUCCUGUGAUAGUGGUGGAG | 588 | CCACCACUAUCACAGGAAG | 988 |
| LPA-4272 | CACCACUAUCACAGGAAGAACAUGT | 189 | ACAUGUUCUUCCUGUGAUAGUGGUGGA | 589 | CACCACUAUCACAGGAAGA | 989 |
| LPA-4273 | ACCACUAUCACAGGAAGAAAAUGTC | 190 | GACAUUUUCUUCCUGUGAUAGUGGUGG | 590 | ACCACUAUCACAGGAAGAA | 990 |
| LPA-4274 | CCACUAUCACAGGAAGAACAUGUCA | 191 | UGACAUGUUCUUCCUGUGAUAGUGGUG | 591 | CCACUAUCACAGGAAGAAC | 991 |
| LPA-4275 | CACUAUCACAGGAAGAACAAGUCAG | 192 | CUGACUUGUUCUUCCUGUGAUAGUGGU | 592 | CACUAUCACAGGAAGAACA | 992 |
| LPA-4276 | ACUAUCACAGGAAGAACAUAUCAGT | 193 | ACUGAUAUGUUCUUCCUGUGAUAGUGG | 593 | ACUAUCACAGGAAGAACAU | 993 |
| LPA-4277 | CUAUCACAGGAAGAACAUGACAGTC | 194 | GACUGUCAUGUUCUUCCUGUGAUAGUG | 594 | CUAUCACAGGAAGAACAUG | 994 |
| LPA-4278 | UAUCACAGGAAGAACAUGUAAGUCT | 195 | AGACUUACAUGUUCUUCCUGUGAUAGU | 595 | UAUCACAGGAAGAACAUGU | 995 |
| LPA-4279 | AUCACAGGAAGAACAUGUCAGUCTT | 196 | AAGACUGACAUGUUCUUCCUGUGAUAG | 596 | AUCACAGGAAGAACAUGUC | 996 |
| LPA-4280 | UCACAGGAAGAACAUGUCAAUCUTG | 197 | CAAGAUUGACAUGUUCUUCCUGUGAUA | 597 | UCACAGGAAGAACAUGUCA | 997 |
| LPA-4281 | CACAGGAAGAACAUGUCAGACUUGG | 198 | CCAAGUCUGACAUGUUCUUCCUGUGAU | 598 | CACAGGAAGAACAUGUCAG | 998 |

TABLE 2-continued

DsiRNAs Targeting Human LPA mRNA and Controls Evaluated in Cells

| | Passenger (Sense) | SEQ ID NO: | Guide (Antisense) | SEQ ID NO: | Target Sequence | SEQ ID NO: |
|---|---|---|---|---|---|---|
| LPA-4282 | ACAGGAAGAACAUGUCAGUAUUGGT | 199 | ACCAAUACUGACAUGUUCUUCCUGUGA | 599 | ACAGGAAGAACAUGUCAGU | 999 |
| LPA-4285 | GGAAGAACAUGUCAGUCUUAGUCGT | 200 | ACGACUAAGACUGACAUGUUCUUCCUG | 600 | GGAAGAACAUGUCAGUCUU | 1000 |
| LPA-4286 | GAAGAACAUGUCAGUCUUGAUCGTC | 201 | GACGAUCAAGACUGACAUGUUCUUCCU | 601 | GAAGAACAUGUCAGUCUUG | 1001 |
| LPA-4287 | AAGAACAUGUCAGUCUUGGACGUCT | 202 | AGACGUCCAAGACUGACAUGUUCUUCC | 602 | AAGAACAUGUCAGUCUUGG | 1002 |
| LPA-4288 | AGAACAUGUCAGUCUUGGUAGUCTA | 203 | UAGACUACCAAGACUGACAUGUUCUUC | 603 | AGAACAUGUCAGUCUUGGU | 1003 |
| LPA-4325 | GGCAUCGGAGGAUCCCAUUAUACTA | 204 | UAGUAUAAUGGGAUCCUCCGAUGCCAA | 604 | GGCAUCGGAGGAUCCCAUU | 1004 |
| LPA-4346 | ACUAUCCAAAUGCUGGCCUAACCAG | 205 | CUGGUUAGGCCAGCAUUUGGAUAGUAU | 605 | ACUAUCCAAAUGCUGGCCU | 1005 |
| LPA-4517 | GCACAGAGGCUCCUUCUGAACAAGC | 206 | GCUUGUUCAGAAGGAGCCUCUGUGCUU | 606 | GCACAGAGGCUCCUUCUGA | 1006 |
| LPA-4527 | UCCUUCUGAACAAGCACCAACUGAG | 207 | CUCAGUUGGUGCUUGUUCAGAAGGAGC | 607 | UCCUUCUGAACAAGCACCA | 1007 |
| LPA-4528 | CCUUCUGAACAAGCACCACAUGAGA | 208 | UCUCAUGUGGUGCUUGUUCAGAAGGAG | 608 | CCUUCUGAACAAGCACCAC | 1008 |
| LPA-4529 | CUUCUGAACAAGCACCACCAGAGAA | 209 | UUCUCUGGUGGUGCUUGUUCAGAAGGA | 609 | CUUCUGAACAAGCACCACC | 1009 |
| LPA-4530 | UUCUGAACAAGCACCACCUAAGAAA | 210 | UUUCUUAGGUGGUGCUUGUUCAGAAGG | 610 | UUCUGAACAAGCACCACCU | 1010 |
| LPA-4531 | UCUGAACAAGCACCACCUGAGAAAA | 211 | UUUUCUCAGGUGGUGCUUGUUCAGAAG | 611 | UCUGAACAAGCACCACCUG | 1011 |
| LPA-4532 | CUGAACAAGCACCACCUGAAAAAAG | 212 | CUUUUUUCAGGUGGUGCUUGUUCAGAA | 612 | CUGAACAAGCACCACCUGA | 1012 |
| LPA-4533 | UGAACAAGCACCACCUGAGAAAAGC | 213 | GCUUUUCUCAGGUGGUGCUUGUUCAGA | 613 | UGAACAAGCACCACCUGAG | 1013 |
| LPA-4531 | GAACAAGCACCACCUGAGAAAAGCC | 214 | GGCUUUUCUCAGGUGGUGCUUGUUCAG | 614 | GAACAAGCACCACCUGAGA | 1014 |
| LPA-4535 | AACAAGCACCACCUGAGAAAAGCCC | 215 | GGGCUUUUCUCAGGUGGUGCUUGUUCA | 615 | AACAAGCACCACCUGAGAA | 1015 |
| LPA-4537 | CAAGCACCACCUGAGAAAAACCCTG | 216 | CAGGGUUUUUCUCAGGUGGUGCUUGUU | 616 | CAAGCACCACCUGAGAAAA | 1016 |
| LPA-4538 | AAGCACCACCUGAGAAAAGACCUGT | 217 | ACAGGUCUUUUCUCAGGUGGUGCUUGU | 617 | AAGCACCACCUGAGAAAAG | 1017 |
| LPA-4539 | AGCACCACCUGAGAAAAGCACUGTG | 218 | CACAGUGCUUUUCUCAGGUGGUGCUUG | 618 | AGCACCACCUGAGAAAAGC | 1018 |
| LPA-4547 | CUGAGAAAAGCCCUGUGGUACAGGA | 219 | UCCUGUACCACAGGGCUUUUCUCAGGU | 619 | CUGAGAAAAGCCCUGUGGU | 1019 |
| LPA-4556 | GCCCUGUGGUCCAGGAUUGAUACCA | 220 | UGGUAUCAAUCCUGGACCACAGGGCUU | 620 | GCCCUGUGGUCCAGGAUUG | 1020 |
| LPA-4559 | CUGUGGUCCAGGAUUGCUAACAUGG | 221 | CCAUGUUAGCAAUCCUGGACCACAGGG | 621 | CUGUGGUCCAGGAUUGCUA | 1021 |
| LPA-4611 | CUCCACCACUGUCACAGGAAGGACC | 222 | GGUCCUUCCUGUGACAGUGGUGGAGGA | 622 | CUCCACCACUGUCACAGGA | 1022 |

TABLE 2-continued

DsiRNAs Targeting Human LPA mRNA and Controls Evaluated in Cells

| | Passenger (Sense) | SEQ ID NO: | Guide (Antisense) | SEQ ID NO: | Target Sequence | SEQ ID NO: |
|---|---|---|---|---|---|---|
| LPA-4612 | UCCACCACUGUCACAGGAAAGACCT | 223 | AGGUCUUUCCUGUGACAGUGGUGGAGG | 623 | UCCACCACUGUCACAGGAA | 1023 |
| LPA-4642 | UCUUGGUCAUCUAUGAUACAACACT | 224 | AGUGUUGUAUCAUAGAUGACCAAGAUU | 624 | UCUUGGUCAUCUAUGAUAC | 1024 |
| LPA-4643 | CUUGGUCAUCUAUGAUACCACACTG | 225 | CAGUGUGGUAUCAUAGAUGACCAAGAU | 625 | CUUGGUCAUCUAUGAUACC | 1025 |
| LPA-4644 | UUGGUCAUCUAUGAUACCAAACUGG | 226 | CCAGUUUGGUAUCAUAGAUGACCAAGA | 626 | UUGGUCAUCUAUGAUACCA | 1026 |
| LPA-4645 | UGGUCAUCUAUGAUACCACACUGGC | 227 | GCCAGUGUGGUAUCAUAGAUGACCAAG | 627 | UGGUCAUCUAUGAUACCAC | 1027 |
| LPA-4646 | GGUCAUCUAUGAUACCACAAUGGCA | 228 | UGCCAUUGUGGUAUCAUAGAUGACCAA | 628 | GGUCAUCUAUGAUACCACA | 1028 |
| LPA-4647 | GUCAUCUAUGAUACCACACAGGCAT | 229 | AUGCCUGUGUGGUAUCAUAGAUGACCA | 629 | GUCAUCUAUGAUACCACAC | 1029 |
| LPA-4648 | UCAUCUAUGAUACCACACUAGCATC | 230 | GAUGCUAGUGUGGUAUCAUAGAUGACC | 630 | UCAUCUAUGAUACCACACU | 1030 |
| LPA-4649 | CAUCUAUGAUACCACACUGACAUCA | 231 | UGAUGUCAGUGUGGUAUCAUAGAUGAC | 631 | CAUCUAUGAUACCACACUG | 1031 |
| LPA-4650 | AUCUAUGAUACCACACUGGAAUCAG | 232 | CUGAUUCCAGUGUGGUAUCAUAGAUGA | 632 | AUCUAUGAUACCACACUGG | 1032 |
| LPA-4651 | UCUAUGAUACCACACUGGCAUCAGA | 233 | UCUGAUGCCAGUGUGGUAUCAUAGAUG | 633 | UCUAUGAUACCACACUGGC | 1033 |
| LPA-4652 | CUAUGAUACCACACUGGCAACAGAG | 234 | CUCUGUUGCCAGUGUGGUAUCAUAGAU | 634 | CUAUGAUACCACACUGGCA | 1034 |
| LPA-4655 | UGAUACCACACUGGCAUCAAAGGAC | 235 | GUCCUUUGAUGCCAGUGUGGUAUCAUA | 635 | UGAUACCACACUGGCAUCA | 1035 |
| LPA-4657 | AUACCACACUGGCAUCAGAAGACCC | 236 | GGGUCUUCUGAUGCCAGUGUGGUAUCA | 636 | AUACCACACUGGCAUCAGA | 1036 |
| LPA-4673 | AGAGGACCCCAGAAAACUAACCAAA | 237 | UUUGGUUAGUUUUCUGGGGUCCUCUGA | 637 | AGAGGACCCCAGAAAACUA | 1037 |
| LPA-4674 | GAGGACCCCAGAAAACUACACAAAT | 238 | AUUUGUGUAGUUUUCUGGGGUCCUCUG | 638 | GAGGACCCCAGAAAACUAC | 1038 |
| LPA-4712 | AGAACUACUGCAGGAAUCCAGAUTC | 239 | GAAUCUGGAUUCCUGCAGUAGUUCUCG | 639 | AGAACUACUGCAGGAAUCC | 1039 |
| LPA-4715 | ACUACUGCAGGAAUCCAGAAUCUGG | 240 | CCAGAUUCUGGAUUCCUGCAGUAGUUC | 640 | ACUACUGCAGGAAUCCAGA | 1040 |
| LPA-4717 | UACUGCAGGAAUCCAGAUUAUGGGA | 241 | UCCCAUAAUCUGGAUUCCUGCAGUAGU | 641 | UACUGCAGGAAUCCAGAUU | 1041 |
| LPA-4718 | ACUGCAGGAAUCCAGAUUCAGGGAA | 242 | UUCCCUGAAUCUGGAUUCCUGCAGUAG | 642 | ACUGCAGGAAUCCAGAUUC | 1042 |
| LPA-4719 | CUGCAGGAAUCCAGAUUCUAGGAAA | 243 | UUUCCUAGAAUCUGGAUUCCUGCAGUA | 643 | CUGCAGGAAUCCAGAUUCU | 1043 |
| LPA-4720 | UGCAGGAAUCCAGAUUCUGAGAAAC | 244 | GUUUCUCAGAAUCUGGAUUCCUGCAGU | 644 | UGCAGGAAUCCAGAUUCUG | 1044 |
| LPA-4721 | GCAGGAAUCCAGAUUCUGGAAAACA | 245 | UGUUUUCCAGAAUCUGGAUUCCUGCAG | 645 | GCAGGAAUCCAGAUUCUGG | 1045 |
| LPA-4724 | GGAAUCCAGAUUCUGGGAAACAACC | 246 | GGUUGUUUCCCAGAAUCUGGAUUCCUG | 646 | GGAAUCCAGAUUCUGGGAA | 1046 |

TABLE 2-continued

DsiRNAs Targeting Human LPA mRNA and Controls Evaluated in Cells

| | Passenger (Sense) | SEQ ID NO: | Guide (Antisense) | SEQ ID NO: | Target Sequence | SEQ ID NO: |
|---|---|---|---|---|---|---|
| LPA-4738 | GGGAAACAACCCUGGUGUUACACAA | 247 | UUGUGUAACACCAGGGUUGUUUCCCAG | 647 | GGGAAACAACCCUGGUGUU | 1047 |
| LPA-4739 | GGAAACAACCCUGGUGUUAAACAAC | 248 | GUUGUUUAACACCAGGGUUGUUUCCCA | 648 | GGAAACAACCCUGGUGUUA | 1048 |
| LPA-4771 | UGUGUGAGGUGGGAGUACUACAATC | 249 | GAUUGUAGUACUCCCACCUCACACACG | 649 | UGUGUGAGGUGGGAGUACU | 1049 |
| LPA-4772 | GUGUGAGGUGGGAGUACUGAAAUCT | 250 | AGAUUUCAGUACUCCCACCUCACACAC | 650 | GUGUGAGGUGGGAGUACUG | 1050 |
| LPA-4774 | GUGAGGUGGGAGUACUGCAAUCUGA | 251 | UCAGAUUGCAGUACUCCCACCUCACAC | 651 | GUGAGGUGGGAGUACUGCA | 1051 |
| LPA-4775 | UGAGGUGGGAGUACUGCAAACUGAC | 252 | GUCAGUUUGCAGUACUCCCACCUCACA | 652 | UGAGGUGGGAGUACUGCAA | 1052 |
| LPA-4795 | CUGACACAAUGCUCAGAAAAAGAAT | 253 | AUUCUUUUUCUGAGCAUUGUGUCAGAU | 653 | CUGACACAAUGCUCAGAAA | 1053 |
| LPA-4796 | UGACACAAUGCUCAGAAACAGAATC | 254 | GAUUCUGUUUCUGAGCAUUGUGUCAGA | 654 | UGACACAAUGCUCAGAAAC | 1054 |
| LPA-4797 | GACACAAUGCUCAGAAACAAAAUCA | 255 | UGAUUUUGUUUCUGAGCAUUGUGUCAG | 655 | GACACAAUGCUCAGAAACA | 1055 |
| LPA-4798 | ACACAAUGCUCAGAAACAGAAUCAG | 256 | CUGAUUCUGUUUCUGAGCAUUGUGUCA | 656 | ACACAAUGCUCAGAAACAG | 1056 |
| LPA-4799 | CACAAUGCUCAGAAACAGAAUCAGG | 257 | CCUGAUUCUGUUUCUGAGCAUUGUGUC | 657 | CACAAUGCUCAGAAACAGA | 1057 |
| LPA-4800 | ACAAUGCUCAGAAACAGAAACAGGT | 258 | ACCUGUUUCUGUUUCUGAGCAUUGUGU | 658 | ACAAUGCUCAGAAACAGAA | 1058 |
| LPA-4801 | CAAUGCUCAGAAACAGAAUAAGGTG | 259 | CACCUUAUUCUGUUUCUGAGCAUUGUG | 659 | CAAUGCUCAGAAACAGAAU | 1059 |
| LPA-4802 | AAUGCUCAGAAACAGAAUCAGGUGT | 260 | ACACCUGAUUCUGUUUCUGAGCAUUGU | 660 | AAUGCUCAGAAACAGAAUC | 1060 |
| LPA-4803 | AUGCUCAGAAACAGAAUCAAGUGTC | 261 | GACACUUGAUUCUGUUUCUGAGCAUUG | 661 | AUGCUCAGAAACAGAAUCA | 1061 |
| LPA-4804 | UGCUCAGAAACAGAAUCAGAUGUCC | 262 | GGACAUCUGAUUCUGUUUCUGAGCAUU | 662 | UGCUCAGAAACAGAAUCAG | 1062 |
| LPA-4806 | CUCAGAAACAGAAUCAGGUAUCCTA | 263 | UAGGAUACCUGAUUCUGUUUCUGAGCA | 663 | CUCAGAAACAGAAUCAGGU | 1063 |
| LPA-4808 | CAGAAACAGAAUCAGGUGUACUAGA | 264 | UCUAGUACACCUGAUUCUGUUUCUGAG | 664 | CAGAAACAGAAUCAGGUGU | 1064 |
| LPA-4809 | AGAAACAGAAUCAGGUGUCAUAGAG | 265 | CUCUAUGACACCUGAUUCUGUUUCUGA | 665 | AGAAACAGAAUCAGGUGUC | 1065 |
| LPA-4810 | GAAACAGAAUCAGGUGUCCAAGAGA | 266 | UCUCUUGGACACCUGAUUCUGUUUCUG | 666 | GAAACAGAAUCAGGUGUCC | 1066 |
| LPA-4811 | AAACAGAAUCAGGUGUCCUAGAGAC | 267 | GUCUCUAGGACACCUGAUUCUGUUUCU | 667 | AAACAGAAUCAGGUGUCCU | 1067 |
| LPA-4812 | AACAGAAUCAGGUGUCCUAAAGACT | 268 | AGUCUUUAGGACACCUGAUUCUGUUUC | 668 | AACAGAAUCAGGUGUCCUA | 1068 |
| LPA-4814 | CAGAAUCAGGUGUCCUAGAAACUCC | 269 | GGAGUUUCUAGGACACCUGAUUCUGUU | 669 | CAGAAUCAGGUGUCCUAGA | 1069 |
| LPA-4816 | GAAUCAGGUGUCCUAGAGAAUCCCA | 270 | UGGGAUUCUCUAGGACACCUGAUUCUG | 670 | GAAUCAGGUGUCCUAGAGA | 1070 |

TABLE 2-continued

DsiRNAs Targeting Human LPA mRNA and Controls Evaluated in Cells

| | Passenger (Sense) | SEQ ID NO: | Guide (Antisense) | SEQ ID NO: | Target Sequence | SEQ ID NO: |
|---|---|---|---|---|---|---|
| LPA-4818 | AUCAGGUGUCCUAGAGACUACCACT | 271 | AGUGGUAGUCUCUAGGACACCUGAUUC | 671 | AUCAGGUGUCCUAGAGACU | 1071 |
| LPA-4822 | GGUGUCCUAGAGACUCCCAAUGUTG | 272 | CAACAUUGGGAGUCUCUAGGACACCUG | 672 | GGUGUCCUAGAGACUCCCA | 1072 |
| LPA-4827 | CCUAGAGACUCCCACUGUUAUUCCA | 273 | UGGAAUAACAGUGGGAGUCUCUAGGAC | 673 | CCUAGAGACUCCCACUGUU | 1073 |
| LPA-4828 | CUAGAGACUCCCACUGUUGAUCCAG | 274 | CUGGAUCAACAGUGGGAGUCUCUAGGA | 674 | CUAGAGACUCCCACUGUUG | 1074 |
| LPA-4829 | UAGAGACUCCCACUGUUGUACCAGT | 275 | ACUGGUACAACAGUGGGAGUCUCUAGG | 675 | UAGAGACUCCCACUGUUGU | 1075 |
| LPA-4830 | AGAGACUCCCACUGUUGUUACAGTT | 276 | AACUGUAACAACAGUGGGAGUCUCUAG | 676 | AGAGACUCCCACUGUUGUU | 1076 |
| LPA-4831 | GAGACUCCCACUGUUGUUCAAGUTC | 277 | GAACUUGAACAACAGUGGGAGUCUCUA | 677 | GAGACUCCCACUGUUGUUC | 1077 |
| LPA-4832 | AGACUCCCACUGUUGUUCCAGUUCC | 278 | GGAACUGGAACAACAGUGGGAGUCUCU | 678 | AGACUCCCACUGUUGUUCC | 1078 |
| LPA-4867 | GCUCAUUCUGAAGCAGCACAAACTG | 279 | CAGUUUGUGCUGCUUCAGAAUGAGCCU | 679 | GCUCAUUCUGAAGCAGCAC | 1079 |
| LPA-4868 | CUCAUUCUGAAGCAGCACCAACUGA | 280 | UCAGUUGGUGCUGCUUCAGAAUGAGCC | 680 | CUCAUUCUGAAGCAGCACC | 1080 |
| LPA-4869 | UCAUUCUGAAGCAGCACCAACUGAG | 281 | CUCAGUUGGUGCUGCUUCAGAAUGAGC | 681 | UCAUUCUGAAGCAGCACCA | 1081 |
| LPA-4870 | CAUUCUGAAGCAGCACCAAAUGAGC | 282 | GCUCAUUUGGUGCUGCUUCAGAAUGAG | 682 | CAUUCUGAAGCAGCACCAA | 1082 |
| LPA-4871 | AUUCUGAAGCAGCACCAACAGAGCA | 283 | UGCUCUGUUGGUGCUGCUUCAGAAUGA | 683 | AUUCUGAAGCAGCACCAAC | 1083 |
| LPA-4872 | UUCUGAAGCAGCACCAACUAAGCAA | 284 | UUGCUUAGUUGGUGCUGCUUCAGAAUG | 684 | UUCUGAAGCAGCACCAACU | 1084 |
| LPA-4873 | UCUGAAGCAGCACCAACUGAGCAAA | 285 | UUUGCUCAGUUGGUGCUGCUUCAGAAU | 685 | UCUGAAGCAGCACCAACUG | 1085 |
| LPA-4874 | CUGAAGCAGCACCAACUGAACAAAC | 286 | GUUUGUUCAGUUGGUGCUGCUUCAGAA | 686 | CUGAAGCAGCACCAACUGA | 1086 |
| LPA-4875 | UGAAGCAGCACCAACUGAGAAAACC | 287 | GGUUUUCUCAGUUGGUGCUGCUUCAGA | 687 | UGAAGCAGCACCAACUGAG | 1087 |
| LPA-4876 | GAAGCAGCACCAACUGAGCAAACCC | 288 | GGGUUUGCUCAGUUGGUGCUGCUUCAG | 688 | GAAGCAGCACCAACUGAGC | 1088 |
| LPA-4877 | AAGCAGCACCAACUGAGCAAACCCC | 289 | GGGGUUUGCUCAGUUGGUGCUGCUUCA | 689 | AAGCAGCACCAACUGAGCA | 1089 |
| LPA-4912 | CAGUGCUACCAUGGUAAUGACCAGA | 290 | UCUGGUCAUUACCAUGGUAGCACUGCC | 690 | CAGUGCUACCAUGGUAAUG | 1090 |
| LPA-4913 | AGUGCUACCAUGGUAAUGGACAGAG | 291 | CUCUGUCCAUUACCAUGGUAGCACUGC | 691 | AGUGCUACCAUGGUAAUGG | 1091 |
| LPA-4948 | ACAUUCUCCACCACUGUCAAAGGAA | 292 | UUCCUUUGACAGUGGUGGAGAAUGUGC | 692 | ACAUUCUCCACCACUGUCA | 1092 |
| LPA-4959 | CACUGUCACAGGAAGGACAAGUCAA | 293 | UUGACUUGUCCUUCCUGUGACAGUGGU | 693 | CACUGUCACAGGAAGGACA | 1093 |
| LPA-4960 | ACUGUCACAGGAAGGACAUAUCAAT | 294 | AUUGAUAUGUCCUUCCUGUGACAGUGG | 694 | ACUGUCACAGGAAGGACAU | 1094 |

TABLE 2-continued

DsiRNAs Targeting Human LPA mRNA and Controls Evaluated in Cells

| | Passenger (Sense) | SEQ ID NO: | Guide (Antisense) | SEQ ID NO: | Target Sequence | SEQ ID NO: |
|---|---|---|---|---|---|---|
| LPA-4961 | CUGUCACAGGAAGGACAUG ACAATC | 295 | GAUUGUCAUGUCCU UCCUGUGACAGUG | 695 | CUGUCACAGG AAGGACAUG | 1095 |
| LPA-4962 | UGUCACAGGAAGGACAUGU AAAUCT | 296 | AGAUUUACAUGUCC UUCCUGUGACAGU | 696 | UGUCACAGGA AGGACAUGU | 1096 |
| LPA-4963 | GUCACAGGAAGGACAUGUC AAUCTT | 297 | AAGAUUGACAUGUC CUUCCUGUGACAG | 697 | GUCACAGGAA GGACAUGUC | 1097 |
| LPA-4964 | UCACAGGAAGGACAUGUCA AUCUTG | 298 | CAAGAUUGACAUGU CCUUCCUGUGACA | 698 | UCACAGGAAG GACAUGUCA | 1098 |
| LPA-4966 | ACAGGAAGGACAUGUCAAU AUUGGT | 299 | ACCAAUAUUGACAU GUCCUUCCUGUGA | 699 | ACAGGAAGGA CAUGUCAAU | 1099 |
| LPA-4967 | CAGGAAGGACAUGUCAAUC AUGGTC | 300 | GACCAUGAUUGACA UGUCCUUCCUGUG | 700 | CAGGAAGGAC AUGUCAAUC | 1100 |
| LPA-4968 | AGGAAGGACAUGUCAAUCU AGGUCA | 301 | UGACCUAGAUUGAC AUGUCCUUCCUGU | 701 | AGGAAGGACA UGUCAAUCU | 1101 |
| LPA-4969 | GGAAGGACAUGUCAAUCUU AGUCAT | 302 | AUGACUAAGAUUGA CAUGUCCUUCCUG | 702 | GGAAGGACAU GUCAAUCUU | 1102 |
| LPA-4970 | GAAGGACAUGUCAAUCUUG AUCATC | 303 | GAUGAUCAAGAUUG ACAUGUCCUUCCU | 703 | GAAGGACAUG UCAAUCUUG | 1103 |
| LPA-4971 | AAGGACAUGUCAAUCUUGG ACAUCC | 304 | GGAUGUCCAAGAUU GACAUGUCCUUCC | 704 | AAGGACAUGU CAAUCUUGG | 1104 |
| LPA-4972 | AGGACAUGUCAAUCUUGGU AAUCCA | 305 | UGGAUUACCAAGAU UGACAUGUCCUUC | 705 | AGGACAUGUC AAUCUUGGU | 1105 |
| LPA-4973 | GGACAUGUCAAUCUUGGUC AUCCAT | 306 | AUGGAUGACCAAGA UUGACAUGUCCUU | 706 | GGACAUGUCA AUCUUGGUC | 1106 |
| LPA-4974 | GACAUGUCAAUCUUGGUCA ACCATG | 307 | CAUGGUUGACCAAG AUUGACAUGUCCU | 707 | GACAUGUCAA UCUUGGUCA | 1107 |
| LPA-4975 | ACAUGUCAAUCUUGGUCAU ACAUGA | 308 | UCAUGUAUGACCAA GAUUGACAUGUCC | 708 | ACAUGUCAAU CUUGGUCAU | 1108 |
| LPA-4976 | CAUGUCAAUCUUGGUCAUC AAUGAC | 309 | GUCAUUGAUGACCA AGAUUGACAUGUC | 709 | CAUGUCAAUC UUGGUCAUC | 1109 |
| LPA-4977 | AUGUCAAUCUUGGUCAUCC AUGACA | 310 | UGUCAUGGAUGACC AAGAUUGACAUGU | 710 | AUGUCAAUCU UGGUCAUCC | 1110 |
| LPA-4978 | UGUCAAUCUUGGUCAUCCA AGACAC | 311 | GUGUCUUGGAUGAC CAAGAUUGACAUG | 711 | UGUCAAUCUU GGUCAUCCA | 1111 |
| LPA-4979 | GUCAAUCUUGGUCAUCCAU AACACC | 312 | GGUGUUAUGGAUGA CCAAGAUUGACAU | 712 | GUCAAUCUUG GUCAUCCAU | 1112 |
| LPA-4980 | UCAAUCUUGGUCAUCCAUG ACACCA | 313 | UGGUGUCAUGGAUG ACCAAGAUUGACA | 713 | UCAAUCUUGG UCAUCCAUG | 1113 |
| LPA-4981 | CAAUCUUGGUCAUCCAUGA AACCAC | 314 | GUGGUUUCAUGGAU GACCAAGAUUGAC | 714 | CAAUCUUGGU CAUCCAUGA | 1114 |
| LPA-4982 | AAUCUUGGUCAUCCAUGAC ACCACA | 315 | UGUGGUGUCAUGGA UGACCAAGAUUGA | 715 | AAUCUUGGUC AUCCAUGAC | 1115 |
| LPA-4983 | AUCUUGGUCAUCCAUGACA ACACAC | 316 | GUGUGUUGUCAUGG AUGACCAAGAUUG | 716 | AUCUUGGUCA UCCAUGACA | 1116 |
| LPA-5048 | UGACAAUGAACUACUGCAG AAAUCC | 317 | GGAUUUCUGCAGUA GUUCAUUGUCAGG | 717 | UGACAAUGAA CUACUGCAG | 1117 |
| LPA-5049 | GACAAUGAACUACUGCAGG AAUCCA | 318 | UGGAUUCCUGCAGU AGUUCAUUGUCAG | 718 | GACAAUGAAC UACUGCAGG | 1118 |

TABLE 2-continued

DsiRNAs Targeting Human LPA mRNA and Controls Evaluated in Cells

| | Passenger (Sense) | SEQ ID NO: | Guide (Antisense) | SEQ ID NO: | Target Sequence | SEQ ID NO: |
|---|---|---|---|---|---|---|
| LPA-5050 | ACAAUGAACUACUGCAGGAAUCCAG | 319 | CUGGAUUCCUGCAGUAGUUCAUUGUCA | 719 | ACAAUGAACUACUGCAGGA | 1119 |
| LPA-5051 | CAAUGAACUACUGCAGGAAACCAGA | 320 | UCUGGUUUCCUGCAGUAGUUCAUUGUC | 720 | CAAUGAACUACUGCAGGAA | 1120 |
| LPA-5052 | AAUGAACUACUGCAGGAAUACAGAT | 321 | AUCUGUAUUCCUGCAGUAGUUCAUUGU | 721 | AAUGAACUACUGCAGGAAU | 1121 |
| LPA-5053 | AUGAACUACUGCAGGAAUCAAGATG | 322 | CAUCUUGAUUCCUGCAGUAGUUCAUUG | 722 | AUGAACUACUGCAGGAAUC | 1122 |
| LPA-5054 | UGAACUACUGCAGGAAUCCAGAUGC | 323 | GCAUCUGGAUUCCUGCAGUAGUUCAUU | 723 | UGAACUACUGCAGGAAUCC | 1123 |
| LPA-5058 | CUACUGCAGGAAUCCAGAUACCGAT | 324 | AUCGGUAUCUGGAUUCCUGCAGUAGUU | 724 | CUACUGCAGGAAUCCAGAU | 1124 |
| LPA-5084 | CAGGCCCUUGGUGUUUUACAAUGGA | 325 | UCCAUUGUAAAACACCAAGGGCCUGUA | 725 | CAGGCCCUUGGUGUUUUAC | 1125 |
| LPA-5090 | CUUGGUGUUUUACCAUGGAACCCAG | 326 | CUGGGUUCCAUGGUAAAACACCAAGGG | 726 | CUUGGUGUUUUACCAUGGA | 1126 |
| LPA-5091 | UUGGUGUUUUACCAUGGACACCAGC | 327 | GCUGGUGUCCAUGGUAAAACACCAAGG | 727 | UUGGUGUUUUACCAUGGAC | 1127 |
| LPA-5092 | UGGUGUUUUACCAUGGACCACAGCA | 328 | UGCUGUGGUCCAUGGUAAAACACCAAG | 728 | UGGUGUUUUACCAUGGACC | 1128 |
| LPA-5093 | GGUGUUUUACCAUGGACCCAAGCAT | 329 | AUGCUUGGGUCCAUGGUAAAACACCAA | 729 | GGUGUUUUACCAUGGACCC | 1129 |
| LPA-5094 | GUGUUUUACCAUGGACCCCAGCATC | 330 | GAUGCUGGGGUCCAUGGUAAAACACCA | 730 | GUGUUUUACCAUGGACCCC | 1130 |
| LPA-5096 | GUUUUACCAUGGACCCCAGAAUCAG | 331 | CUGAUUCUGGGGUCCAUGGUAAAACAC | 731 | GUUUUACCAUGGACCCCAG | 1131 |
| LPA-5124 | GGAGUACUGCAACCUGACGAGAUGC | 332 | GCAUCUCGUCAGGUUGCAGUACUCCCA | 732 | GGAGUACUGCAACCUGACG | 1132 |
| LPA-5125 | GAGUACUGCAACCUGACGCAAUGCT | 333 | AGCAUUGCGUCAGGUUGCAGUACUCCC | 733 | GAGUACUGCAACCUGACGC | 1133 |
| LPA-5127 | GUACUGCAACCUGACGCGAAGCUCA | 334 | UGAGCUUCGCGUCAGGUUGCAGUACUC | 734 | GUACUGCAACCUGACGCGA | 1134 |
| LPA-5128 | UACUGCAACCUGACGCGAUACUCAG | 335 | CUGAGUAUCGCGUCAGGUUGCAGUACU | 735 | UACUGCAACCUGACGCGAU | 1135 |
| LPA-5131 | UGCAACCUGACGCGAUGCUAAGACA | 336 | UGUCUUAGCAUCGCGUCAGGUUGCAGU | 736 | UGCAACCUGACGCGAUGCU | 1136 |
| LPA-5136 | CCUGACGCGAUGCUCAGACACAGAA | 337 | UUCUGUGUCUGAGCAUCGCGUCAGGUU | 737 | CCUGACGCGAUGCUCAGAC | 1137 |
| LPA-5137 | CUGACGCGAUGCUCAGACAAAGAAG | 338 | CUUCUUUGUCUGAGCAUCGCGUCAGGU | 738 | CUGACGCGAUGCUCAGACA | 1138 |
| LPA-5144 | GAUGCUCAGACACAGAAGGAACUGT | 339 | ACAGUUCCUUCUGUGUCUGAGCAUCGC | 739 | GAUGCUCAGACACAGAAGG | 1139 |
| LPA-5145 | AUGCUCAGACACAGAAGGGACUGTG | 340 | CACAGUCCCUUCUGUGUCUGAGCAUCG | 740 | AUGCUCAGACACAGAAGGG | 1140 |
| LPA-5151 | AGACACAGAAGGGACUGUGAUCGCT | 341 | AGCGAUCACAGUCCCUUCUGUGUCUGA | 741 | AGACACAGAAGGGACUGUG | 1141 |
| LPA-5467 | GCAUCCUCUUCAUUUGAUUAUGGGA | 342 | UCCCAUAAUCAAAUGAAGAGGAUGCAC | 742 | GCAUCCUCUUCAUUUGAUU | 1142 |

TABLE 2-continued

DsiRNAs Targeting Human LPA mRNA and Controls Evaluated in Cells

| | Passenger (Sense) | SEQ ID NO: | Guide (Antisense) | SEQ ID NO: | Target Sequence | SEQ ID NO: |
|---|---|---|---|---|---|---|
| LPA-5468 | CAUCCUCUUCAUUUGAUUGAGGGAA | 343 | UUCCCUCAAUCAAAUGAAGAGGAUGCA | 743 | CAUCCUCUUCAUUUGAUUG | 1143 |
| LPA-5469 | AUCCUCUUCAUUUGAUUGUAGGAAG | 344 | CUUCCUACAAUCAAAUGAAGAGGAUGC | 744 | AUCCUCUUCAUUUGAUUGU | 1144 |
| LPA-5470 | UCCUCUUCAUUUGAUUGUGAGAAGC | 345 | GCUUCUCACAAUCAAAUGAAGAGGAUG | 745 | UCCUCUUCAUUUGAUUGUG | 1145 |
| LPA-5471 | CCUCUUCAUUUGAUUGUGGAAAGCC | 346 | GGCUUUCCACAAUCAAAUGAAGAGGAU | 746 | CCUCUUCAUUUGAUUGUGG | 1146 |
| LPA-5474 | CUUCAUUUGAUUGUGGGAAACCUCA | 347 | UGAGGUUUCCCACAAUCAAAUGAAGAG | 747 | CUUCAUUUGAUUGUGGGAA | 1147 |
| LPA-5475 | UUCAUUUGAUUGUGGGAAGACUCAA | 348 | UUGAGUCUUCCCACAAUCAAAUGAAGA | 748 | UUCAUUUGAUUGUGGGAAG | 1148 |
| LPA-5476 | UCAUUUGAUUGUGGGAAGCAUCAAG | 349 | CUUGAUGCUUCCCACAAUCAAAUGAAG | 749 | UCAUUUGAUUGUGGGAAGC | 1149 |
| LPA-5477 | CAUUUGAUUGUGGGAAGCCACAAGT | 350 | ACUUGUGGCUUCCCACAAUCAAAUGAA | 750 | CAUUUGAUUGUGGGAAGCC | 1150 |
| LPA-5478 | AUUUGAUUGUGGGAAGCCUAAAGTG | 351 | CACUUUAGGCUUCCCACAAUCAAAUGA | 751 | AUUUGAUUGUGGGAAGCCU | 1151 |
| LPA-5486 | GUGGGAAGCCUCAAGUGGAACCGAA | 352 | UUCGGUUCCACUUGAGGCUUCCCACAA | 752 | GUGGGAAGCCUCAAGUGGA | 1152 |
| LPA-5509 | AAGAAAUGUCCUGGAAGCAAUGUAG | 353 | CUACAUUGCUUCCAGGACAUUUCUUCG | 753 | AAGAAAUGUCCUGGAAGCA | 1153 |
| LPA-5510 | AGAAAUGUCCUGGAAGCAUAGUAGG | 354 | CCUACUAUGCUUCCAGGACAUUUCUUC | 754 | AGAAAUGUCCUGGAAGCAU | 1154 |
| LPA-5511 | GAAAUGUCCUGGAAGCAUUAUAGGG | 355 | CCCUAUAAUGCUUCCAGGACAUUUCUU | 755 | GAAAUGUCCUGGAAGCAUU | 1155 |
| LPA-5513 | AAUGUCCUGGAAGCAUUGUAGGGGG | 356 | CCCCCUACAAUGCUUCCAGGACAUUUC | 756 | AAUGUCCUGGAAGCAUUGU | 1156 |
| LPA-5514 | AUGUCCUGGAAGCAUUGUAAGGGGG | 357 | CCCCCUUACAAUGCUUCCAGGACAUUU | 757 | AUGUCCUGGAAGCAUUGUA | 1157 |
| LPA-5581 | AGAACAAGGUUUGGAAAGCACUUCT | 358 | AGAAGUGCUUUCCAAACCUUGUUCUGA | 758 | AGAACAAGGUUUGGAAAGC | 1158 |
| LPA-5582 | GAACAAGGUUUGGAAAGCAAUUCTG | 359 | CAGAAUUGCUUUCCAAACCUUGUUCUG | 759 | GAACAAGGUUUGGAAAGCA | 1159 |
| LPA-5583 | AACAAGGUUUGGAAAGCACAUCUGT | 360 | ACAGAUGUGCUUUCCAAACCUUGUUCU | 760 | AACAAGGUUUGGAAAGCAC | 1160 |
| LPA-5584 | ACAAGGUUUGGAAAGCACUACUGTG | 361 | CACAGUAGUGCUUUCCAAACCUUGUUC | 761 | ACAAGGUUUGGAAAGCACU | 1161 |
| LPA-5585 | CAAGGUUUGGAAAGCACUUAUGUGG | 362 | CCACAUAAGUGCUUUCCAAACCUUGUU | 762 | CAAGGUUUGGAAAGCACUU | 1162 |
| LPA-5586 | AAGGUUUGGAAAGCACUUCAGUGGA | 363 | UCCACUGAAGUGCUUUCCAAACCUUGU | 763 | AAGGUUUGGAAAGCACUUC | 1163 |
| LPA-5587 | AGGUUUGGAAAGCACUUCUAUGGAG | 364 | CUCCAUAGAAGUGCUUUCCAAACCUUG | 764 | AGGUUUGGAAAGCACUUCU | 1164 |
| LPA-5592 | UGGAAAGCACUUCUGUGGAAGCACC | 365 | GGUGCUUCCACAGAAGUGCUUUCCAAA | 765 | UGGAAAGCACUUCUGUGGA | 1165 |
| LPA-5606 | GUGGAGGCACCUUAAUAUCACCAGA | 366 | UCUGGUGAUAUUAAGGUGCCUCCACAG | 766 | GUGGAGGCACCUUAAUAUC | 1166 |

TABLE 2-continued

DsiRNAs Targeting Human LPA mRNA and Controls Evaluated in Cells

| | Passenger (Sense) | SEQ ID NO: | Guide (Antisense) | SEQ ID NO: | Target Sequence | SEQ ID NO: |
|---|---|---|---|---|---|---|
| LPA-5616 | CUUAAUAUCCCCAGAGUGGAUGCTG | 367 | CAGCAUCCACUCUGGGGAUAUUAAGGU | 767 | CUUAAUAUCCCCAGAGUGG | 1167 |
| LPA-5618 | UAAUAUCCCCAGAGUGGGUACUGAC | 36 | GUCAGUACCCACUCUGGGGAUAUUAAG | 768 | UAAUAUCCCCAGAGUGGGU | 1168 |
| LPA-5628 | AGAGUGGGUGCUGACUGCUACUCAC | 369 | GUGAGUAGCAGUCAGCACCCACUCUGG | 769 | AGAGUGGGUGCUGACUGCU | 1169 |
| LPA-5685 | CAAGGUCAUCCUGGGUGCAAACCAA | 370 | UUGGUUUGCACCCAGGAUGACCUUGUA | 770 | CAAGGUCAUCCUGGGUGCA | 1170 |
| LPA-5694 | CCUGGGUGCACACCAAGAAAUGAAC | 371 | GUUCAUUUCUUGGUGUGCACCCAGGAU | 771 | CCUGGGUGCACACCAAGAA | 1171 |
| LPA-5699 | GUGCACACCAAGAAGUGAAACUCGA | 372 | UCGAGUUUCACUUCUUGGUGUGCACCC | 772 | GUGCACACCAAGAAGUGAA | 1172 |
| LPA-5775 | AGCAGAUAUUGCCUUGCUAAAGCTA | 373 | UAGCUUUAGCAAGGCAAUAUCUGCUUG | 773 | AGCAGAUAUUGCCUUGCUA | 1173 |
| LPA-5776 | GCAGAUAUUGCCUUGCUAAAGCUAA | 374 | UUAGCUUUAGCAAGGCAAUAUCUGCUU | 774 | GCAGAUAUUGCCUUGCUAA | 1174 |
| LPA-5777 | CAGAUAUUGCCUUGCUAAAACUAAG | 375 | CUUAGUUUUAGCAAGGCAAUAUCUGCU | 775 | CAGAUAUUGCCUUGCUAAA | 1175 |
| LPA-5778 | AGAUAUUGCCUUGCUAAAGAUAAGC | 376 | GCUUAUCUUUAGCAAGGCAAUAUCUGC | 776 | AGAUAUUGCCUUGCUAAAG | 1176 |
| LPA-5779 | GAUAUUGCCUUGCUAAAGCAAAGCA | 377 | UGCUUUGCUUUAGCAAGGCAAUAUCUG | 777 | GAUAUUGCCUUGCUAAAGC | 1177 |
| LPA-5780 | AUAUUGCCUUGCUAAAGCUAAGCAG | 378 | CUGCUUAGCUUUAGCAAGGCAAUAUCU | 778 | AUAUUGCCUUGCUAAAGCU | 1178 |
| LPA-5781 | UAUUGCCUUGCUAAAGCUAAGCAGG | 379 | CCUGCUUAGCUUUAGCAAGGCAAUAUC | 779 | UAUUGCCUUGCUAAAGCUA | 1179 |
| LPA-5813 | UCAUCACUGACAAAGUAAUACCAGC | 380 | GCUGGUAUUACUUUGUCAGUGAUGACG | 780 | UCAUCACUGACAAAGUAAU | 1180 |
| LPA-5873 | GGACUGAAUGUUACAUCACAGGCTG | 381 | CAGCCUGUGAUGUAACAUUCAGUCCUG | 781 | GGACUGAAUGUUACAUCAC | 1181 |
| LPA-5874 | GACUGAAUGUUACAUCACUAGCUGG | 382 | CCAGCUAGUGAUGUAACAUUCAGUCCU | 782 | GACUGAAUGUUACAUCACU | 1182 |
| LPA-5875 | ACUGAAUGUUACAUCACUGACUGGG | 383 | CCCAGUCAGUGAUGUAACAUUCAGUCC | 783 | ACUGAAUGUUACAUCACUG | 1183 |
| LPA-5876 | CUGAAUGUUACAUCACUGGAUGGGG | 384 | CCCCAUCCAGUGAUGUAACAUUCAGUC | 784 | CUGAAUGUUACAUCACUGG | 1184 |
| LPA-5877 | UGAAUGUUACAUCACUGGCAGGGGA | 385 | UCCCCUGCCAGUGAUGUAACAUUCAGU | 785 | UGAAUGUUACAUCACUGGC | 1185 |
| LPA-5879 | AAUGUUACAUCACUGGCUGAGGAGA | 386 | UCUCCUCAGCCAGUGAUGUAACAUUCA | 786 | AAUGUUACAUCACUGGCUG | 1186 |
| LPA-5902 | GAAACCCAAGGUACCUUUGAGACTG | 387 | CAGUCUCAAAGGUACCUUGGGUUUCUC | 787 | GAAACCCAAGGUACCUUUG | 1187 |
| Control | | | | | | |
| Gal XC-LPA-3675 | GACAACAGAAUAUUAUCCAAGCAGCCGAAAGGCUGC | 1188 | UUGGAUAAUAUUCUGUUGUCGG | 1189 | GACAACAGAAUAUUAUCCA | 1190 |
| NC1 | CGUUAAUCGCGUAUAAUACGCGUAT | 1191 | AUACGCGUAUUAUACGCGAUUAACGAC | 1192 | N/A | |

TABLE 2-continued

DsiRNAs Targeting Human LPA mRNA and Controls Evaluated in Cells

| | Passenger (Sense) | SEQ ID NO: | Guide (Antisense) | SEQ ID NO: | Target Sequence | SEQ ID NO: |
|---|---|---|---|---|---|---|
| NC5 | CAUAUUGCGCGUAUAGUCG CGUUAG | 1193 | CUAACGCGACUAUA CGCGCAAUAUGGU | 1194 | N/A | |
| NC7 | GGCGCGUAUAGUCGCGCGU AUAGTC | 1195 | GACUAUACGCGCGA CUAUACGCGCCUC | 1196 | N/A | |

In Vitro Cell-Based Assays

The ability of each of the DsiRINAs listed in Table 2 to inhibit LPA expression was determined using in vitro cell-based assays. Briefly, human embryonic kidney 293 (HEK293) or HepG2 cells stably expressing a human LPA gene were transfected with each of the DsiRNAs listed in Table 2 at 0.5 nM in separate wells of a multi-well cell-culture plate. Cells were maintained for 24 hours following transfection, and then the amount of remaining LPA mRNA from the transfected cells was determined using TAQMAN®-based qPCR assays. Two qPCR assays, a 3' assay and a 5' assay, were used to determine LPA mRNA levels as measured using PCR probes conjugated to 6-carboxyfluorescein (6-FAM).

The results of the HEK293 and HepG2 cell-based assays to evaluate the ability of the DsiRNAs listed in Table 2 to inhibit LPA expression are shown in FIGS. 1-4 and FIG. 5, respectively. Cells transfected with a GalNAc-conjugated LPA oligonucleotide (GalXC-LPA-3675 SEQ ID NO: 1188 and 1189) were used as a positive control. DsiRNAs that resulted in less than or equal to about 15%-20% LPA mRNA remaining in DsiRNA-transfected cells when compared to mock-transfected cells were generally considered to comprise sequences that provide a suitable amount of knockdown or reduction of target mRNA expression for further evaluation. In FIGS. 1-5, the percent of LPA mRNA remaining in cells transfected with DsiRNAs, as indicated, relative to time-matched control cells is shown (3' assay=circle shapes; 5' assay=triangle shapes).

Figure 6:
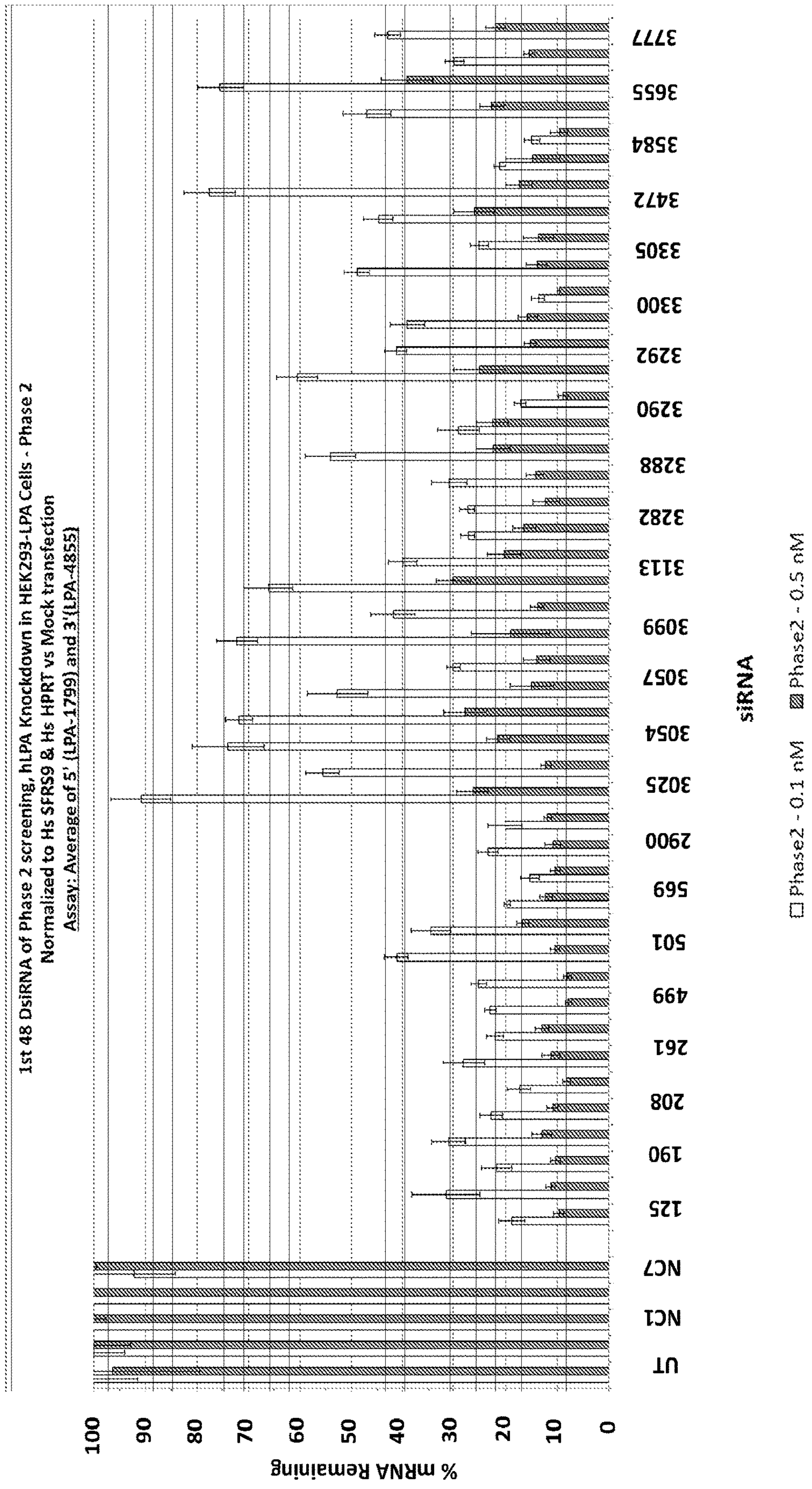
FIGS. 6-7 provide graphs depicting the percent (%) of LPA mRNA in HEK293-LPA cells transfected with the indicated DsiRNAs relative to the % of LPA mRNA control mock-treated cells.
Figure 7:
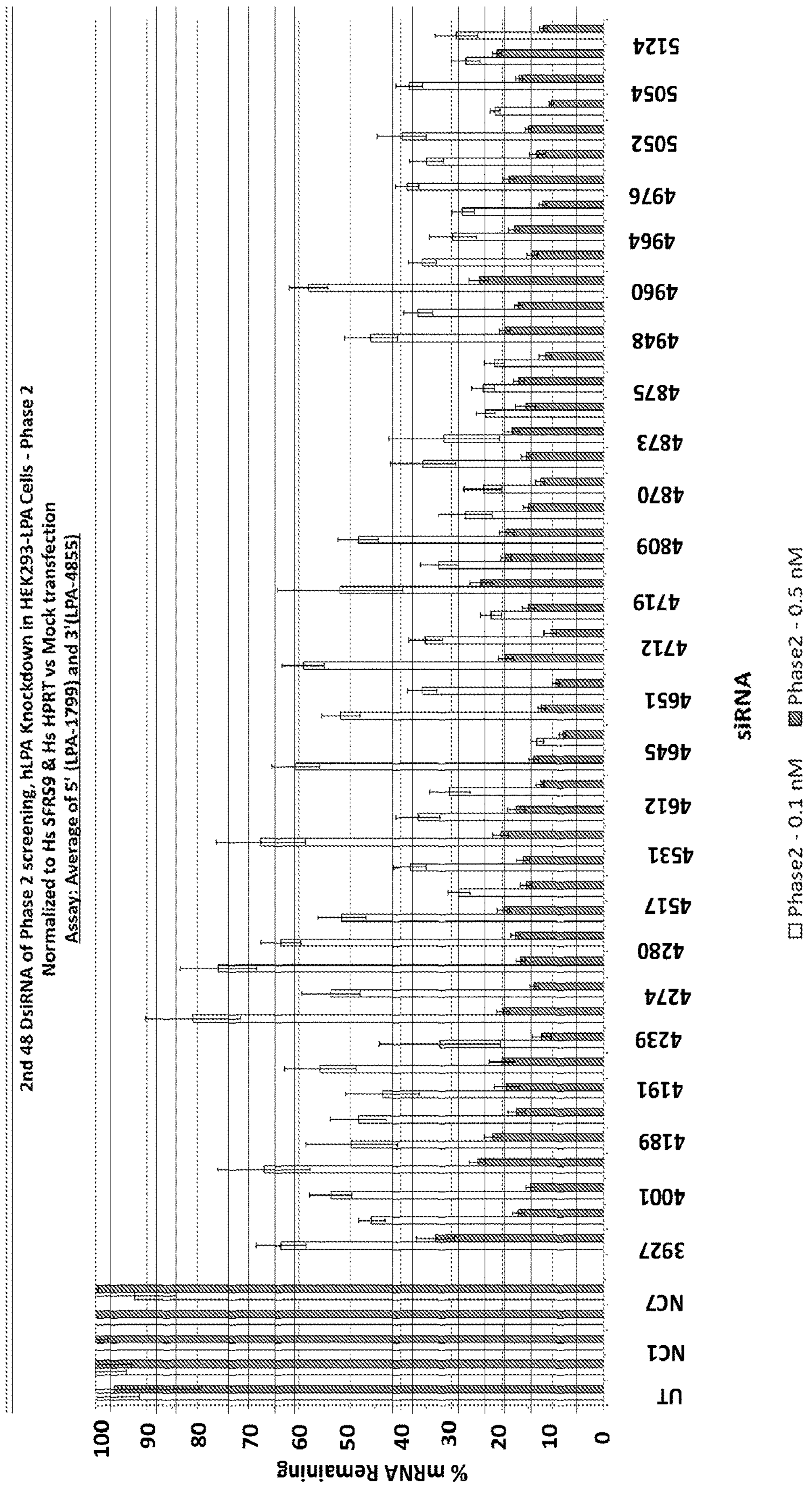

To further evaluate the DsiRNA hits, a subset of the DsiRNAs listed in Table 2 were tested to determine their ability to inhibit LPA expression using in vitro cell-based assays at two different DsiRNA concentrations (FIG. 6 and FIG. 7). Briefly, HEK293 cells stably expressing a human LPA gene were transfected with DsiRNAs at 0.1 nM and 0.5 nM in separate wells of a multi-well cell-culture plate. Cells were maintained for 24 hr. following transfection, and then the amount of remaining LPA mRNA from the transfected cells was determined using TAQMAN®-based qPCR assays. Two qPCR assays, a 3' assay and a 5' assay, were used to determine LPA mRNA levels as measured using PCR probes conjugated to hexachloro-fluorescein (HEX). Untransfected cells (UT), mock-transfected cells (Mock), and cells transfected with control oligonucleotides (NC1, SEQ ID NOs: 1191 and 1192; NC5, SEQ ID NO: 1193 and 1194; and NC7, SEQ ID NO: 1195 and 1196) were used as negative controls. As shown in FIGS. 6 and 7, the percent of LPA mRNA remaining in HEK293 cells transfected with the indicated DsiRNAs is an average of the LPA mRNA levels from the 3' assay and 5' assay and is normalized to time-matched, mock-transfected control HEK293 cells.

Taken together, these results show that DsiRNAs designed to target human LPA mRNA inhibit LPA expression in cells, as determined by a reduced amount of LPA mRNA in DsiRNA-transfected cells relative to control cells. These results demonstrate that the nucleotide sequences comprising the DsiRNA are useful for generating RNAi oligonucleotides to inhibit LPA expression. Further, these results demonstrate that multiple LPA mRNA target sequences are suitable for the RNAi-mediated inhibition of LPA expression.

Example 3: RNAi Oligonucleotide Inhibition of LPA Expression In Vivo

Of the DsiRNAs screened in the cell-based assays described in Example 2, the nucleotide sequences of 14 DsiRNAs were selected for further evaluation in vivo. Briefly, the nucleotide sequences of the 14 selected DsiRNAs were used to generate 14 corresponding double-stranded RNAi oligonucleotides comprising a nicked tetraloop GalNAc-conjugated structure (referred to herein as "GalNAc-conjugated LPA oligonucleotides") having a 36-mer passenger strand and a 22-mer guide strand (Table 3). Further, the nucleotide sequences comprising the passenger strand and guide strand of the GalNAc-conjugated LPA oligonucleotides have a distinct pattern of modified nucleotides and phosphorothioate linkages (e.g., see FIG. 10 for a schematic of the generic structure and chemical modification patterns (M1, M2, and M3) of the GalNAc-conjugated LPA oligonucleotides). The three adenosine nucleotides comprising the tetraloop are each conjugated to a GalNAc moiety (CAS #: 14131-60-3).

TABLE 3

GalNAc-Conjugated LPA Oligonucleotides Evaluated in Mice

| Oligonucleotide | DP# | SEQ ID NO (Sense) | SEQ ID NO (Antisense) |
|---|---|---|---|
| LPA-0190-M1 | DP15791P:DP15790G | 388 | 788 |
| LPA-0501-M1 | DP15634P:DP15633G | 389 | 789 |
| LPA-3100-M1 | DP15639P:DP15638G | 390 | 790 |
| LPA-3286-M1 | DP15643P:DP15642G | 391 | 791 |
| LPA-3288-M1 | DP15645P:DP15644G | 392 | 792 |
| LPA-3291-M1 | DP15647P:DP15646G | 393 | 793 |
| LPA-3584-M1 | DP15651P:DP15650G | 394 | 794 |
| LPA-3585-M1 | DP15653P:DP15652G | 395 | 795 |
| LPA-4645-M1 | DP15657P:DP15656G | 396 | 796 |
| LPA-4717-M1 | DP15801P:DP15800G | 397 | 797 |
| LPA-5510-M1 | DP15815P:DP15814G | 398 | 798 |
| LPA-3750-M1 | DP13346P:DP13385G | 399 | 799 |
| LPA-2900-M2 | DP13351P:DP14623G | 400 | 800 |
| LPA-3675-M2 | DP13346P:DP14624G | 401 | 801 |
| LPA-2900-M3 | DP13351P:DP13387G | 402 | 802 |
| LPA-3675-M3 | DP13346P:DP13385G | 403 | 803 |

Mouse Studies

The GalNAc-conjugated LPA oligonucleotides listed in Table 3 were evaluated in an HDI mouse model, wherein HDI mice were engineered to transiently express human LPA mRNA in hepatocytes. The GalNAc-conjugated LPA oligonucleotide LPA-3675-M2 was used as a benchmark control. Briefly, 6-8-week-old female CD-1 mice (n=5) were treated subcutaneously with the indicated GalNAc-conjugated LPA oligonucleotides at a dose level of 0.5 mg/kg (FIG. 8) or at a dose level of 0.25 mg/kg, 0.5 mg/kg, and 1 mg/kg (FIG. 9). Three days later (72 h), the mice were hydrodynamically injected (HDI) with a DNA plasmid encoding the full human LPA gene under control of a ubiquitous cytomegalovirus (CMV) promoter sequence. One day after introduction of the DNA plasmid, liver samples from mice were collected. Total RNA derived from these mice were subjected to qRT-PCR analysis for LPA mRNA, relative to mice treated only with an identical volume of PBS. The values were normalized for transfection efficiency using the NeoR gene included on the plasmid.

Figure 8:
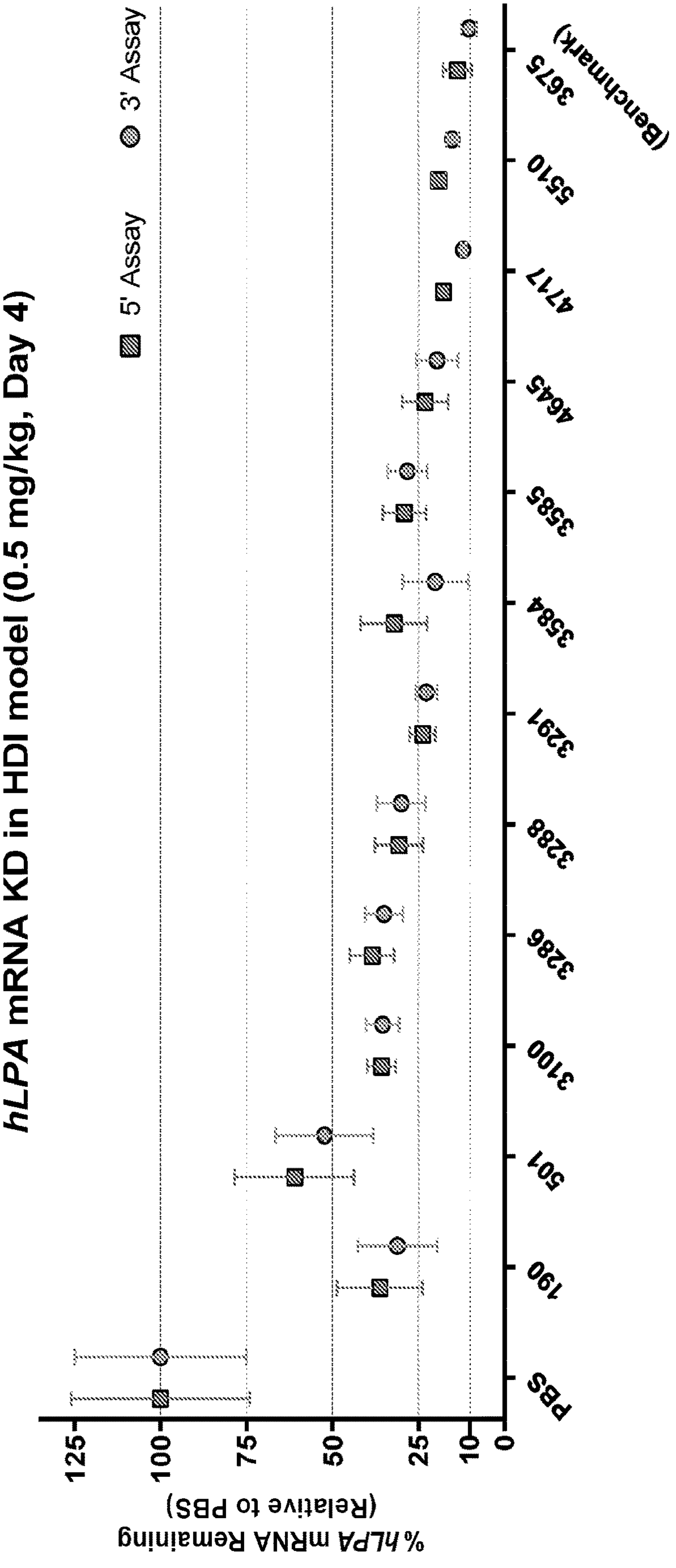
FIGS. 8-9 provide graphs depicting the percent (%) of LPA mRNA in liver samples from mice treated with the indicated GalNAc-conjugated LPA oligonucleotides relative to mice treated with phosphate buffered saline (PBS).
Figure 9:
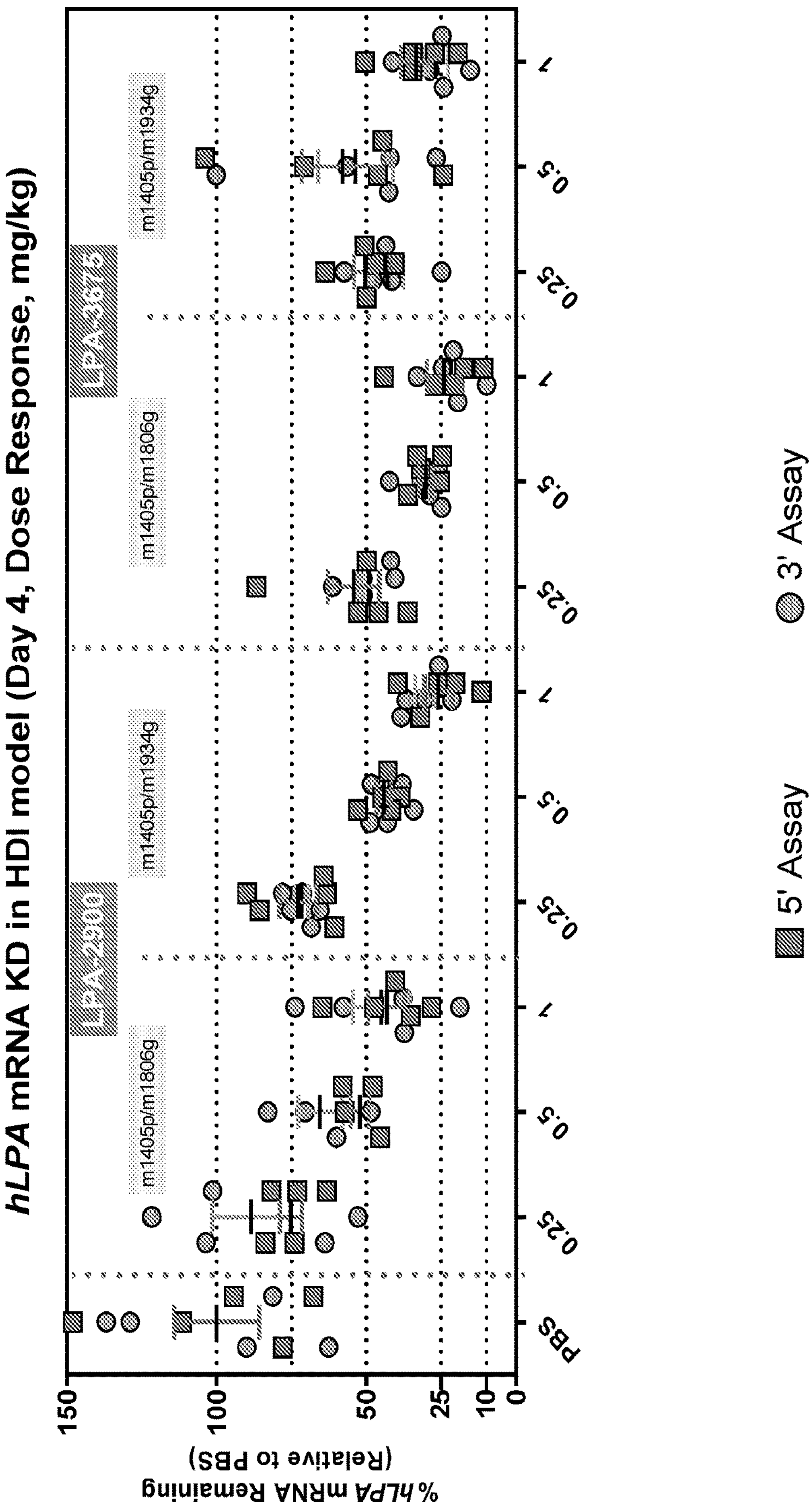

As shown in FIG. 8, the indicated GalNAc-conjugated LPA oligonucleotides inhibited LPA expression, as determined by a reduction in the amount of LPA mRNA in liver samples from oligonucleotide-treated HDI mice relative to mice treated with PBS. To further evaluate the ability of GalNAc-conjugated LPA oligonucleotides to inhibit LPA expression, two of the GalNAc-conjugated LPA oligonucleotide sequences (LPA-2900 and LPA-3675) each having a different chemical modification pattern (M2 and M3) were tested for their ability to inhibit LPA expression in the HDI mice described above at three different concentrations (0.25 mg/kg, 0.5 mg/kg, and 1.0 mg/kg). As shown in FIG. 9, the indicated GalNAc-conjugated LPA oligonucleotides inhibited LPA expression in HDI mice in a dose-dependent manner.

Taken together, these results show that GalNAc-conjugated LPA oligonucleotides designed to target human LPA mRNA inhibit LPA expression in mice, as determined by a reduction in the amount of LPA mRNA in HDI mouse livers relative to control mice treated with PBS. Based on these results, 10 of the 14 GalNAc-conjugated LPA oligonucleotides evaluated in HDI mice were selected for evaluation of their ability to inhibit LPA expression in non-human primates (NHPs). The 10 GalNAc-conjugated LPA oligonucleotides listed in Table 4 comprise chemically modified nucleotides having pattern M1, M2, or M3 as described in FIG. 10.

TABLE 4

GalNAc-Conjugated LPA Oligonucleotides Evaluated in NHPs

| Oligonucleotide | DP# | SEQ ID NO (Sense) | SEQ ID NO (Antisense) |
|---|---|---|---|
| LPA-0190-M1 | DP15791P:DP15790G | 388 | 788 |
| LPA-3100-M1 | DP15639P:DP15638G | 390 | 790 |
| LPA-3288-M1 | DP15645P:DP15644G | 392 | 792 |
| LPA-3291-M1 | DP15647P:DP15646G | 393 | 793 |
| LPA-3585-M1 | DP15653P:DP15652G | 395 | 795 |

TABLE 4-continued

GalNAc-Conjugated LPA Oligonucleotides Evaluated in NHPs

| Oligonucleotide | DP# | SEQ ID NO (Sense) | SEQ ID NO (Antisense) |
|---|---|---|---|
| LPA-4645-M1 | DP15657P:DP15656G | 396 | 796 |
| LPA-4717-M1 | DP15801P:DP15800G | 397 | 797 |
| LPA-5510-M1 | DP15815P:DP15814G | 398 | 798 |
| LPA-2900-M2 | DP13351P:DP14623G | 400 | 800 |
| LPA-3675-M3 | DP13346P:DP13385G | 403 | 803 |

Non-Human Primate (NHP) Studies

Figure 11A:
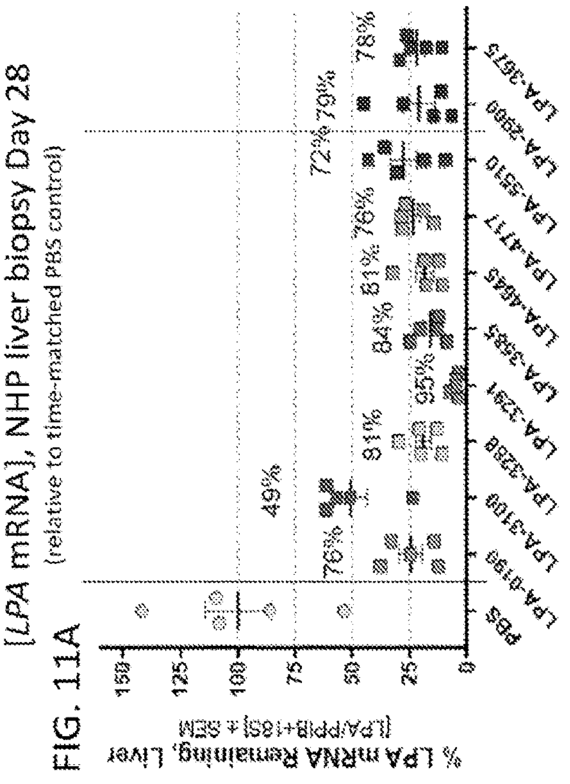
FIGS. 11A-11C provide graphs depicting the percent (%) of LPA mRNA in liver samples from non-human primates (NHPs) treated with the indicated GalNAc-conjugated LPA oligonucleotides relative to NHPs treated with PBS on day 28 (FIG. 11A), day 56 (FIG. 11B) and day 84 (FIG. 11C) following treatment.
Figure 11B:
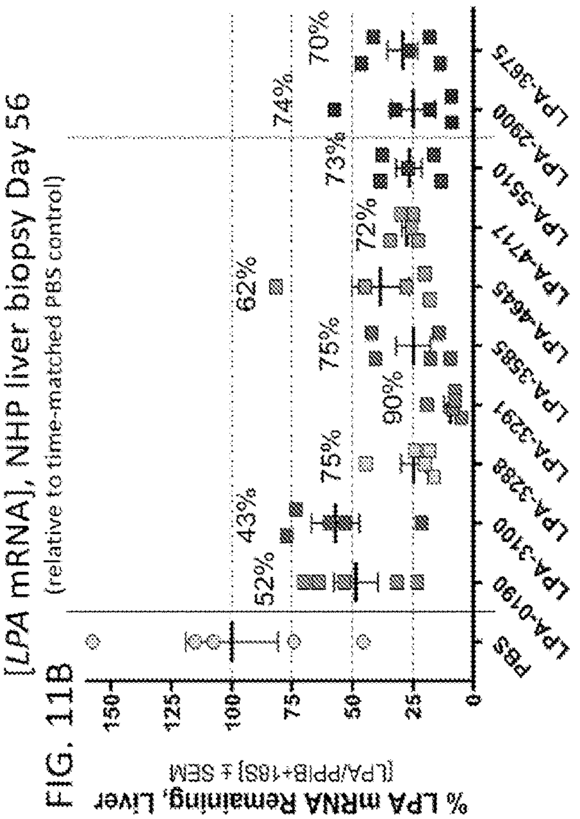
Figure 11C:
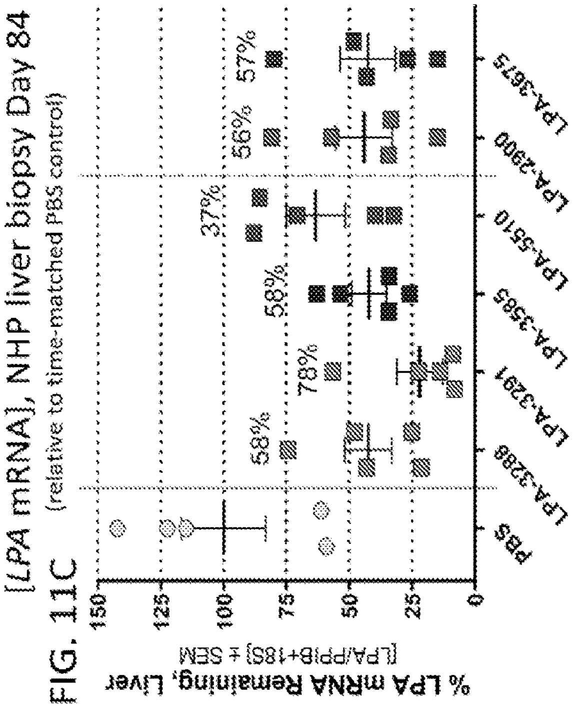
Figure 11D:
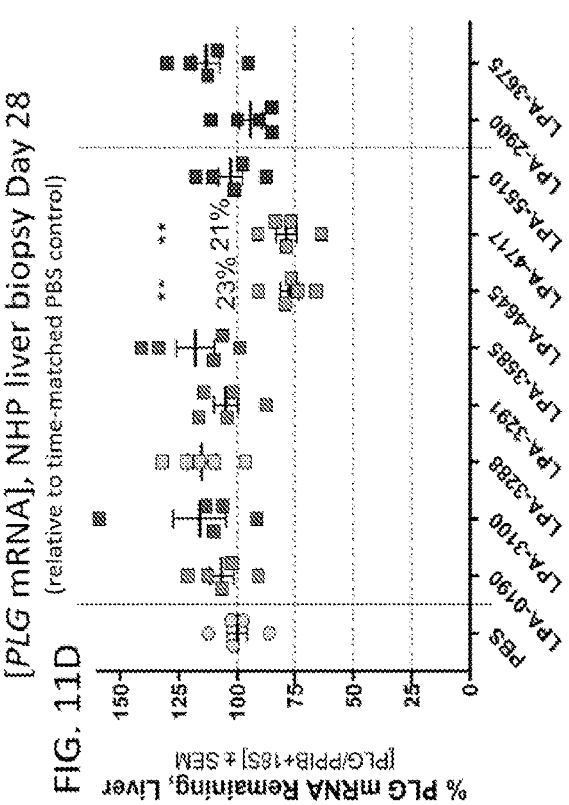
FIG. 11D provides a graph depicting the percent (%) of PLG mRNA in liver samples from NHPs treated with the indicated GalNAc-conjugated LPA oligonucleotides relative to NHPs treated with PBS on day 28.
Figure 12:
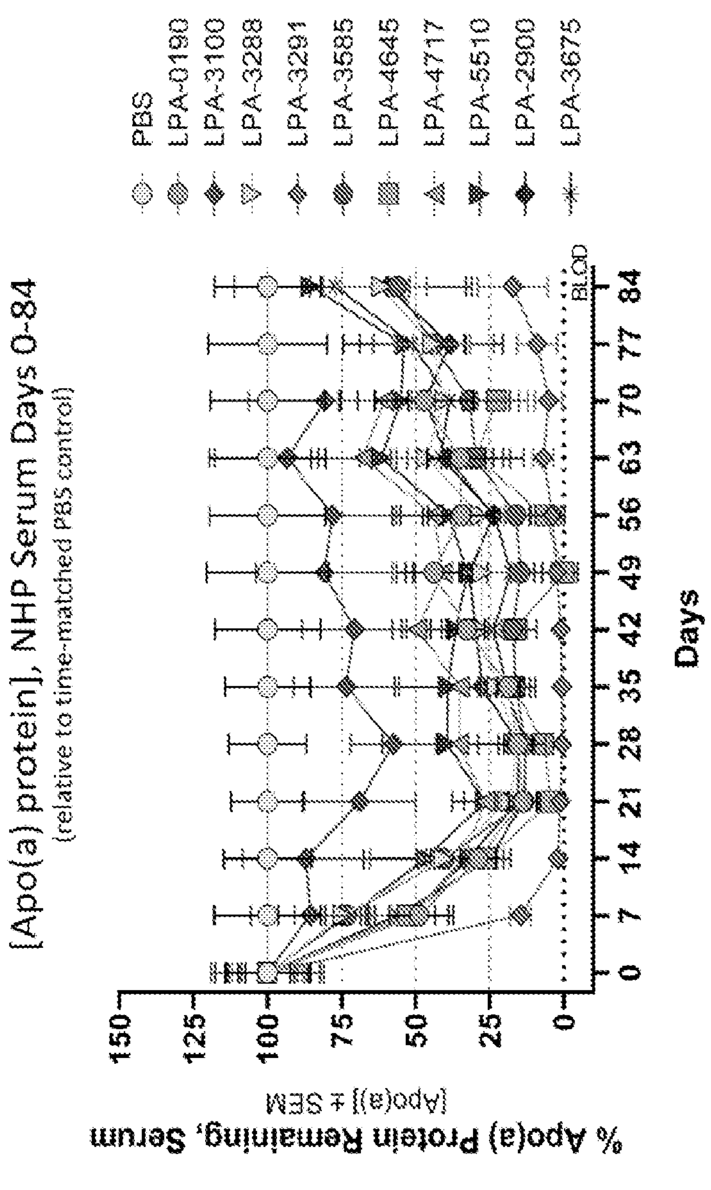
FIG. 12 provides a graph depicting the mean percent (%) of apo(a) protein in serum from NHPs treated with the indicated GalNAc-conjugated LPA oligonucleotides relative to NHPs treated with PBS over time.

The GalNAc-conjugated LPA oligonucleotides listed in Table 4 were evaluated in cynomolgus monkeys (*Macaca fascicularis*). In this study, the monkeys are grouped so that their mean body weights (about 5.4 kg) are comparable between the control and experimental groups. Each cohort contains two male and three female subjects. The GalNAc-conjugated LPA oligonucleotides were administered subcutaneously on Study Day 0. Blood samples were collected on Study Days −8, −5 and 0, and weekly after dosing. Ultrasound-guided core needle liver biopsies were collected on Study Days 28, 56 and 84. At each time point, total RNA derived from the liver biopsy samples was subjected to qRT-PCR analysis to measure LPA mRNA in oligonucleotide-treated monkeys relative to monkeys treated with a comparable volume of PBS. To normalize the data, the measurements were made relative to the geometric mean of two reference genes, PPIB and 18S rRNA. As shown in FIG. 11A (Day 28), FIG. 11B (Day 56), and FIG. 11C (Day 84), treatment of NHPs with the GalNAc-conjugated LPA oligonucleotides listed in Table 4 inhibited LPA expression in the liver, as determined by a reduction in the amount of LPA mRNA in liver samples from oligonucleotide-treated NHPs relative to NHPs treated with PBS. The amount of plasminogen (PLG) mRNA in the liver samples of treated NHPs was also determined and is shown in FIG. 11D. From the same NHP study, inhibition of LPA expression was also determined by measuring apo(a) protein serum from treated NHPs by ELISA. As shown in FIG. 12, a significant reduction in serum apo(a) protein was observed in NHPs treated with GalNAc-conjugated LPA oligonucleotides compared to NHPs treated with PBS. Values from three pre-dose samples are averaged and set to 100%, and data are reported as relative values compared to the pre-dose average. Taken together, these results demonstrate that treatment of NHPs with GalNAc-conjugated LPA oligonucleotides reduced the amount of LPA mRNA in the liver and reduced the amount of apo(a) protein in the serum.

Taken together, these results show that GalNAc-conjugated LPA oligonucleotides designed to target human LPA mRNA inhibit LPA expression in vivo (as determined by the reduction of the amount of LPA mRNA and apo(a) protein in treated animals).

SEQUENCE LISTING

The following nucleic and/or amino acid sequences are referred to in the disclosure above and are provided below for reference.

TABLE 5

| LPA Oligonucleotide Sequences (Unmodified) | | | | |
|---|---|---|---|---|
| Oligonucleotide | Sequence (Sense Strand) | SEQ ID NO: | Sequence (Antisense Strand) | SEQ ID NO: |
| LPA-125 | CUGAGCAAAGCCAUGUGGUACAGGA | 4 | UCCUGUACCACAUGGCUUUGCUCAGGU | 404 |
| LPA-128 | AGCAAAGCCAUGUGGUCCAAGAUTG | 5 | CAAUCUUGGACCACAUGGCUUUGCUCA | 405 |
| LPA-132 | AAGCCAUGUGGUCCAGGAUAGCUAC | 6 | GUAGCUAUCCUGGACCACAUGGCUUUG | 406 |
| LPA-133 | AGCCAUGUGGUCCAGGAUUACUACC | 7 | GGUAGUAAUCCUGGACCACAUGGCUUU | 407 |
| LPA-134 | GCCAUGUGGUCCAGGAUUGAUACCA | 8 | UGGUAUCAAUCCUGGACCACAUGGCUU | 408 |
| LPA-135 | CCAUGUGGUCCAGGAUUGCAACCAT | 9 | AUGGUUGCAAUCCUGGACCACAUGGCU | 409 |
| LPA-136 | CAUGUGGUCCAGGAUUGCUACCATG | 10 | CAUGGUAGCAAUCCUGGACCACAUGGC | 410 |
| LPA-137 | AUGUGGUCCAGGAUUGCUAACAUGG | 11 | CCAUGUUAGCAAUCCUGGACCACAUGG | 411 |
| LPA-138 | UGUGGUCCAGGAUUGCUACAAUGGT | 12 | ACCAUUGUAGCAAUCCUGGACCACAUG | 412 |
| LPA-160 | GGUGAUGGACAGAGUUAUCAAGGCA | 13 | UGCCUUGAUAACUCUGUCCAUCACCAU | 413 |
| LPA-190 | UCCACCACUGUCACAGGAAAGACCT | 14 | AGGUCUUUCCUGUGACAGUGGUGGAGU | 414 |
| LPA-191 | CCACCACUGUCACAGGAAGAACCTG | 15 | CAGGUUCUUCCUGUGACAGUGGUGGAG | 415 |
| LPA-197 | CUGUCACAGGAAGGACCUGACAAGC | 16 | GCUUGUCAGGUCCUUCCUGUGACAGUG | 416 |
| LPA-205 | GGAAGGACCUGCCAAGCUUAGUCAT | 17 | AUGACUAAGCUUGGCAGGUCCUUCCUG | 417 |
| LPA-206 | GAAGGACCUGCCAAGCUUGAUCATC | 18 | GAUGAUCAAGCUUGGCAGGUCCUUCCU | 418 |
| LPA-208 | AGGACCUGCCAAGCUUGGUAAUCTA | 19 | UAGAUUACCAAGCUUGGCAGGUCCUUC | 419 |
| LPA-209 | GGACCUGCCAAGCUUGGUCAUCUAT | 20 | AUAGAUGACCAAGCUUGGCAGGUCCUU | 420 |
| LPA-210 | GACCUGCCAAGCUUGGUCAACUATG | 21 | CAUAGUUGACCAAGCUUGGCAGGUCCU | 421 |
| LPA-211 | ACCUGCCAAGCUUGGUCAUAUAUGA | 22 | UCAUAUAUGACCAAGCUUGGCAGGUCC | 422 |
| LPA-212 | CCUGCCAAGCUUGGUCAUCAAUGAC | 23 | GUCAUUGAUGACCAAGCUUGGCAGGUC | 423 |
| LPA-219 | AGCUUGGUCAUCUAUGACAACACAT | 24 | AUGUGUUGUCAUAGAUGACCAAGCUUG | 424 |
| LPA-225 | GUCAUCUAUGACACCACAUAAACAT | 25 | AUGUUUAUGUGGUGUCAUAGAUGACCA | 425 |
| LPA-258 | CACAGAAAACUACCCAAAUACUGGC | 26 | GCCAGUAUUUGGGUAGUUUUCUGUGGU | 426 |
| LPA-261 | AGAAAACUACCCAAAUGCUAGCUTG | 27 | CAAGCUAGCAUUUGGGUAGUUUUCUGU | 427 |
| LPA-263 | AAAACUACCCAAAUGCUGGAUUGAT | 28 | AUCAAUCCAGCAUUUGGGUAGUUUUCU | 428 |

TABLE 5-continued

| | | | | |
|---|---|---|---|---|
| LPA-269 | ACCCAAAUGCUGGCUUGAUAAUGAA | 29 | UUCAUUAUCAAGCCAGCAUUUGGGUAG | 429 |
| LPA-270 | CCCAAAUGCUGGCUUGAUCAUGAAC | 30 | GUUCAUGAUCAAGCCAGCAUUUGGGUA | 430 |
| LPA-291 | GAACUACUGCAGGAAUCCAAAUGCT | 31 | AGCAUUUGGAUUCCUGCAGUAGUUCAU | 431 |
| LPA-295 | UACUGCAGGAAUCCAGAUGAUGUGG | 32 | CCACAUCAUCUGGAUUCCUGCAGUAGU | 432 |
| LPA-296 | ACUGCAGGAAUCCAGAUGCAGUGGC | 33 | GCCACUGCAUCUGGAUUCCUGCAGUAG | 433 |
| LPA-298 | UGCAGGAAUCCAGAUGCUGAGGCAG | 34 | CUGCCUCAGCAUCUGGAUUCCUGCAGU | 434 |
| LPA-355 | AGGUGGGAGUACUGCAACCAGACGC | 35 | GCGUCUGGUUGCAGUACUCCCACCUGA | 435 |
| LPA-380 | AAUGCUCAGACGCAGAAGGAACUGC | 36 | GCAGUUCCUUCUGCGUCUGAGCAUUGC | 436 |
| LPA-417 | GACUGUUACCCCGGUUCCAAGCCTA | 37 | UAGGCUUGGAACCGGGGUAACAGUCGG | 437 |
| LPA-418 | ACUGUUACCCCGGUUCCAAACCUAG | 38 | CUAGGUUUGGAACCGGGGUAACAGUCG | 438 |
| LPA-419 | CUGUUACCCCGGUUCCAAGACUAGA | 39 | UCUAGUCUUGGAACCGGGGUAACAGUC | 439 |
| LPA-420 | UGUUACCCCGGUUCCAAGCAUAGAG | 40 | CUCUAUGCUUGGAACCGGGGUAACAGU | 440 |
| LPA-421 | GUUACCCCGGUUCCAAGCCAAGAGG | 41 | CCUCUUGGCUUGGAACCGGGGUAACAG | 441 |
| LPA-422 | UUACCCCGGUUCCAAGCCUAGAGGC | 42 | GCCUCUAGGCUUGGAACCGGGGUAACA | 442 |
| LPA-423 | UACCCCGGUUCCAAGCCUAAAGGCT | 43 | AGCCUUUAGGCUUGGAACCGGGGUAAC | 443 |
| LPA-492 | GUGCUACCAUGGUAAUGGAAAGAGT | 44 | ACUCUUUCCAUUACCAUGGUAGCACUC | 444 |
| LPA-493 | UGCUACCAUGGUAAUGGACAGAGTT | 45 | AACUCUGUCCAUUACCAUGGUAGCACU | 445 |
| LPA-494 | GCUACCAUGGUAAUGGACAAAGUTA | 46 | UAACUUUGUCCAUUACCAUGGUAGCAC | 446 |
| LPA-495 | CUACCAUGGUAAUGGACAGAGUUAT | 47 | AUAACUCUGUCCAUUACCAUGGUAGCA | 447 |
| LPA-496 | UACCAUGGUAAUGGACAGAAUUATC | 48 | GAUAAUUCUGUCCAUUACCAUGGUAGC | 448 |
| LPA-497 | ACCAUGGUAAUGGACAGAGAUAUCG | 49 | CGAUAUCUCUGUCCAUUACCAUGGUAG | 449 |
| LPA-498 | CCAUGGUAAUGGACAGAGUAAUCGA | 50 | UCGAUUACUCUGUCCAUUACCAUGGUA | 450 |
| LPA-499 | CAUGGUAAUGGACAGAGUUAUCGAG | 51 | CUCGAUAACUCUGUCCAUUACCAUGGU | 451 |
| LPA-500 | AUGGUAAUGGACAGAGUUAACGAGG | 52 | CCUCGUUAACUCUGUCCAUUACCAUGG | 452 |
| LPA-501 | UGGUAAUGGACAGAGUUAUAGAGGC | 53 | GCCUCUAUAACUCUGUCCAUUACCAUG | 453 |
| LPA-502 | GGUAAUGGACAGAGUUAUCAAGGCA | 54 | UGCCUUGAUAACUCUGUCCAUUACCAU | 454 |

TABLE 5-continued

| | | | | |
|---|---|---|---|---|
| LPA-503 | GUAAUGGACAGAGUUAUCGAG GCAC | 55 | GUGCCUCGAUAACUCUGUCCAUUA CCA | 455 |
| LPA-523 | GGCACAUACUCCACCACUGAC ACAG | 56 | CUGUGUCAGUGGUGGAGUAUGUGC CUC | 456 |
| LPA-563 | CUUGGUCAUCUAUGACACCAC ACTC | 57 | GAGUGUGGUGUCAUAGAUGACCAA GCU | 457 |
| LPA-567 | GUCAUCUAUGACACCACACAC GCAT | 58 | AUGCGUGUGUGGUGUCAUAGAUGA CCA | 458 |
| LPA-568 | UCAUCUAUGACACCACACUAG CATA | 59 | UAUGCUAGUGUGGUGUCAUAGAUG ACC | 459 |
| LPA-569 | CAUCUAUGACACCACACUCAC AUAG | 60 | CUAUGUGAGUGUGGUGUCAUAGAU GAC | 460 |
| LPA-1208 | GCACAUACUCCACCACUGUAA CUGG | 61 | CCAGUUACAGUGGUGGAGUAUGUG CCU | 461 |
| LPA-2715 | AGCCCCUUAUUGUUAUACGAG GGAT | 62 | AUCCCUCGUAUAACAAUAAGGGGC UGC | 462 |
| LPA-2716 | GCCCCUUAUUGUUAUACGAAG GATC | 63 | GAUCCUUCGUAUAACAAUAAGGGG CUG | 463 |
| LPA-2827 | CCAAGCCUAGAGGCUCCUUAU GAAC | 64 | GUUCAUAAGGAGCCUCUAGGCUUG GAA | 464 |
| LPA-2837 | AGGCUCCUUCUGAACAAGCAC CAAC | 65 | GUUGGUGCUUGUUCAGAAGGAGCC UCU | 465 |
| LPA-2900 | AUGGACAGAGUUAUCAAGGAA CATA | 66 | UAUGUUCCUUGAUAACUCUGUCCA UUU | 466 |
| LPA-2901 | UGGACAGAGUUAUCAAGGCAC AUAC | 67 | GUAUGUGCCUUGAUAACUCUGUCC AUU | 467 |
| LPA-2902 | GGACAGAGUUAUCAAGGCAAA UACT | 68 | AGUAUUUGCCUUGAUAACUCUGUC CAU | 468 |
| LPA-2903 | GACAGAGUUAUCAAGGCACAU ACTT | 69 | AAGUAUGUGCCUUGAUAACUCUGU CCA | 469 |
| LPA-2904 | ACAGAGUUAUCAAGGCACAAA CUTC | 70 | GAAGUUUGUGCCUUGAUAACUCUG UCC | 470 |
| LPA-2905 | CAGAGUUAUCAAGGCACAUAC UUCA | 71 | UGAAGUAUGUGCCUUGAUAACUCU GUC | 471 |
| LPA-3004 | UACCCAAAUGCUGGCUUGAAC AAGA | 72 | UCUUGUUCAAGCCAGCAUUUGGGU AGU | 472 |
| LPA-3007 | CCAAAUGCUGGCUUGAUCAAG AACT | 73 | AGUUCUUGAUCAAGCCAGCAUUUG GGU | 473 |
| LPA-3023 | UCAAGAACUACUGCCGAAAAC CAGA | 74 | UCUGGUUUUCGGCAGUAGUUCUUG AUC | 474 |
| LPA-3024 | CAAGAACUACUGCCGAAAUAC AGAT | 75 | AUCUGUAUUUCGGCAGUAGUUCUU GAU | 475 |
| LPA-3025 | AAGAACUACUGCCGAAAUCAA GATC | 76 | GAUCUUGAUUUCGGCAGUAGUUCU UGA | 476 |
| LPA-3027 | GAACUACUGCCGAAAUCCAAA UCCT | 77 | AGGAUUUGGAUUUCGGCAGUAGUU CUU | 477 |
| LPA-3030 | CUACUGCCGAAAUCCAGAUAC UGTG | 78 | CACAGUAUCUGGAUUUCGGCAGUA GUU | 478 |
| LPA-3051 | UGUGGCAGCCCCUUGGUGUAA UACA | 79 | UGUAUUACACCAAGGGGCUGCCAC AGG | 479 |
| LPA-3052 | GUGGCAGCCCCUUGGUGUUAU ACAA | 80 | UUGUAUAACACCAAGGGGCUGCCA CAG | 480 |

TABLE 5-continued

| | | | | |
|---|---|---|---|---|
| LPA-3053 | UGGCAGCCCCUUGGUGUUAAA CAAC | 81 | GUUGUUUAACACCAAGGGGCUGCC ACA | 481 |
| LPA-3054 | GGCAGCCCCUUGGUGUUAUAC AACA | 82 | UGUUGUAUAACACCAAGGGGCUGC CAC | 482 |
| LPA-3055 | GCAGCCCCUUGGUGUUAUAAA ACAG | 83 | CUGUUUUAUAACACCAAGGGGCUG CCA | 483 |
| LPA-3056 | CAGCCCCUUGGUGUUAUACAA CAGA | 84 | UCUGUUGUAUAACACCAAGGGGCU GCC | 484 |
| LPA-3057 | AGCCCCUUGGUGUUAUACAAC AGAT | 85 | AUCUGUUGUAUAACACCAAGGGGC UGC | 485 |
| LPA-3058 | GCCCCUUGGUGUUAUACAAAA GATC | 86 | GAUCUUUUGUAUAACACCAAGGGG CUG | 486 |
| LPA-3059 | CCCCUUGGUGUUAUACAACAG AUCC | 87 | GGAUCUGUUGUAUAACACCAAGGG GCU | 487 |
| LPA-3092 | GGUGGGAGUACUGCAACCUAA CACG | 88 | CGUGUUAGGUUGCAGUACUCCCAC CUG | 488 |
| LPA-3093 | GUGGGAGUACUGCAACCUGAC ACGA | 89 | UCGUGUCAGGUUGCAGUACUCCCA CCU | 489 |
| LPA-3096 | GGAGUACUGCAACCUGACAAG AUGC | 90 | GCAUCUUGUCAGGUUGCAGUACUC CCA | 490 |
| LPA-3097 | GAGUACUGCAACCUGACACAA UGCT | 91 | AGCAUUGUGUCAGGUUGCAGUACU CCC | 491 |
| LPA-3099 | GUACUGCAACCUGACACGAAG CUCA | 92 | UGAGCUUCGUGUCAGGUUGCAGUA CUC | 492 |
| LPA-3100 | UACUGCAACCUGACACGAUAC UCAG | 93 | CUGAGUAUCGUGUCAGGUUGCAGU ACU | 493 |
| LPA-3101 | ACUGCAACCUGACACGAUGAU CAGA | 94 | UCUGAUCAUCGUGUCAGGUUGCAG UAC | 494 |
| LPA-3102 | CUGCAACCUGACACGAUGCAC AGAT | 95 | AUCUGUGCAUCGUGUCAGGUUGCA GUA | 495 |
| LPA-3103 | UGCAACCUGACACGAUGCUAA GATG | 96 | CAUCUUAGCAUCGUGUCAGGUUGC AGU | 496 |
| LPA-3105 | CAACCUGACACGAUGCUCAAA UGCA | 97 | UGCAUUUGAGCAUCGUGUCAGGUU GCA | 497 |
| LPA-3107 | ACCUGACACGAUGCUCAGAAG CAGA | 98 | UCUGCUUCUGAGCAUCGUGUCAGG UUG | 498 |
| LPA-3108 | CCUGACACGAUGCUCAGAUAC AGAA | 99 | UUCUGUAUCUGAGCAUCGUGUCAG GUU | 499 |
| LPA-3109 | CUGACACGAUGCUCAGAUGAA GAAT | 100 | AUUCUUCAUCUGAGCAUCGUGUCA GGU | 500 |
| LPA-3110 | UGACACGAUGCUCAGAUGCAG AATG | 101 | CAUUCUGCAUCUGAGCAUCGUGUC AGG | 501 |
| LPA-3111 | GACACGAUGCUCAGAUGCAAA AUGG | 102 | CCAUUUUGCAUCUGAGCAUCGUGU CAG | 502 |
| LPA-3112 | ACACGAUGCUCAGAUGCAGAA UGGA | 103 | UCCAUUCUGCAUCUGAGCAUCGUG UCA | 503 |
| LPA-3113 | CACGAUGCUCAGAUGCAGAAU GGAC | 104 | GUCCAUUCUGCAUCUGAGCAUCGU GUC | 504 |
| LPA-3229 | UGCUACUACCAUUAUGGACAG AGTT | 105 | AACUCUGUCCAUAAUGGUAGUAGC AGU | 505 |
| LPA-3230 | GCUACUACCAUUAUGGACAAA GUTA | 106 | UAACUUUGUCCAUAAUGGUAGUAG CAG | 506 |

TABLE 5-continued

| | | | | |
|---|---|---|---|---|
| LPA-3231 | CUACUACCAUUAUGGACAGAG UUAC | 107 | GUAACUCUGUCCAUAAUGGUAGUA GCA | 507 |
| LPA-3232 | UACUACCAUUAUGGACAGAAU UACC | 108 | GGUAAUUCUGUCCAUAAUGGUAGU AGC | 508 |
| LPA-3233 | ACUACCAUUAUGGACAGAGAU ACCG | 109 | CGGUAUCUCUGUCCAUAAUGGUAG UAG | 509 |
| LPA-3234 | CUACCAUUAUGGACAGAGUAA CCGA | 110 | UCGGUUACUCUGUCCAUAAUGGUA GUA | 510 |
| LPA-3235 | UACCAUUAUGGACAGAGUUAC CGAG | 111 | CUCGGUAACUCUGUCCAUAAUGGU AGU | 511 |
| LPA-3236 | ACCAUUAUGGACAGAGUUAAC GAGG | 112 | CCUCGUUAACUCUGUCCAUAAUGG UAG | 512 |
| LPA-3257 | GAGGCACAUACUCCACCACAG UCAC | 113 | GUGACUGUGGUGGAGUAUGUGCCU CGG | 513 |
| LPA-3267 | CUCCACCACUGUCACAGGAAG AACT | 114 | AGUUCUUCCUGUGACAGUGGUGGA GUA | 514 |
| LPA-3280 | ACAGGAAGAACUUGCCAAGAU UGGT | 115 | ACCAAUCUUGGCAAGUUCUUCCUG UGA | 515 |
| LPA-3281 | CAGGAAGAACUUGCCAAGCAU GGTC | 116 | GACCAUGCUUGGCAAGUUCUUCCU GUG | 516 |
| LPA-3282 | AGGAAGAACUUGCCAAGCUAG GUCA | 117 | UGACCUAGCUUGGCAAGUUCUUCC UGU | 517 |
| LPA-3283 | GGAAGAACUUGCCAAGCUUAG UCAT | 118 | AUGACUAAGCUUGGCAAGUUCUUC CUG | 518 |
| LPA-3284 | GAAGAACUUGCCAAGCUUGAU CATC | 119 | GAUGAUCAAGCUUGGCAAGUUCUU CCU | 519 |
| LPA-3285 | AAGAACUUGCCAAGCUUGGAC AUCT | 120 | AGAUGUCCAAGCUUGGCAAGUUCU UCC | 520 |
| LPA-3286 | AGAACUUGCCAAGCUUGGUAA UCTA | 121 | UAGAUUACCAAGCUUGGCAAGUUC UUC | 521 |
| LPA-3287 | GAACUUGCCAAGCUUGGUCAU CUAT | 122 | AUAGAUGACCAAGCUUGGCAAGUU CUU | 522 |
| LPA-3288 | AACUUGCCAAGCUUGGUCAAC UATG | 123 | CAUAGUUGACCAAGCUUGGCAAGU UCU | 523 |
| LPA-3289 | ACUUGCCAAGCUUGGUCAUAU AUGA | 124 | UCAUAUAUGACCAAGCUUGGCAAG UUC | 524 |
| LPA-3290 | CUUGCCAAGCUUGGUCAUCAA UGAC | 125 | GUCAUUGAUGACCAAGCUUGGCAA GUU | 525 |
| LPA-3291 | UUGCCAAGCUUGGUCAUCUAU GACA | 126 | UGUCAUAGAUGACCAAGCUUGGCA AGU | 526 |
| LPA-3292 | UGCCAAGCUUGGUCAUCUAAG ACAC | 127 | GUGUCUUAGAUGACCAAGCUUGGC AAG | 527 |
| LPA-3298 | GCUUGGUCAUCUAUGACACAA CACC | 128 | GGUGUUGUGUCAUAGAUGACCAAG CUU | 528 |
| LPA-3300 | UUGGUCAUCUAUGACACCAAA CCAG | 129 | CUGGUUUGGUGUCAUAGAUGACCA AGC | 529 |
| LPA-3301 | UGGUCAUCUAUGACACCACAC CAGC | 130 | GCUGGUGUGGUGUCAUAGAUGACC AAG | 530 |
| LPA-3303 | GUCAUCUAUGACACCACACAA GCAT | 131 | AUGCUUGUGUGGUGUCAUAGAUGA CCA | 531 |
| LPA-3305 | CAUCUAUGACACCACACCAAC AUAG | 132 | CUAUGUUGGUGUGGUGUCAUAGAU GAC | 532 |

TABLE 5-continued

| | | | | |
|---|---|---|---|---|
| LPA-3306 | AUCUAUGACACCACACCAGAA UAGT | 133 | ACUAUUCUGGUGUGGUGUCAUAGA UGA | 533 |
| LPA-3308 | CUAUGACACCACACCAGCAAA GUCG | 134 | CGACUUUGCUGGUGUGGUGUCAUA GAU | 534 |
| LPA-3329 | GUCGGACCCCAGAAAACUAAC CAAA | 135 | UUUGGUUAGUUUUCUGGGGUCCGA CUA | 535 |
| LPA-3330 | UCGGACCCCAGAAAACUACAC AAAT | 136 | AUUUGUGUAGUUUUCUGGGGUCCG ACU | 536 |
| LPA-3340 | GAAAACUACCCAAAUGCUGAC CUGA | 137 | UCAGGUCAGCAUUUGGGUAGUUUU CUG | 537 |
| LPA-3391 | GCUGAGAUUCGCCCUUGGUAU UACA | 138 | UGUAAUACCAAGGGCGAAUCUCAG CAU | 538 |
| LPA-3392 | CUGAGAUUCGCCCUUGGUGAU ACAC | 139 | GUGUAUCACCAAGGGCGAAUCUCA GCA | 539 |
| LPA-3394 | GAGAUUCGCCCUUGGUGUUAC ACCA | 140 | UGGUGUAACACCAAGGGCGAAUCU CAG | 540 |
| LPA-3395 | AGAUUCGCCCUUGGUGUUAAA CCAT | 141 | AUGGUUUAACACCAAGGGCGAAUC UCA | 541 |
| LPA-3398 | UUCGCCCUUGGUGUUACACAA UGGA | 142 | UCCAUUGUGUAACACCAAGGGCGA AUC | 542 |
| LPA-3404 | CUUGGUGUUACACCAUGGAAC CCAG | 143 | CUGGGUUCCAUGGUGUAACACCAA GGG | 543 |
| LPA-3405 | UUGGUGUUACACCAUGGAUAC CAGT | 144 | ACUGGUAUCCAUGGUGUAACACCA AGG | 544 |
| LPA-3406 | UGGUGUUACACCAUGGAUCAC AGTG | 145 | CACUGUGAUCCAUGGUGUAACACC AAG | 545 |
| LPA-3407 | GGUGUUACACCAUGGAUCCAA GUGT | 146 | ACACUUGGAUCCAUGGUGUAACAC CAA | 546 |
| LPA-3409 | UGUUACACCAUGGAUCCCAAU GUCA | 147 | UGACAUUGGGAUCCAUGGUGUAAC ACC | 547 |
| LPA-3472 | GAAUCAAGUGUCCUUGCAAAU CUCA | 148 | UGAGAUUUGCAAGGACACUUGAUU CUG | 548 |
| LPA-3473 | AAUCAAGUGUCCUUGCAACAC UCAC | 149 | GUGAGUGUUGCAAGGACACUUGAU UCU | 549 |
| LPA-3474 | AUCAAGUGUCCUUGCAACUAU CACG | 150 | CGUGAUAGUUGCAAGGACACUUGA UUC | 550 |
| LPA-3584 | AUGGACAGAGUUAUCGAGGAU CATT | 151 | AAUGAUCCUCGAUAACUCUGUCCA UCA | 551 |
| LPA-3585 | UGGACAGAGUUAUCGAGGCAC AUTC | 152 | GAAUGUGCCUCGAUAACUCUGUCC AUC | 552 |
| LPA-3655 | ACACCACACUGGCAUCAGAAG ACAA | 153 | UUGUCUUCUGAUGCCAGUGUGGUG UCA | 553 |
| LPA-3747 | UUGGUGUUAUACCAUGGAUAC CAAT | 154 | AUUGGUAUCCAUGGUAUAACACCA AGG | 554 |
| LPA-3748 | UGGUGUUAUACCAUGGAUCAC AATG | 155 | CAUUGUGAUCCAUGGUAUAACACC AAG | 555 |
| LPA-3749 | GGUGUUAUACCAUGGAUCCAA AUGT | 156 | ACAUUUGGAUCCAUGGUAUAACAC CAA | 556 |
| LPA-3750 | GUGUUAUACCAUGGAUCCCAA UGTC | 157 | GACAUUGGGAUCCAUGGUAUAACA CCA | 557 |
| LPA-3773 | UCAGAUGGGAGUACUGCAAAC UGAC | 158 | GUCAGUUUGCAGUACUCCCAUCUG ACA | 558 |

TABLE 5-continued

| | | | | |
|---|---|---|---|---|
| LPA-3776 | GAUGGGAGUACUGCAACCUAACACA | 159 | UGUGUUAGGUUGCAGUACUCCCAUCUG | 559 |
| LPA-3777 | AUGGGAGUACUGCAACCUGACACAA | 160 | UUGUGUCAGGUUGCAGUACUCCCAUCU | 560 |
| LPA-3778 | UGGGAGUACUGCAACCUGAAACAAT | 161 | AUUGUUUCAGGUUGCAGUACUCCCAUC | 561 |
| LPA-3779 | GGGAGUACUGCAACCUGACACAATG | 162 | CAUUGUGUCAGGUUGCAGUACUCCCAU | 562 |
| LPA-3840 | GGCUGUUUCUGAACAAGCAACAACG | 163 | CGUUGUUGCUUGUUCAGAAACAGCCGU | 563 |
| LPA-3844 | GUUUCUGAACAAGCACCAAAGGAGC | 164 | GCUCCUUUGGUGCUUGUUCAGAAACAG | 564 |
| LPA-3927 | CUCCACCACUGUUACAGGAAGGACA | 165 | UGUCCUUCCUGUAACAGUGGUGGAGAA | 565 |
| LPA-3928 | UCCACCACUGUUACAGGAAAGACAT | 166 | AUGUCUUUCCUGUAACAGUGGUGGAGA | 566 |
| LPA-3929 | CCACCACUGUUACAGGAAGAACATG | 167 | CAUGUUCUUCCUGUAACAGUGGUGGAG | 567 |
| LPA-3972 | GACACCACACUGGCAUCAGAGAACC | 168 | GGUUCUCUGAUGCCAGUGUGGUGUCAU | 568 |
| LPA-3973 | ACACCACACUGGCAUCAGAAAACCA | 169 | UGGUUUUCUGAUGCCAGUGUGGUGUCA | 569 |
| LPA-3999 | AGAAUACUACCCAAAUGGUAGCCTG | 170 | CAGGCUACCAUUUGGGUAGUAUUCUGU | 570 |
| LPA-4000 | GAAUACUACCCAAAUGGUGACCUGA | 171 | UCAGGUCACCAUUUGGGUAGUAUUCUG | 571 |
| LPA-4001 | AAUACUACCCAAAUGGUGGACUGAC | 172 | GUCAGUCCACCAUUUGGGUAGUAUUCU | 572 |
| LPA-4185 | UCCUUCUGAAGAAGCACCAACUGAA | 173 | UUCAGUUGGUGCUUCUUCAGAAGGAAG | 573 |
| LPA-4186 | CCUUCUGAAGAAGCACCAAAUGAAA | 174 | UUUCAUUUGGUGCUUCUUCAGAAGGAA | 574 |
| LPA-4187 | CUUCUGAAGAAGCACCAACAGAAAA | 175 | UUUUCUGUUGGUGCUUCUUCAGAAGGA | 575 |
| LPA-4188 | UUCUGAAGAAGCACCAACUAAAAAC | 176 | GUUUUUAGUUGGUGCUUCUUCAGAAGG | 576 |
| LPA-4189 | UCUGAAGAAGCACCAACUGAAAACA | 177 | UGUUUUCAGUUGGUGCUUCUUCAGAAG | 577 |
| LPA-4190 | CUGAAGAAGCACCAACUGAAAACAG | 178 | CUGUUUUCAGUUGGUGCUUCUUCAGAA | 578 |
| LPA-4191 | UGAAGAAGCACCAACUGAAAACAGC | 179 | GCUGUUUUCAGUUGGUGCUUCUUCAGA | 579 |
| LPA-4192 | GAAGAAGCACCAACUGAAAACAGCA | 180 | UGCUGUUUUCAGUUGGUGCUUCUUCAG | 580 |
| LPA-4193 | AAGAAGCACCAACUGAAAAAAGCAC | 181 | GUGCUUUUUUCAGUUGGUGCUUCUUCA | 581 |
| LPA-4194 | AGAAGCACCAACUGAAAACAGCACT | 182 | AGUGCUGUUUUCAGUUGGUGCUUCUUC | 582 |
| LPA-4195 | GAAGCACCAACUGAAAACAACACTG | 183 | CAGUGUUGUUUUCAGUUGGUGCUUCUU | 583 |
| LPA-4196 | AAGCACCAACUGAAAACAGAACUGG | 184 | CCAGUUCUGUUUUCAGUUGGUGCUUCU | 584 |

TABLE 5-continued

| | | | | |
|---|---|---|---|---|
| LPA-4239 | AGGUGAUGGACAGAGUUAUAG AGGC | 185 | GCCUCUAUAACUCUGUCCAUCACC UCG | 585 |
| LPA-4269 | CUCCACCACUAUCACAGGAAG AACA | 186 | UGUUCUUCCUGUGAUAGUGGUGGA GAG | 586 |
| LPA-4270 | UCCACCACUAUCACAGGAAAA ACAT | 187 | AUGUUUUUCCUGUGAUAGUGGUGG AGA | 587 |
| LPA-4271 | CCACCACUAUCACAGGAAGAA CATG | 188 | CAUGUUCUUCCUGUGAUAGUGGUG GAG | 588 |
| LPA-4272 | CACCACUAUCACAGGAAGAAC AUGT | 189 | ACAUGUUCUUCCUGUGAUAGUGGU GGA | 589 |
| LPA-4273 | ACCACUAUCACAGGAAGAAAA UGTC | 190 | GACAUUUUCUUCCUGUGAUAGUGG UGG | 590 |
| LPA-4274 | CCACUAUCACAGGAAGAACAU GUCA | 191 | UGACAUGUUCUUCCUGUGAUAGUG GUG | 591 |
| LPA-4275 | CACUAUCACAGGAAGAACAAG UCAG | 192 | CUGACUUGUUCUUCCUGUGAUAGU GGU | 592 |
| LPA-4276 | ACUAUCACAGGAAGAACAUAU CAGT | 193 | ACUGAUAUGUUCUUCCUGUGAUAG UGG | 593 |
| LPA-4277 | CUAUCACAGGAAGAACAUGAC AGTC | 194 | GACUGUCAUGUUCUUCCUGUGAUA GUG | 594 |
| LPA-4278 | UAUCACAGGAAGAACAUGUAA GUCT | 195 | AGACUUACAUGUUCUUCCUGUGAU AGU | 595 |
| LPA-4279 | AUCACAGGAAGAACAUGUCAG UCTT | 196 | AAGACUGACAUGUUCUUCCUGUGA UAG | 596 |
| LPA-4280 | UCACAGGAAGAACAUGUCAAU CUTG | 197 | CAAGAUUGACAUGUUCUUCCUGUG AUA | 597 |
| LPA-4281 | CACAGGAAGAACAUGUCAGAC UUGG | 198 | CCAAGUCUGACAUGUUCUUCCUGU GAU | 598 |
| LPA-4282 | ACAGGAAGAACAUGUCAGUAU UGGT | 199 | ACCAAUACUGACAUGUUCUUCCUG UGA | 599 |
| LPA-4285 | GGAAGAACAUGUCAGUCUUAG UCGT | 200 | ACGACUAAGACUGACAUGUUCUUC CUG | 600 |
| LPA-4286 | GAAGAACAUGUCAGUCUUGAU CGTC | 201 | GACGAUCAAGACUGACAUGUUCUU CCU | 601 |
| LPA-4287 | AAGAACAUGUCAGUCUUGGAC GUCT | 202 | AGACGUCCAAGACUGACAUGUUCU UCC | 602 |
| LPA-4288 | AGAACAUGUCAGUCUUGGUAG UCTA | 203 | UAGACUACCAAGACUGACAUGUUC UUC | 603 |
| LPA-4325 | GGCAUCGGAGGAUCCCAUUAU ACTA | 204 | UAGUAUAAUGGGAUCCUCCGAUGC CAA | 604 |
| LPA-4346 | ACUAUCCAAAUGCUGGCCUAA CCAG | 205 | CUGGUUAGGCCAGCAUUUGGAUAG UAU | 605 |
| LPA-4517 | GCACAGAGGCUCCUUCUGAAC AAGC | 206 | GCUUGUUCAGAAGGAGCCUCUGUG CUU | 606 |
| LPA-4527 | UCCUUCUGAACAAGCACCAAC UGAG | 207 | CUCAGUUGGUGCUUGUUCAGAAGG AGC | 607 |
| LPA-4528 | CCUUCUGAACAAGCACCACAU GAGA | 208 | UCUCAUGUGGUGCUUGUUCAGAAG GAG | 608 |
| LPA-4529 | CUUCUGAACAAGCACCACCAG AGAA | 209 | UUCUCUGGUGGUGCUUGUUCAGAA GGA | 609 |
| LPA-4530 | UUCUGAACAAGCACCACCUAA GAAA | 210 | UUUCUUAGGUGGUGCUUGUUCAGA AGG | 610 |

TABLE 5-continued

| | | | | |
|---|---|---|---|---|
| LPA-4531 | UCUGAACAAGCACCACCUGAGAAAA | 211 | UUUUCUCAGGUGGUGCUUGUUCAGAAG | 611 |
| LPA-4532 | CUGAACAAGCACCACCUGAAAAAAG | 212 | CUUUUUUCAGGUGGUGCUUGUUCAGAA | 612 |
| LPA-4533 | UGAACAAGCACCACCUGAGAAAAGC | 213 | GCUUUUCUCAGGUGGUGCUUGUUCAGA | 613 |
| LPA-4534 | GAACAAGCACCACCUGAGAAAAGCC | 214 | GGCUUUUCUCAGGUGGUGCUUGUUCAG | 614 |
| LPA-4535 | AACAAGCACCACCUGAGAAAAGCCC | 215 | GGGCUUUUCUCAGGUGGUGCUUGUUCA | 615 |
| LPA-4537 | CAAGCACCACCUGAGAAAAACCCTG | 216 | CAGGGUUUUUCUCAGGUGGUGCUUGUU | 616 |
| LPA-4538 | AAGCACCACCUGAGAAAAGACCUGT | 217 | ACAGGUCUUUUCUCAGGUGGUGCUUGU | 617 |
| LPA-4539 | AGCACCACCUGAGAAAAGCACUGTG | 218 | CACAGUGCUUUUCUCAGGUGGUGCUUG | 618 |
| LPA-4547 | CUGAGAAAAGCCCUGUGGUACAGGA | 219 | UCCUGUACCACAGGGCUUUUCUCAGGU | 619 |
| LPA-4556 | GCCCUGUGGUCCAGGAUUGAUACCA | 220 | UGGUAUCAAUCCUGGACCACAGGGCUU | 620 |
| LPA-4559 | CUGUGGUCCAGGAUUGCUAACAUGG | 221 | CCAUGUUAGCAAUCCUGGACCACAGGG | 621 |
| LPA-4611 | CUCCACCACUGUCACAGGAAGGACC | 222 | GGUCCUUCCUGUGACAGUGGUGGAGGA | 622 |
| LPA-4612 | UCCACCACUGUCACAGGAAAGACCT | 223 | AGGUCUUUCCUGUGACAGUGGUGGAGG | 623 |
| LPA-4642 | UCUUGGUCAUCUAUGAUACAACACT | 224 | AGUGUUGUAUCAUAGAUGACCAAGAUU | 624 |
| LPA-4643 | CUUGGUCAUCUAUGAUACCACACTG | 225 | CAGUGUGGUAUCAUAGAUGACCAAGAU | 625 |
| LPA-4644 | UUGGUCAUCUAUGAUACCAAACUGG | 226 | CCAGUUUGGUAUCAUAGAUGACCAAGA | 626 |
| LPA-4645 | UGGUCAUCUAUGAUACCACACUGGC | 227 | GCCAGUGUGGUAUCAUAGAUGACCAAG | 627 |
| LPA-4646 | GGUCAUCUAUGAUACCACAAUGGCA | 228 | UGCCAUUGUGGUAUCAUAGAUGACCAA | 628 |
| LPA-4647 | GUCAUCUAUGAUACCACACAGGCAT | 229 | AUGCCUGUGUGGUAUCAUAGAUGACCA | 629 |
| LPA-4648 | UCAUCUAUGAUACCACACUAGCATC | 230 | GAUGCUAGUGUGGUAUCAUAGAUGACC | 630 |
| LPA-4649 | CAUCUAUGAUACCACACUGACAUCA | 231 | UGAUGUCAGUGUGGUAUCAUAGAUGAC | 631 |
| LPA-4650 | AUCUAUGAUACCACACUGGAAUCAG | 232 | CUGAUUCCAGUGUGGUAUCAUAGAUGA | 632 |
| LPA-4651 | UCUAUGAUACCACACUGGCAUCAGA | 233 | UCUGAUGCCAGUGUGGUAUCAUAGAUG | 633 |
| LPA-4652 | CUAUGAUACCACACUGGCAACAGAG | 234 | CUCUGUUGCCAGUGUGGUAUCAUAGAU | 634 |
| LPA-4655 | UGAUACCACACUGGCAUCAAAGGAC | 235 | GUCCUUUGAUGCCAGUGUGGUAUCAUA | 635 |
| LPA-4657 | AUACCACACUGGCAUCAGAAGACCC | 236 | GGGUCUUCUGAUGCCAGUGUGGUAUCA | 636 |

TABLE 5-continued

| | | | | |
|---|---|---|---|---|
| LPA-4673 | AGAGGACCCCAGAAAACUAACCAAA | 237 | UUUGGUUAGUUUUCUGGGGUCCUCUGA | 637 |
| LPA-4674 | GAGGACCCCAGAAAACUACACAAAT | 238 | AUUUGUGUAGUUUUCUGGGGUCCUCUG | 638 |
| LPA-4712 | AGAACUACUGCAGGAAUCCAGAUTC | 239 | GAAUCUGGAUUCCUGCAGUAGUUCUCG | 639 |
| LPA-4715 | ACUACUGCAGGAAUCCAGAAUCUGG | 240 | CCAGAUUCUGGAUUCCUGCAGUAGUUC | 640 |
| LPA-4717 | UACUGCAGGAAUCCAGAUUAUGGGA | 241 | UCCCAUAAUCUGGAUUCCUGCAGUAGU | 641 |
| LPA-4718 | ACUGCAGGAAUCCAGAUUCAGGGAA | 242 | UUCCCUGAAUCUGGAUUCCUGCAGUAG | 642 |
| LPA-4719 | CUGCAGGAAUCCAGAUUCUAGGAAA | 243 | UUUCCUAGAAUCUGGAUUCCUGCAGUA | 643 |
| LPA-4720 | UGCAGGAAUCCAGAUUCUGAGAAAC | 244 | GUUUCUCAGAAUCUGGAUUCCUGCAGU | 644 |
| LPA-4721 | GCAGGAAUCCAGAUUCUGGAAAACA | 245 | UGUUUUCCAGAAUCUGGAUUCCUGCAG | 645 |
| LPA-4724 | GGAAUCCAGAUUCUGGGAAACAACC | 246 | GGUUGUUUCCCAGAAUCUGGAUUCCUG | 646 |
| LPA-4738 | GGGAAACAACCCUGGUGUUACACAA | 247 | UUGUGUAACACCAGGGUUGUUUCCCAG | 647 |
| LPA-4739 | GGAAACAACCCUGGUGUUAAACAAC | 248 | GUUGUUUAACACCAGGGUUGUUUCCCA | 648 |
| LPA-4771 | UGUGUGAGGUGGGAGUACUACAATC | 249 | GAUUGUAGUACUCCCACCUCACACACG | 649 |
| LPA-4772 | GUGUGAGGUGGGAGUACUGAAAUCT | 250 | AGAUUUCAGUACUCCCACCUCACACAC | 650 |
| LPA-4774 | GUGAGGUGGGAGUACUGCAAUCUGA | 251 | UCAGAUUGCAGUACUCCCACCUCACAC | 651 |
| LPA-4775 | UGAGGUGGGAGUACUGCAAACUGAC | 252 | GUCAGUUUGCAGUACUCCCACCUCACA | 652 |
| LPA-4795 | CUGACACAAUGCUCAGAAAAAGAAT | 253 | AUUCUUUUUCUGAGCAUUGUGUCAGAU | 653 |
| LPA-4796 | UGACACAAUGCUCAGAAACAGAATC | 254 | GAUUCUGUUUCUGAGCAUUGUGUCAGA | 654 |
| LPA-4797 | GACACAAUGCUCAGAAACAAAAUCA | 255 | UGAUUUUGUUUCUGAGCAUUGUGUCAG | 655 |
| LPA-4798 | ACACAAUGCUCAGAAACAGAAUCAG | 256 | CUGAUUCUGUUUCUGAGCAUUGUGUCA | 656 |
| LPA-4799 | CACAAUGCUCAGAAACAGAAUCAGG | 257 | CCUGAUUCUGUUUCUGAGCAUUGUGUC | 657 |
| LPA-4800 | ACAAUGCUCAGAAACAGAAACAGGT | 258 | ACCUGUUUCUGUUUCUGAGCAUUGUGU | 658 |
| LPA-4801 | CAAUGCUCAGAAACAGAAUAAGGTG | 259 | CACCUUAUUCUGUUUCUGAGCAUUGUG | 659 |
| LPA-4802 | AAUGCUCAGAAACAGAAUCAGGUGT | 260 | ACACCUGAUUCUGUUUCUGAGCAUUGU | 660 |
| LPA-4803 | AUGCUCAGAAACAGAAUCAAGUGTC | 261 | GACACUUGAUUCUGUUUCUGAGCAUUG | 661 |
| LPA-4804 | UGCUCAGAAACAGAAUCAGAUGUCC | 262 | GGACAUCUGAUUCUGUUUCUGAGCAUU | 662 |

TABLE 5-continued

| | | | | |
|---|---|---|---|---|
| LPA-4806 | CUCAGAAACAGAAUCAGGUAUCCTA | 263 | UAGGAUACCUGAUUCUGUUUCUGAGCA | 663 |
| LPA-4808 | CAGAAACAGAAUCAGGUGUACUAGA | 264 | UCUAGUACACCUGAUUCUGUUUCUGAG | 664 |
| LPA-4809 | AGAAACAGAAUCAGGUGUCAUAGAG | 265 | CUCUAUGACACCUGAUUCUGUUUCUGA | 665 |
| LPA-4810 | GAAACAGAAUCAGGUGUCCAAGAGA | 266 | UCUCUUGGACACCUGAUUCUGUUUCUG | 666 |
| LPA-4811 | AAACAGAAUCAGGUGUCCUAGAGAC | 267 | GUCUCUAGGACACCUGAUUCUGUUUCU | 667 |
| LPA-4812 | AACAGAAUCAGGUGUCCUAAAGACT | 268 | AGUCUUUAGGACACCUGAUUCUGUUUC | 668 |
| LPA-4814 | CAGAAUCAGGUGUCCUAGAAACUCC | 269 | GGAGUUUCUAGGACACCUGAUUCUGUU | 669 |
| LPA-4816 | GAAUCAGGUGUCCUAGAGAAUCCCA | 270 | UGGGAUUCUCUAGGACACCUGAUUCUG | 670 |
| LPA-4818 | AUCAGGUGUCCUAGAGACUACCACT | 271 | AGUGGUAGUCUCUAGGACACCUGAUUC | 671 |
| LPA-4822 | GGUGUCCUAGAGACUCCCAAUGUTG | 272 | CAACAUUGGGAGUCUCUAGGACACCUG | 672 |
| LPA-4827 | CCUAGAGACUCCCACUGUUAUUCCA | 273 | UGGAAUAACAGUGGGAGUCUCUAGGAC | 673 |
| LPA-4828 | CUAGAGACUCCCACUGUUGAUCCAG | 274 | CUGGAUCAACAGUGGGAGUCUCUAGGA | 674 |
| LPA-4829 | UAGAGACUCCCACUGUUGUACCAGT | 275 | ACUGGUACAACAGUGGGAGUCUCUAGG | 675 |
| LPA-4830 | AGAGACUCCCACUGUUGUUACAGTT | 276 | AACUGUAACAACAGUGGGAGUCUCUAG | 676 |
| LPA-4831 | GAGACUCCCACUGUUGUUCAAGUTC | 277 | GAACUUGAACAACAGUGGGAGUCUCUA | 677 |
| LPA-4832 | AGACUCCCACUGUUGUUCCAGUUCC | 278 | GGAACUGGAACAACAGUGGGAGUCUCU | 678 |
| LPA-4867 | GCUCAUUCUGAAGCAGCACAAACTG | 279 | CAGUUUGUGCUGCUUCAGAAUGAGCCU | 679 |
| LPA-4868 | CUCAUUCUGAAGCAGCACCAACUGA | 280 | UCAGUUGGUGCUGCUUCAGAAUGAGCC | 680 |
| LPA-4869 | UCAUUCUGAAGCAGCACCAACUGAG | 281 | CUCAGUUGGUGCUGCUUCAGAAUGAGC | 681 |
| LPA-4870 | CAUUCUGAAGCAGCACCAAAUGAGC | 282 | GCUCAUUUGGUGCUGCUUCAGAAUGAG | 682 |
| LPA-4871 | AUUCUGAAGCAGCACCAACAGAGCA | 283 | UGCUCUGUUGGUGCUGCUUCAGAAUGA | 683 |
| LPA-4872 | UUCUGAAGCAGCACCAACUAAGCAA | 284 | UUGCUUAGUUGGUGCUGCUUCAGAAUG | 684 |
| LPA-4873 | UCUGAAGCAGCACCAACUGAGCAAA | 285 | UUUGCUCAGUUGGUGCUGCUUCAGAAU | 685 |
| LPA-4874 | CUGAAGCAGCACCAACUGAACAAAC | 286 | GUUUGUUCAGUUGGUGCUGCUUCAGAA | 686 |
| LPA-4875 | UGAAGCAGCACCAACUGAGAAAACC | 287 | GGUUUUCUCAGUUGGUGCUGCUUCAGA | 687 |
| LPA-4876 | GAAGCAGCACCAACUGAGCAAACCC | 288 | GGGUUUGCUCAGUUGGUGCUGCUUCAG | 688 |

TABLE 5-continued

| | | | | |
|---|---|---|---|---|
| LPA-4877 | AAGCAGCACCAACUGAGCAAACCCC | 289 | GGGGUUUGCUCAGUUGGUGCUGCUUCA | 689 |
| LPA-4912 | CAGUGCUACCAUGGUAAUGACCAGA | 290 | UCUGGUCAUUACCAUGGUAGCACUGCC | 690 |
| LPA-4913 | AGUGCUACCAUGGUAAUGGACAGAG | 291 | CUCUGUCCAUUACCAUGGUAGCACUGC | 691 |
| LPA-4948 | ACAUUCUCCACCACUGUCAAAGGAA | 292 | UUCCUUUGACAGUGGUGGAGAAUGUGC | 692 |
| LPA-4959 | CACUGUCACAGGAAGGACAAGUCAA | 293 | UUGACUUGUCCUUCCUGUGACAGUGGU | 693 |
| LPA-4960 | ACUGUCACAGGAAGGACAUAUCAAT | 294 | AUUGAUAUGUCCUUCCUGUGACAGUGG | 694 |
| LPA-4961 | CUGUCACAGGAAGGACAUGACAATC | 295 | GAUUGUCAUGUCCUUCCUGUGACAGUG | 695 |
| LPA-4962 | UGUCACAGGAAGGACAUGUAAAUCT | 296 | AGAUUUACAUGUCCUUCCUGUGACAGU | 696 |
| LPA-4963 | GUCACAGGAAGGACAUGUCAAUCTT | 297 | AAGAUUGACAUGUCCUUCCUGUGACAG | 697 |
| LPA-4964 | UCACAGGAAGGACAUGUCAAUCUTG | 298 | CAAGAUUGACAUGUCCUUCCUGUGACA | 698 |
| LPA-4966 | ACAGGAAGGACAUGUCAAUAUUGGT | 299 | ACCAAUAUUGACAUGUCCUUCCUGUGA | 699 |
| LPA-4967 | CAGGAAGGACAUGUCAAUCAUGGTC | 300 | GACCAUGAUUGACAUGUCCUUCCUGUG | 700 |
| LPA-4968 | AGGAAGGACAUGUCAAUCUAGGUCA | 301 | UGACCUAGAUUGACAUGUCCUUCCUGU | 701 |
| LPA-4969 | GGAAGGACAUGUCAAUCUUAGUCAT | 302 | AUGACUAAGAUUGACAUGUCCUUCCUG | 702 |
| LPA-4970 | GAAGGACAUGUCAAUCUUGAUCATC | 303 | GAUGAUCAAGAUUGACAUGUCCUUCCU | 703 |
| LPA-4971 | AAGGACAUGUCAAUCUUGGACAUCC | 304 | GGAUGUCCAAGAUUGACAUGUCCUUCC | 704 |
| LPA-4972 | AGGACAUGUCAAUCUUGGUAAUCCA | 305 | UGGAUUACCAAGAUUGACAUGUCCUUC | 705 |
| LPA-4973 | GGACAUGUCAAUCUUGGUCAUCCAT | 306 | AUGGAUGACCAAGAUUGACAUGUCCUU | 706 |
| LPA-4974 | GACAUGUCAAUCUUGGUCAACCATG | 307 | CAUGGUUGACCAAGAUUGACAUGUCCU | 707 |
| LPA-4975 | ACAUGUCAAUCUUGGUCAUACAUGA | 308 | UCAUGUAUGACCAAGAUUGACAUGUCC | 708 |
| LPA-4976 | CAUGUCAAUCUUGGUCAUCAAUGAC | 309 | GUCAUUGAUGACCAAGAUUGACAUGUC | 709 |
| LPA-4977 | AUGUCAAUCUUGGUCAUCCAUGACA | 310 | UGUCAUGGAUGACCAAGAUUGACAUGU | 710 |
| LPA-4978 | UGUCAAUCUUGGUCAUCCAAGACAC | 311 | GUGUCUUGGAUGACCAAGAUUGACAUG | 711 |
| LPA-4979 | GUCAAUCUUGGUCAUCCAUAACACC | 312 | GGUGUUAUGGAUGACCAAGAUUGACAU | 712 |
| LPA-4980 | UCAAUCUUGGUCAUCCAUGACACCA | 313 | UGGUGUCAUGGAUGACCAAGAUUGACA | 713 |
| LPA-4981 | CAAUCUUGGUCAUCCAUGAAACCAC | 314 | GUGGUUUCAUGGAUGACCAAGAUUGAC | 714 |

TABLE 5-continued

| | | | | |
|---|---|---|---|---|
| LPA-4982 | AAUCUUGGUCAUCCAUGACACCACA | 315 | UGUGGUGUCAUGGAUGACCAAGAUUGA | 715 |
| LPA-4983 | AUCUUGGUCAUCCAUGACAACACAC | 316 | GUGUGUUGUCAUGGAUGACCAAGAUUG | 716 |
| LPA-5048 | UGACAAUGAACUACUGCAGAAAUCC | 317 | GGAUUUCUGCAGUAGUUCAUUGUCAGG | 717 |
| LPA-5049 | GACAAUGAACUACUGCAGGAAUCCA | 318 | UGGAUUCCUGCAGUAGUUCAUUGUCAG | 718 |
| LPA-5050 | ACAAUGAACUACUGCAGGAAUCCAG | 319 | CUGGAUUCCUGCAGUAGUUCAUUGUCA | 719 |
| LPA-5051 | CAAUGAACUACUGCAGGAAACCAGA | 320 | UCUGGUUUCCUGCAGUAGUUCAUUGUC | 720 |
| LPA-5052 | AAUGAACUACUGCAGGAAUACAGAT | 321 | AUCUGUAUUCCUGCAGUAGUUCAUUGU | 721 |
| LPA-5053 | AUGAACUACUGCAGGAAUCAAGATG | 322 | CAUCUUGAUUCCUGCAGUAGUUCAUUG | 722 |
| LPA-5054 | UGAACUACUGCAGGAAUCCAGAUGC | 323 | GCAUCUGGAUUCCUGCAGUAGUUCAUU | 723 |
| LPA-5058 | CUACUGCAGGAAUCCAGAUACCGAT | 324 | AUCGGUAUCUGGAUUCCUGCAGUAGUU | 724 |
| LPA-5084 | CAGGCCCUUGGUGUUUUACAAUGGA | 325 | UCCAUUGUAAAACACCAAGGGCCUGUA | 725 |
| LPA-5090 | CUUGGUGUUUUACCAUGGAACCCAG | 326 | CUGGGUUCCAUGGUAAAACACCAAGGG | 726 |
| LPA-5091 | UUGGUGUUUUACCAUGGACACCAGC | 327 | GCUGGUGUCCAUGGUAAAACACCAAGG | 727 |
| LPA-5092 | UGGUGUUUUACCAUGGACCACAGCA | 328 | UGCUGUGGUCCAUGGUAAAACACCAAG | 728 |
| LPA-5093 | GGUGUUUUACCAUGGACCCAAGCAT | 329 | AUGCUUGGGUCCAUGGUAAAACACCAA | 729 |
| LPA-5094 | GUGUUUUACCAUGGACCCCAGCATC | 330 | GAUGCUGGGGUCCAUGGUAAAACACCA | 730 |
| LPA-5096 | GUUUUACCAUGGACCCCAGAAUCAG | 331 | CUGAUUCUGGGGUCCAUGGUAAAACAC | 731 |
| LPA-5124 | GGAGUACUGCAACCUGACGAGAUGC | 332 | GCAUCUCGUCAGGUUGCAGUACUCCCA | 732 |
| LPA-5125 | GAGUACUGCAACCUGACGCAAUGCT | 333 | AGCAUUGCGUCAGGUUGCAGUACUCCC | 733 |
| LPA-5127 | GUACUGCAACCUGACGCGAAGCUCA | 334 | UGAGCUUCGCGUCAGGUUGCAGUACUC | 734 |
| LPA-5128 | UACUGCAACCUGACGCGAUACUCAG | 335 | CUGAGUAUCGCGUCAGGUUGCAGUACU | 735 |
| LPA-5131 | UGCAACCUGACGCGAUGCUAAGACA | 336 | UGUCUUAGCAUCGCGUCAGGUUGCAGU | 736 |
| LPA-5136 | CCUGACGCGAUGCUCAGACACAGAA | 337 | UUCUGUGUCUGAGCAUCGCGUCAGGUU | 737 |
| LPA-5137 | CUGACGCGAUGCUCAGACAAAGAAG | 338 | CUUCUUUGUCUGAGCAUCGCGUCAGGU | 738 |
| LPA-5144 | GAUGCUCAGACACAGAAGGAACUGT | 339 | ACAGUUCCUUCUGUGUCUGAGCAUCGC | 739 |
| LPA-5145 | AUGCUCAGACACAGAAGGGACUGTG | 340 | CACAGUCCCUUCUGUGUCUGAGCAUCG | 740 |

TABLE 5-continued

| | | | | |
|---|---|---|---|---|
| LPA-5151 | AGACACAGAAGGGACUGUGAUCGCT | 341 | AGCGAUCACAGUCCCUUCUGUGUCUGA | 741 |
| LPA-5467 | GCAUCCUCUUCAUUUGAUUAUGGGA | 342 | UCCCAUAAUCAAAUGAAGAGGAUGCAC | 742 |
| LPA-5468 | CAUCCUCUUCAUUUGAUUGAGGGAA | 343 | UUCCCUCAAUCAAAUGAAGAGGAUGCA | 743 |
| LPA-5469 | AUCCUCUUCAUUUGAUUGUAGGAAG | 344 | CUUCCUACAAUCAAAUGAAGAGGAUGC | 744 |
| LPA-5470 | UCCUCUUCAUUUGAUUGUGAGAAGC | 345 | GCUUCUCACAAUCAAAUGAAGAGGAUG | 745 |
| LPA-5471 | CCUCUUCAUUUGAUUGUGGAAAGCC | 346 | GGCUUUCCACAAUCAAAUGAAGAGGAU | 746 |
| LPA-5474 | CUUCAUUUGAUUGUGGGAAACCUCA | 347 | UGAGGUUUCCCACAAUCAAAUGAAGAG | 747 |
| LPA-5475 | UUCAUUUGAUUGUGGGAAGACUCAA | 348 | UUGAGUCUUCCCACAAUCAAAUGAAGA | 748 |
| LPA-5476 | UCAUUUGAUUGUGGGAAGCAUCAAG | 349 | CUUGAUGCUUCCCACAAUCAAAUGAAG | 749 |
| LPA-5477 | CAUUUGAUUGUGGGAAGCCACAAGT | 350 | ACUUGUGGCUUCCCACAAUCAAAUGAA | 750 |
| LPA-5478 | AUUUGAUUGUGGGAAGCCUAAAGTG | 351 | CACUUUAGGCUUCCCACAAUCAAAUGA | 751 |
| LPA-5486 | GUGGGAAGCCUCAAGUGGAACCGAA | 352 | UUCGGUUCCACUUGAGGCUUCCCACAA | 752 |
| LPA-5509 | AAGAAAUGUCCUGGAAGCAAUGUAG | 353 | CUACAUUGCUUCCAGGACAUUUCUUCG | 753 |
| LPA-5510 | AGAAAUGUCCUGGAAGCAUAGUAGG | 354 | CCUACUAUGCUUCCAGGACAUUUCUUC | 754 |
| LPA-5511 | GAAAUGUCCUGGAAGCAUUAUAGGG | 355 | CCCUAUAAUGCUUCCAGGACAUUUCUU | 755 |
| LPA-5513 | AAUGUCCUGGAAGCAUUGUAGGGGG | 356 | CCCCCUACAAUGCUUCCAGGACAUUUC | 756 |
| LPA-5514 | AUGUCCUGGAAGCAUUGUAAGGGGG | 357 | CCCCCUUACAAUGCUUCCAGGACAUUU | 757 |
| LPA-5581 | AGAACAAGGUUUGGAAAGCACUUCT | 358 | AGAAGUGCUUUCCAAACCUUGUUCUGA | 758 |
| LPA-5582 | GAACAAGGUUUGGAAAGCAAUUCTG | 359 | CAGAAUUGCUUUCCAAACCUUGUUCUG | 759 |
| LPA-5583 | AACAAGGUUUGGAAAGCACAUCUGT | 360 | ACAGAUGUGCUUUCCAAACCUUGUUCU | 760 |
| LPA-5584 | ACAAGGUUUGGAAAGCACUACUGTG | 361 | CACAGUAGUGCUUUCCAAACCUUGUUC | 761 |
| LPA-5585 | CAAGGUUUGGAAAGCACUUAUGUGG | 362 | CCACAUAAGUGCUUUCCAAACCUUGUU | 762 |
| LPA-5586 | AAGGUUUGGAAAGCACUUCAGUGGA | 363 | UCCACUGAAGUGCUUUCCAAACCUUGU | 763 |
| LPA-5587 | AGGUUUGGAAAGCACUUCUAUGGAG | 364 | CUCCAUAGAAGUGCUUUCCAAACCUUG | 764 |
| LPA-5592 | UGGAAAGCACUUCUGUGGAAGCACC | 365 | GGUGCUUCCACAGAAGUGCUUUCCAAA | 765 |
| LPA-5606 | GUGGAGGCACCUUAAUAUCACCAGA | 366 | UCUGGUGAUAUUAAGGUGCCUCCACAG | 766 |

TABLE 5-continued

| | | | | |
|---|---|---|---|---|
| LPA-5616 | CUUAAUAUCCCCAGAGUGGAUGCTG | 367 | CAGCAUCCACUCUGGGGAUAUUAAGGU | 767 |
| LPA-5618 | UAAUAUCCCCAGAGUGGGUACUGAC | 368 | GUCAGUACCCACUCUGGGGAUAUUAAG | 768 |
| LPA-5628 | AGAGUGGGUGCUGACUGCUACUCAC | 369 | GUGAGUAGCAGUCAGCACCCACUCUGG | 769 |
| LPA-5685 | CAAGGUCAUCCUGGGUGCAAACCAA | 370 | UUGGUUUGCACCCAGGAUGACCUUGUA | 770 |
| LPA-5694 | CCUGGGUGCACACCAAGAAAUGAAC | 371 | GUUCAUUUCUUGGUGUGCACCCAGGAU | 771 |
| LPA-5699 | GUGCACACCAAGAAGUGAAACUCGA | 372 | UCGAGUUUCACUUCUUGGUGUGCACCC | 772 |
| LPA-5775 | AGCAGAUAUUGCCUUGCUAAAGCTA | 373 | UAGCUUUAGCAAGGCAAUAUCUGCUUG | 773 |
| LPA-5776 | GCAGAUAUUGCCUUGCUAAAGCUAA | 374 | UUAGCUUUAGCAAGGCAAUAUCUGCUU | 774 |
| LPA-5777 | CAGAUAUUGCCUUGCUAAAACUAAG | 375 | CUUAGUUUUAGCAAGGCAAUAUCUGCU | 775 |
| LPA-5778 | AGAUAUUGCCUUGCUAAAGAUAAGC | 376 | GCUUAUCUUUAGCAAGGCAAUAUCUGC | 776 |
| LPA-5779 | GAUAUUGCCUUGCUAAAGCAAAGCA | 377 | UGCUUUGCUUUAGCAAGGCAAUAUCUG | 777 |
| LPA-5780 | AUAUUGCCUUGCUAAAGCUAAGCAG | 378 | CUGCUUAGCUUUAGCAAGGCAAUAUCU | 778 |
| LPA-5781 | UAUUGCCUUGCUAAAGCUAAGCAGG | 379 | CCUGCUUAGCUUUAGCAAGGCAAUAUC | 779 |
| LPA-5813 | UCAUCACUGACAAAGUAAUACCAGC | 380 | GCUGGUAUUACUUUGUCAGUGAUGACG | 780 |
| LPA-5873 | GGACUGAAUGUUACAUCACAGGCTG | 381 | CAGCCUGUGAUGUAACAUUCAGUCCUG | 781 |
| LPA-5874 | GACUGAAUGUUACAUCACUAGCUGG | 382 | CCAGCUAGUGAUGUAACAUUCAGUCCU | 782 |
| LPA-5875 | ACUGAAUGUUACAUCACUGACUGGG | 383 | CCCAGUCAGUGAUGUAACAUUCAGUCC | 783 |
| LPA-5876 | CUGAAUGUUACAUCACUGGAUGGGG | 384 | CCCCAUCCAGUGAUGUAACAUUCAGUC | 784 |
| LPA-5877 | UGAAUGUUACAUCACUGGCAGGGGA | 385 | UCCCCUGCCAGUGAUGUAACAUUCAGU | 785 |
| LPA-5879 | AAUGUUACAUCACUGGCUGAGGAGA | 386 | UCUCCUCAGCCAGUGAUGUAACAUUCA | 786 |
| LPA-5902 | GAAACCCAAGGUACCUUUGAGACTG | 387 | CAGUCUCAAAGGUACCUUGGGUUUCUC | 787 |
| LPA-0190-M1 | UCCACCACUGUCACAGGAAAGCAGCCGAAAGGCUGC | 388 | UUUCCUGUGACAGUGGUGGAGG | 788 |
| LPA-0501-M1 | UGGUAAUGGACAGAGUUAUAGCAGCCGAAAGGCUGC | 389 | UAUAACUCUGUCCAUUACCAGG | 789 |
| LPA-3100-M1 | UACUGCAACCUGACACGAUAGCAGCCGAAAGGCUGC | 390 | UAUCGUGUCAGGUUGCAGUAGG | 790 |
| LPA-3286-M1 | AGAACUUGCCAAGCUUGGUAGCAGCCGAAAGGCUGC | 391 | UACCAAGCUUGGCAAGUUCUGG | 791 |
| LPA-3288-M1 | AACUUGCCAAGCUUGGUCAAGCAGCCGAAAGGCUGC | 392 | UUGACCAAGCUUGGCAAGUUGG | 792 |

TABLE 5-continued

| | | | | |
|---|---|---|---|---|
| LPA-3291-M1 | UUGCCAAGCUUGGUCAUCUAG CAGCCGAAAGGCUGC | 393 | UAGAUGACCAAGCUUGGCAAGG | 793 |
| LPA-3584-M1 | AUGGACAGAGUUAUCGAGGAG CAGCCGAAAGGCUGC | 394 | UCCUCGAUAACUCUGUCCAUGG | 794 |
| LPA-3585-M1 | UGGACAGAGUUAUCGAGGCAG CAGCCGAAAGGCUGC | 395 | UGCCUCGAUAACUCUGUCCAGG | 795 |
| LPA-4645-M1 | UGGUCAUCUAUGAUACCACAG CAGCCGAAAGGCUGC | 396 | UGUGGUAUCAUAGAUGACCAGG | 796 |
| LPA-4717-M1 | UACUGCAGGAAUCCAGAUUAG CAGCCGAAAGGCUGC | 397 | UAAUCUGGAUUCCUGCAGUAGG | 797 |
| LPA-5510-M1 | AGAAAUGUCCUGGAAGCAUAG CAGCCGAAAGGCUGC | 398 | UAUGCUUCCAGGACAUUUCUGG | 798 |
| LPA-3750-M1 | GACAACAGAAUAUUAUCCAAG CAGCCGAAAGGCUGC | 399 | UUGGAUAAUAUUCUGUUGUCGG | 799 |
| LPA-2900-M2 | AUGGACAGAGUUAUCAAGGAG CAGCCGAAAGGCUGC | 400 | UCCUUGAUAACUCUGUCCAUGG | 800 |
| LPA-3675-M2 | GACAACAGAAUAUUAUCCAAG CAGCCGAAAGGCUGC | 401 | UUGGAUAAUAUUCUGUUGUCGG | 801 |
| LPA-2900-M3 | AUGGACAGAGUUAUCAAGGAG CAGCCGAAAGGCUGC | 402 | UCCUUGAUAACUCUGUCCAUGG | 802 |
| LPA-3675-M3 | GACAACAGAAUAUUAUCCAAG CAGCCGAAAGGCUGC | 403 | UUGGAUAAUAUUCUGUUGUCGG | 803 |

Human (Hs): NM_005577.3 (SEQ ID NO: 1)
CTGGGATTGG GACACACTTT CTGGGCACTG CTGGCCAGTC CCAAAATGGA ACATAAGGAA
GTGGTTCTTC TACTTCTTTT ATTTCTGAAA TCAGCAGCAC CTGAGCAAAG CCATGTGGTC
CAGGATTGCT ACCATGGTGA TGGACAGAGT TATCGAGGCA CGTACTCCAC CACTGTCACA
GGAAGGACCT GCCAAGCTTG GTCATCTATG ACACCACATC AACATAATAG GACCACAGAA
AACTACCCAA ATGCTGGCTT GATCATGAAC TACTGCAGGA ATCCAGATGC TGTGGCAGCT
CCTTATTGTT ATACGAGGGA TCCCGGTGTC AGGTGGGAGT ACTGCAACCT GACGCAATGC
TCAGACGCAG AAGGGACTGC CGTCGCGCCT CCGACTGTTA CCCCGGTTCC AAGCCTAGAG
GCTCCTTCCG AACAAGCACC GACTGAGCAA AGGCCTGGGG TGCAGGAGTG CTACCATGGT
AATGGACAGA GTTATCGAGG CACATACTCC ACCACTGTCA CAGGAAGAAC CTGCCAAGCT
TGGTCATCTA TGACACCACA CTCGCATAGT CGGACCCCAG AATACTACCC AAATGCTGGC
TTGATCATGA ACTACTGCAG GAATCCAGAT GCTGTGGCAG CTCCTTATTG TTATACGAGG
GATCCCGGTG TCAGGTGGGA GTACTGCAAC CTGACGCAAT GCTCAGACGC AGAAGGGACT
GCCGTCGCGC CTCCGACTGT TACCCCGGTT CCAAGCCTAG AGGCTCCTTC CGAACAAGCA
CCGACTGAGC AAAGGCCTGG GGTGCAGGAG TGCTACCATG GTAATGGACA GAGTTATCGA
GGCACATACT CCACCACTGT CACAGGAAGA ACCTGCCAAG CTTGGTCATC TATGACACCA
CACTCGCATA GTCGGACCCC AGAATACTAC CCAAATGCTG GCTTGATCAT GAACTACTGC
AGGAATCCAG ATGCTGTGGC AGCTCCTTAT TGTTATACGA GGGATCCCGG TGTCAGGTGG
GAGTACTGCA ACCTGACGCA ATGCTCAGAC GCAGAAGGGA CTGCCGTCGC GCCTCCGACT
GTTACCCCGG TTCCAAGCCT AGAGGCTCCT TCCGAACAAG CACCGACTGA GCAGAGGCCT
GGGGTGCAGG AGTGCTACCA CGGTAATGGA CAGAGTTATC GAGGCACATA CTCCACCACT
GTCACTGGAA GAACCTGCCA AGCTTGGTCA TCTATGACAC CACACTCGCA TAGTCGGACC
CCAGAATACT ACCCAAATGC TGGCTTGATC ATGAACTACT GCAGGAATCC AGATGCTGTG
GCAGCTCCTT ATTGTTATAC GAGGGATCCC GGTGTCAGGT GGGAGTACTG CAACCTGACG
CAATGCTCAG ACGCAGAAGG GACTGCCGTC GCGCCTCCGA CTGTTACCCC GGTTCCAAGC
CTAGAGGCTC CTTCCGAACA AGCACCGACT GAGCAAAGGC CTGGGGTGCA GGAGTGCTAC
CATGGTAATG GACAGAGTTA TCGAGGCACA TACTCCACCA CTGTCACAGG AAGAACCTGC
CAAGCTTGGT CATCTATGAC ACCACACTCG CATAGTCGGA CCCCAGAATA CTACCCAAAT
GCTGGCTTGA TCATGAACTA CTGCAGGAAT CCAGATGCTG TGGCAGCTCC TTATTGTTAT
ACGAGGGATC CCGGTGTCAG GTGGGAGTAC TGCAACCTGA CGCAATGCTC AGACGCAGAA
GGGACTGCCG TCGCGCCTCC GACTGTTACC CCGGTTCCAA GCCTAGAGGC TCCTTCCGAA
CAAGCACCGA CTGAGCAAAG GCCTGGGGTG CAGGAGTGCT ACCATGGTAA TGGACAGAGT
TATCGAGGCA CATACTCCAC CACTGTCACA GGAAGAACCT GCCAAGCTTG GTCATCTATG
ACACCACACT CGCATAGTCG GACCCCAGAA TACTACCCAA ATGCTGGCTT GATCATGAAC
TACTGCAGGA ATCCAGATGC TGTGGCAGCT CCTTATTGTT ATACGAGGGA TCCCGGTGTC
AGGTGGGAGT ACTGCAACCT GACGCAATGC TCAGACGCAG AAGGGACTGC CGTCGCGCCT
CCGACTGTTA CCCCGGTTCC AAGCCTAGAG GCTCCTTCCG AACAAGCACC GACTGAGCAA
AGGCCTGGGG TGCAGGAGTG CTACCATGGT AATGGACAGA GTTATCGAGG CACATACTCC
ACCACTGTCA CAGGAAGAAC CTGCCAAGCT TGGTCATCTA TGACACCACA CTCGCATAGT
CGGACCCCAG AATACTACCC AAATGCTGGC TTGATCATGA ACTACTGCAG GAATCCAGAT
GCTGTGGCAG CTCCTTATTG TTATACGAGG GATCCCGGTG TCAGGTGGGA GTACTGCAAC
CTGACGCAAT GCTCAGACGC AGAAGGGACT GCCGTCGCGC CTCCGACTGT TACCCCGGTT
CCAAGCCTAG AGGCTCCTTC CGAACAAGCA CCGACTGAGC AGAGGCCTGG GGTGCAGGAG
TGCTACCACG GTAATGGACA GAGTTATCGA GGCACATACT CCACCACTGT CACTGGAAGA
ACCTGCCAAG CTTGGTCATC TATGACACCA CACTCGCATA GTCGGACCCC AGAATACTAC
CCAAATGCTG GCTTGATCAT GAACTACTGC AGGAATCCAG ATCCTGTGGC AGCCCCTTAT TABLE 5-continued TGTTATACGA GGGATCCCAG TGTCAGGTGG GAGTACTGCA ACCTGACACA ATGCTCAGAC
GCAGAAGGGA CTGCCGTCGC GCCTCCAACT ATTACCCCGA TTCCAAGCCT AGAGGCTCCT
TCTGAACAAG CACCAACTGA GCAAAGGCCT GGGGTGCAGG AGTGCTACCA CGGAAATGGA
CAGAGTTATC AAGGCACATA CTTCATTACT GTCACAGGAA GAACCTGCCA AGCTTGGTCA
TCTATGACAC CACACTCGCA TAGTCGGACC CCAGCATACT ACCCAAATGC TGGCTTGATC
AAGAACTACT GCCGAAATCC AGATCCTGTG GCAGCCCCTT GGTGTTATAC AACAGATCCC
AGTGTCAGGT GGGAGTACTG CAACCTGACA CGATGCTCAG ATGCAGAATG GACTGCCTTC
GTCCCTCCGA ATGTTATTCT GGCTCCAAGC CTAGAGGCTT TTTTTGAACA AGCACTGACT
GAGGAAACCC CCGGGGTACA GGACTGCTAC TACCATTATG GACAGAGTTA CCGAGGCACA
TACTCCACCA CTGTCACAGG AAGAACTTGC CAAGCTTGGT CATCTATGAC ACCACACCAG
CATAGTCGGA CCCCAGAAAA CTACCCAAAT GCTGGCCTGA CCAGGAACTA CTGCAGGAAT
CCAGATGCTG AGATTCGCCC TTGGTGTTAC ACCATGGATC CCAGTGTCAG GTGGGAGTAC
TGCAACCTGA CACAATGCCT GGTGACAGAA TCAAGTGTCC TTGCAACTCT CACGGTGGTC
CCAGATCCAA GCACAGAGGC TTCTTCTGAA GAAGCACCAA CGGAGCAAAG CCCCGGGGTC
CAGGATTGCT ACCATGGTGA TGGACAGAGT TATCGAGGCT CATTCTCTAC CACTGTCACA
GGAAGGACAT GTCAGTCTTG GTCCTCTATG ACACCACACT GGCATCAGAG GACAACAGAA
TATTATCCAA ATGGTGGCCT GACCAGGAAC TACTGCAGGA ATCCAGATGC TGAGATTAGT
CCTTGGTGTT ATACCATGGA TCCCAATGTC AGATGGGAGT ACTGCAACCT GACACAATGT
CCAGTGACAG AATCAAGTGT CCTTGCGACG TCCACGGCTG TTTCTGAACA AGCACCAACG
GAGCAAAGCC CCACAGTCCA GGACTGCTAC CATGGTGATG GACAGAGTTA TCGAGGCTCA
TTCTCCACCA CTGTTACAGG AAGGACATGT CAGTCTTGGT CCTCTATGAC ACCACACTGG
CATCAGAGAA CCACAGAATA CTACCCAAAT GGTGGCCTGA CCAGGAACTA CTGCAGGAAT
CCAGATGCTG AGATTCGCCC TTGGTGTTAT ACCATGGATC CCAGTGTCAG ATGGGAGTAC
TGCAACCTGA CGCAATGTCC AGTGATGGAA TCAACTCTCC TCACAACTCC CACGGTGGTC
CCAGTTCCAA GCACAGAGCT TCCTTCTGAA GAAGCACCAA CTGAAAACAG CACTGGGGTC
CAGGACTGCT ACCGAGGTGA TGGACAGAGT TATCGAGGCA CACTCTCCAC CACTATCACA
GGAAGAACAT GTCAGTCTTG GTCGTCTATG ACACCACATT GGCATCGGAG GATCCCATTA
TACTATCCAA ATGCTGGCCT GACCAGGAAC TACTGCAGGA ATCCAGATGC TGAGATTCGC
CCTTGGTGTT ACACCATGGA TCCCAGTGTC AGGTGGGAGT ACTGCAACCT GACACGATGT
CCAGTGACAG AATCGAGTGT CCTCACAACT CCCACAGTGG CCCCGGTTCC AAGCACAGAG
GCTCCTTCTG AACAAGCACC ACCTGAGAAA AGCCCTGTGG TCCAGGATTG CTACCATGGT
GATGGACGGA GTTATCGAGG CATATCCTCC ACCACTGTCA CAGGAAGGAC CTGTCAATCT
TGGTCATCTA TGATACCACA CTGGCATCAG AGGACCCCAG AAAACTACCC AAATGCTGGC
CTGACCGAGA ACTACTGCAG GAATCCAGAT TCTGGGAAAC AACCCTGGTG TTACACAACC
GATCCGTGTG TGAGGTGGGA GTACTGCAAT CTGACACAAT GCTCAGAAAC AGAATCAGGT
GTCCTAGAGA CTCCCACTGT TGTTCCAGTT CCAAGCATGG AGGCTCATTC TGAAGCAGCA
CCAACTGAGC AAACCCCTGT GGTCCGGCAG TGCTACCATG GTAATGGCCA GAGTTATCGA
GGCACATTCT CCACCACTGT CACAGGAAGG ACATGTCAAT CTTGGTCATC CATGACACCA
CACCGGCATC AGAGGACCCC AGAAAACTAC CCAAATGATG GCCTGACAAT GAACTACTGC
AGGAATCCAG ATGCCGATAC AGGCCCTTGG TGTTTTACCA TGGACCCCAG CATCAGGTGG
GAGTACTGCA ACCTGACGCG ATGCTCAGAC ACAGAAGGGA CTGTGGTCGC TCCTCCGACT
GTCATCCAGG TTCCAAGCCT AGGGCCTCCT TCTGAACAAG ACTGTATGTT TGGGAATGGG
AAAGGATACC GGGGCAAGAA GGCAACCACT GTTACTGGGA CGCCATGCCA GGAATGGGCT
GCCCAGGAGC CCCATAGACA CAGCACGTTC ATTCCAGGGA CAAATAAATG GGCAGGTCTG
GAAAAAAATT ACTGCCGTAA CCCTGATGGT GACATCAATG GTCCCTGGTG CTACACAATG
AATCCAAGAA AACTTTTTGA CTACTGTGAT ATCCCTCTCT GTGCATCCTC TTCATTTGAT
TGTGGGAAGC CTCAAGTGGA GCCGAAGAAA TGTCCTGGAA GCATTGTAGG GGGGTGTGTG
GCCCACCCAC ATTCCTGGCC CTGGCAAGTC AGTCTCAGAA CAAGGTTTGG AAAGCACTTC
TGTGGAGGCA CCTTAATATC CCCAGAGTGG GTGCTGACTG CTGCTCACTG CTTGAAGAAG
TCCTCAAGGC CTTCATCCTA CAAGGTCATC CTGGGTGCAC ACCAAGAAGT GAACCTCGAA
TCTCATGTTC AGGAAATAGA AGTGTCTAGG CTGTTCTTGG AGCCCACACA AGCAGATATT
GCCTTGCTAA AGCTAAGCAG GCCTGCCGTC ATCACTGACA AAGTAATGCC AGCTTGTCTG
CCATCCCCAG ACTACATGGT CACCGCCAGG ACTGAATGTT ACATCACTGG CTGGGGAGAA
ACCCAAGGTA CCTTTGGGAC TGGCCTTCTC AAGGAAGCCC AGCTCCTTGT TATTGAGAAT
GAAGTGTGCA ATCACTATAA GTATATTTGT GCTGAGCATT TGGCCAGAGG CACTGACAGT
TGCCAGGGTG ACAGTGGAGG GCCTCTGGTT TGCTTCGAGA AGGACAAATA CATTTTACAA
GGAGTCACTT CTTGGGGTCT TGGCTGTGCA CGCCCCAATA AGCCTGGTGT CTATGCTCGT
GTTTCAAGGT TTGTTACTTG GATTGAGGGA ATGATGAGAA ATAATTAATT GGACGGGAGA
CAGAGTGAAG CATCAACCTA CTTAGAAGCT GAAACGTGGG TAAGGATTTA GCATGCTGGA
AATAATAGAC AGCAATCAAA CGAAGACACT GTTCCCAGCT ACCAGCTATG CCAAACCTTG
GCATTTTTGG TATTTTTGTG TATAAGCTTT TAAGGTCTGA CTGACAAATT CTGTATTAAG
GTGTCATAGC TATGACATTT GTTAAAAATA AACTCTGCAC TTATTTTGAT TTGA Cynomolgus monkey (Mf): XM_015448517. 1 (SEQ ID NO: 2)
GATGCTGCAT ACTTAATGTC GAAAGGTTGC TTCATCCAAG AGCCTGGAGT TTTCAGAGAC
ACTGTCCTGA AACTATGTCC TGAAACTATG TCATTGAAAC TGAAACATTG TCCTGAAGCT
GGTATTGGGC AATACCAGCG CCTGCAGGCA ACAGCTCGGA TGCACTTAAG ATTTAAATAT
TACCCACAGA AGTTCTGGCT TGTCTGGGAA AACCTTTTGC TAAACAGAAG AGCAACATTT
TTTTTTTTTT CTTTTCTGGA ATTTGTAAAC AGCATTTATT CTCAGCCTTA CCTTCCAAAC
GTTGCACTTG GAACATTGCT GGGCCCCGTG GAAACAGAAG CGAACGTCAG CCAGGCCGGC
AGGGGGCGGC AGACCCCACA CTTCGCCGGG CGCCCTCACC TCCCTGGGAG GGAGTGTGCA
GCTGCCAAAA TCTTCGGCGG GGTTCAGTCC AAGCGACTTC AGCCAGCAGA TGGTCATTCT
CCTGTGACCG TGTGTACTAC AGACTGTTTC AAAACCGGGC AGGCAATTAA CAATGGGAAT
TCTGCCATCA TCGCTGACAA AGTCATCCCA GTTTGTCTGC CATCCCCAAA TTATGTGGTC
GCCAACCAGA CTGAATGTTA TGTCACTGGC TGGGGAGAAA CCCAAGCACT ACCTGAGCAA
AGCCATGTGG TCCAGGATTG CTACCATGGT GATGGACAGA GTTATCAAGG CACATCCTCC
ACCACTGTCA CAGGAAGGAC CTGCCAAGCT TGGTCATCTA TGGAACCACA TCAGCATAAT
AGAACCACAG AAAACTACCC AAATGCTGGC TTGATCAGGA ACTACTGCAG GAATCCAGAT
CCTGTGGCAG CCCCTTATTG TTATACGATG GATCCCAATG TCAGGTGGGA GTACTGCAAC
CTGACACAAT GCTCAGACGC AGAAGGGACT GCCGTCGCAC CTCCGAATGT CACCCCGGTT TABLE 5-continued CCAAGCCTAG AGGCTCCTTC CGAACAAGCA CCGACTGAGC AAAGGCCTGG GGTGCAGGAG
TGCTACCACG GTAATGGACA GAGTTATCGA GGCACATACT TCACCACTGT GACAGGAAGA
ACCTGCCAAG CTTGGTCATC TATGACACCG CACTCTCATA GTCGGACCCC GGAAAACTAC
CCAAATGGTG GCTTGATCAG GAACTACTGC AGGAATCCAG ATCCTGTGGC AGCCCCTTAT
TGTTATACCA TGGATCCCAA TGTCAGGTGG GAGTACTGCA ACCTGACACA ATGCTCAGAC
GCAGAAGGGA TTGCCGTCAC ACCTCTGACT GTTACCCCGG TTCCAAGCCT AGAGGCTCCT
TCCAAGCAAG CACCAACTGA GCAAAGGCCT GGTGTCCAGG AGTGCTACCA CGGTAATGGA
CAGAGTTATC GAGGCACATA CTTCACCACT GTGACAGGAA GAACCTGCCA AGCTTGGTCA
TCTATGACAC CACATTCTCA TAGTCGTACC CCAGAAAACT ACCCAAATGG TGGCTTGATC
AGGAACTACT GCAGGAATCC AGATCCTGTG GCAGCCCCTT ATTGTTATAC CATGGATCCC
AATGTCAGGT GGGAGTACTG CAACCTGACA CAATGCTCAG ACGCAGAAGG GACTGCCGTC
GCACCTCCGA CTGTCACCCC GGTTCCAAGC CTAGAGGCTC CTTCCGAACA AGCACCGACT
GAGCAAAGGC CTGGGGTGCA GGAGTGCTAC CACGGTAATG GACAGAGTTA TCGAGGCACA
TACTTCACCA CTGTGACAGG AAGAACCTGC CAAGCTTGGT CATCTATGAC ACCGCACTCT
CATAGTCGGA CCCCGGAAAA CTACCCAAAT GGTGGCTTGA TCAGGAACTA CTGCAGGAAT
CCAGATCCTG TGGCAGCCCC TTATTGTTAT ACCATGGATC CCAATGTCAG GTGGGAGTAC
TGCAACCTGA CACAATGCTC AGACGCAGAA GGGACTGCCG TCGCACCTCC GAATGTCACC
CCGGTTCCAA GCCTAGAGGC TCCTTCTGAG CAAGCACCAA CTGAGCAAAG GCTTGGGGTG
CAGGAGTGCT ACCACGGTAA TGGACAGAGT TATCGAGGCA CATACTTCAC CACTGTGACA
GGAAGAACCT GCCAAGCTTG GTCATCTATG ACACCACACT CTCATAGTCG GACCCCAGAA
AACTACCCAA ATGCTGGCTT GGTCAAGAAC TACTGCCGAA ATCCAGATCC TGTGGCAGCC
CCTTGGTGTT ATACAACGGA TCCCAGTGTC AGGTGGGAGT ACTGCAACCT GACACGATGC
TCAGATGCAG AAGGGACTGC TGTTGTGCCT CCAAATATTA TTCCGGTTCC AAGCCTAGAG
GCTTTTCTTG AACAAGAACC GACTGAGGAA ACCCCCGGGG TACAGGAGTG CTACTACCAT
TATGGACAGA GTTATAGAGG CACATACTCC ACCACTGTTA CAGGAAGAAC TTGCCAAGCT
TGGTCATCTA TGACACCACA CCAGCATAGT CGGACCCCAA AAAACTATCC AAATGCTGGC
CTGACCAGGA ACTACTGCAG GAATCCAGAT GCTGAGATTC GCCCTTGGTG TTATACCATG
GATCCCAGTG TCAGGTGGGA GTACTGCAAC CTGACACAAT GTCTGGTGAC AGAATCAAGT
GTCCTTGAAA CTCTCACAGT GGTCCCAGAT CCAAGCACAC AGGCTTCTTC TGAAGAAGCA
CCAACGGAGC AAAGTCCCGA GGTCCAGGAC TGCTACCATG GTGATGGACA GAGTTATCGA
GGCTCATTCT CCACCACTGT CACAGGAAGG ACATGTCAGT CTTGGTCCTC TATGACACCA
CACTGGCATC AGAGGACAAC AGAATATTAT CCAGATGGTG GCCTGACCAG GAACTACTGC
AGGAATCCAG ATGCTGAGAT TCGCCCTTGG TGTTATACCA TGGATCCCAG TGTCAGGTGG
GAGTACTGCA ACCTGACACA ATGTCCAGTG ACAGAATCAA GTGTCCTCGC AACGTCCATG
GCTGTTTCTG AACAAGCACC AATGGAGCAA AGCCCCGGGG TCCAGGACTG CTACCATGGT
GATGGACAGA GTTATCGAGG TTCATTCTCC ACCACTGTCA CAGGAAGGAC ATGTCAGTCT
TGGTCCTCTA TGACACCACA CTGGCATCAG AGGACCATAG AATACTACCC AAATGGTGGC
CTGACCAAGA ACTACTGCAG GAATCCAGAT GCTGAGATTC GCCCTTGGTG TTATACCATG
GATCCCAGAG TCAGATGGGA GTACTGCAAC CTGACACAAT GTGTGGTGAT GGAATCAAGT
GTCCTTGCAA CTCCCATGGT GGTCCCAGTT CCAAGCAGAG AGGTTCCTTC TGAAGAAGCA
CCAACTGAAA ACAGCCCTGG GGTCCAGGAC TGCTACCAAG GTGATGGACA GAGTTATCGA
GGCACATTCT CCACCACTAT CACAGGAAGA ACATGTCAGT CTTGGTTGTC TATGACACCA
CATCGGCATC GGAGGATCCC ATTACGCTAT CCAAATGCTG GCCTGACCAG GAACTATTGC
AGAAATCCAG ATGCTGAGAT TCGCCCTTGG TGTTACACCA TGGATCCCAG TGTCAGGTGG
GAGTACTGCA ACCTGACACA ATGTCCAGTG ACAGAATCAA GTGTCCTCAC AACTCCCACG
GTGGTCCCGG TTCCAAGCAC AGAGGCTCCT TCTGAACAAG CACCACCTGA GAAAAGCCCT
GTGGTCCAGG ATTGCTACCA TGGTGATGGA CAGAGTTATC GAGGCACATC CTCCACCACT
GTCACAGGAA GGAACTGTCA GTCTTGGTCA TCTATGATAC CACACTGGCA TCAGAGGACC
CCAGAAAACT ACCCAAATGC TGGCCTGACC AGGAACTACT GCAGGAATCC AGATTCTGGG
AAACAACCCT GGTGTTACAC GACTGATCCA TGTGTGAGGT GGGAGTACTG CAACCTGACA
CAATGCTCAG AAACAGAATC AGGTGTCCTA GAGACTCCCA CTGTTGTTCC GGTTCCAAGC
ATGGAAGCTC ATTCTGAAGC AGCACCAACT GAGCAAACTC CTGTGGTCCA GCAGTGCTAC
CATGGTAATG GACAGAGTTA TCGAGGCACA TTCTCCACCA CTGTCACAGG AAGGACATGT
CAATCTTGGT CATCCATGAC ACCACACCAG CATAAGAGGA CCCCGGAAAA CCACCCAAAT
GATGACTTGA CAATGAACTA CTGCAGGAAT CCAGATGCTG ACACAGGCCC TTGGTGTTTT
ACCATGGACC CCAGCGTCAG GCGGGAGTAC TGCAACCTGA CGCGATGCTC AGACACAGAA
GGGACTGTGG TCACACCTCC GACTGTTATC CCGGTTCCAA GCCTAGAGGC TCCTTCTGAA
CAAGCATCCT CTTCATTTGA TTGTGGGAAG CCTCAAGTGG AGCCAAAGAA ATGTCCTGGA
AGCATTGTAG GTGGGTGTGT GGCCCACCCA CATTCCTGGC CCTGGCAAGT CAGTCTTAGA
ACAAGGTTTG GAAAGCACTT CTGTGGAGGC ACCTTAATAT CCCCAGAGTG GGTGCTGACT
GCTGCTTGCT GCTTGGAGAC GTTCTCAAGG CCTTCCTTCT ACAAGGTCAT CCTGGGTGCA
CACCAAGAAG TGAATCTCGA ATCTCACGTT CAAGAAATAG AAGTGTCTAG GTTGTTCTTG
GAGCCCATAG GAGCAGATAT TGCCTTGCTA AAGCTAAGCA GGCCTGCCAT CATCACTGAC
AAAGTAATCC CAGCCTGTCT GCCGTCTCCA AATTACGTGA TCACCGTCTG GACTGAATGT
TACATCACTG GCTGGGGAGA AACCCAAGGT ACCTTTGGGG CTGGCCTTCT CAAGGAAGCC
CAGCTTCATG TGATTGAGAA TACAGTGTGC AATCACTACG AGTTTCTGAA TGGAAGAGTC
AAATCCACCG AGCTCTGTGC TGGGCATTTG GCCGGAGGCA CTGACAGATG CCAGGGTGAC
AGTGGAGGGC CTGTGGTTTG CTTCGACAAG GACAAATACA TTTTACGAGG AATAACTTCT
TGGGGTCCTG GCTGTGCATG CCCCAATAAG CCTGGTGTCT ATGTTCGTGT TTCAAGCTTT
GTCACTTGGA TTGAGGGAGT GATGAGAAAT AATTAATTGA ACAAGAGACA GAGTGAAGCA
TTGACTCACC TAGAGGCTAG AATGGGGGTA GGGATTTAGC ACGCTGGAAA TAACGGACAG
TAATCAAACG AAGACACTGT CCCCAGCTAC CAACTATGCC AAACCTCAGC ATTTTTGGTA
TTATTGTGTA TAAGCTTTTC CCGTCTGACT GCTGGGTTCT CCAATAAGGT GACATAGCTA
TGCCATTTGT TAAAAATAAA CTCTGTACTT ATTTTGATTT GAGTAAA Rhesus monkey: XM_028847001.1 (SEQ ID NO: 3)
AGCCTTGCCT TTGAAATGTT CCAGTTGGAA CATTGCTGGG CAGCGTGCAA ACAGGAGCGA
ACGTCAGCCG GGGCGGCAGG GGGCAGCAGA CCCCACACTT TGTCCATGCC TCAGGTGGGA
GGAAGTGTCC GGCTCCAGAA ACCTGCCGCG GGCTTTATCC CAAGCGACTT CAGCCAGCAG
ACGGTTCATG TCCTGAGGCT GCAAAATACG AGTTCTGCCA TCATCGCTGA CAAAGTCATC TABLE 5-continued CCAGTTTGTC TGCCATCCCC AAATTATGCG ATCGCCAACC AGACTGAATG TTATGTCACT
GGCTGGGGAG AAACCCAAGC ACTACCTGAG CAAAGCCATG TGGTCCAGGA TTGCTACCAT
GGTGATGGAC AGAGTTATCA AGGCACATCC TCCACCACTG TCACAGGAAG GACCTGCCAA
GCTTGGTCAT CTATGGAACC ACATCAGCAT AATAGAACCA CAGAAAACTA CCCAAATGCT
GGCTTGATCA GGAACTACTG CAGGAATCCA GATCCTGTGG CAGCCCCTTA TTGTTATACG
ATGGATCCCA ATGTCAGGTG GGAGTACTGC AACCTGACAC AATGCTCAGA CGCAGAAGGG
ACTGCCGTCG CACCTCCGAA TGTCACCCCG GTTCCAAGCC TAGAGGCTCT TTCCGAACAA
GCACCGACTG AGCAAAGGCC TGGGGTGCAG GAGTGCTACC ACGGTAATGG ACAGAGTTAT
CGAGGCACAT ACTTCACCAC TGTGACAGGA AGAACCTGCC AAGCTTGGTC ATCTATGACA
CCACATTCTC ATAGTCGTAC CCCAGAAAAC TACCCAAATG GTGGCTTGAT CAGGAACTAC
TGCAGGAATC CAGATCCTGT GGCAGCCCCT TATTGTTATA CCATGGATCC CAATGTCAGG
TGGGAGTACT GCAACCTGAC ACAATGCTCA GACGCAGAAG GGACTGCCGT CGCACCTCCG
AATGTCACCC CGGTTCCAAG CCTAGAGGCT CCTTCCGAAC AAGCACCGAC TGAGCAAAGG
CCTGGGGTGC AGGAGTGCTA CCACGGTAAT GGACAGAGTT ATCGAGGCAC ATACTTCACC
ACTGTGACAG GAAGAACCTG CCAAGCTTGG TCATCTATGA CACCACATTC TCATAGTCGT
ACCCCAGAAA ACTACCCAAA TGGTGGCTTG ATCAGGAACT ACTGCAGGAA TCCAGATCCT
GTGGCAGCCC CTTATTGTTA TACCATGGAT CCCAATGTCA GGTGGGAGTA CTGCAACCTG
ACACAATGCT CAGACGCAGA GGGGACTGCC GTCGCACCTC CGACTGTCAC CCCGGTTCCA
AGCCTAGAGG CTCCTTCTGA GCAAGCACCG ACTGAGCAAA GGCCTGGGGT GCAGGAGTGC
TACCACGGTA ATGGACAGAG TTATCGAGGC ACATACTTCA CCACTGTGAC AGGAAGAACC
TGCCAAGCTT GGTCATCTAT GACACCGCAC TCTCATAGTC GGACCCCGGA AAACTACCCA
AATGGTGGCT TGATCAGGAA CTACTGCAGG AATCCAGATC CTGTGGCAGC CCCTTATTGT
TATACGATGG ATCCCAATGT CAGGTGGGAG TACTGCAACC TGACACAATG CTCAGACGCA
GAAGGGACTG CCGTCGCACC TCCGAATGTC ACCCCGGTTC CAAGCCTAGA GGCTCCTTCC
GAACAAGCAC CGACTGAGCA AAGGCCTGGG GTGCAGGAGT GCTACCACGG TAATGGACAG
AGTTATCGAG GCACATACTT CACCACTGTG ACAGGAAGAA CCTGCCAAGC TTGGTCATCT
ATGACACCGC ACTCTCATAG TCGGACCCCG GAAAACTACC CAAATGGTGG CTTGATCAGG
AACTACTGCA GGAATCCAGA TCCTGTGGCA GCCCCTTATT GTTATACGAT GGATCCCAAT
GTCAGGTGGG AGTACTGCAA CCTGACACAA TGCTCAGACG CAGAAGGGAC TGCCGTCGCA
CCTCCGAATG TCACCCCGGT TCCAAGCCTA GAGGCTCCTT CCGAACAAGC ACCAACTGAG
CAAAGGCCTG GGNTGCAGGA GTGCTACCAT GGTAATGGAC AGAGTTATCG AGGCACATAC
TTCACCACTG TGACAGGAAG AACCTGCCAA GCTTGGTCAT CTATGACACC GCACTCTCAT
AGTCGGACCC CGGAAAACTA CCCAAATGGT GGCTTGATCA GGAACTACTG CAGGAATCCA
GATCCTGTGG CAGCCCCTTA TTGTTATACC ATGGATCCCA ATGTCAGGTG GNAGTACTGC
AACCTGACAC AATGCTCAGA CGCAGAAGGG ACTGCCGTCG CACCTCCGAC TGTCACCCCG
GTTCCAAGCC TAGAGGCTCC TTCGAGCAAG GCACCGACTG AGCAAAGGCC TGGGNTGCAG
GAGTGCTACC ACGGTAATGG ACAGAGTTAT CGAGGCACAT ACTTCACCAC TGTGACAGGA
AGAACCTGCC AAGCTTGGTC ATCTATGACA CCGCACTCTC ATAGTCGGAC CCCGGAAAAC
TACCCAAATG GTGGCTTGAT CAGGAACTAC TGCAGGAATC CAGATCCTGT GGCAGCCCCT
TATTGTTATA CGATGGATCC CAATGTCAGG TGGGAGTACT GCAACCTGAC ACAATGCTCA
GACGCAGAAG GGACTGCCGT CGCACCTCCG AATGTCACCC CGGTTCCAAG CCTAGAGGCT
CCTTCCGAAC AAGCACCGAC TGAGCAAAGG CCTGGGGTGC AGGAGTGCTA CCACGGTAAT
GGACAGAGTT ATCGAGGCAC ATACTTCACC ACTGTGACAG GAAGAACCTG CCAAGCTTGG
TCATCTATGA CACCGCACTC TCATAGTCGG ACCCCGGAAA ACTACCCAAA TGGTGGCTTG
ATCAGGAACT ACTGCAGGAA TCCAGATCCT GTGGCAGCCC CTTATTGTTA TACCATGGAT
CCCAATGTCA GGTGGGAGTA CTGCAACCTG ACACAATGCT CAGACGCAGA AGGGACTGCC
GTCGCACCTC CGAATGTCAC CCCGGTTCCA AGCCTAGAGG CTCCTTCTGA GCAAGCACCA
ACTGAGCAAA GGCTTGGGGT GCAGGAGTGC TACCACAGTA ATGGACAGAG TTATCGAGGC
ACATACTTCA CCACTGTGAC AGGAAGAACC TGCCAAGCTT GGTCATCTAT GACACCACAC
TCTCATAGTC GGACCCCAGA AAACTACCCA AATGCTGGCT TGGTCAAGAA CTACTGCCGA
AATCCAGATC CTGTGGCAGC CCCTTGGTGT TATACAACGG ATCCCAGTGT CAGGTGGGAG
TACTGCAACC TGACACGATG CTCAGATGCA GAAGGGACTG CTGTCATGCC TCCAAATATT
ATTCCGGTTC CAAGCCTAGA GGCTTTTCTT GAACAAGAAC CTACTGAGGA AACCCCCGGG
GTACAGGAGT GCTACTACCA TTATGGACAG AGTTATCGAG GCACATACTC CACCACTGTT
ACAGGAAGAA CTTGCCAAGC TTGGTCATCT ATGACACCAC ACCAGCATAG TCGGACCCCA
AAAAACTATC CAAATGCTGG CCTGACCAGG AACTACTGCA GGAATCCAGA TGCTGAGATT
CGCCCTTGGT GTTATACCAT GGATCCCAGT GTCAGGTGGG AGTACTGCAA CCTGACACAA
TGTCTGGTGA CAGAATCAAG TGTCCTTGAA ACTCTCACAG TGGTCCCAGA TCCAAGCACA
CAGGCTTCTT CTGAAGAAGC ACCAACGGAG CAAAGTCCCG AGGTCCAGGA CTGCTACCAT
GGTGATGGAC AGAGTTATCG AGGCTCATTC TCCACCACTG TCACAGGAAG GACATGTCAG
TCTTGGTCCT CTATGACACC ACACTGGCAT CAGAGGACAA CAGAATATTA TCCAGATGGT
GGCCTGACCA GGAACTACTG CAGGAATCCA GATGCTGAGA TTCGCCCTTG GTGTTATACC
ATGGATCCCA GTGTCAGGTG GGAGTACTGC AACCTGACAC AATGTCCAGT GACAGAATCA
AGTGTCCTCG CAACGTCCAT GGCTGTTTCT GAACAAGCAC CAATGGAGCA AAGCCCCGGG
GTCCAGGACT GCTACCATGG TGATGGACAG AGTTATCGAG GTTCATTCTC CACCACTGTC
ACAGGAAGGA CATGTCAGTC TTGGTCCTCT ATGACACCAC ACTGGCATCA GAGGACCATA
GAATACTACC CAAATGGTGG CCTGACCAAG AACTACTGCA GGAATCCAGA TGCTGAGATT
CGCCCTTGGT GTTATACCAT GGATCCCAGA GTCAGATGGG AGTACTGCAA CCTGACACAA
TGTGTGGTGA TGGAATCAAG TGTCCTTGCA ACTCCCATGG TGGTCCCAGT TCCAAGCAGA
GAGGTTCCTT CTGAAGAAGC ACCAACTGAA AACAGCCCTG GGGTCCAGGA CTGCTACCAA
GGTGATGGAC AGAGTTATCG AGGCACATTC TCCACCACTA TCACAGGAAG AACATGTCAG
TCTTGGTTGT CTATGACACC ACATCGGCAT CGGAGGATCC CATTACGCTA TCCAAATGCT
GGCCTGACCA GGAACTATTG CAGAAATCCA GATGCTGAGA TTCGCCCTTG GTGTTACACC
ATGGATCCCA GTGTCAGGTG GGAGTACTGC AACCTGACAC AATGTCCAGT GACAGAATCA
AGTGTCCTCA CAACTCCCAC GGTGGTCCCG GTTCCAAGCA CAGAGGCTCC TTCTGAACAA
GCACCACCTG AGAAAAGCCC TGTGGTCCAG GATTGCTACC ATGGTGATGG ACAGAGTTAT
CGAGGCACAT CCTCCACCAC TGTCACAGGA AGGAACTGTC AATCTTGGTC ATCTATGATA
CCACACTGGC ATCAGAGGAC CCCAGAAAAC TACCCAAATG CTGGCCTGAC CAGGAACTAC
TGCAGGAATC CAGATTCTGG GAAACAACCC TGGTGTTACA CGACTGATCC ATGTGTGAGG
TGGGAGTACT GCAACCTGAC ACAATGCTCA GAAACAGAAT CAGGTGTCCT AGAGACTCCC TABLE 5-continued

| |
|---|
| ACTGTTGTTC CGGTTCCAAG CATGGAAGCT CATTCTGAAG CAGCACCAAC TGAGCAAACC |
| CCTGTGGTCC AGCAGTGCTA CCATGGTAAT GGACAGAGTT ATCGAGGCAC ATTCTCCACC |
| ACTGTCACAG GAAGGACATG TCAATCTTGG TCATCCATGA CACCACACCA GCATAAGAGG |
| ACCCCGGAAA ACCACCCAAA TGATGACTTG ACAATGAACT ACTGCAGGAA TCCAGATGCT |
| GACACAGGCC CTTGGTGTTT TACCATGGAC CCCAGCGTCA GGCGGGAGTA CTGCAACCTG |
| ACGCGATGCT CAGACACAGA AGGGACTGTG GTCACACCTC CGACTGTTAT CCCGGTTCCA |
| AGCCTAGAGG CTCCTTCTGA ACAAGCATCC TCTTCATTTG ATTGTGGGAA GCCTCAAGTG |
| GAGCCAAAGA AATGTCCTGG AAGCATTGTA GGTGGGTGTG TGGCCCACCC ACATTCCTGG |
| CCCTGGCAAG TCAGTCTTAG AACAAGGTTT GGAAAGCACT TCTGTGGAGG CACCTTAATA |
| TCCCCAGAGT GGGTGCTGAC TGCTGCTTGC TGCTTGGAGA CGTTCTCAAG GCCTTCCTTC |
| TACAAGGTCA TCCTGGGTGC ACACCAAGAA GTGAATCTCG AATCTCATGT TCAAGAAATA |
| GAAGTGTCTA GGTTGTTCTT GGAGCCCATA GGAGCAGATA TTGCCTTGCT AAAGCTAAGC |
| AGGCCTGCCA TCATCACTGA CAAAGTAATC CCAGCCTGTC TGCCGTCTCC AAATTACGTG |
| ATCACCGCCT GGACTGAATG TTACATCACT GGCTGGGGAG AAACCCAAGG TACCTTTGGG |
| GCTGGCCTTC TCAAGGAAGC CCAGCTTCAT GTGATTGAGA ATACAGTGTG CAATCACTAC |
| GAGTTTCTGA ATGGAAGAGT CAAATCCACT GAGCTCTGTG CTGGGCATTT GGCCGGAGGC |
| ACTGACAGAT GCCAGGGTGA CAATGGAGGG CCTGTGGTTT GCTTCGACAA GGACAAATAC |
| ATTTTACGAG GAATAACTTC TTGGGGTCCT GGCTGTGCAT GCCCCAATAA GCCTGGTGTC |
| TATGTTCGTG TTTCAAGCTT TGTCACTTGG ATTGAGGGAG TGATGAGAAA TAATTAATTG |
| AACAAGAGAC AGAGTGAAGC ATTGACTCAC CTAGAGGCTA GAATGGGGGT AGGGATTTAG |
| CACGCTGGAA ATAACGGACA GTAATCAAAC GAAGACACTG TCCCCAGCTA CCAACTATGC |
| CAAACCTCAG CATTTTTGGT ATTATTGTGT ATAAGCTTTT CCTGTCTGAC TGCTGGGTTC |
| TCCAATAAGG TGACATAGCT ATGCCATTTG TTAAAAATAA ACTCTGTACT TATTTTGATT |
| TGAGTAAA |

TABLE 6

LPA Oligonucleotide Sequences (modified)

| Oligonucleotide | Sequence (Sense Strand) | SEQ ID NO: | Sequence (Antisense Strand) | SEQ ID NO: |
|---|---|---|---|---|
| LPA-0190-M1 | [mUs][mC][mC][mA][mC][mC][mA][fC][fU][fG][fU][mC][mA][mC][mA][mG][mG][mA][mA][mA][mG][mC][mA][mG][mC][mC][mG][ademA-GalNAc][ademA-GalNAc][ademA-GalNAc][mG][mG][mC][mU][mG][mC] | 388 | [Me Phosphonate-4O-mUs][fUs][fUs][fC][fC][mU][fG][mU][mG][fA][mC][mA][mG][fU][mG][mG][mU][mG][mG][mAs][mGs][mG] | 788 |
| LPA-0501-M1 | [mUs][mG][mG][mU][mA][mA][mU][fG][fG][fA][fC][mA][mG][mA][mG][mU][mU][mA][mU][mA][mG][mC][mA][mG][mC][mC][mG][ademA-GalNAc][ademA-GalNAc][ademA-GalNAc][mG][mG][mC][mU][mG][mC] | 389 | [Me Phosphonate-4O-mUs][fAs][fUs][fA][fA][mC][fU][mC][mU][fG][mU][mC][mC][fA][mU][mU][mA][mC][mC][mAs][mGs][mG] | 789 |
| LPA-3100-M1 | [mUs][mA][mC][mU][mG][mC][mA][fA][fC][fC][fU][mG][mA][mC][mA][mC][mG][mA][mU][mA][mG][mC][mA][mG][mC][mC][mG][ademA-GalNAc][ademA-GalNAc][ademA-GalNAc][mG][mG][mC][mU][mG][mC] | 390 | [Me Phosphonate-4O-mUs][fAs][fUs][fC][fG][mU][fG][mU][mC][fA][mG][mG][mU][fU][mG][mC][mA][mG][mU][mAs][mGs][mG] | 790 |
| LPA-3286-M1 | [mAs][mG][mA][mA][mC][mU][mU][fG][fC][fC][fA][mA][mG][mC][mU][mU][mG][mG][mU][mA][mG][mC][mA][mG][mC][mC][mG][ademA-GalNAc][ademA-GalNAc][ademA-GalNAc][mG][mG][mC][mU][mG][mC] | 391 | [Me Phosphonate-4O-mUs][fAs][fCs][fC][fA][mA][fG][mC][mU][fU][mG][mG][mC][fA][mA][mG][mU][mU][mC][mUs][mGs][mG] | 791 |

TABLE 6-continued

| LPA Oligonucleotide Sequences (modified) | | | | |
|---|---|---|---|---|
| Oligonucleotide | Sequence (Sense Strand) | SEQ ID NO: | Sequence (Antisense Strand) | SEQ ID NO: |
| LPA-3288-M1 | [mAs][mA][mC][mU][mU][mG][mC][fC][fA][fA][fG][mC][mU][mU][mG][mG][mU][mC][mA][mA][mG][mC][mA][mG][mC][mC][mG][ademA-GalNAc][ademA-GalNAc][ademA-GalNAc][mG][mG][mC][mU][mG][mC] | 392 | [Me Phosphonate-4O-mUs][fUs][fGs][fA][fC][mC][FA][mA][mG][fC][mU][mU][mG][fG][mC][mA][mA][mG][mU][mUs][mGs][mG] | 792 |
| LPA-3291-M1 | [mUs][mU][mG][mC][mC][mA][mA][fG][fC][fU][fU][mG][mG][mU][mC][mA][mU][mC][mU][mA][mG][mC][mA][mG][mC][mC][mG][ademA-GalNAc][ademA-GalNAc][ademA-GalNAc][mG][mG][mC][mU][mG][mC] | 393 | [Me Phosphonate-4O-mUs][fAs][fGs][fA][fU][mG][fA][mC][mC][fA][mA][mG][mC][fU][mU][mG][mG][mC][mA][mAs][mGs][mG] | 793 |
| LPA-3584-M1 | [mAs][mU][mG][mG][mA][mC][mA][fG][fA][fG][fU][mU][mA][mU][mC][mG][mA][mG][mG][mA][mG][mC][mA][mG][mC][mC][mG][ademA-GalNAc][ademA-GalNAc][ademA-GalNAc][mG][mG][mC][mU][mG][mC] | 394 | [Me Phosphonate-4O-mUs][fCs][fCs][fU][fC][mG][fA][mU][mA][fA][mC][mU][mC][fU][mG][mU][mC][mC][mA][mUs][mGs][mG] | 794 |
| LPA-3585-M1 | [mUs][mG][mG][mA][mC][mA][mG][fA][fG][fU][fU][mA][mU][mC][mG][mA][mG][mG][mC][mA][mG][mC][mA][mG][mC][mC][mG][ademA-GalNAc][ademA-GalNAc][ademA-GalNAc][mG][mG][mC][mU][mG][mC] | 395 | [Me Phosphonate-4O-mUs][fGs][fCs][fC][fU][mC][fG][mA][mU][fA][mA][mC][mU][fC][mU][mG][mU][mC][mC][mAs][mGs][mG] | 795 |
| LPA-4645-M1 | [mUs][mG][mG][mU][mC][mA][mU][fC][fU][fA][fU][mG][mA][mU][mA][mC][mC][mA][mC][mA][mG][mC][mA][mG][mC][mC][mG][ademA-GalNAc][ademA-GalNAc][ademA-GalNAc][mG][mG][mC][mU][mG][mC] | 396 | [Me Phosphonate-4O-mUs][fGs][fUs][fG][fG][mU][fA][mU][mC][fA][mU][mA][mG][fA][mU][mG][mA][mC][mC][mAs][mGs][mG] | 796 |
| LPA-4717-M1 | [mUs][mA][mC][mU][mG][mC][mA][fG][fG][fA][fA][mU][mC][mC][mA][mG][mA][mU][mU][mA][mG][mC][mA][mG][mC][mC][mG][ademA-GalNAc][ademA-GalNAc][ademA-GalNAc][mG][mG][mC][mU][mG][mC] | 397 | [Me Phosphonate-4O-mUs][fAs][fAs][fU][fC][mU][fG][mG][mA][fU][mU][mC][mC][fU][mG][mC][mA][mG][mU][mAs][mGs][mG] | 797 |

TABLE 6-continued

| LPA Oligonucleotide Sequences (modified) | | | | |
|---|---|---|---|---|
| Oligonucleotide | Sequence (Sense Strand) | SEQ ID NO: | Sequence (Antisense Strand) | SEQ ID NO: |
| LPA-5510-M1 | [mAs][mG][mA][mA][mA][mU][mG][fU][fC][fC][fU][mG][mG][mA][mA][mG][mC][mA][mU][mA][mG][mC][mA][mG][mC][mC][mG][ademA-GalNAc][ademA-GalNAc][ademA-GalNAc][mG][mG][mC][mU][mG][mC] | 398 | [Me Phosphonate-4O-mUs][fAs][fUs][fG][fC][mU][fU][mC][mC][fA][mG][mG][mA][fC][mA][mU][mU][mU][mC][mUs][mGs][mG] | 798 |
| LPA-3750-M1 | [mGs][mA][mC][mA][mA][mC][mA][fG][fA][fA][fU][mA][mU][mU][mA][mU][mC][mC][mA][mA][mG][mC][mA][mG][mC][mC][mG][ademA-GalNAc][ademA-GalNAc][ademA-GalNAc][mG][mG][mC][mU][mG][mC] | 399 | [Me Phosphonate-4O-mUs][fUs][fGs][fG][fA][mU][fA][mA][mU][fA][mU][mU][mC][fU][mG][mU][mU][mG][mU][mCs][mGs][mG] | 799 |
| LPA-2900-M2 | [mAs][mU][mG][mG][mA][mC][mA][fG][fA][fG][fU][mU][mA][mU][mC][mA][mA][mG][mG][mA][mG][mC][mA][mG][mC][mC][mG][ademA-GalNAc][ademA-GalNAc][ademA-GalNAc][mG][mG][mC][mU][mG][mC] | 400 | [Me Phosphonate-4O-mUs][fCs][fC][fU][fU][mG][fA][mU][mA][fA][mC][mU][mC][fU][mG][mU][mC][mC][mA][mUs][mGs][mG] | 800 |
| LPA-3675-M2 | [mGs][mA][mC][mA][mA][mC][mA][fG][fA][fA][fU][mA][mU][mU][mA][mU][mC][mC][mA][mA][mG][mC][mA][mG][mC][mC][mG][ademA-GalNAc][ademA-GalNAc][ademA-GalNAc][mG][mG][mC][mU][mG][mC] | 401 | [Me Phosphonate-4O-mUs][fUs][fG][fG][fA][mU][fA][mA][mU][fA][mU][mU][mC][fU][mG][mU][mU][mG][mU][mCs][mGs][mG] | 801 |
| LPA-2900-M3 | [mAs][mU][mG][mG][mA][mC][mA][fG][fA][fG][fU][mU][mA][mU][mC][mA][mA][mG][mG][mA][mG][mC][mA][mG][mC][mC][mG][ademA-GalNAc][ademA-GalNAc][ademA-GalNAc][mG][mG][mC][mU][mG][mC] | 402 | [Me Phosphonate-4O-mUs][fCs][fC][mU][fU][mG][fA][mU][mA][fA][mC][mU][mC][fU][mG][mU][mC][mC][mA][mUs][mGs][mG] | 802 |
| LPA-3675-M3 | [mGs][mA][mC][mA][mA][mC][mA][fG][fA][fA][fU][mA][mU][mU][mA][mU][mC][mC][mA][mA][mG][mC][mA][mG][mC][mC][mG][ademA-GalNAc][ademA-GalNAc][ademA-GalNAc][mG][mG][mC][mU][mG][mC] | 403 | [Me Phosphonate-4O-mUs][fUs][fG][mG][fA][mU][fA][mA][mU][fA][mU][mU][mC][fU][mG][mU][mU][mG][mU][mCs][mGs][mG] | 803 |

Modifications in Table 6:

mC, mA, mG, mU=2'-OMe ribonucleosides; fA, fC, fG, fU=2'-F ribonucleosides; s=phosphorothioate; MePhosphonate-40-mUs=

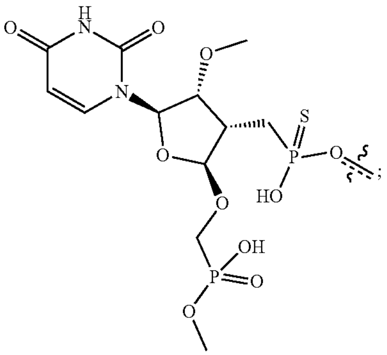

ademA-GalNAc=GalNAc attached to an adenine nucleotide:

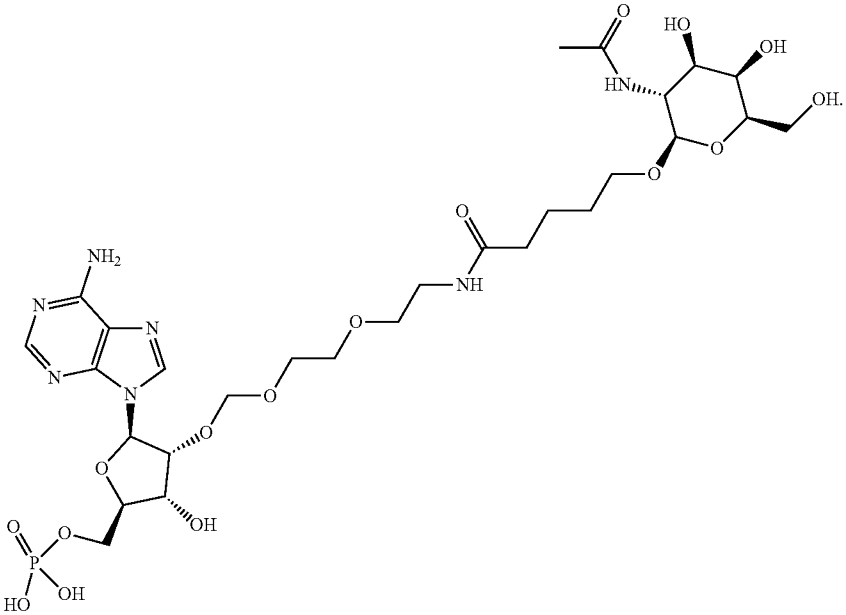 [SMILES: CC(=O)N[C@H]1[C@H](OCCCCC(=O)NCCOCCOCO[C@@H]2[C@H](O)[C@@H](COP(=O)(O)O)O[C@H]2n2cnc3c(N)ncnc32)O[C@H](CO)[C@H](O)[C@@H]1O]

What is claimed is:

1. A method for treating a subject having a disease, disorder or condition associated with increased LPA expression, the method comprising administering to the subject a therapeutically effective amount of an RNAi oligonucleotide, the oligonucleotide comprising a sense strand and an antisense strand, wherein the sense strand and the antisense strand form a duplex region, wherein the antisense strand is:

(SEQ ID NO: 793)
5'-[MePhosphonate-4O-mUs][fAs][fGs][fA][fU][mG]
[fA][mC][mC][fA][mA][mG][mC][fU][mU][mG][mG][mC]
[mA][mAs][mGs][mG]-3', and the sense strand is:

(SEQ ID NO: 393)
5'-[mUs][mU][mG][mC][mC][mA][mA][fG][fC][fU][fU]
[mG][mG][mU][mC][mA][mU][mC][mU][mA][mG][mC][mA]
[mG][mC][mC][mG][ademA-GalNAc][ademA-GalNAc]
[ademA-GalNAc][mG][mG][mC][mU][mG][mC]-3', wherein:

mA represents 2'-OMe adenosine;
mC represents 2'-OMe cytosine;
mG represents 2'-OMe guanosine;
mU represents 2'-OMe uridine;
fA represents 2'-F adenosine;
fC represents 2'-F cytosine;
fG represents 2'-F guanosine;
fU represents 2'-F uridine;
fAs represents 2'-F adenosine with a 3'-phosphorothioate linkage;
fGs represents 2'-F guanosine with a 3'-phosphorothioate linkage;
mAs represents 2'-OMe adenosine with a 3'-phosphorothioate linkage;
mGs represents 2'-OMe guanosine with a 3'-phosphorothioate linkage;
mUs represents 2'-OMe uridine with a 3'-phosphorothioate linkage;
ademA-GalNAc represents 2'-aminodiethoxymethanol-adenine-GalNAc:

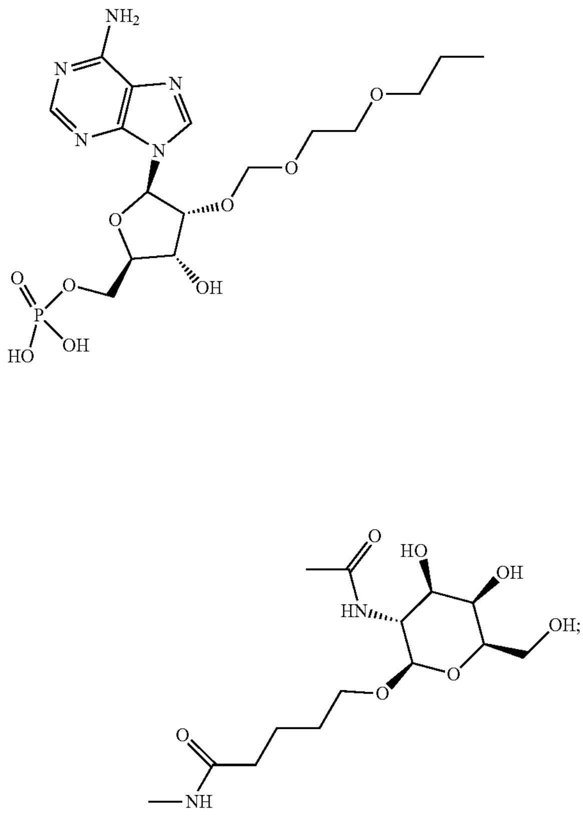;

and

MePhosphonate-40-mUs represents

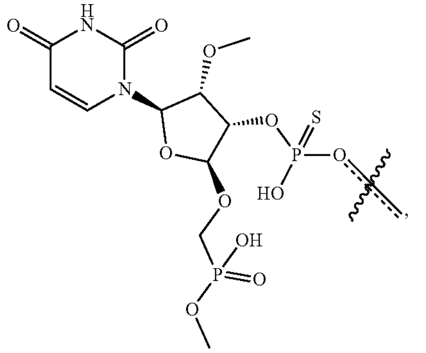

thereby treating the subject.

2. A method for reducing LPA expression in a subject, the method comprising the step of:

administering to the subject an RNAi oligonucleotide, the oligonucleotide comprising a sense strand and an antisense strand, wherein the sense strand and the antisense strand form a duplex region, wherein the antisense strand is:

```
                                        (SEQ ID NO: 793)
5'-[MePhosphonate-40-mUs][fAs][fGs][fA][fU][mG]

[fA][mC][mC][fA][mA][mG][mC][fU][mU][mG][mG][mC]

[mA][mAs][mGs][mG]-3', and
```

the sense strand is:

```
                                        (SEQ ID NO: 393)
5'-[mUs][mU][mG][mC][mC][mA][mA][fG][fC][fU][fU]

[mG][mG][mU][mC][mA][mU][mC][mU][mA][mG][mC][mA]

[mG][mC][mC][mG][ademA-GalNAc][ademA-GalNAc]

[ademA-GalNAc][mG][mG][mC][mU][mG][mC]-3',
```

wherein:

mA represents 2'-OMe adenosine;

mC represents 2'-OMe cytosine;

mG represents 2'-OMe guanosine;

mU represents 2'-OMe uridine;

fA represents 2'-F adenosine;

fC represents 2'-F cytosine;

fG represents 2'-F guanosine;

fU represents 2'-F uridine;

fAs represents 2'-F adenosine with a 3'-phosphorothioate linkage;

fGs represents 2'-F guanosine with a 3'-phosphorothioate linkage;

mAs represents 2'-OMe adenosine with a 3'-phosphorothioate linkage;

mGs represents 2'-OMe guanosine with a 3'-phosphorothioate linkage;

mUs represents 2'-OMe uridine with a 3'-phosphorothioate linkage;

ademA-GalNAc represents 2'-aminodiethoxymethanol-adenine-GalNAc:

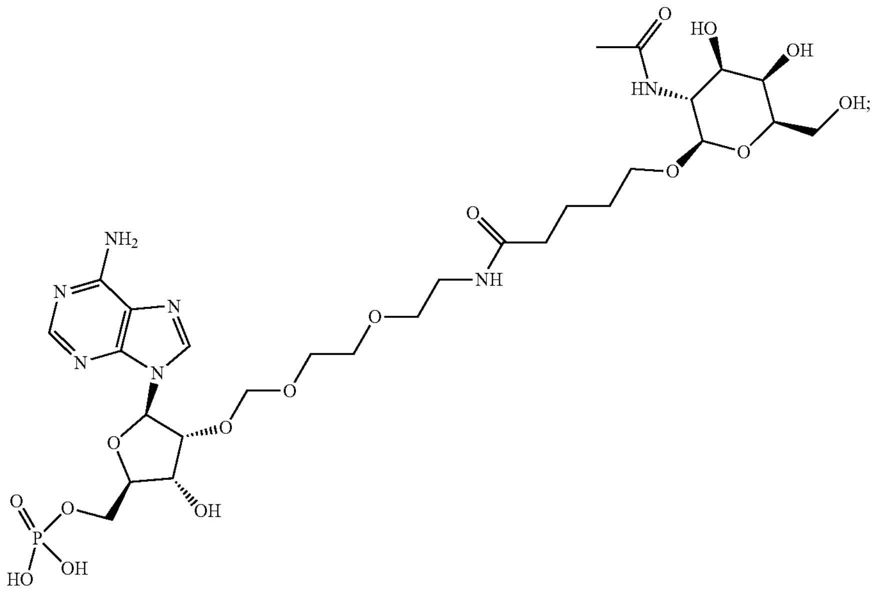 [SMILES: CC(=O)N[C@H]1[C@H](OCCCCC(=O)NCCOCCOCO[C@@H]2[C@H](O)[C@@H](COP(=O)(O)O)O[C@H]2n2cnc3c(N)ncnc32)O[C@H](CO)[C@H](O)[C@@H]1O]

and MePhosphonate-40-mUs represents

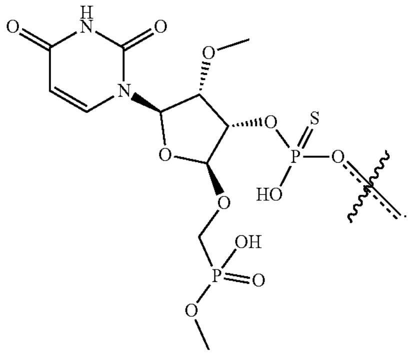

3. The method of claim 1, further comprising the step of reducing LPA expression, and wherein the reducing LPA expression comprises reducing an amount or level of LPA mRNA, an amount or level of apolipoprotein(a) (apo(a)), an amount or level of apo(a) activity, an amount or level of lipoprotein(a) (Lp(a)), or a combination thereof.

4. The method of claim 1, wherein LPA expression is reduced in the subject by about 75% when compared to LPA expression prior to the administering or when compared to LPA expression in a reference or control subject.

5. The method of claim 1, wherein an amount or level of cholesterol is reduced in the subject following the administering, and wherein the cholesterol is selected from the group consisting of total cholesterol, LDL cholesterol and HDL cholesterol.

6. The method of claim 1, wherein an amount or level of apolipoprotein B (ApoB-100) is reduced in the subject following the administering.

7. The method of claim 1, wherein the disease, disorder or condition associated with increased LPA expression is selected from the group consisting of cardiometabolic diseases, atherosclerosis, dyslipidemia, nonalcoholic fatty liver disease (NAFLD) and nonalcoholic steatohepatitis (NASH).

8. The method of claim 1, wherein the subject is treated therapeutically.

9. The method of claim 1, wherein the subject is treated prophylactically.

10. The method of claim 1, wherein the administering comprises a subcutaneous injection.

11. The method of claim 1, further comprising the step of administering to the subject a second composition or therapeutic agent.

12. The method of claim 1, wherein LPA expression is reduced in the subject by at least 75% when compared to LPA expression prior to the administering or when compared to LPA expression in a reference or control subject.

13. The method of claim 2, wherein the reducing LPA expression comprises reducing an amount or level of LPA mRNA, an amount or level of apolipoprotein(a) (apo(a)), an amount or level of apo(a) activity, an amount or level of lipoprotein(a) (Lp(a)), or a combination thereof.

14. The method of claim 2, wherein LPA expression is reduced in the subject by about 75% when compared to LPA expression prior to the administering or when compared to LPA expression in a reference or control subject.

15. The method of claim 2, wherein LPA expression is reduced in the subject by at least 75% when compared to LPA expression prior to the administering or when compared to LPA expression in a reference or control subject.

16. The method of claim 2, wherein an amount or level of cholesterol is reduced in the subject following the administering, and wherein the cholesterol is selected from the group consisting of total cholesterol, LDL cholesterol and HDL cholesterol.

17. The method of claim 2, wherein an amount or level of apolipoprotein B (ApoB-100) is reduced in the subject following the administering.

18. The method of claim 2, wherein the subject has a disease, disorder or condition associated with increased LPA expression selected from the group consisting of cardiometabolic diseases, atherosclerosis, dyslipidemia, nonalcoholic fatty liver disease (NAFLD) and nonalcoholic steatohepatitis (NASH).

19. The method of claim 2, wherein the subject is treated therapeutically.

20. The method of claim 2, wherein the subject is treated prophylactically.

21. The method of claim 2, wherein the administering comprises a subcutaneous injection.

22. The method of claim 2, further comprising the step of administering to the subject a second composition or therapeutic agent.

* * * * *

SEQUENCE LISTING

<160> NUMBER OF SEQ ID NOS: 1197

<210> SEQ ID NO 1
<211> LENGTH: 6414
<212> TYPE: DNA
<213> ORGANISM: Homo sapiens

<400> SEQUENCE: 1
ctgggattgg gacacacttt ctgggcactg ctggccagtc ccaaaatgga acataaggaa 60
gtggttcttc tacttctttt atttctgaaa tcagcagcac ctgagcaaag ccatgtggtc 120
caggattgct accatggtga tggacagagt tatcgaggca cgtactccac cactgtcaca 180
ggaaggacct gccaagcttg gtcatctatg acaccacatc aacataatag gaccacagaa 240

-continued

```
aactacccaa atgctggctt gatcatgaac tactgcagga atccagatgc tgtggcagct    300
ccttattgtt atacgaggga tcccggtgtc aggtgggagt actgcaacct gacgcaatgc    360
tcagacgcag aagggactgc cgtcgcgcct ccgactgtta ccccggttcc aagcctagag    420
gctccttccg aacaagcacc gactgagcaa aggcctgggg tgcaggagtg ctaccatggt    480
aatggacaga gttatcgagg cacatactcc accactgtca caggaagaac ctgccaagct    540
tggtcatcta tgacaccaca ctcgcatagt cggaccccag aatactaccc aaatgctggc    600
ttgatcatga actactgcag gaatccagat gctgtggcag ctccttattg ttatacgagg    660
gatcccggtg tcaggtggga gtactgcaac ctgacgcaat gctcagacgc agaagggact    720
gccgtcgcgc ctccgactgt taccccggtt ccaagcctag aggctccttc cgaacaagca    780
ccgactgagc aaaggcctgg ggtgcaggag tgctaccatg gtaatggaca gagttatcga    840
ggcacatact ccaccactgt cacaggaaga acctgccaag cttggtcatc tatgacacca    900
cactcgcata gtcggacccc agaatactac ccaaatgctg gcttgatcat gaactactgc    960
aggaatccag atgctgtggc agctccttat tgttatacga gggatcccgg tgtcaggtgg   1020
gagtactgca acctgacgca atgctcagac gcagaaggga ctgccgtcgc gcctccgact   1080
gttaccccgg ttccaagcct agaggctcct tccgaacaag caccgactga gcagaggcct   1140
ggggtgcagg agtgctacca cggtaatgga cagagttatc gaggcacata ctccaccact   1200
gtcactggaa gaacctgcca agcttggtca tctatgacac cacactcgca tagtcggacc   1260
ccagaatact acccaaatgc tggcttgatc atgaactact gcaggaatcc agatgctgtg   1320
gcagctcctt attgttatac gagggatccc ggtgtcaggt gggagtactg caacctgacg   1380
caatgctcag acgcagaagg gactgccgtc gcgcctccga ctgttacccc ggttccaagc   1440
ctagaggctc cttccgaaca agcaccgact gagcaaaggc ctggggtgca ggagtgctac   1500
catggtaatg gacagagtta tcgaggcaca tactccacca ctgtcacagg aagaacctgc   1560
caagcttggt catctatgac accacactcg catagtcgga ccccagaata ctacccaaat   1620
gctggcttga tcatgaacta ctgcaggaat ccagatgctg tggcagctcc ttattgttat   1680
acgagggatc ccggtgtcag gtgggagtac tgcaacctga cgcaatgctc agacgcagaa   1740
gggactgccg tcgcgcctcc gactgttacc ccggttccaa gcctagaggc tccttccgaa   1800
caagcaccga ctgagcaaag gcctggggtg caggagtgct accatggtaa tggacagagt   1860
tatcgaggca catactccac cactgtcaca ggaagaacct gccaagcttg gtcatctatg   1920
acaccacact cgcatagtcg gaccccagaa tactacccaa atgctggctt gatcatgaac   1980
tactgcagga atccagatgc tgtggcagct ccttattgtt atacgaggga tcccggtgtc   2040
aggtgggagt actgcaacct gacgcaatgc tcagacgcag aagggactgc cgtcgcgcct   2100
ccgactgtta ccccggttcc aagcctagag gctccttccg aacaagcacc gactgagcaa   2160
aggcctgggg tgcaggagtg ctaccatggt aatggacaga gttatcgagg cacatactcc   2220
accactgtca caggaagaac ctgccaagct tggtcatcta tgacaccaca ctcgcatagt   2280
cggaccccag aatactaccc aaatgctggc ttgatcatga actactgcag gaatccagat   2340
gctgtggcag ctccttattg ttatacgagg gatcccggtg tcaggtggga gtactgcaac   2400
ctgacgcaat gctcagacgc agaagggact gccgtcgcgc ctccgactgt taccccggtt   2460
ccaagcctag aggctccttc cgaacaagca ccgactgagc agaggcctgg ggtgcaggag   2520
tgctaccacg gtaatggaca gagttatcga ggcacatact ccaccactgt cactggaaga   2580
```

-continued

```
acctgccaag cttggtcatc tatgacacca cactcgcata gtcggacccc agaatactac   2640
ccaaatgctg gcttgatcat gaactactgc aggaatccag atcctgtggc agccccttat   2700
tgttatacga gggatcccag tgtcaggtgg gagtactgca acctgacaca atgctcagac   2760
gcagaaggga ctgccgtcgc gcctccaact attaccccga ttccaagcct agaggctcct   2820
tctgaacaag caccaactga gcaaaggcct ggggtgcagg agtgctacca cggaaatgga   2880
cagagttatc aaggcacata cttcattact gtcacaggaa gaacctgcca agcttggtca   2940
tctatgacac cacactcgca tagtcggacc ccagcatact acccaaatgc tggcttgatc   3000
aagaactact gccgaaatcc agatcctgtg gcagcccctt ggtgttatac aacagatccc   3060
agtgtcaggt gggagtactg caacctgaca cgatgctcag atgcagaatg gactgccttc   3120
gtccctccga atgttattct ggctccaagc ctagaggctt tttttgaaca agcactgact   3180
gaggaaaccc ccggggtaca ggactgctac taccattatg gacagagtta ccgaggcaca   3240
tactccacca ctgtcacagg aagaacttgc caagcttggt catctatgac accacaccag   3300
catagtcgga ccccagaaaa ctacccaaat gctggcctga ccaggaacta ctgcaggaat   3360
ccagatgctg agattcgccc ttggtgttac accatggatc ccagtgtcag gtgggagtac   3420
tgcaacctga cacaatgcct ggtgacagaa tcaagtgtcc ttgcaactct cacggtggtc   3480
ccagatccaa gcacagaggc ttcttctgaa gaagcaccaa cggagcaaag ccccggggtc   3540
caggattgct accatggtga tggacagagt tatcgaggct cattctctac cactgtcaca   3600
ggaaggacat gtcagtcttg gtcctctatg acaccacact ggcatcagag gacaacagaa   3660
tattatccaa atggtggcct gaccaggaac tactgcagga atccagatgc tgagattagt   3720
ccttggtgtt ataccatgga tcccaatgtc agatgggagt actgcaacct gacacaatgt   3780
ccagtgacag aatcaagtgt ccttgcgacg tccacggctg tttctgaaca agcaccaacg   3840
gagcaaagcc ccacagtcca ggactgctac catggtgatg gacagagtta tcgaggctca   3900
ttctccacca ctgttacagg aaggacatgt cagtcttggt cctctatgac accacactgg   3960
catcagagaa ccacagaata ctacccaaat ggtggcctga ccaggaacta ctgcaggaat   4020
ccagatgctg agattcgccc ttggtgttat accatggatc ccagtgtcag atgggagtac   4080
tgcaacctga cgcaatgtcc agtgatggaa tcaactctcc tcacaactcc cacggtggtc   4140
ccagttccaa gcacagagct tccttctgaa gaagcaccaa ctgaaaacag cactggggtc   4200
caggactgct accgaggtga tggacagagt tatcgaggca cactctccac cactatcaca   4260
ggaagaacat gtcagtcttg gtcgtctatg acaccacatt ggcatcggag gatcccatta   4320
tactatccaa atgctggcct gaccaggaac tactgcagga atccagatgc tgagattcgc   4380
ccttggtgtt acaccatgga tcccagtgtc aggtgggagt actgcaacct gacacgatgt   4440
ccagtgacag aatcgagtgt cctcacaact cccacagtgg ccccggttcc aagcacagag   4500
gctccttctg aacaagcacc acctgagaaa agccctgtgg tccaggattg ctaccatggt   4560
gatggacgga gttatcgagg catatcctcc accactgtca caggaaggac ctgtcaatct   4620
tggtcatcta tgataccaca ctggcatcag aggaccccag aaaactaccc aaatgctggc   4680
ctgaccgaga actactgcag gaatccagat tctgggaaac aaccctggtg ttacacaacc   4740
gatccgtgtg tgaggtggga gtactgcaat ctgacacaat gctcagaaac agaatcaggt   4800
gtcctagaga ctcccactgt tgttccagtt ccaagcatgg aggctcattc tgaagcagca   4860
ccaactgagc aaacccctgt ggtccggcag tgctaccatg gtaatggcca gagttatcga   4920
ggcacattct ccaccactgt cacaggaagg acatgtcaat cttggtcatc catgacacca   4980
```

caccggcatc agaggacccc agaaaactac ccaaatgatg gcctgacaat gaactactgc 5040
aggaatccag atgccgatac aggcccttgg tgttttacca tggaccccag catcaggtgg 5100
gagtactgca acctgacgcg atgctcagac acagaaggga ctgtggtcgc tcctccgact 5160
gtcatccagg ttccaagcct agggcctcct tctgaacaag actgtatgtt tgggaatggg 5220
aaaggatacc ggggcaagaa ggcaaccact gttactggga cgccatgcca ggaatgggct 5280
gcccaggagc cccatagaca cagcacgttc attccaggga caaataaatg ggcaggtctg 5340
gaaaaaaatt actgccgtaa ccctgatggt gacatcaatg gtccctggtg ctacacaatg 5400
aatccaagaa aactttttga ctactgtgat atccctctct gtgcatcctc ttcatttgat 5460
tgtgggaagc ctcaagtgga gccgaagaaa tgtcctggaa gcattgtagg ggggtgtgtg 5520
gcccacccac attcctggcc ctggcaagtc agtctcagaa caaggtttgg aaagcacttc 5580
tgtggaggca ccttaatatc cccagagtgg gtgctgactg ctgctcactg cttgaagaag 5640
tcctcaaggc cttcatccta caaggtcatc ctgggtgcac accaagaagt gaacctcgaa 5700
tctcatgttc aggaaataga agtgtctagg ctgttcttgg agcccacaca agcagatatt 5760
gccttgctaa agctaagcag gcctgccgtc atcactgaca aagtaatgcc agcttgtctg 5820
ccatccccag actacatggt caccgccagg actgaatgtt acatcactgg ctggggagaa 5880
acccaaggta cctttgggac tggccttctc aaggaagccc agctccttgt tattgagaat 5940
gaagtgtgca atcactataa gtatatttgt gctgagcatt tggccagagg cactgacagt 6000
tgccagggtg acagtggagg gcctctggtt tgcttcgaga aggacaaata cattttacaa 6060
ggagtcactt cttggggtct tggctgtgca cgccccaata agcctggtgt ctatgctcgt 6120
gtttcaaggt ttgttacttg gattgaggga atgatgagaa ataattaatt ggacgggaga 6180
cagagtgaag catcaaccta cttagaagct gaaacgtggg taaggattta gcatgctgga 6240
aataatagac agcaatcaaa cgaagacact gttcccagct accagctatg ccaaaccttg 6300
gcatttttgg tatttttgtg tataagcttt taaggtctga ctgacaaatt ctgtattaag 6360
gtgtcatagc tatgacattt gttaaaaata aactctgcac ttattttgat ttga 6414

<210> SEQ ID NO 2
<211> LENGTH: 5387
<212> TYPE: DNA
<213> ORGANISM: Macaca fascicularis

<400> SEQUENCE: 2
gatgctgcat acttaatgtc gaaaggttgc ttcatccaag agcctggagt tttcagagac 60
actgtcctga aactatgtcc tgaaactatg tcattgaaac tgaaacattg tcctgaagct 120
ggtattgggc aataccagcg cctgcaggca acagctcgga tgcacttaag atttaaatat 180
tacccacaga agttctggct tgtctgggaa aacctttttgc taaacagaag agcaacattt 240 ttttttttt cttttctgga atttgtaaac agcatttatt ctcagcctta ccttccaaac 300
gttgcacttg gaacattgct gggccccgtg gaaacagaag cgaacgtcag ccaggccggc 360
agggggcggc agaccccaca cttcgccggg cgccctcacc tccctgggag ggagtgtgca 420
gctgccaaaa tcttcggcgg ggttcagtcc aagcgacttc agccagcaga tggtcattct 480
cctgtgaccg tgtgtactac agactgtttc aaaaccgggc aggcaattaa caatgggaat 540
tctgccatca tcgctgacaa agtcatccca gtttgtctgc catccccaaa ttatgtggtc 600
gccaaccaga ctgaatgtta tgtcactggc tggggagaaa cccaagcact acctgagcaa 660

-continued

```
agccatgtgg tccaggattg ctaccatggt gatggacaga gttatcaagg cacatcctcc    720
accactgtca caggaaggac ctgccaagct tggtcatcta tggaaccaca tcagcataat    780
agaaccacag aaaactaccc aaatgctggc ttgatcagga actactgcag gaatccagat    840
cctgtggcag cccettattg ttatacgatg gatcccaatg tcaggtggga gtactgcaac    900
ctgacacaat gctcagacgc agaagggact gccgtcgcac ctccgaatgt caccccggtt    960
ccaagcctag aggctccttc cgaacaagca ccgactgagc aaaggcctgg ggtgcaggag   1020
tgctaccacg gtaatggaca gagttatcga ggcacatact tcaccactgt gacaggaaga   1080
acctgccaag cttggtcatc tatgacaccg cactctcata gtcggacccc ggaaaactac   1140
ccaaatggtg gcttgatcag gaactactgc aggaatccag atcctgtggc agccccttat   1200
tgttatacca tggatcccaa tgtcaggtgg gagtactgca acctgacaca atgctcagac   1260
gcagaaggga ttgccgtcac acctctgact gttaccccgg ttccaagcct agaggctcct   1320
tccaagcaag caccaactga gcaaaggcct ggtgtccagg agtgctacca cggtaatgga   1380
cagagttatc gaggcacata cttcaccact gtgacaggaa gaacctgcca agcttggtca   1440
tctatgacac cacattctca tagtcgtacc ccagaaaact acccaaatgg tggcttgatc   1500
aggaactact gcaggaatcc agatcctgtg gcagcccctt attgttatac catggatccc   1560
aatgtcaggt gggagtactg caacctgaca caatgctcag acgcagaagg gactgccgtc   1620
gcacctccga ctgtcacccc ggttccaagc ctagaggctc cttccgaaca agcaccgact   1680
gagcaaaggc ctggggtgca ggagtgctac cacggtaatg gacagagtta tcgaggcaca   1740
tacttcacca ctgtgacagg aagaacctgc caagcttggt catctatgac accgcactct   1800
catagtcgga ccccggaaaa ctacccaaat ggtggcttga tcaggaacta ctgcaggaat   1860
ccagatcctg tggcagcccc ttattgttat accatggatc ccaatgtcag gtgggagtac   1920
tgcaacctga cacaatgctc agacgcagaa gggactgccg tcgcacctcc gaatgtcacc   1980
ccggttccaa gcctagaggc tccttctgag caagcaccaa ctgagcaaag gcttggggtg   2040
caggagtgct accacggtaa tggacagagt tatcgaggca catacttcac cactgtgaca   2100
ggaagaacct gccaagcttg gtcatctatg acaccacact ctcatagtcg gaccccagaa   2160
aactacccaa atgctggctt ggtcaagaac tactgccgaa atccagatcc tgtggcagcc   2220
ccttggtgtt atacaacgga tcccagtgtc aggtgggagt actgcaacct gacacgatgc   2280
tcagatgcag aagggactgc tgttgtgcct ccaaatatta ttccggttcc aagcctagag   2340
gcttttcttg aacaagaacc gactgaggaa accccccggg tacaggagtg ctactaccat   2400
tatggacaga gttatagagg cacatactcc accactgtta caggaagaac ttgccaagct   2460
tggtcatcta tgacaccaca ccagcatagt cggaccccaa aaaactatcc aaatgctggc   2520
ctgaccagga actactgcag gaatccagat gctgagattc gcccttggtg ttataccatg   2580
gatcccagtg tcaggtggga gtactgcaac ctgacacaat gtctggtgac agaatcaagt   2640
gtccttgaaa ctctcacagt ggtcccagat ccaagcacac aggcttcttc tgaagaagca   2700
ccaacggagc aaagtcccga ggtccaggac tgctaccatg gtgatggaca gagttatcga   2760
ggctcattct ccaccactgt cacaggaagg acatgtcagt cttggtcctc tatgacacca   2820
cactggcatc agaggacaac agaatattat ccagatggtg gcctgaccag gaactactgc   2880
aggaatccag atgctgagat tcgcccttgg tgttatacca tggatcccag tgtcaggtgg   2940
gagtactgca acctgacaca atgtccagtg acagaatcaa gtgtcctcgc aacgtccatg   3000
gctgtttctg aacaagcacc aatggagcaa agccccgggg tccaggactg ctaccatggt   3060
```

-continued

```
gatggacaga gttatcgagg ttcattctcc accactgtca caggaaggac atgtcagtct   3120
tggtcctcta tgacaccaca ctggcatcag aggaccatag aatactaccc aaatggtggc   3180
ctgaccaaga actactgcag gaatccagat gctgagattc gcccttggtg ttataccatg   3240
gatcccagag tcagatggga gtactgcaac ctgacacaat gtgtggtgat ggaatcaagt   3300
gtccttgcaa ctcccatggt ggtcccagtt ccaagcagag aggttccttc tgaagaagca   3360
ccaactgaaa acagccctgg ggtccaggac tgctaccaag gtgatggaca gagttatcga   3420
ggcacattct ccaccactat cacaggaaga acatgtcagt cttggttgtc tatgacacca   3480
catcggcatc ggaggatccc attacgctat ccaaatgctg gcctgaccag gaactattgc   3540
agaaatccag atgctgagat tcgcccttgg tgttacacca tggatcccag tgtcaggtgg   3600
gagtactgca acctgacaca atgtccagtg acagaatcaa gtgtcctcac aactcccacg   3660
gtggtcccgg ttccaagcac agaggctcct tctgaacaag caccacctga gaaaagccct   3720
gtggtccagg attgctacca tggtgatgga cagagttatc gaggcacatc ctccaccact   3780
gtcacaggaa ggaactgtca gtcttggtca tctatgatac cacactggca tcagaggacc   3840
ccagaaaact acccaaatgc tggcctgacc aggaactact gcaggaatcc agattctggg   3900
aaacaaccct ggtgttacac gactgatcca tgtgtgaggt gggagtactg caacctgaca   3960
caatgctcag aaacagaatc aggtgtccta gagactccca ctgttgttcc ggttccaagc   4020
atggaagctc attctgaagc agcaccaact gagcaaactc ctgtggtcca gcagtgctac   4080
catggtaatg gacagagtta tcgaggcaca ttctccacca ctgtcacagg aaggacatgt   4140
caatcttggt catccatgac accacaccag cataagagga ccccggaaaa ccacccaaat   4200
gatgacttga caatgaacta ctgcaggaat ccagatgctg acacaggccc ttggtgtttt   4260
accatggacc ccagcgtcag gcgggagtac tgcaacctga cgcgatgctc agacacagaa   4320
gggactgtgg tcacacctcc gactgttatc ccggttccaa gcctagaggc tccttctgaa   4380
caagcatcct cttcatttga ttgtgggaag cctcaagtgg agccaaagaa atgtcctgga   4440
agcattgtag gtgggtgtgt ggcccaccca cattcctggc cctggcaagt cagtcttaga   4500
acaaggtttg gaaagcactt ctgtggaggc accttaatat ccccagagtg ggtgctgact   4560
gctgcttgct gcttggagac gttctcaagg ccttccttct acaaggtcat cctgggtgca   4620
caccaagaag tgaatctcga atctcacgtt caagaaatag aagtgtctag gttgttcttg   4680
gagcccatag gagcagatat tgccttgcta aagctaagca ggcctgccat catcactgac   4740
aaagtaatcc cagcctgtct gccgtctcca aattacgtga tcaccgtctg gactgaatgt   4800
tacatcactg gctggggaga aacccaaggt acctttgggg ctggccttct caaggaagcc   4860
cagcttcatg tgattgagaa tacagtgtgc aatcactacg agtttctgaa tggaagagtc   4920
aaatccaccg agctctgtgc tgggcatttg gccggaggca ctgacagatg ccagggtgac   4980
agtggagggc ctgtggtttg cttcgacaag gacaaataca ttttacgagg aataacttct   5040
tggggtcctg gctgtgcatg ccccaataag cctggtgtct atgttcgtgt ttcaagcttt   5100
gtcacttgga ttgagggagt gatgagaaat aattaattga acaagagaca gagtgaagca   5160
ttgactcacc tagaggctag aatgggggta gggatttagc acgctggaaa taacggacag   5220
taatcaaacg aagacactgt ccccagctac caactatgcc aaacctcagc atttttggta   5280
ttattgtgta taagcttttc ccgtctgact gctgggttct ccaataaggt gacatagcta   5340
tgccatttgt taaaaataaa ctctgtactt attttgattt gagtaaa                 5387
```

<210> SEQ ID NO 3
<211> LENGTH: 6428
<212> TYPE: DNA
<213> ORGANISM: Macaca mulatta
<220> FEATURE:
<221> NAME/KEY: misc_feature
<222> LOCATION: (2053)..(2053)
<223> OTHER INFORMATION: n is a, c, g, or t
<220> FEATURE:
<221> NAME/KEY: misc_feature
<222> LOCATION: (2272)..(2272)
<223> OTHER INFORMATION: n is a, c, g, or t
<220> FEATURE:
<221> NAME/KEY: misc_feature
<222> LOCATION: (2395)..(2395)
<223> OTHER INFORMATION: n is a, c, g, or t

<400> SEQUENCE: 3
agccttgcct ttgaaatgtt ccagttggaa cattgctggg cagcgtgcaa acaggagcga 60
acgtcagccg gggcggcagg gggcagcaga ccccacactt tgtccatgcc tcaggtggga 120
ggaagtgtcc ggctccagaa acctgccgcg ggctttatcc caagcgactt cagccagcag 180
acggttcatg tcctgaggct gcaaaatacg agttctgcca tcatcgctga caaagtcatc 240
ccagtttgtc tgccatcccc aaattatgcg atcgccaacc agactgaatg ttatgtcact 300
ggctggggag aaacccaagc actacctgag caaagccatg tggtccagga ttgctaccat 360
ggtgatggac agagttatca aggcacatcc tccaccactg tcacaggaag gacctgccaa 420
gcttggtcat ctatggaacc acatcagcat aatagaacca cagaaaacta cccaaatgct 480
ggcttgatca ggaactactg caggaatcca gatcctgtgg cagcccctta ttgttatacg 540
atggatccca atgtcaggtg ggagtactgc aacctgacac aatgctcaga cgcagaaggg 600
actgccgtcg cacctccgaa tgtcaccccg gttccaagcc tagaggctct ttccgaacaa 660
gcaccgactg agcaaaggcc tggggtgcag gagtgctacc acggtaatgg acagagttat 720
cgaggcacat acttcaccac tgtgacagga agaacctgcc aagcttggtc atctatgaca 780
ccacattctc atagtcgtac cccagaaaac tacccaaatg gtggcttgat caggaactac 840
tgcaggaatc cagatcctgt ggcagcccct tattgttata ccatggatcc caatgtcagg 900
tgggagtact gcaacctgac acaatgctca gacgcagaag ggactgccgt cgcacctccg 960
aatgtcaccc cggttccaag cctagaggct ccttccgaac aagcaccgac tgagcaaagg 1020
cctggggtgc aggagtgcta ccacggtaat ggacagagtt atcgaggcac atacttcacc 1080
actgtgacag gaagaacctg ccaagcttgg tcatctatga caccacattc tcatagtcgt 1140
accccagaaa actacccaaa tggtggcttg atcaggaact actgcaggaa tccagatcct 1200
gtggcagccc cttattgtta taccatggat cccaatgtca ggtgggagta ctgcaacctg 1260
acacaatgct cagacgcaga ggggactgcc gtcgcacctc cgactgtcac cccggttcca 1320
agcctagagg ctccttctga gcaagcaccg actgagcaaa ggcctggggt gcaggagtgc 1380
taccacggta atggacagag ttatcgaggc acatacttca ccactgtgac aggaagaacc 1440
tgccaagctt ggtcatctat gacaccgcac tctcatagtc ggaccccgga aaactaccca 1500
aatggtggct tgatcaggaa ctactgcagg aatccagatc ctgtggcagc cccttattgt 1560
tatacgatgg atcccaatgt caggtgggag tactgcaacc tgacacaatg ctcagacgca 1620
gaagggactg ccgtcgcacc tccgaatgtc accccggttc caagcctaga ggctccttcc 1680
gaacaagcac cgactgagca aaggcctggg gtgcaggagt gctaccacgg taatggacag 1740
agttatcgag gcacatactt caccactgtg acaggaagaa cctgccaagc ttggtcatct 1800

-continued

```
atgacaccgc actctcatag tcggaccccg gaaaactacc caaatggtgg cttgatcagg   1860
aactactgca ggaatccaga tcctgtggca gccccttatt gttatacgat ggatcccaat   1920
gtcaggtggg agtactgcaa cctgacacaa tgctcagacg cagaagggac tgccgtcgca   1980
cctccgaatg tcaccccggt tccaagccta gaggctcctt ccgaacaagc accaactgag   2040
caaaggcctg ggntgcagga gtgctaccat ggtaatggac agagttatcg aggcacatac   2100
ttcaccactg tgacaggaag aacctgccaa gcttggtcat ctatgacacc gcactctcat   2160
agtcggaccc cggaaaacta cccaaatggt ggcttgatca ggaactactg caggaatcca   2220
gatcctgtgg cagcccctta ttgttatacc atggatccca atgtcaggtg gnagtactgc   2280
aacctgacac aatgctcaga cgcagaaggg actgccgtcg cacctccgac tgtcaccccg   2340
gttccaagcc tagaggctcc ttcgagcaag gcaccgactg agcaaaggcc tgggntgcag   2400
gagtgctacc acggtaatgg acagagttat cgaggcacat acttcaccac tgtgacagga   2460
agaacctgcc aagcttggtc atctatgaca ccgcactctc atagtcggac cccggaaaac   2520
tacccaaatg gtggcttgat caggaactac tgcaggaatc cagatcctgt ggcagcccct   2580
tattgttata cgatggatcc caatgtcagg tgggagtact gcaacctgac acaatgctca   2640
gacgcagaag ggactgccgt cgcacctccg aatgtcaccc cggttccaag cctagaggct   2700
ccttccgaac aagcaccgac tgagcaaagg cctggggtgc aggagtgcta ccacggtaat   2760
ggacagagtt atcgaggcac atacttcacc actgtgacag gaagaacctg ccaagcttgg   2820
tcatctatga caccgcactc tcatagtcgg accccggaaa actacccaaa tggtggcttg   2880
atcaggaact actgcaggaa tccagatcct gtggcagccc cttattgtta taccatggat   2940
cccaatgtca ggtgggagta ctgcaacctg acacaatgct cagacgcaga agggactgcc   3000
gtcgcacctc cgaatgtcac cccggttcca agcctagagg ctccttctga gcaagcacca   3060
actgagcaaa ggcttggggt gcaggagtgc taccacagta atggacagag ttatcgaggc   3120
acatacttca ccactgtgac aggaagaacc tgccaagctt ggtcatctat gacaccacac   3180
tctcatagtc ggaccccaga aaactaccca aatgctggct tggtcaagaa ctactgccga   3240
aatccagatc ctgtggcagc cccttggtgt tatacaacgg atcccagtgt caggtgggag   3300
tactgcaacc tgacacgatg ctcagatgca gaagggactg ctgtcatgcc tccaaatatt   3360
attccggttc caagcctaga ggcttttctt gaacaagaac ctactgagga aaccccccggg   3420
gtacaggagt gctactacca ttatggacag agttatcgag gcacatactc caccactgtt   3480
acaggaagaa cttgccaagc ttggtcatct atgacaccac accagcatag tcggacccca   3540
aaaaactatc caaatgctgg cctgaccagg aactactgca ggaatccaga tgctgagatt   3600
cgcccttggt gttataccat ggatcccagt gtcaggtggg agtactgcaa cctgacacaa   3660
tgtctggtga cagaatcaag tgtccttgaa actctcacag tggtcccaga tccaagcaca   3720
caggcttctt ctgaagaagc accaacggag caaagtcccg aggtccagga ctgctaccat   3780
ggtgatggac agagttatcg aggctcattc tccaccactg tcacaggaag gacatgtcag   3840
tcttggtcct ctatgacacc acactggcat cagaggacaa cagaatatta tccagatggt   3900
ggcctgacca ggaactactg caggaatcca gatgctgaga ttcgcccttg gtgttatacc   3960
atggatccca gtgtcaggtg ggagtactgc aacctgacac aatgtccagt gacagaatca   4020
agtgtcctcg caacgtccat ggctgtttct gaacaagcac caatggagca aagccccggg   4080
gtccaggact gctaccatgg tgatggacag agttatcgag gttcattctc caccactgtc   4140
```

-continued

```
acaggaagga catgtcagtc ttggtcctct atgacaccac actggcatca gaggaccata   4200
gaatactacc caaatggtgg cctgaccaag aactactgca ggaatccaga tgctgagatt   4260
cgcccttggt gttataccat ggatcccaga gtcagatggg agtactgcaa cctgacacaa   4320
tgtgtggtga tggaatcaag tgtccttgca actcccatgg tggtcccagt tccaagcaga   4380
gaggttcctt ctgaagaagc accaactgaa aacagccctg ggtccagga ctgctaccaa    4440
ggtgatggac agagttatcg aggcacattc tccaccacta tcacaggaag aacatgtcag   4500
tcttggttgt ctatgacacc acatcggcat cggaggatcc cattacgcta tccaaatgct   4560
ggcctgacca ggaactattg cagaaatcca gatgctgaga ttcgcccttg gtgttacacc   4620
atggatccca gtgtcaggtg ggagtactgc aacctgacac aatgtccagt gacagaatca   4680
agtgtcctca caactcccac ggtggtcccg gttccaagca cagaggctcc ttctgaacaa   4740
gcaccacctg agaaaagccc tgtggtccag gattgctacc atggtgatgg acagagttat   4800
cgaggcacat cctccaccac tgtcacagga aggaactgtc aatcttggtc atctatgata   4860
ccacactggc atcagaggac cccagaaaac tacccaaatg ctggcctgac caggaactac   4920
tgcaggaatc cagattctgg gaaacaaccc tggtgttaca cgactgatcc atgtgtgagg   4980
tgggagtact gcaacctgac acaatgctca gaaacagaat caggtgtcct agagactccc   5040
actgttgttc cggttccaag catggaagct cattctgaag cagcaccaac tgagcaaacc   5100
cctgtggtcc agcagtgcta ccatggtaat ggacagagtt atcgaggcac attctccacc   5160
actgtcacag gaaggacatg tcaatcttgg tcatccatga caccacacca gcataagagg   5220
accccggaaa accacccaaa tgatgacttg acaatgaact actgcaggaa tccagatgct   5280
gacacaggcc cttggtgttt taccatggac cccagcgtca ggcgggagta ctgcaacctg   5340
acgcgatgct cagacacaga agggactgtg gtcacacctc cgactgttat cccggttcca   5400
agcctagagg ctccttctga acaagcatcc tcttcatttg attgtgggaa gcctcaagtg   5460
gagccaaaga aatgtcctgg aagcattgta ggtgggtgtg tggcccaccc acattcctgg   5520
ccctggcaag tcagtcttag aacaaggttt ggaaagcact tctgtggagg caccttaata   5580
tccccagagt gggtgctgac tgctgcttgc tgcttggaga cgttctcaag gccttccttc   5640
tacaaggtca tcctgggtgc acaccaagaa gtgaatctcg aatctcatgt tcaagaaata   5700
gaagtgtcta ggttgttctt ggagcccata ggagcagata ttgccttgct aaagctaagc   5760
aggcctgcca tcatcactga caaagtaatc ccagcctgtc tgccgtctcc aaattacgtg   5820
atcaccgcct ggactgaatg ttacatcact ggctggggag aaacccaagg tacctttggg   5880
gctggccttc tcaaggaagc ccagcttcat gtgattgaga atacagtgtg caatcactac   5940
gagtttctga atggaagagt caaatccact gagctctgtg ctgggcattt ggccggaggc   6000
actgacagat gccagggtga caatggaggg cctgtggttt gcttcgacaa ggacaaatac   6060
attttacgag gaataacttc ttggggtcct ggctgtgcat gccccaataa gcctggtgtc   6120
tatgttcgtg tttcaagctt tgtcacttgg attgagggag tgatgagaaa taattaattg   6180
aacaagagac agagtgaagc attgactcac ctagaggcta gaatgggggt agggatttag   6240
cacgctggaa ataacggaca gtaatcaaac gaagacactg tccccagcta ccaactatgc   6300
caaacctcag catttttggt attattgtgt ataagctttt cctgtctgac tgctgggttc   6360
tccaataagg tgacatagct atgccatttg ttaaaaataa actctgtact tattttgatt   6420
tgagtaaa                                                            6428
```

<210> SEQ ID NO 4
<211> LENGTH: 25
<212> TYPE: RNA
<213> ORGANISM: Artificial Sequence
<220> FEATURE:
<223> OTHER INFORMATION: Synthetic

<400> SEQUENCE: 4
cugagcaaag ccauguggua cagga 25

<210> SEQ ID NO 5
<211> LENGTH: 25
<212> TYPE: DNA
<213> ORGANISM: Artificial Sequence
<220> FEATURE:
<223> OTHER INFORMATION: Synthetic

<400> SEQUENCE: 5
agcaaagcca uguggucca a gautg 25

<210> SEQ ID NO 6
<211> LENGTH: 25
<212> TYPE: RNA
<213> ORGANISM: Artificial Sequence
<220> FEATURE:
<223> OTHER INFORMATION: Synthetic

<400> SEQUENCE: 6
aagccaugug guccaggaua gcuac 25

<210> SEQ ID NO 7
<211> LENGTH: 25
<212> TYPE: RNA
<213> ORGANISM: Artificial Sequence
<220> FEATURE:
<223> OTHER INFORMATION: Synthetic

<400> SEQUENCE: 7
agccaugugg uccaggauua cuacc 25

<210> SEQ ID NO 8
<211> LENGTH: 25
<212> TYPE: RNA
<213> ORGANISM: Artificial Sequence
<220> FEATURE:
<223> OTHER INFORMATION: Synthetic

<400> SEQUENCE: 8 gccaugugggu ccaggauuga uacca 25

<210> SEQ ID NO 9
<211> LENGTH: 25
<212> TYPE: DNA
<213> ORGANISM: Artificial Sequence
<220> FEATURE:
<223> OTHER INFORMATION: Synthetic

<400> SEQUENCE: 9 ccauguggucc caggauugca accat 25

<210> SEQ ID NO 10
<211> LENGTH: 25
<212> TYPE: DNA
<213> ORGANISM: Artificial Sequence
<220> FEATURE:
<223> OTHER INFORMATION: Synthetic

<400> SEQUENCE: 10
cauguggucc aggauugcua ccatg 25

<210> SEQ ID NO 11
<211> LENGTH: 25
<212> TYPE: RNA
<213> ORGANISM: Artificial Sequence
<220> FEATURE:
<223> OTHER INFORMATION: Synthetic

<400> SEQUENCE: 11
auguggucca ggauugcuaa caugg 25

<210> SEQ ID NO 12
<211> LENGTH: 25
<212> TYPE: DNA
<213> ORGANISM: Artificial Sequence
<220> FEATURE:
<223> OTHER INFORMATION: Synthetic

<400> SEQUENCE: 12
ugugguccag gauugcuaca auggt 25

<210> SEQ ID NO 13
<211> LENGTH: 25
<212> TYPE: RNA
<213> ORGANISM: Artificial Sequence
<220> FEATURE:
<223> OTHER INFORMATION: Synthetic

<400> SEQUENCE: 13
ggugauggac agaguuauca aggca 25

<210> SEQ ID NO 14
<211> LENGTH: 25
<212> TYPE: DNA
<213> ORGANISM: Artificial Sequence
<220> FEATURE:
<223> OTHER INFORMATION: Synthetic

<400> SEQUENCE: 14
uccaccacug ucacaggaaa gacct 25

<210> SEQ ID NO 15
<211> LENGTH: 25
<212> TYPE: DNA
<213> ORGANISM: Artificial Sequence
<220> FEATURE:
<223> OTHER INFORMATION: Synthetic

<400> SEQUENCE: 15
ccaccacugu cacaggaaga acctg 25

<210> SEQ ID NO 16
<211> LENGTH: 25
<212> TYPE: RNA
<213> ORGANISM: Artificial Sequence
<220> FEATURE:
<223> OTHER INFORMATION: Synthetic

<400> SEQUENCE: 16
cugucacagg aaggaccuga caagc 25

<210> SEQ ID NO 17
<211> LENGTH: 25

<212> TYPE: DNA
<213> ORGANISM: Artificial Sequence
<220> FEATURE:
<223> OTHER INFORMATION: Synthetic

<400> SEQUENCE: 17
ggaaggaccu gccaagcuua gucat 25

<210> SEQ ID NO 18
<211> LENGTH: 25
<212> TYPE: DNA
<213> ORGANISM: Artificial Sequence
<220> FEATURE:
<223> OTHER INFORMATION: Synthetic

<400> SEQUENCE: 18
gaaggaccug ccaagcuuga ucatc 25

<210> SEQ ID NO 19
<211> LENGTH: 25
<212> TYPE: DNA
<213> ORGANISM: Artificial Sequence
<220> FEATURE:
<223> OTHER INFORMATION: Synthetic

<400> SEQUENCE: 19
aggaccugcc aagcuuggua aucta 25

<210> SEQ ID NO 20
<211> LENGTH: 25
<212> TYPE: DNA
<213> ORGANISM: Artificial Sequence
<220> FEATURE:
<223> OTHER INFORMATION: Synthetic

<400> SEQUENCE: 20
ggaccugcca agcuugguca ucuat 25

<210> SEQ ID NO 21
<211> LENGTH: 25
<212> TYPE: DNA
<213> ORGANISM: Artificial Sequence
<220> FEATURE:
<223> OTHER INFORMATION: Synthetic

<400> SEQUENCE: 21
gaccugccaa gcuuggucaa cuatg 25

<210> SEQ ID NO 22
<211> LENGTH: 25
<212> TYPE: RNA
<213> ORGANISM: Artificial Sequence
<220> FEATURE:
<223> OTHER INFORMATION: Synthetic

<400> SEQUENCE: 22
accugccaag cuuggucaua uauga 25

<210> SEQ ID NO 23
<211> LENGTH: 25
<212> TYPE: RNA
<213> ORGANISM: Artificial Sequence
<220> FEATURE:
<223> OTHER INFORMATION: Synthetic

<400> SEQUENCE: 23
ccugccaagc uuggucauca augac 25

<210> SEQ ID NO 24
<211> LENGTH: 25
<212> TYPE: DNA
<213> ORGANISM: Artificial Sequence
<220> FEATURE:
<223> OTHER INFORMATION: Synthetic

<400> SEQUENCE: 24
agcuugguca ucuaugacaa cacat 25

<210> SEQ ID NO 25
<211> LENGTH: 25
<212> TYPE: DNA
<213> ORGANISM: Artificial Sequence
<220> FEATURE:
<223> OTHER INFORMATION: Synthetic

<400> SEQUENCE: 25
gucaucuaug acaccacaua aacat 25

<210> SEQ ID NO 26
<211> LENGTH: 25
<212> TYPE: RNA
<213> ORGANISM: Artificial Sequence
<220> FEATURE:
<223> OTHER INFORMATION: Synthetic

<400> SEQUENCE: 26
cacagaaaac uacccaaaua cuggc 25

<210> SEQ ID NO 27
<211> LENGTH: 25
<212> TYPE: DNA
<213> ORGANISM: Artificial Sequence
<220> FEATURE:
<223> OTHER INFORMATION: Synthetic

<400> SEQUENCE: 27
agaaaacuac ccaaaugcua gcutg 25

<210> SEQ ID NO 28
<211> LENGTH: 25
<212> TYPE: DNA
<213> ORGANISM: Artificial Sequence
<220> FEATURE:
<223> OTHER INFORMATION: Synthetic

<400> SEQUENCE: 28
aaaacuaccc aaaugcugga uugat 25

<210> SEQ ID NO 29
<211> LENGTH: 25
<212> TYPE: RNA
<213> ORGANISM: Artificial Sequence
<220> FEATURE:
<223> OTHER INFORMATION: Synthetic

<400> SEQUENCE: 29
acccaaaugc uggcuugaua augaa 25

<210> SEQ ID NO 30
<211> LENGTH: 25
<212> TYPE: RNA
<213> ORGANISM: Artificial Sequence
<220> FEATURE:
<223> OTHER INFORMATION: Synthetic

<400> SEQUENCE: 30
cccaaaugcu ggcuugauca ugaac 25

<210> SEQ ID NO 31
<211> LENGTH: 25
<212> TYPE: DNA
<213> ORGANISM: Artificial Sequence
<220> FEATURE:
<223> OTHER INFORMATION: Synthetic

<400> SEQUENCE: 31
gaacuacugc aggaauccaa augct 25

<210> SEQ ID NO 32
<211> LENGTH: 25
<212> TYPE: RNA
<213> ORGANISM: Artificial Sequence
<220> FEATURE:
<223> OTHER INFORMATION: Synthetic

<400> SEQUENCE: 32
uacugcagga auccagauga ugugg 25

<210> SEQ ID NO 33
<211> LENGTH: 25
<212> TYPE: RNA
<213> ORGANISM: Artificial Sequence
<220> FEATURE:
<223> OTHER INFORMATION: Synthetic

<400> SEQUENCE: 33
acugcaggaa uccagaugca guggc 25

<210> SEQ ID NO 34
<211> LENGTH: 25
<212> TYPE: RNA
<213> ORGANISM: Artificial Sequence
<220> FEATURE:
<223> OTHER INFORMATION: Synthetic

<400> SEQUENCE: 34
ugcaggaauc cagaugcuga ggcag 25

<210> SEQ ID NO 35
<211> LENGTH: 25
<212> TYPE: RNA
<213> ORGANISM: Artificial Sequence
<220> FEATURE:
<223> OTHER INFORMATION: Synthetic

<400> SEQUENCE: 35
aggugggagu acugcaacca gacgc 25

<210> SEQ ID NO 36
<211> LENGTH: 25
<212> TYPE: RNA
<213> ORGANISM: Artificial Sequence
<220> FEATURE:
<223> OTHER INFORMATION: Synthetic

<400> SEQUENCE: 36
aaugcucaga cgcagaagga acugc 25

<210> SEQ ID NO 37
<211> LENGTH: 25
<212> TYPE: DNA
<213> ORGANISM: Artificial Sequence
<220> FEATURE:
<223> OTHER INFORMATION: Synthetic

<400> SEQUENCE: 37
gacuguuacc ccgguuccaa gccta 25

<210> SEQ ID NO 38
<211> LENGTH: 25
<212> TYPE: RNA
<213> ORGANISM: Artificial Sequence
<220> FEATURE:
<223> OTHER INFORMATION: Synthetic

<400> SEQUENCE: 38
acuguuaccc cgguuccaaa ccuag 25

<210> SEQ ID NO 39
<211> LENGTH: 25
<212> TYPE: RNA
<213> ORGANISM: Artificial Sequence
<220> FEATURE:
<223> OTHER INFORMATION: Synthetic

<400> SEQUENCE: 39
cuguuacccc gguuccaaga cuaga 25

<210> SEQ ID NO 40
<211> LENGTH: 25
<212> TYPE: RNA
<213> ORGANISM: Artificial Sequence
<220> FEATURE:
<223> OTHER INFORMATION: Synthetic

<400> SEQUENCE: 40
uguuaccccg guuccaagca uagag 25

<210> SEQ ID NO 41
<211> LENGTH: 25
<212> TYPE: RNA
<213> ORGANISM: Artificial Sequence
<220> FEATURE:
<223> OTHER INFORMATION: Synthetic

<400> SEQUENCE: 41
guuaccccgg uuccaagcca agagg 25

<210> SEQ ID NO 42
<211> LENGTH: 25
<212> TYPE: RNA
<213> ORGANISM: Artificial Sequence
<220> FEATURE:
<223> OTHER INFORMATION: Synthetic

<400> SEQUENCE: 42
uuaccccggu uccaagccua gaggc 25

<210> SEQ ID NO 43
<211> LENGTH: 25
<212> TYPE: DNA
<213> ORGANISM: Artificial Sequence
<220> FEATURE:
<223> OTHER INFORMATION: Synthetic

<400> SEQUENCE: 43
uaccccgguu ccaagccuaa aggct 25

<210> SEQ ID NO 44
<211> LENGTH: 25
<212> TYPE: DNA
<213> ORGANISM: Artificial Sequence
<220> FEATURE:
<223> OTHER INFORMATION: Synthetic

<400> SEQUENCE: 44
gugcuaccau gguaauggaa agagt 25

<210> SEQ ID NO 45
<211> LENGTH: 25
<212> TYPE: DNA
<213> ORGANISM: Artificial Sequence
<220> FEATURE:
<223> OTHER INFORMATION: Synthetic

<400> SEQUENCE: 45
ugcuaccaug guaauggaca gagtt 25

<210> SEQ ID NO 46
<211> LENGTH: 25
<212> TYPE: DNA
<213> ORGANISM: Artificial Sequence
<220> FEATURE:
<223> OTHER INFORMATION: Synthetic

<400> SEQUENCE: 46
gcuaccaugg uaauggacaa aguta 25

<210> SEQ ID NO 47
<211> LENGTH: 25
<212> TYPE: DNA
<213> ORGANISM: Artificial Sequence
<220> FEATURE:
<223> OTHER INFORMATION: Synthetic

<400> SEQUENCE: 47
cuaccauggu aauggacaga guuat 25

<210> SEQ ID NO 48
<211> LENGTH: 25
<212> TYPE: DNA
<213> ORGANISM: Artificial Sequence
<220> FEATURE:
<223> OTHER INFORMATION: Synthetic

<400> SEQUENCE: 48
uaccauggua auggacagaa uuatc 25

<210> SEQ ID NO 49
<211> LENGTH: 25
<212> TYPE: RNA
<213> ORGANISM: Artificial Sequence
<220> FEATURE:
<223> OTHER INFORMATION: Synthetic

<400> SEQUENCE: 49
accaugguaa uggacagaga uaucg 25

<210> SEQ ID NO 50

<211> LENGTH: 25
<212> TYPE: RNA
<213> ORGANISM: Artificial Sequence
<220> FEATURE:
<223> OTHER INFORMATION: Synthetic

<400> SEQUENCE: 50
ccaugguaau ggacagagua aucga 25

<210> SEQ ID NO 51
<211> LENGTH: 25
<212> TYPE: RNA
<213> ORGANISM: Artificial Sequence
<220> FEATURE:
<223> OTHER INFORMATION: Synthetic

<400> SEQUENCE: 51
caugguaaug gacagaguua ucgag 25

<210> SEQ ID NO 52
<211> LENGTH: 25
<212> TYPE: RNA
<213> ORGANISM: Artificial Sequence
<220> FEATURE:
<223> OTHER INFORMATION: Synthetic

<400> SEQUENCE: 52
augguaaugg acagaguuaa cgagg 25

<210> SEQ ID NO 53
<211> LENGTH: 25
<212> TYPE: RNA
<213> ORGANISM: Artificial Sequence
<220> FEATURE:
<223> OTHER INFORMATION: Synthetic

<400> SEQUENCE: 53
ugguaaugga cagaguuaua gaggc 25

<210> SEQ ID NO 54
<211> LENGTH: 25
<212> TYPE: RNA
<213> ORGANISM: Artificial Sequence
<220> FEATURE:
<223> OTHER INFORMATION: Synthetic

<400> SEQUENCE: 54
gguaauggac agaguuauca aggca 25

<210> SEQ ID NO 55
<211> LENGTH: 25
<212> TYPE: RNA
<213> ORGANISM: Artificial Sequence
<220> FEATURE:
<223> OTHER INFORMATION: Synthetic

<400> SEQUENCE: 55
guaauggaca gaguuaucga ggcac 25

<210> SEQ ID NO 56
<211> LENGTH: 25
<212> TYPE: RNA
<213> ORGANISM: Artificial Sequence
<220> FEATURE:
<223> OTHER INFORMATION: Synthetic

<400> SEQUENCE: 56
ggcacauacu ccaccacuga cacag 25

<210> SEQ ID NO 57
<211> LENGTH: 25
<212> TYPE: DNA
<213> ORGANISM: Artificial Sequence
<220> FEATURE:
<223> OTHER INFORMATION: Synthetic

<400> SEQUENCE: 57
cuuggucauc uaugacacca cactc 25

<210> SEQ ID NO 58
<211> LENGTH: 25
<212> TYPE: DNA
<213> ORGANISM: Artificial Sequence
<220> FEATURE:
<223> OTHER INFORMATION: Synthetic

<400> SEQUENCE: 58
gucaucuaug acaccacaca cgcat 25

<210> SEQ ID NO 59
<211> LENGTH: 25
<212> TYPE: DNA
<213> ORGANISM: Artificial Sequence
<220> FEATURE:
<223> OTHER INFORMATION: Synthetic

<400> SEQUENCE: 59
ucaucuauga caccacacua gcata 25

<210> SEQ ID NO 60
<211> LENGTH: 25
<212> TYPE: RNA
<213> ORGANISM: Artificial Sequence
<220> FEATURE:
<223> OTHER INFORMATION: Synthetic

<400> SEQUENCE: 60
caucuaugac accacacuca cauag 25

<210> SEQ ID NO 61
<211> LENGTH: 25
<212> TYPE: RNA
<213> ORGANISM: Artificial Sequence
<220> FEATURE:
<223> OTHER INFORMATION: Synthetic

<400> SEQUENCE: 61
gcacauacuc caccacugua acugg 25

<210> SEQ ID NO 62
<211> LENGTH: 25
<212> TYPE: DNA
<213> ORGANISM: Artificial Sequence
<220> FEATURE:
<223> OTHER INFORMATION: Synthetic

<400> SEQUENCE: 62
agccccuuau uguuauacga gggat 25

<210> SEQ ID NO 63
<211> LENGTH: 25
<212> TYPE: DNA

<213> ORGANISM: Artificial Sequence
<220> FEATURE:
<223> OTHER INFORMATION: Synthetic

<400> SEQUENCE: 63
gccccuuauu guuauacgaa ggatc 25

<210> SEQ ID NO 64
<211> LENGTH: 25
<212> TYPE: RNA
<213> ORGANISM: Artificial Sequence
<220> FEATURE:
<223> OTHER INFORMATION: Synthetic

<400> SEQUENCE: 64
ccaagccuag aggcuccuua ugaac 25

<210> SEQ ID NO 65
<211> LENGTH: 25
<212> TYPE: RNA
<213> ORGANISM: Artificial Sequence
<220> FEATURE:
<223> OTHER INFORMATION: Synthetic

<400> SEQUENCE: 65
aggcuccuuc ugaacaagca ccaac 25

<210> SEQ ID NO 66
<211> LENGTH: 25
<212> TYPE: DNA
<213> ORGANISM: Artificial Sequence
<220> FEATURE:
<223> OTHER INFORMATION: Synthetic

<400> SEQUENCE: 66
auggacagag uuaucaagga acata 25

<210> SEQ ID NO 67
<211> LENGTH: 25
<212> TYPE: RNA
<213> ORGANISM: Artificial Sequence
<220> FEATURE:
<223> OTHER INFORMATION: Synthetic

<400> SEQUENCE: 67
uggacagagu uaucaaggca cauac 25

<210> SEQ ID NO 68
<211> LENGTH: 25
<212> TYPE: DNA
<213> ORGANISM: Artificial Sequence
<220> FEATURE:
<223> OTHER INFORMATION: Synthetic

<400> SEQUENCE: 68
ggacagaguu aucaaggcaa auact 25

<210> SEQ ID NO 69
<211> LENGTH: 25
<212> TYPE: DNA
<213> ORGANISM: Artificial Sequence
<220> FEATURE:
<223> OTHER INFORMATION: Synthetic

<400> SEQUENCE: 69
gacagaguua ucaaggcaca uactt 25

<210> SEQ ID NO 70
<211> LENGTH: 25
<212> TYPE: DNA
<213> ORGANISM: Artificial Sequence
<220> FEATURE:
<223> OTHER INFORMATION: Synthetic

<400> SEQUENCE: 70
acagaguuau caaggcacaa acutc 25

<210> SEQ ID NO 71
<211> LENGTH: 25
<212> TYPE: RNA
<213> ORGANISM: Artificial Sequence
<220> FEATURE:
<223> OTHER INFORMATION: Synthetic

<400> SEQUENCE: 71
cagaguuauc aaggcacaua cuuca 25

<210> SEQ ID NO 72
<211> LENGTH: 25
<212> TYPE: RNA
<213> ORGANISM: Artificial Sequence
<220> FEATURE:
<223> OTHER INFORMATION: Synthetic

<400> SEQUENCE: 72
uacccaaaug cuggcuugaa caaga 25

<210> SEQ ID NO 73
<211> LENGTH: 25
<212> TYPE: DNA
<213> ORGANISM: Artificial Sequence
<220> FEATURE:
<223> OTHER INFORMATION: Synthetic

<400> SEQUENCE: 73
ccaaaugcug gcuugaucaa gaact 25

<210> SEQ ID NO 74
<211> LENGTH: 25
<212> TYPE: RNA
<213> ORGANISM: Artificial Sequence
<220> FEATURE:
<223> OTHER INFORMATION: Synthetic

<400> SEQUENCE: 74
ucaagaacua cugccgaaaa ccaga 25

<210> SEQ ID NO 75
<211> LENGTH: 25
<212> TYPE: DNA
<213> ORGANISM: Artificial Sequence
<220> FEATURE:
<223> OTHER INFORMATION: Synthetic

<400> SEQUENCE: 75
caagaacuac ugccgaaaua cagat 25

<210> SEQ ID NO 76
<211> LENGTH: 25
<212> TYPE: DNA
<213> ORGANISM: Artificial Sequence
<220> FEATURE:

-continued

<223> OTHER INFORMATION: Synthetic

<400> SEQUENCE: 76
aagaacuacu gccgaaauca agatc 25

<210> SEQ ID NO 77
<211> LENGTH: 25
<212> TYPE: DNA
<213> ORGANISM: Artificial Sequence
<220> FEATURE:
<223> OTHER INFORMATION: Synthetic

<400> SEQUENCE: 77
gaacuacugc cgaaauccaa aucct 25

<210> SEQ ID NO 78
<211> LENGTH: 25
<212> TYPE: DNA
<213> ORGANISM: Artificial Sequence
<220> FEATURE:
<223> OTHER INFORMATION: Synthetic

<400> SEQUENCE: 78
cuacugccga aauccagaua cugtg 25

<210> SEQ ID NO 79
<211> LENGTH: 25
<212> TYPE: RNA
<213> ORGANISM: Artificial Sequence
<220> FEATURE:
<223> OTHER INFORMATION: Synthetic

<400> SEQUENCE: 79
uguggcagcc ccuuggugua auaca 25

<210> SEQ ID NO 80
<211> LENGTH: 25
<212> TYPE: RNA
<213> ORGANISM: Artificial Sequence
<220> FEATURE:
<223> OTHER INFORMATION: Synthetic

<400> SEQUENCE: 80
guggcagccc cuugguguua uacaa 25

<210> SEQ ID NO 81
<211> LENGTH: 25
<212> TYPE: RNA
<213> ORGANISM: Artificial Sequence
<220> FEATURE:
<223> OTHER INFORMATION: Synthetic

<400> SEQUENCE: 81
uggcagcccc uugguguuaa acaac 25

<210> SEQ ID NO 82
<211> LENGTH: 25
<212> TYPE: RNA
<213> ORGANISM: Artificial Sequence
<220> FEATURE:
<223> OTHER INFORMATION: Synthetic

<400> SEQUENCE: 82
ggcagccccu ugguguuaua caaca 25

<210> SEQ ID NO 83
<211> LENGTH: 25
<212> TYPE: RNA
<213> ORGANISM: Artificial Sequence
<220> FEATURE:
<223> OTHER INFORMATION: Synthetic

<400> SEQUENCE: 83
gcagccccuu gguguuauaa aacag 25

<210> SEQ ID NO 84
<211> LENGTH: 25
<212> TYPE: RNA
<213> ORGANISM: Artificial Sequence
<220> FEATURE:
<223> OTHER INFORMATION: Synthetic

<400> SEQUENCE: 84
cagccccuug guguuauaca acaga 25

<210> SEQ ID NO 85
<211> LENGTH: 25
<212> TYPE: DNA
<213> ORGANISM: Artificial Sequence
<220> FEATURE:
<223> OTHER INFORMATION: Synthetic

<400> SEQUENCE: 85
agccccuugg uguuauacaa cagat 25

<210> SEQ ID NO 86
<211> LENGTH: 25
<212> TYPE: DNA
<213> ORGANISM: Artificial Sequence
<220> FEATURE:
<223> OTHER INFORMATION: Synthetic

<400> SEQUENCE: 86
gccccuuggu guuauacaaa agatc 25

<210> SEQ ID NO 87
<211> LENGTH: 25
<212> TYPE: RNA
<213> ORGANISM: Artificial Sequence
<220> FEATURE:
<223> OTHER INFORMATION: Synthetic

<400> SEQUENCE: 87
ccccuuggug uuauacaaca gaucc 25

<210> SEQ ID NO 88
<211> LENGTH: 25
<212> TYPE: RNA
<213> ORGANISM: Artificial Sequence
<220> FEATURE:
<223> OTHER INFORMATION: Synthetic

<400> SEQUENCE: 88
ggugggagua cugcaaccua acacg 25

<210> SEQ ID NO 89
<211> LENGTH: 25
<212> TYPE: RNA
<213> ORGANISM: Artificial Sequence
<220> FEATURE:
<223> OTHER INFORMATION: Synthetic

<400> SEQUENCE: 89
gugggaguac ugcaaccuga cacga 25

<210> SEQ ID NO 90
<211> LENGTH: 25
<212> TYPE: RNA
<213> ORGANISM: Artificial Sequence
<220> FEATURE:
<223> OTHER INFORMATION: Synthetic

<400> SEQUENCE: 90
ggaguacugc aaccugacaa gaugc 25

<210> SEQ ID NO 91
<211> LENGTH: 25
<212> TYPE: DNA
<213> ORGANISM: Artificial Sequence
<220> FEATURE:
<223> OTHER INFORMATION: Synthetic

<400> SEQUENCE: 91
gaguacugca accugacaca augct 25

<210> SEQ ID NO 92
<211> LENGTH: 25
<212> TYPE: RNA
<213> ORGANISM: Artificial Sequence
<220> FEATURE:
<223> OTHER INFORMATION: Synthetic

<400> SEQUENCE: 92
guacugcaac cugacacgaa gcuca 25

<210> SEQ ID NO 93
<211> LENGTH: 25
<212> TYPE: RNA
<213> ORGANISM: Artificial Sequence
<220> FEATURE:
<223> OTHER INFORMATION: Synthetic

<400> SEQUENCE: 93
uacugcaacc ugacacgaua cucag 25

<210> SEQ ID NO 94
<211> LENGTH: 25
<212> TYPE: RNA
<213> ORGANISM: Artificial Sequence
<220> FEATURE:
<223> OTHER INFORMATION: Synthetic

<400> SEQUENCE: 94
acugcaaccu gacacgauga ucaga 25

<210> SEQ ID NO 95
<211> LENGTH: 25
<212> TYPE: DNA
<213> ORGANISM: Artificial Sequence
<220> FEATURE:
<223> OTHER INFORMATION: Synthetic

<400> SEQUENCE: 95
cugcaaccug acacgaugca cagat 25

<210> SEQ ID NO 96
<211> LENGTH: 25

<212> TYPE: DNA
<213> ORGANISM: Artificial Sequence
<220> FEATURE:
<223> OTHER INFORMATION: Synthetic

<400> SEQUENCE: 96
ugcaaccuga cacgaugcua agatg 25

<210> SEQ ID NO 97
<211> LENGTH: 25
<212> TYPE: RNA
<213> ORGANISM: Artificial Sequence
<220> FEATURE:
<223> OTHER INFORMATION: Synthetic

<400> SEQUENCE: 97
caaccugaca cgaugcucaa augca 25

<210> SEQ ID NO 98
<211> LENGTH: 25
<212> TYPE: RNA
<213> ORGANISM: Artificial Sequence
<220> FEATURE:
<223> OTHER INFORMATION: Synthetic

<400> SEQUENCE: 98
accugacacg augcucagaa gcaga 25

<210> SEQ ID NO 99
<211> LENGTH: 25
<212> TYPE: RNA
<213> ORGANISM: Artificial Sequence
<220> FEATURE:
<223> OTHER INFORMATION: Synthetic

<400> SEQUENCE: 99
ccugacacga ugcucagaua cagaa 25

<210> SEQ ID NO 100
<211> LENGTH: 25
<212> TYPE: DNA
<213> ORGANISM: Artificial Sequence
<220> FEATURE:
<223> OTHER INFORMATION: Synthetic

<400> SEQUENCE: 100
cugacacgau gcucagauga agaat 25

<210> SEQ ID NO 101
<211> LENGTH: 25
<212> TYPE: DNA
<213> ORGANISM: Artificial Sequence
<220> FEATURE:
<223> OTHER INFORMATION: Synthetic

<400> SEQUENCE: 101
ugacacgaug cucagaugca gaatg 25

<210> SEQ ID NO 102
<211> LENGTH: 25
<212> TYPE: RNA
<213> ORGANISM: Artificial Sequence
<220> FEATURE:
<223> OTHER INFORMATION: Synthetic

<400> SEQUENCE: 102

-continued gacacgaugc ucagaugcaa aaugg 25

<210> SEQ ID NO 103
<211> LENGTH: 25
<212> TYPE: RNA
<213> ORGANISM: Artificial Sequence
<220> FEATURE:
<223> OTHER INFORMATION: Synthetic

<400> SEQUENCE: 103
acacgaugcu cagaugcaga augga 25

<210> SEQ ID NO 104
<211> LENGTH: 25
<212> TYPE: RNA
<213> ORGANISM: Artificial Sequence
<220> FEATURE:
<223> OTHER INFORMATION: Synthetic

<400> SEQUENCE: 104
cacgaugcuc agaugcagaa uggac 25

<210> SEQ ID NO 105
<211> LENGTH: 25
<212> TYPE: DNA
<213> ORGANISM: Artificial Sequence
<220> FEATURE:
<223> OTHER INFORMATION: Synthetic

<400> SEQUENCE: 105
ugcuacuacc auuauggaca gagtt 25

<210> SEQ ID NO 106
<211> LENGTH: 25
<212> TYPE: DNA
<213> ORGANISM: Artificial Sequence
<220> FEATURE:
<223> OTHER INFORMATION: Synthetic

<400> SEQUENCE: 106
gcuacuacca uuauggacaa aguta 25

<210> SEQ ID NO 107
<211> LENGTH: 25
<212> TYPE: RNA
<213> ORGANISM: Artificial Sequence
<220> FEATURE:
<223> OTHER INFORMATION: Synthetic

<400> SEQUENCE: 107
cuacuaccau uauggacaga guuac 25

<210> SEQ ID NO 108
<211> LENGTH: 25
<212> TYPE: RNA
<213> ORGANISM: Artificial Sequence
<220> FEATURE:
<223> OTHER INFORMATION: Synthetic

<400> SEQUENCE: 108
uacuaccauu auggacagaa uuacc 25

<210> SEQ ID NO 109
<211> LENGTH: 25
<212> TYPE: RNA
<213> ORGANISM: Artificial Sequence

```
<220> FEATURE:
<223> OTHER INFORMATION: Synthetic

<400> SEQUENCE: 109

acuaccauua uggacagaga uaccg                                          25


<210> SEQ ID NO 110
<211> LENGTH: 25
<212> TYPE: RNA
<213> ORGANISM: Artificial Sequence
<220> FEATURE:
<223> OTHER INFORMATION: Synthetic

<400> SEQUENCE: 110

cuaccauuau ggacagagua accga                                          25


<210> SEQ ID NO 111
<211> LENGTH: 25
<212> TYPE: RNA
<213> ORGANISM: Artificial Sequence
<220> FEATURE:
<223> OTHER INFORMATION: Synthetic

<400> SEQUENCE: 111

uaccauuaug gacagaguua ccgag                                          25


<210> SEQ ID NO 112
<211> LENGTH: 25
<212> TYPE: RNA
<213> ORGANISM: Artificial Sequence
<220> FEATURE:
<223> OTHER INFORMATION: Synthetic

<400> SEQUENCE: 112

accauuaugg acagaguuaa cgagg                                          25


<210> SEQ ID NO 113
<211> LENGTH: 25
<212> TYPE: RNA
<213> ORGANISM: Artificial Sequence
<220> FEATURE:
<223> OTHER INFORMATION: Synthetic

<400> SEQUENCE: 113

gaggcacaua cuccaccaca gucac                                          25


<210> SEQ ID NO 114
<211> LENGTH: 25
<212> TYPE: DNA
<213> ORGANISM: Artificial Sequence
<220> FEATURE:
<223> OTHER INFORMATION: Synthetic

<400> SEQUENCE: 114

cuccaccacu gucacaggaa gaact                                          25


<210> SEQ ID NO 115
<211> LENGTH: 25
<212> TYPE: DNA
<213> ORGANISM: Artificial Sequence
<220> FEATURE:
<223> OTHER INFORMATION: Synthetic

<400> SEQUENCE: 115

acaggaagaa cuugccaaga uuggt                                          25
```

<210> SEQ ID NO 116
<211> LENGTH: 25
<212> TYPE: DNA
<213> ORGANISM: Artificial Sequence
<220> FEATURE:
<223> OTHER INFORMATION: Synthetic

<400> SEQUENCE: 116
caggaagaac uugccaagca uggtc 25

<210> SEQ ID NO 117
<211> LENGTH: 25
<212> TYPE: RNA
<213> ORGANISM: Artificial Sequence
<220> FEATURE:
<223> OTHER INFORMATION: Synthetic

<400> SEQUENCE: 117
aggaagaacu ugccaagcua gguca 25

<210> SEQ ID NO 118
<211> LENGTH: 25
<212> TYPE: DNA
<213> ORGANISM: Artificial Sequence
<220> FEATURE:
<223> OTHER INFORMATION: Synthetic

<400> SEQUENCE: 118
ggaagaacuu gccaagcuua gucat 25

<210> SEQ ID NO 119
<211> LENGTH: 25
<212> TYPE: DNA
<213> ORGANISM: Artificial Sequence
<220> FEATURE:
<223> OTHER INFORMATION: Synthetic

<400> SEQUENCE: 119
gaagaacuug ccaagcuuga ucatc 25

<210> SEQ ID NO 120
<211> LENGTH: 25
<212> TYPE: DNA
<213> ORGANISM: Artificial Sequence
<220> FEATURE:
<223> OTHER INFORMATION: Synthetic

<400> SEQUENCE: 120
aagaacuugc caagcuugga cauct 25

<210> SEQ ID NO 121
<211> LENGTH: 25
<212> TYPE: DNA
<213> ORGANISM: Artificial Sequence
<220> FEATURE:
<223> OTHER INFORMATION: Synthetic

<400> SEQUENCE: 121
agaacuugcc aagcuuggua aucta 25

<210> SEQ ID NO 122
<211> LENGTH: 25
<212> TYPE: DNA
<213> ORGANISM: Artificial Sequence
<220> FEATURE:
<223> OTHER INFORMATION: Synthetic

<400> SEQUENCE: 122
gaacuugcca agcuugguca ucuat 25

<210> SEQ ID NO 123
<211> LENGTH: 25
<212> TYPE: DNA
<213> ORGANISM: Artificial Sequence
<220> FEATURE:
<223> OTHER INFORMATION: Synthetic

<400> SEQUENCE: 123
aacuugccaa gcuuggucaa cuatg 25

<210> SEQ ID NO 124
<211> LENGTH: 25
<212> TYPE: RNA
<213> ORGANISM: Artificial Sequence
<220> FEATURE:
<223> OTHER INFORMATION: Synthetic

<400> SEQUENCE: 124
acuugccaag cuuggucaua uauga 25

<210> SEQ ID NO 125
<211> LENGTH: 25
<212> TYPE: RNA
<213> ORGANISM: Artificial Sequence
<220> FEATURE:
<223> OTHER INFORMATION: Synthetic

<400> SEQUENCE: 125
cuugccaagc uuggucauca augac 25

<210> SEQ ID NO 126
<211> LENGTH: 25
<212> TYPE: RNA
<213> ORGANISM: Artificial Sequence
<220> FEATURE:
<223> OTHER INFORMATION: Synthetic

<400> SEQUENCE: 126
uugccaagcu uggucaucua ugaca 25

<210> SEQ ID NO 127
<211> LENGTH: 25
<212> TYPE: RNA
<213> ORGANISM: Artificial Sequence
<220> FEATURE:
<223> OTHER INFORMATION: Synthetic

<400> SEQUENCE: 127
ugccaagcuu ggucaucuaa gacac 25

<210> SEQ ID NO 128
<211> LENGTH: 25
<212> TYPE: RNA
<213> ORGANISM: Artificial Sequence
<220> FEATURE:
<223> OTHER INFORMATION: Synthetic

<400> SEQUENCE: 128
gcuuggucau cuaugacaca acacc 25

<210> SEQ ID NO 129

<211> LENGTH: 25
<212> TYPE: RNA
<213> ORGANISM: Artificial Sequence
<220> FEATURE:
<223> OTHER INFORMATION: Synthetic

<400> SEQUENCE: 129
uuggucaucu augacaccaa accag 25

<210> SEQ ID NO 130
<211> LENGTH: 25
<212> TYPE: RNA
<213> ORGANISM: Artificial Sequence
<220> FEATURE:
<223> OTHER INFORMATION: Synthetic

<400> SEQUENCE: 130
uggucaucua ugacaccaca ccagc 25

<210> SEQ ID NO 131
<211> LENGTH: 25
<212> TYPE: DNA
<213> ORGANISM: Artificial Sequence
<220> FEATURE:
<223> OTHER INFORMATION: Synthetic

<400> SEQUENCE: 131
gucaucuaug acaccacaca agcat 25

<210> SEQ ID NO 132
<211> LENGTH: 25
<212> TYPE: RNA
<213> ORGANISM: Artificial Sequence
<220> FEATURE:
<223> OTHER INFORMATION: Synthetic

<400> SEQUENCE: 132
caucuaugac accacaccaa cauag 25

<210> SEQ ID NO 133
<211> LENGTH: 25
<212> TYPE: DNA
<213> ORGANISM: Artificial Sequence
<220> FEATURE:
<223> OTHER INFORMATION: Synthetic

<400> SEQUENCE: 133
aucuaugaca ccacaccaga auagt 25

<210> SEQ ID NO 134
<211> LENGTH: 25
<212> TYPE: DNA
<213> ORGANISM: Artificial Sequence
<220> FEATURE:
<223> OTHER INFORMATION: Synthetic

<400> SEQUENCE: 134
cuaugacacc acaccagcaa agucg 25

<210> SEQ ID NO 135
<211> LENGTH: 25
<212> TYPE: RNA
<213> ORGANISM: Artificial Sequence
<220> FEATURE:
<223> OTHER INFORMATION: Synthetic

<400> SEQUENCE: 135
gucggacccc agaaaacuaa ccaaa 25

<210> SEQ ID NO 136
<211> LENGTH: 25
<212> TYPE: DNA
<213> ORGANISM: Artificial Sequence
<220> FEATURE:
<223> OTHER INFORMATION: Synthetic

<400> SEQUENCE: 136
ucggacccca gaaaacuaca caaat 25

<210> SEQ ID NO 137
<211> LENGTH: 25
<212> TYPE: RNA
<213> ORGANISM: Artificial Sequence
<220> FEATURE:
<223> OTHER INFORMATION: Synthetic

<400> SEQUENCE: 137
gaaaacuacc caaaugcuga ccuga 25

<210> SEQ ID NO 138
<211> LENGTH: 25
<212> TYPE: RNA
<213> ORGANISM: Artificial Sequence
<220> FEATURE:
<223> OTHER INFORMATION: Synthetic

<400> SEQUENCE: 138
gcugagauuc gcccuuggua uuaca 25

<210> SEQ ID NO 139
<211> LENGTH: 25
<212> TYPE: RNA
<213> ORGANISM: Artificial Sequence
<220> FEATURE:
<223> OTHER INFORMATION: Synthetic

<400> SEQUENCE: 139
cugagauucg cccuuggugu uacac 25

<210> SEQ ID NO 140
<211> LENGTH: 25
<212> TYPE: RNA
<213> ORGANISM: Artificial Sequence
<220> FEATURE:
<223> OTHER INFORMATION: Synthetic

<400> SEQUENCE: 140
gagauucgcc cuuggguuua cacca 25

<210> SEQ ID NO 141
<211> LENGTH: 25
<212> TYPE: DNA
<213> ORGANISM: Artificial Sequence
<220> FEATURE:
<223> OTHER INFORMATION: Synthetic

<400> SEQUENCE: 141
agauucgccc uugguguuaa accat 25

<210> SEQ ID NO 142
<211> LENGTH: 25
<212> TYPE: RNA

<213> ORGANISM: Artificial Sequence
<220> FEATURE:
<223> OTHER INFORMATION: Synthetic

<400> SEQUENCE: 142
uucgcccuug guguuacaca augga 25

<210> SEQ ID NO 143
<211> LENGTH: 25
<212> TYPE: RNA
<213> ORGANISM: Artificial Sequence
<220> FEATURE:
<223> OTHER INFORMATION: Synthetic

<400> SEQUENCE: 143
cuugguguua caccauggaa cccag 25

<210> SEQ ID NO 144
<211> LENGTH: 25
<212> TYPE: DNA
<213> ORGANISM: Artificial Sequence
<220> FEATURE:
<223> OTHER INFORMATION: Synthetic

<400> SEQUENCE: 144
uugguguuac accauggaua ccagt 25

<210> SEQ ID NO 145
<211> LENGTH: 25
<212> TYPE: DNA
<213> ORGANISM: Artificial Sequence
<220> FEATURE:
<223> OTHER INFORMATION: Synthetic

<400> SEQUENCE: 145
ugguguuaca ccauggauca cagtg 25

<210> SEQ ID NO 146
<211> LENGTH: 25
<212> TYPE: DNA
<213> ORGANISM: Artificial Sequence
<220> FEATURE:
<223> OTHER INFORMATION: Synthetic

<400> SEQUENCE: 146
gguguuacac cauggaucca agugt 25

<210> SEQ ID NO 147
<211> LENGTH: 25
<212> TYPE: RNA
<213> ORGANISM: Artificial Sequence
<220> FEATURE:
<223> OTHER INFORMATION: Synthetic

<400> SEQUENCE: 147
uguuacacca uggaucccaa uguca 25

<210> SEQ ID NO 148
<211> LENGTH: 25
<212> TYPE: RNA
<213> ORGANISM: Artificial Sequence
<220> FEATURE:
<223> OTHER INFORMATION: Synthetic

<400> SEQUENCE: 148
gaaucaagug uccuugcaaa ucuca 25

<210> SEQ ID NO 149
<211> LENGTH: 25
<212> TYPE: RNA
<213> ORGANISM: Artificial Sequence
<220> FEATURE:
<223> OTHER INFORMATION: Synthetic

<400> SEQUENCE: 149
aaucaagugu ccuugcaaca cucac 25

<210> SEQ ID NO 150
<211> LENGTH: 25
<212> TYPE: RNA
<213> ORGANISM: Artificial Sequence
<220> FEATURE:
<223> OTHER INFORMATION: Synthetic

<400> SEQUENCE: 150
aucaaguguc cuugcaacua ucacg 25

<210> SEQ ID NO 151
<211> LENGTH: 25
<212> TYPE: DNA
<213> ORGANISM: Artificial Sequence
<220> FEATURE:
<223> OTHER INFORMATION: Synthetic

<400> SEQUENCE: 151
auggacagag uuaucgagga ucatt 25

<210> SEQ ID NO 152
<211> LENGTH: 25
<212> TYPE: DNA
<213> ORGANISM: Artificial Sequence
<220> FEATURE:
<223> OTHER INFORMATION: Synthetic

<400> SEQUENCE: 152
uggacagagu uaucgaggca cautc 25

<210> SEQ ID NO 153
<211> LENGTH: 25
<212> TYPE: DNA
<213> ORGANISM: Artificial Sequence
<220> FEATURE:
<223> OTHER INFORMATION: Synthetic

<400> SEQUENCE: 153
acaccacacu ggcaucagaa gacaa 25

<210> SEQ ID NO 154
<211> LENGTH: 25
<212> TYPE: DNA
<213> ORGANISM: Artificial Sequence
<220> FEATURE:
<223> OTHER INFORMATION: Synthetic

<400> SEQUENCE: 154
uugguguuau accauggaua ccaat 25

<210> SEQ ID NO 155
<211> LENGTH: 25
<212> TYPE: DNA
<213> ORGANISM: Artificial Sequence
<220> FEATURE:

<223> OTHER INFORMATION: Synthetic

<400> SEQUENCE: 155
ugguguuaua ccauggauca caatg 25

<210> SEQ ID NO 156
<211> LENGTH: 25
<212> TYPE: DNA
<213> ORGANISM: Artificial Sequence
<220> FEATURE:
<223> OTHER INFORMATION: Synthetic

<400> SEQUENCE: 156
gguguuauac cauggaucca aaugt 25

<210> SEQ ID NO 157
<211> LENGTH: 25
<212> TYPE: DNA
<213> ORGANISM: Artificial Sequence
<220> FEATURE:
<223> OTHER INFORMATION: Synthetic

<400> SEQUENCE: 157
guguuauacc auggauccca augtc 25

<210> SEQ ID NO 158
<211> LENGTH: 25
<212> TYPE: RNA
<213> ORGANISM: Artificial Sequence
<220> FEATURE:
<223> OTHER INFORMATION: Synthetic

<400> SEQUENCE: 158
ucagauggga guacugcaaa cugac 25

<210> SEQ ID NO 159
<211> LENGTH: 25
<212> TYPE: RNA
<213> ORGANISM: Artificial Sequence
<220> FEATURE:
<223> OTHER INFORMATION: Synthetic

<400> SEQUENCE: 159
gaugggagua cugcaaccua acaca 25

<210> SEQ ID NO 160
<211> LENGTH: 25
<212> TYPE: RNA
<213> ORGANISM: Artificial Sequence
<220> FEATURE:
<223> OTHER INFORMATION: Synthetic

<400> SEQUENCE: 160
augggaguac ugcaaccuga cacaa 25

<210> SEQ ID NO 161
<211> LENGTH: 25
<212> TYPE: DNA
<213> ORGANISM: Artificial Sequence
<220> FEATURE:
<223> OTHER INFORMATION: Synthetic

<400> SEQUENCE: 161
ugggaguacu gcaaccugaa acaat 25

<210> SEQ ID NO 162
<211> LENGTH: 25
<212> TYPE: DNA
<213> ORGANISM: Artificial Sequence
<220> FEATURE:
<223> OTHER INFORMATION: Synthetic

<400> SEQUENCE: 162
gggaguacug caaccugaca caatg 25

<210> SEQ ID NO 163
<211> LENGTH: 25
<212> TYPE: RNA
<213> ORGANISM: Artificial Sequence
<220> FEATURE:
<223> OTHER INFORMATION: Synthetic

<400> SEQUENCE: 163
ggcuguuucu gaacaagcaa caacg 25

<210> SEQ ID NO 164
<211> LENGTH: 25
<212> TYPE: RNA
<213> ORGANISM: Artificial Sequence
<220> FEATURE:
<223> OTHER INFORMATION: Synthetic

<400> SEQUENCE: 164
guuucugaac aagcaccaaa ggagc 25

<210> SEQ ID NO 165
<211> LENGTH: 25
<212> TYPE: RNA
<213> ORGANISM: Artificial Sequence
<220> FEATURE:
<223> OTHER INFORMATION: Synthetic

<400> SEQUENCE: 165
cuccaccacu guuacaggaa ggaca 25

<210> SEQ ID NO 166
<211> LENGTH: 24
<212> TYPE: RNA
<213> ORGANISM: Artificial Sequence
<220> FEATURE:
<223> OTHER INFORMATION: Synthetic

<400> SEQUENCE: 166
uccaccacug uuacaggaaa gaca 24

<210> SEQ ID NO 167
<211> LENGTH: 24
<212> TYPE: RNA
<213> ORGANISM: Artificial Sequence
<220> FEATURE:
<223> OTHER INFORMATION: Synthetic

<400> SEQUENCE: 167
ccaccacugu uacaggaaga acag 24

<210> SEQ ID NO 168
<211> LENGTH: 25
<212> TYPE: RNA
<213> ORGANISM: Artificial Sequence
<220> FEATURE:
<223> OTHER INFORMATION: Synthetic

<400> SEQUENCE: 168
gacaccacac uggcaucaga gaacc 25

<210> SEQ ID NO 169
<211> LENGTH: 25
<212> TYPE: RNA
<213> ORGANISM: Artificial Sequence
<220> FEATURE:
<223> OTHER INFORMATION: Synthetic

<400> SEQUENCE: 169
acaccacacu ggcaucagaa aacca 25

<210> SEQ ID NO 170
<211> LENGTH: 24
<212> TYPE: RNA
<213> ORGANISM: Artificial Sequence
<220> FEATURE:
<223> OTHER INFORMATION: Synthetic

<400> SEQUENCE: 170
agaauacuac ccaaauggua gccg 24

<210> SEQ ID NO 171
<211> LENGTH: 25
<212> TYPE: RNA
<213> ORGANISM: Artificial Sequence
<220> FEATURE:
<223> OTHER INFORMATION: Synthetic

<400> SEQUENCE: 171
gaauacuacc caaaugguga ccuga 25

<210> SEQ ID NO 172
<211> LENGTH: 25
<212> TYPE: RNA
<213> ORGANISM: Artificial Sequence
<220> FEATURE:
<223> OTHER INFORMATION: Synthetic

<400> SEQUENCE: 172
aauacuaccc aaauggugga cugac 25

<210> SEQ ID NO 173
<211> LENGTH: 25
<212> TYPE: RNA
<213> ORGANISM: Artificial Sequence
<220> FEATURE:
<223> OTHER INFORMATION: Synthetic

<400> SEQUENCE: 173
uccuucugaa gaagcaccaa cugaa 25

<210> SEQ ID NO 174
<211> LENGTH: 25
<212> TYPE: RNA
<213> ORGANISM: Artificial Sequence
<220> FEATURE:
<223> OTHER INFORMATION: Synthetic

<400> SEQUENCE: 174
ccuucugaag aagcaccaaa ugaaa 25

<210> SEQ ID NO 175
<211> LENGTH: 25

<212> TYPE: RNA
<213> ORGANISM: Artificial Sequence
<220> FEATURE:
<223> OTHER INFORMATION: Synthetic

<400> SEQUENCE: 175
cuucugaaga agcaccaaca gaaaa 25

<210> SEQ ID NO 176
<211> LENGTH: 25
<212> TYPE: RNA
<213> ORGANISM: Artificial Sequence
<220> FEATURE:
<223> OTHER INFORMATION: Synthetic

<400> SEQUENCE: 176
uucugaagaa gcaccaacua aaaac 25

<210> SEQ ID NO 177
<211> LENGTH: 25
<212> TYPE: RNA
<213> ORGANISM: Artificial Sequence
<220> FEATURE:
<223> OTHER INFORMATION: Synthetic

<400> SEQUENCE: 177
ucugaagaag caccaacuga aaaca 25

<210> SEQ ID NO 178
<211> LENGTH: 25
<212> TYPE: RNA
<213> ORGANISM: Artificial Sequence
<220> FEATURE:
<223> OTHER INFORMATION: Synthetic

<400> SEQUENCE: 178
cugaagaagc accaacugaa aacag 25

<210> SEQ ID NO 179
<211> LENGTH: 25
<212> TYPE: RNA
<213> ORGANISM: Artificial Sequence
<220> FEATURE:
<223> OTHER INFORMATION: Synthetic

<400> SEQUENCE: 179
ugaagaagca ccaacugaaa acagc 25

<210> SEQ ID NO 180
<211> LENGTH: 25
<212> TYPE: RNA
<213> ORGANISM: Artificial Sequence
<220> FEATURE:
<223> OTHER INFORMATION: Synthetic

<400> SEQUENCE: 180
gaagaagcac caacugaaaa cagca 25

<210> SEQ ID NO 181
<211> LENGTH: 25
<212> TYPE: RNA
<213> ORGANISM: Artificial Sequence
<220> FEATURE:
<223> OTHER INFORMATION: Synthetic

<400> SEQUENCE: 181

-continued aagaagcacc aacugaaaaa agcac 25

<210> SEQ ID NO 182
<211> LENGTH: 24
<212> TYPE: RNA
<213> ORGANISM: Artificial Sequence
<220> FEATURE:
<223> OTHER INFORMATION: Synthetic

<400> SEQUENCE: 182
agaagcacca acugaaaaca gcac 24

<210> SEQ ID NO 183
<211> LENGTH: 24
<212> TYPE: RNA
<213> ORGANISM: Artificial Sequence
<220> FEATURE:
<223> OTHER INFORMATION: Synthetic

<400> SEQUENCE: 183
gaagcaccaa cugaaaacaa cacg 24

<210> SEQ ID NO 184
<211> LENGTH: 25
<212> TYPE: RNA
<213> ORGANISM: Artificial Sequence
<220> FEATURE:
<223> OTHER INFORMATION: Synthetic

<400> SEQUENCE: 184
aagcaccaac ugaaaacaga acugg 25

<210> SEQ ID NO 185
<211> LENGTH: 25
<212> TYPE: RNA
<213> ORGANISM: Artificial Sequence
<220> FEATURE:
<223> OTHER INFORMATION: Synthetic

<400> SEQUENCE: 185
aggugaugga cagaguuaua gaggc 25

<210> SEQ ID NO 186
<211> LENGTH: 25
<212> TYPE: RNA
<213> ORGANISM: Artificial Sequence
<220> FEATURE:
<223> OTHER INFORMATION: Synthetic

<400> SEQUENCE: 186
cuccaccacu aucacaggaa gaaca 25

<210> SEQ ID NO 187
<211> LENGTH: 24
<212> TYPE: RNA
<213> ORGANISM: Artificial Sequence
<220> FEATURE:
<223> OTHER INFORMATION: Synthetic

<400> SEQUENCE: 187
uccaccacua ucacaggaaa aaca 24

<210> SEQ ID NO 188
<211> LENGTH: 24
<212> TYPE: RNA
<213> ORGANISM: Artificial Sequence
<220> FEATURE:
<223> OTHER INFORMATION: Synthetic

<400> SEQUENCE: 188
ccaccacuau cacaggaaga acag 24

<210> SEQ ID NO 189
<211> LENGTH: 24
<212> TYPE: RNA
<213> ORGANISM: Artificial Sequence
<220> FEATURE:
<223> OTHER INFORMATION: Synthetic

<400> SEQUENCE: 189
caccacuauc acaggaagaa caug 24

<210> SEQ ID NO 190
<211> LENGTH: 24
<212> TYPE: RNA
<213> ORGANISM: Artificial Sequence
<220> FEATURE:
<223> OTHER INFORMATION: Synthetic

<400> SEQUENCE: 190
accacuauca caggaagaaa augc 24

<210> SEQ ID NO 191
<211> LENGTH: 25
<212> TYPE: RNA
<213> ORGANISM: Artificial Sequence
<220> FEATURE:
<223> OTHER INFORMATION: Synthetic

<400> SEQUENCE: 191
ccacuaucac aggaagaaca uguca 25

<210> SEQ ID NO 192
<211> LENGTH: 25
<212> TYPE: RNA
<213> ORGANISM: Artificial Sequence
<220> FEATURE:
<223> OTHER INFORMATION: Synthetic

<400> SEQUENCE: 192
cacuaucaca ggaagaacaa gucag 25

<210> SEQ ID NO 193
<211> LENGTH: 24
<212> TYPE: RNA
<213> ORGANISM: Artificial Sequence
<220> FEATURE:
<223> OTHER INFORMATION: Synthetic

<400> SEQUENCE: 193
acuaucacag gaagaacaua ucag 24

<210> SEQ ID NO 194
<211> LENGTH: 24
<212> TYPE: RNA
<213> ORGANISM: Artificial Sequence
<220> FEATURE:
<223> OTHER INFORMATION: Synthetic

<400> SEQUENCE: 194
cuaucacagg aagaacauga cagc 24

-continued

<210> SEQ ID NO 195
<211> LENGTH: 24
<212> TYPE: RNA
<213> ORGANISM: Artificial Sequence
<220> FEATURE:
<223> OTHER INFORMATION: Synthetic

<400> SEQUENCE: 195
uaucacagga agaacaugua aguc 24

<210> SEQ ID NO 196
<211> LENGTH: 23
<212> TYPE: RNA
<213> ORGANISM: Artificial Sequence
<220> FEATURE:
<223> OTHER INFORMATION: Synthetic

<400> SEQUENCE: 196
aucacaggaa gaacauguca guc 23

<210> SEQ ID NO 197
<211> LENGTH: 24
<212> TYPE: RNA
<213> ORGANISM: Artificial Sequence
<220> FEATURE:
<223> OTHER INFORMATION: Synthetic

<400> SEQUENCE: 197
ucacaggaag aacaugucaa ucug 24

<210> SEQ ID NO 198
<211> LENGTH: 25
<212> TYPE: RNA
<213> ORGANISM: Artificial Sequence
<220> FEATURE:
<223> OTHER INFORMATION: Synthetic

<400> SEQUENCE: 198
cacaggaaga acaugucaga cuugg 25

<210> SEQ ID NO 199
<211> LENGTH: 24
<212> TYPE: RNA
<213> ORGANISM: Artificial Sequence
<220> FEATURE:
<223> OTHER INFORMATION: Synthetic

<400> SEQUENCE: 199
acaggaagaa caugucagua uugg 24

<210> SEQ ID NO 200
<211> LENGTH: 24
<212> TYPE: RNA
<213> ORGANISM: Artificial Sequence
<220> FEATURE:
<223> OTHER INFORMATION: Synthetic

<400> SEQUENCE: 200
ggaagaacau gucagucuua gucg 24

<210> SEQ ID NO 201
<211> LENGTH: 24
<212> TYPE: RNA
<213> ORGANISM: Artificial Sequence
<220> FEATURE:
<223> OTHER INFORMATION: Synthetic

<400> SEQUENCE: 201
gaagaacaug ucagucuuga ucgc 24

<210> SEQ ID NO 202
<211> LENGTH: 24
<212> TYPE: RNA
<213> ORGANISM: Artificial Sequence
<220> FEATURE:
<223> OTHER INFORMATION: Synthetic

<400> SEQUENCE: 202
aagaacaugu cagucuugga cguc 24

<210> SEQ ID NO 203
<211> LENGTH: 24
<212> TYPE: RNA
<213> ORGANISM: Artificial Sequence
<220> FEATURE:
<223> OTHER INFORMATION: Synthetic

<400> SEQUENCE: 203
agaacauguc agucuuggua guca 24

<210> SEQ ID NO 204
<211> LENGTH: 24
<212> TYPE: RNA
<213> ORGANISM: Artificial Sequence
<220> FEATURE:
<223> OTHER INFORMATION: Synthetic

<400> SEQUENCE: 204
ggcaucggag gaucccauua uaca 24

<210> SEQ ID NO 205
<211> LENGTH: 25
<212> TYPE: RNA
<213> ORGANISM: Artificial Sequence
<220> FEATURE:
<223> OTHER INFORMATION: Synthetic

<400> SEQUENCE: 205
acuauccaaa ugcuggccua accag 25

<210> SEQ ID NO 206
<211> LENGTH: 25
<212> TYPE: RNA
<213> ORGANISM: Artificial Sequence
<220> FEATURE:
<223> OTHER INFORMATION: Synthetic

<400> SEQUENCE: 206
gcacagaggc uccuucugaa caagc 25

<210> SEQ ID NO 207
<211> LENGTH: 25
<212> TYPE: RNA
<213> ORGANISM: Artificial Sequence
<220> FEATURE:
<223> OTHER INFORMATION: Synthetic

<400> SEQUENCE: 207
uccuucugaa caagcaccaa cugag 25

<210> SEQ ID NO 208

<211> LENGTH: 25
<212> TYPE: RNA
<213> ORGANISM: Artificial Sequence
<220> FEATURE:
<223> OTHER INFORMATION: Synthetic

<400> SEQUENCE: 208
ccuucugaac aagcaccaca ugaga 25

<210> SEQ ID NO 209
<211> LENGTH: 25
<212> TYPE: RNA
<213> ORGANISM: Artificial Sequence
<220> FEATURE:
<223> OTHER INFORMATION: Synthetic

<400> SEQUENCE: 209
cuucugaaca agcaccacca gagaa 25

<210> SEQ ID NO 210
<211> LENGTH: 25
<212> TYPE: RNA
<213> ORGANISM: Artificial Sequence
<220> FEATURE:
<223> OTHER INFORMATION: Synthetic

<400> SEQUENCE: 210
uucugaacaa gcaccaccua agaaa 25

<210> SEQ ID NO 211
<211> LENGTH: 25
<212> TYPE: RNA
<213> ORGANISM: Artificial Sequence
<220> FEATURE:
<223> OTHER INFORMATION: Synthetic

<400> SEQUENCE: 211
ucugaacaag caccaccuga gaaaa 25

<210> SEQ ID NO 212
<211> LENGTH: 25
<212> TYPE: RNA
<213> ORGANISM: Artificial Sequence
<220> FEATURE:
<223> OTHER INFORMATION: Synthetic

<400> SEQUENCE: 212
cugaacaagc accaccugaa aaaag 25

<210> SEQ ID NO 213
<211> LENGTH: 25
<212> TYPE: RNA
<213> ORGANISM: Artificial Sequence
<220> FEATURE:
<223> OTHER INFORMATION: Synthetic

<400> SEQUENCE: 213
ugaacaagca ccaccugaga aaagc 25

<210> SEQ ID NO 214
<211> LENGTH: 25
<212> TYPE: RNA
<213> ORGANISM: Artificial Sequence
<220> FEATURE:
<223> OTHER INFORMATION: Synthetic

<400> SEQUENCE: 214
gaacaagcac caccugagaa aagcc 25

<210> SEQ ID NO 215
<211> LENGTH: 25
<212> TYPE: RNA
<213> ORGANISM: Artificial Sequence
<220> FEATURE:
<223> OTHER INFORMATION: Synthetic

<400> SEQUENCE: 215
aacaagcacc accugagaaa agccc 25

<210> SEQ ID NO 216
<211> LENGTH: 24
<212> TYPE: RNA
<213> ORGANISM: Artificial Sequence
<220> FEATURE:
<223> OTHER INFORMATION: Synthetic

<400> SEQUENCE: 216
caagcaccac cugagaaaaa cccg 24

<210> SEQ ID NO 217
<211> LENGTH: 24
<212> TYPE: RNA
<213> ORGANISM: Artificial Sequence
<220> FEATURE:
<223> OTHER INFORMATION: Synthetic

<400> SEQUENCE: 217
aagcaccacc ugagaaaaga ccug 24

<210> SEQ ID NO 218
<211> LENGTH: 24
<212> TYPE: RNA
<213> ORGANISM: Artificial Sequence
<220> FEATURE:
<223> OTHER INFORMATION: Synthetic

<400> SEQUENCE: 218
agcaccaccu gagaaaagca cugg 24

<210> SEQ ID NO 219
<211> LENGTH: 25
<212> TYPE: RNA
<213> ORGANISM: Artificial Sequence
<220> FEATURE:
<223> OTHER INFORMATION: Synthetic

<400> SEQUENCE: 219
cugagaaaag cccuguggua cagga 25

<210> SEQ ID NO 220
<211> LENGTH: 25
<212> TYPE: RNA
<213> ORGANISM: Artificial Sequence
<220> FEATURE:
<223> OTHER INFORMATION: Synthetic

<400> SEQUENCE: 220
gcccuguggu ccaggauuga uacca 25

<210> SEQ ID NO 221
<211> LENGTH: 25
<212> TYPE: RNA

<213> ORGANISM: Artificial Sequence
<220> FEATURE:
<223> OTHER INFORMATION: Synthetic

<400> SEQUENCE: 221
cuguggucca ggauugcuaa caugg 25

<210> SEQ ID NO 222
<211> LENGTH: 25
<212> TYPE: RNA
<213> ORGANISM: Artificial Sequence
<220> FEATURE:
<223> OTHER INFORMATION: Synthetic

<400> SEQUENCE: 222
cuccaccacu gucacaggaa ggacc 25

<210> SEQ ID NO 223
<211> LENGTH: 24
<212> TYPE: RNA
<213> ORGANISM: Artificial Sequence
<220> FEATURE:
<223> OTHER INFORMATION: Synthetic

<400> SEQUENCE: 223
uccaccacug ucacaggaaa gacc 24

<210> SEQ ID NO 224
<211> LENGTH: 24
<212> TYPE: RNA
<213> ORGANISM: Artificial Sequence
<220> FEATURE:
<223> OTHER INFORMATION: Synthetic

<400> SEQUENCE: 224
ucuuggucau cuaugauaca acac 24

<210> SEQ ID NO 225
<211> LENGTH: 24
<212> TYPE: RNA
<213> ORGANISM: Artificial Sequence
<220> FEATURE:
<223> OTHER INFORMATION: Synthetic

<400> SEQUENCE: 225
cuuggucauc uaugauacca cacg 24

<210> SEQ ID NO 226
<211> LENGTH: 25
<212> TYPE: RNA
<213> ORGANISM: Artificial Sequence
<220> FEATURE:
<223> OTHER INFORMATION: Synthetic

<400> SEQUENCE: 226
uuggucaucu augauaccaa acugg 25

<210> SEQ ID NO 227
<211> LENGTH: 25
<212> TYPE: RNA
<213> ORGANISM: Artificial Sequence
<220> FEATURE:
<223> OTHER INFORMATION: Synthetic

<400> SEQUENCE: 227
uggucaucua ugauaccaca cuggc 25

<210> SEQ ID NO 228
<211> LENGTH: 25
<212> TYPE: RNA
<213> ORGANISM: Artificial Sequence
<220> FEATURE:
<223> OTHER INFORMATION: Synthetic

<400> SEQUENCE: 228
ggucaucuau gauaccacaa uggca 25

<210> SEQ ID NO 229
<211> LENGTH: 24
<212> TYPE: RNA
<213> ORGANISM: Artificial Sequence
<220> FEATURE:
<223> OTHER INFORMATION: Synthetic

<400> SEQUENCE: 229
gucaucuaug auaccacaca ggca 24

<210> SEQ ID NO 230
<211> LENGTH: 24
<212> TYPE: RNA
<213> ORGANISM: Artificial Sequence
<220> FEATURE:
<223> OTHER INFORMATION: Synthetic

<400> SEQUENCE: 230
ucaucuauga uaccacacua gcac 24

<210> SEQ ID NO 231
<211> LENGTH: 25
<212> TYPE: RNA
<213> ORGANISM: Artificial Sequence
<220> FEATURE:
<223> OTHER INFORMATION: Synthetic

<400> SEQUENCE: 231
caucuaugau accacacuga cauca 25

<210> SEQ ID NO 232
<211> LENGTH: 25
<212> TYPE: RNA
<213> ORGANISM: Artificial Sequence
<220> FEATURE:
<223> OTHER INFORMATION: Synthetic

<400> SEQUENCE: 232
aucuaugaua ccacacugga aucag 25

<210> SEQ ID NO 233
<211> LENGTH: 25
<212> TYPE: RNA
<213> ORGANISM: Artificial Sequence
<220> FEATURE:
<223> OTHER INFORMATION: Synthetic

<400> SEQUENCE: 233
ucuaugauac cacacuggca ucaga 25

<210> SEQ ID NO 234
<211> LENGTH: 25
<212> TYPE: RNA
<213> ORGANISM: Artificial Sequence
<220> FEATURE:

<223> OTHER INFORMATION: Synthetic

<400> SEQUENCE: 234
cuaugauacc acacuggcaa cagag 25

<210> SEQ ID NO 235
<211> LENGTH: 25
<212> TYPE: RNA
<213> ORGANISM: Artificial Sequence
<220> FEATURE:
<223> OTHER INFORMATION: Synthetic

<400> SEQUENCE: 235
ugauaccaca cuggcaucaa aggac 25

<210> SEQ ID NO 236
<211> LENGTH: 25
<212> TYPE: RNA
<213> ORGANISM: Artificial Sequence
<220> FEATURE:
<223> OTHER INFORMATION: Synthetic

<400> SEQUENCE: 236
auaccacacu ggcaucagaa gaccc 25

<210> SEQ ID NO 237
<211> LENGTH: 25
<212> TYPE: RNA
<213> ORGANISM: Artificial Sequence
<220> FEATURE:
<223> OTHER INFORMATION: Synthetic

<400> SEQUENCE: 237
agaggacccc agaaaacuaa ccaaa 25

<210> SEQ ID NO 238
<211> LENGTH: 24
<212> TYPE: RNA
<213> ORGANISM: Artificial Sequence
<220> FEATURE:
<223> OTHER INFORMATION: Synthetic

<400> SEQUENCE: 238
gaggacccca gaaaacuaca caaa 24

<210> SEQ ID NO 239
<211> LENGTH: 24
<212> TYPE: RNA
<213> ORGANISM: Artificial Sequence
<220> FEATURE:
<223> OTHER INFORMATION: Synthetic

<400> SEQUENCE: 239
agaacuacug caggaaucca gauc 24

<210> SEQ ID NO 240
<211> LENGTH: 25
<212> TYPE: RNA
<213> ORGANISM: Artificial Sequence
<220> FEATURE:
<223> OTHER INFORMATION: Synthetic

<400> SEQUENCE: 240
acuacugcag gaauccagaa ucugg 25

<210> SEQ ID NO 241
<211> LENGTH: 25
<212> TYPE: RNA
<213> ORGANISM: Artificial Sequence
<220> FEATURE:
<223> OTHER INFORMATION: Synthetic

<400> SEQUENCE: 241
uacugcagga auccagauua uggga 25

<210> SEQ ID NO 242
<211> LENGTH: 25
<212> TYPE: RNA
<213> ORGANISM: Artificial Sequence
<220> FEATURE:
<223> OTHER INFORMATION: Synthetic

<400> SEQUENCE: 242
acugcaggaa uccagauuca gggaa 25

<210> SEQ ID NO 243
<211> LENGTH: 25
<212> TYPE: RNA
<213> ORGANISM: Artificial Sequence
<220> FEATURE:
<223> OTHER INFORMATION: Synthetic

<400> SEQUENCE: 243
cugcaggaau ccagauucua ggaaa 25

<210> SEQ ID NO 244
<211> LENGTH: 25
<212> TYPE: RNA
<213> ORGANISM: Artificial Sequence
<220> FEATURE:
<223> OTHER INFORMATION: Synthetic

<400> SEQUENCE: 244
ugcaggaauc cagauucuga gaaac 25

<210> SEQ ID NO 245
<211> LENGTH: 25
<212> TYPE: RNA
<213> ORGANISM: Artificial Sequence
<220> FEATURE:
<223> OTHER INFORMATION: Synthetic

<400> SEQUENCE: 245
gcaggaaucc agauucugga aaaca 25

<210> SEQ ID NO 246
<211> LENGTH: 25
<212> TYPE: RNA
<213> ORGANISM: Artificial Sequence
<220> FEATURE:
<223> OTHER INFORMATION: Synthetic

<400> SEQUENCE: 246
ggaauccaga uucugggaaa caacc 25

<210> SEQ ID NO 247
<211> LENGTH: 25
<212> TYPE: RNA
<213> ORGANISM: Artificial Sequence
<220> FEATURE:
<223> OTHER INFORMATION: Synthetic

<400> SEQUENCE: 247
gggaaacaac ccugguguua cacaa 25

<210> SEQ ID NO 248
<211> LENGTH: 25
<212> TYPE: RNA
<213> ORGANISM: Artificial Sequence
<220> FEATURE:
<223> OTHER INFORMATION: Synthetic

<400> SEQUENCE: 248
ggaaacaacc cugguguuaa acaac 25

<210> SEQ ID NO 249
<211> LENGTH: 24
<212> TYPE: RNA
<213> ORGANISM: Artificial Sequence
<220> FEATURE:
<223> OTHER INFORMATION: Synthetic

<400> SEQUENCE: 249
ugugugaggu gggaguacua caac 24

<210> SEQ ID NO 250
<211> LENGTH: 24
<212> TYPE: RNA
<213> ORGANISM: Artificial Sequence
<220> FEATURE:
<223> OTHER INFORMATION: Synthetic

<400> SEQUENCE: 250
gugugaggug ggaguacuga aauc 24

<210> SEQ ID NO 251
<211> LENGTH: 25
<212> TYPE: RNA
<213> ORGANISM: Artificial Sequence
<220> FEATURE:
<223> OTHER INFORMATION: Synthetic

<400> SEQUENCE: 251 gugaggluggg aguacugcaa ucuga 25

<210> SEQ ID NO 252
<211> LENGTH: 25
<212> TYPE: RNA
<213> ORGANISM: Artificial Sequence
<220> FEATURE:
<223> OTHER INFORMATION: Synthetic

<400> SEQUENCE: 252 ugaggugga guacugcaaa cugac 25

<210> SEQ ID NO 253
<211> LENGTH: 24
<212> TYPE: RNA
<213> ORGANISM: Artificial Sequence
<220> FEATURE:
<223> OTHER INFORMATION: Synthetic

<400> SEQUENCE: 253
cugacacaau gcucagaaaa agaa 24

<210> SEQ ID NO 254
<211> LENGTH: 24

<212> TYPE: RNA
<213> ORGANISM: Artificial Sequence
<220> FEATURE:
<223> OTHER INFORMATION: Synthetic

<400> SEQUENCE: 254
ugacacaaug cucagaaaca gaac 24

<210> SEQ ID NO 255
<211> LENGTH: 25
<212> TYPE: RNA
<213> ORGANISM: Artificial Sequence
<220> FEATURE:
<223> OTHER INFORMATION: Synthetic

<400> SEQUENCE: 255
gacacaaugc ucagaaacaa aauca 25

<210> SEQ ID NO 256
<211> LENGTH: 25
<212> TYPE: RNA
<213> ORGANISM: Artificial Sequence
<220> FEATURE:
<223> OTHER INFORMATION: Synthetic

<400> SEQUENCE: 256
acacaaugcu cagaaacaga aucag 25

<210> SEQ ID NO 257
<211> LENGTH: 25
<212> TYPE: RNA
<213> ORGANISM: Artificial Sequence
<220> FEATURE:
<223> OTHER INFORMATION: Synthetic

<400> SEQUENCE: 257
cacaaugcuc agaaacagaa ucagg 25

<210> SEQ ID NO 258
<211> LENGTH: 24
<212> TYPE: RNA
<213> ORGANISM: Artificial Sequence
<220> FEATURE:
<223> OTHER INFORMATION: Synthetic

<400> SEQUENCE: 258
acaaugcuca gaaacagaaa cagg 24

<210> SEQ ID NO 259
<211> LENGTH: 24
<212> TYPE: RNA
<213> ORGANISM: Artificial Sequence
<220> FEATURE:
<223> OTHER INFORMATION: Synthetic

<400> SEQUENCE: 259
caaugcucag aaacagaaua aggg 24

<210> SEQ ID NO 260
<211> LENGTH: 24
<212> TYPE: RNA
<213> ORGANISM: Artificial Sequence
<220> FEATURE:
<223> OTHER INFORMATION: Synthetic

<400> SEQUENCE: 260
aaugcucaga aacagaauca ggug 24

<210> SEQ ID NO 261
<211> LENGTH: 24
<212> TYPE: RNA
<213> ORGANISM: Artificial Sequence
<220> FEATURE:
<223> OTHER INFORMATION: Synthetic

<400> SEQUENCE: 261
augcucagaa acagaaucaa gugc 24

<210> SEQ ID NO 262
<211> LENGTH: 25
<212> TYPE: RNA
<213> ORGANISM: Artificial Sequence
<220> FEATURE:
<223> OTHER INFORMATION: Synthetic

<400> SEQUENCE: 262
ugcucagaaa cagaaucaga ugucc 25

<210> SEQ ID NO 263
<211> LENGTH: 24
<212> TYPE: RNA
<213> ORGANISM: Artificial Sequence
<220> FEATURE:
<223> OTHER INFORMATION: Synthetic

<400> SEQUENCE: 263
cucagaaaca gaaucaggua ucca 24

<210> SEQ ID NO 264
<211> LENGTH: 25
<212> TYPE: RNA
<213> ORGANISM: Artificial Sequence
<220> FEATURE:
<223> OTHER INFORMATION: Synthetic

<400> SEQUENCE: 264
cagaaacaga aucaggugua cuaga 25

<210> SEQ ID NO 265
<211> LENGTH: 25
<212> TYPE: RNA
<213> ORGANISM: Artificial Sequence
<220> FEATURE:
<223> OTHER INFORMATION: Synthetic

<400> SEQUENCE: 265
agaaacagaa ucagguguca uagag 25

<210> SEQ ID NO 266
<211> LENGTH: 25
<212> TYPE: RNA
<213> ORGANISM: Artificial Sequence
<220> FEATURE:
<223> OTHER INFORMATION: Synthetic

<400> SEQUENCE: 266
gaaacagaau caggugucca agaga 25

<210> SEQ ID NO 267
<211> LENGTH: 25
<212> TYPE: RNA
<213> ORGANISM: Artificial Sequence
<220> FEATURE:
<223> OTHER INFORMATION: Synthetic

<400> SEQUENCE: 267
aaacagaauc agguguccua gagac 25

<210> SEQ ID NO 268
<211> LENGTH: 24
<212> TYPE: RNA
<213> ORGANISM: Artificial Sequence
<220> FEATURE:
<223> OTHER INFORMATION: Synthetic

<400> SEQUENCE: 268
aacagaauca gguguccuaa agac 24

<210> SEQ ID NO 269
<211> LENGTH: 25
<212> TYPE: RNA
<213> ORGANISM: Artificial Sequence
<220> FEATURE:
<223> OTHER INFORMATION: Synthetic

<400> SEQUENCE: 269
cagaaucagg uguccuagaa acucc 25

<210> SEQ ID NO 270
<211> LENGTH: 25
<212> TYPE: RNA
<213> ORGANISM: Artificial Sequence
<220> FEATURE:
<223> OTHER INFORMATION: Synthetic

<400> SEQUENCE: 270
gaaucaggug uccuagagaa uccca 25

<210> SEQ ID NO 271
<211> LENGTH: 24
<212> TYPE: RNA
<213> ORGANISM: Artificial Sequence
<220> FEATURE:
<223> OTHER INFORMATION: Synthetic

<400> SEQUENCE: 271 aucaggugucc cuagagacua ccac 24

<210> SEQ ID NO 272
<211> LENGTH: 24
<212> TYPE: RNA
<213> ORGANISM: Artificial Sequence
<220> FEATURE:
<223> OTHER INFORMATION: Synthetic

<400> SEQUENCE: 272
gguguccuag agacucccaa ugug 24

<210> SEQ ID NO 273
<211> LENGTH: 25
<212> TYPE: RNA
<213> ORGANISM: Artificial Sequence
<220> FEATURE:
<223> OTHER INFORMATION: Synthetic

<400> SEQUENCE: 273
ccuagagacu cccacuguua uucca 25

<210> SEQ ID NO 274
<211> LENGTH: 25
<212> TYPE: RNA
<213> ORGANISM: Artificial Sequence
<220> FEATURE:
<223> OTHER INFORMATION: Synthetic

<400> SEQUENCE: 274
cuagagacuc ccacuguuga uccag 25

<210> SEQ ID NO 275
<211> LENGTH: 24
<212> TYPE: RNA
<213> ORGANISM: Artificial Sequence
<220> FEATURE:
<223> OTHER INFORMATION: Synthetic

<400> SEQUENCE: 275
uagagacucc cacuguugua ccag 24

<210> SEQ ID NO 276
<211> LENGTH: 23
<212> TYPE: RNA
<213> ORGANISM: Artificial Sequence
<220> FEATURE:
<223> OTHER INFORMATION: Synthetic

<400> SEQUENCE: 276
agagacuccc acuguuguua cag 23

<210> SEQ ID NO 277
<211> LENGTH: 24
<212> TYPE: RNA
<213> ORGANISM: Artificial Sequence
<220> FEATURE:
<223> OTHER INFORMATION: Synthetic

<400> SEQUENCE: 277
gagacuccca cuguuguuca aguc 24

<210> SEQ ID NO 278
<211> LENGTH: 25
<212> TYPE: RNA
<213> ORGANISM: Artificial Sequence
<220> FEATURE:
<223> OTHER INFORMATION: Synthetic

<400> SEQUENCE: 278
agacucccac uguuguucca guucc 25

<210> SEQ ID NO 279
<211> LENGTH: 24
<212> TYPE: RNA
<213> ORGANISM: Artificial Sequence
<220> FEATURE:
<223> OTHER INFORMATION: Synthetic

<400> SEQUENCE: 279
gcucauucug aagcagcaca aacg 24

<210> SEQ ID NO 280
<211> LENGTH: 25
<212> TYPE: RNA
<213> ORGANISM: Artificial Sequence
<220> FEATURE:
<223> OTHER INFORMATION: Synthetic

<400> SEQUENCE: 280
cucauucuga agcagcacca acuga 25

<210> SEQ ID NO 281
<211> LENGTH: 25
<212> TYPE: RNA
<213> ORGANISM: Artificial Sequence
<220> FEATURE:
<223> OTHER INFORMATION: Synthetic

<400> SEQUENCE: 281
ucauucugaa gcagcaccaa cugag 25

<210> SEQ ID NO 282
<211> LENGTH: 25
<212> TYPE: RNA
<213> ORGANISM: Artificial Sequence
<220> FEATURE:
<223> OTHER INFORMATION: Synthetic

<400> SEQUENCE: 282
cauucugaag cagcaccaaa ugagc 25

<210> SEQ ID NO 283
<211> LENGTH: 25
<212> TYPE: RNA
<213> ORGANISM: Artificial Sequence
<220> FEATURE:
<223> OTHER INFORMATION: Synthetic

<400> SEQUENCE: 283
auucugaagc agcaccaaca gagca 25

<210> SEQ ID NO 284
<211> LENGTH: 25
<212> TYPE: RNA
<213> ORGANISM: Artificial Sequence
<220> FEATURE:
<223> OTHER INFORMATION: Synthetic

<400> SEQUENCE: 284
uucugaagca gcaccaacua agcaa 25

<210> SEQ ID NO 285
<211> LENGTH: 25
<212> TYPE: RNA
<213> ORGANISM: Artificial Sequence
<220> FEATURE:
<223> OTHER INFORMATION: Synthetic

<400> SEQUENCE: 285
ucugaagcag caccaacuga gcaaa 25

<210> SEQ ID NO 286
<211> LENGTH: 25
<212> TYPE: RNA
<213> ORGANISM: Artificial Sequence
<220> FEATURE:
<223> OTHER INFORMATION: Synthetic

<400> SEQUENCE: 286
cugaagcagc accaacugaa caaac 25

<210> SEQ ID NO 287

<211> LENGTH: 25
<212> TYPE: RNA
<213> ORGANISM: Artificial Sequence
<220> FEATURE:
<223> OTHER INFORMATION: Synthetic

<400> SEQUENCE: 287
ugaagcagca ccaacugaga aaacc 25

<210> SEQ ID NO 288
<211> LENGTH: 25
<212> TYPE: RNA
<213> ORGANISM: Artificial Sequence
<220> FEATURE:
<223> OTHER INFORMATION: Synthetic

<400> SEQUENCE: 288
gaagcagcac caacugagca aaccc 25

<210> SEQ ID NO 289
<211> LENGTH: 25
<212> TYPE: RNA
<213> ORGANISM: Artificial Sequence
<220> FEATURE:
<223> OTHER INFORMATION: Synthetic

<400> SEQUENCE: 289
aagcagcacc aacugagcaa acccc 25

<210> SEQ ID NO 290
<211> LENGTH: 25
<212> TYPE: RNA
<213> ORGANISM: Artificial Sequence
<220> FEATURE:
<223> OTHER INFORMATION: Synthetic

<400> SEQUENCE: 290
cagugcuacc augguaauga ccaga 25

<210> SEQ ID NO 291
<211> LENGTH: 25
<212> TYPE: RNA
<213> ORGANISM: Artificial Sequence
<220> FEATURE:
<223> OTHER INFORMATION: Synthetic

<400> SEQUENCE: 291
agugcuacca ugguaaugga cagag 25

<210> SEQ ID NO 292
<211> LENGTH: 25
<212> TYPE: RNA
<213> ORGANISM: Artificial Sequence
<220> FEATURE:
<223> OTHER INFORMATION: Synthetic

<400> SEQUENCE: 292
acauucucca ccacugucaa aggaa 25

<210> SEQ ID NO 293
<211> LENGTH: 25
<212> TYPE: RNA
<213> ORGANISM: Artificial Sequence
<220> FEATURE:
<223> OTHER INFORMATION: Synthetic

<400> SEQUENCE: 293
cacugucaca ggaaggacaa gucaa 25

<210> SEQ ID NO 294
<211> LENGTH: 24
<212> TYPE: RNA
<213> ORGANISM: Artificial Sequence
<220> FEATURE:
<223> OTHER INFORMATION: Synthetic

<400> SEQUENCE: 294
acugucacag gaaggacaua ucaa 24

<210> SEQ ID NO 295
<211> LENGTH: 24
<212> TYPE: RNA
<213> ORGANISM: Artificial Sequence
<220> FEATURE:
<223> OTHER INFORMATION: Synthetic

<400> SEQUENCE: 295
cugucacagg aaggacauga caac 24

<210> SEQ ID NO 296
<211> LENGTH: 24
<212> TYPE: RNA
<213> ORGANISM: Artificial Sequence
<220> FEATURE:
<223> OTHER INFORMATION: Synthetic

<400> SEQUENCE: 296
ugucacagga aggacaugua aauc 24

<210> SEQ ID NO 297
<211> LENGTH: 23
<212> TYPE: RNA
<213> ORGANISM: Artificial Sequence
<220> FEATURE:
<223> OTHER INFORMATION: Synthetic

<400> SEQUENCE: 297
gucacaggaa ggacauguca auc 23

<210> SEQ ID NO 298
<211> LENGTH: 24
<212> TYPE: RNA
<213> ORGANISM: Artificial Sequence
<220> FEATURE:
<223> OTHER INFORMATION: Synthetic

<400> SEQUENCE: 298
ucacaggaag gacaugucaa ucug 24

<210> SEQ ID NO 299
<211> LENGTH: 24
<212> TYPE: RNA
<213> ORGANISM: Artificial Sequence
<220> FEATURE:
<223> OTHER INFORMATION: Synthetic

<400> SEQUENCE: 299
acaggaagga caugucaaua uugg 24

<210> SEQ ID NO 300
<211> LENGTH: 24
<212> TYPE: RNA

-continued

<213> ORGANISM: Artificial Sequence
<220> FEATURE:
<223> OTHER INFORMATION: Synthetic

<400> SEQUENCE: 300
caggaaggac augucaauca uggc 24

<210> SEQ ID NO 301
<211> LENGTH: 25
<212> TYPE: RNA
<213> ORGANISM: Artificial Sequence
<220> FEATURE:
<223> OTHER INFORMATION: Synthetic

<400> SEQUENCE: 301
aggaaggaca ugucaaucua gguca 25

<210> SEQ ID NO 302
<211> LENGTH: 24
<212> TYPE: RNA
<213> ORGANISM: Artificial Sequence
<220> FEATURE:
<223> OTHER INFORMATION: Synthetic

<400> SEQUENCE: 302
ggaaggacau gucaaucuua guca 24

<210> SEQ ID NO 303
<211> LENGTH: 24
<212> TYPE: RNA
<213> ORGANISM: Artificial Sequence
<220> FEATURE:
<223> OTHER INFORMATION: Synthetic

<400> SEQUENCE: 303
gaaggacaug ucaaucuuga ucac 24

<210> SEQ ID NO 304
<211> LENGTH: 25
<212> TYPE: RNA
<213> ORGANISM: Artificial Sequence
<220> FEATURE:
<223> OTHER INFORMATION: Synthetic

<400> SEQUENCE: 304
aaggacaugu caaucuugga caucc 25

<210> SEQ ID NO 305
<211> LENGTH: 25
<212> TYPE: RNA
<213> ORGANISM: Artificial Sequence
<220> FEATURE:
<223> OTHER INFORMATION: Synthetic

<400> SEQUENCE: 305
aggacauguc aaucuuggua aucca 25

<210> SEQ ID NO 306
<211> LENGTH: 24
<212> TYPE: RNA
<213> ORGANISM: Artificial Sequence
<220> FEATURE:
<223> OTHER INFORMATION: Synthetic

<400> SEQUENCE: 306
ggacauguca aucuugguca ucca 24

<210> SEQ ID NO 307
<211> LENGTH: 24
<212> TYPE: RNA
<213> ORGANISM: Artificial Sequence
<220> FEATURE:
<223> OTHER INFORMATION: Synthetic

<400> SEQUENCE: 307
gacaugucaa ucuuggucaa ccag 24

<210> SEQ ID NO 308
<211> LENGTH: 25
<212> TYPE: RNA
<213> ORGANISM: Artificial Sequence
<220> FEATURE:
<223> OTHER INFORMATION: Synthetic

<400> SEQUENCE: 308
acaugucaau cuuggucaua cauga 25

<210> SEQ ID NO 309
<211> LENGTH: 25
<212> TYPE: RNA
<213> ORGANISM: Artificial Sequence
<220> FEATURE:
<223> OTHER INFORMATION: Synthetic

<400> SEQUENCE: 309
caugucaauc uuggucauca augac 25

<210> SEQ ID NO 310
<211> LENGTH: 25
<212> TYPE: RNA
<213> ORGANISM: Artificial Sequence
<220> FEATURE:
<223> OTHER INFORMATION: Synthetic

<400> SEQUENCE: 310
augucaaucu uggucaucca ugaca 25

<210> SEQ ID NO 311
<211> LENGTH: 25
<212> TYPE: RNA
<213> ORGANISM: Artificial Sequence
<220> FEATURE:
<223> OTHER INFORMATION: Synthetic

<400> SEQUENCE: 311
ugucaaucuu ggucauccaa gacac 25

<210> SEQ ID NO 312
<211> LENGTH: 25
<212> TYPE: RNA
<213> ORGANISM: Artificial Sequence
<220> FEATURE:
<223> OTHER INFORMATION: Synthetic

<400> SEQUENCE: 312
gucaaucuug gucauccaua acacc 25

<210> SEQ ID NO 313
<211> LENGTH: 25
<212> TYPE: RNA
<213> ORGANISM: Artificial Sequence
<220> FEATURE:

<223> OTHER INFORMATION: Synthetic

<400> SEQUENCE: 313
ucaaucuugg ucauccauga cacca 25

<210> SEQ ID NO 314
<211> LENGTH: 25
<212> TYPE: RNA
<213> ORGANISM: Artificial Sequence
<220> FEATURE:
<223> OTHER INFORMATION: Synthetic

<400> SEQUENCE: 314
caaucuuggu cauccaugaa accac 25

<210> SEQ ID NO 315
<211> LENGTH: 25
<212> TYPE: RNA
<213> ORGANISM: Artificial Sequence
<220> FEATURE:
<223> OTHER INFORMATION: Synthetic

<400> SEQUENCE: 315
aaucuugguc auccaugaca ccaca 25

<210> SEQ ID NO 316
<211> LENGTH: 25
<212> TYPE: RNA
<213> ORGANISM: Artificial Sequence
<220> FEATURE:
<223> OTHER INFORMATION: Synthetic

<400> SEQUENCE: 316
aucuugguca uccaugacaa cacac 25

<210> SEQ ID NO 317
<211> LENGTH: 25
<212> TYPE: RNA
<213> ORGANISM: Artificial Sequence
<220> FEATURE:
<223> OTHER INFORMATION: Synthetic

<400> SEQUENCE: 317
ugacaaugaa cuacugcaga aaucc 25

<210> SEQ ID NO 318
<211> LENGTH: 25
<212> TYPE: RNA
<213> ORGANISM: Artificial Sequence
<220> FEATURE:
<223> OTHER INFORMATION: Synthetic

<400> SEQUENCE: 318
gacaaugaac uacugcagga aucca 25

<210> SEQ ID NO 319
<211> LENGTH: 25
<212> TYPE: RNA
<213> ORGANISM: Artificial Sequence
<220> FEATURE:
<223> OTHER INFORMATION: Synthetic

<400> SEQUENCE: 319
acaaugaacu acugcaggaa uccag 25

<210> SEQ ID NO 320
<211> LENGTH: 25
<212> TYPE: RNA
<213> ORGANISM: Artificial Sequence
<220> FEATURE:
<223> OTHER INFORMATION: Synthetic

<400> SEQUENCE: 320
caaugaacua cugcaggaaa ccaga 25

<210> SEQ ID NO 321
<211> LENGTH: 24
<212> TYPE: RNA
<213> ORGANISM: Artificial Sequence
<220> FEATURE:
<223> OTHER INFORMATION: Synthetic

<400> SEQUENCE: 321
aaugaacuac ugcaggaaua caga 24

<210> SEQ ID NO 322
<211> LENGTH: 24
<212> TYPE: RNA
<213> ORGANISM: Artificial Sequence
<220> FEATURE:
<223> OTHER INFORMATION: Synthetic

<400> SEQUENCE: 322
augaacuacu gcaggaauca agag 24

<210> SEQ ID NO 323
<211> LENGTH: 25
<212> TYPE: RNA
<213> ORGANISM: Artificial Sequence
<220> FEATURE:
<223> OTHER INFORMATION: Synthetic

<400> SEQUENCE: 323
ugaacuacug caggaaucca gaugc 25

<210> SEQ ID NO 324
<211> LENGTH: 24
<212> TYPE: RNA
<213> ORGANISM: Artificial Sequence
<220> FEATURE:
<223> OTHER INFORMATION: Synthetic

<400> SEQUENCE: 324
cuacugcagg aauccagaua ccga 24

<210> SEQ ID NO 325
<211> LENGTH: 25
<212> TYPE: RNA
<213> ORGANISM: Artificial Sequence
<220> FEATURE:
<223> OTHER INFORMATION: Synthetic

<400> SEQUENCE: 325
caggcccuug guguuuuaca augga 25

<210> SEQ ID NO 326
<211> LENGTH: 25
<212> TYPE: RNA
<213> ORGANISM: Artificial Sequence
<220> FEATURE:
<223> OTHER INFORMATION: Synthetic

<400> SEQUENCE: 326
cuugguguuu uaccauggaa cccag 25

<210> SEQ ID NO 327
<211> LENGTH: 25
<212> TYPE: RNA
<213> ORGANISM: Artificial Sequence
<220> FEATURE:
<223> OTHER INFORMATION: Synthetic

<400> SEQUENCE: 327
uugguguuuu accauggaca ccagc 25

<210> SEQ ID NO 328
<211> LENGTH: 25
<212> TYPE: RNA
<213> ORGANISM: Artificial Sequence
<220> FEATURE:
<223> OTHER INFORMATION: Synthetic

<400> SEQUENCE: 328
ugguguuuua ccauggacca cagca 25

<210> SEQ ID NO 329
<211> LENGTH: 24
<212> TYPE: RNA
<213> ORGANISM: Artificial Sequence
<220> FEATURE:
<223> OTHER INFORMATION: Synthetic

<400> SEQUENCE: 329
gguguuuuac cauggaccca agca 24

<210> SEQ ID NO 330
<211> LENGTH: 24
<212> TYPE: RNA
<213> ORGANISM: Artificial Sequence
<220> FEATURE:
<223> OTHER INFORMATION: Synthetic

<400> SEQUENCE: 330
guguuuuacc auggacccca gcac 24

<210> SEQ ID NO 331
<211> LENGTH: 25
<212> TYPE: RNA
<213> ORGANISM: Artificial Sequence
<220> FEATURE:
<223> OTHER INFORMATION: Synthetic

<400> SEQUENCE: 331
guuuuaccau ggaccccaga aucag 25

<210> SEQ ID NO 332
<211> LENGTH: 25
<212> TYPE: RNA
<213> ORGANISM: Artificial Sequence
<220> FEATURE:
<223> OTHER INFORMATION: Synthetic

<400> SEQUENCE: 332
ggaguacugc aaccugacga gaugc 25

<210> SEQ ID NO 333
<211> LENGTH: 24

<212> TYPE: RNA
<213> ORGANISM: Artificial Sequence
<220> FEATURE:
<223> OTHER INFORMATION: Synthetic

<400> SEQUENCE: 333
gaguacugca accugacgca augc 24

<210> SEQ ID NO 334
<211> LENGTH: 25
<212> TYPE: RNA
<213> ORGANISM: Artificial Sequence
<220> FEATURE:
<223> OTHER INFORMATION: Synthetic

<400> SEQUENCE: 334
guacugcaac cugacgcgaa gcuca 25

<210> SEQ ID NO 335
<211> LENGTH: 25
<212> TYPE: RNA
<213> ORGANISM: Artificial Sequence
<220> FEATURE:
<223> OTHER INFORMATION: Synthetic

<400> SEQUENCE: 335
uacugcaacc ugacgcgaua cucag 25

<210> SEQ ID NO 336
<211> LENGTH: 25
<212> TYPE: RNA
<213> ORGANISM: Artificial Sequence
<220> FEATURE:
<223> OTHER INFORMATION: Synthetic

<400> SEQUENCE: 336
ugcaaccuga cgcgaugcua agaca 25

<210> SEQ ID NO 337
<211> LENGTH: 25
<212> TYPE: RNA
<213> ORGANISM: Artificial Sequence
<220> FEATURE:
<223> OTHER INFORMATION: Synthetic

<400> SEQUENCE: 337
ccugacgcga ugcucagaca cagaa 25

<210> SEQ ID NO 338
<211> LENGTH: 25
<212> TYPE: RNA
<213> ORGANISM: Artificial Sequence
<220> FEATURE:
<223> OTHER INFORMATION: Synthetic

<400> SEQUENCE: 338
cugacgcgau gcucagacaa agaag 25

<210> SEQ ID NO 339
<211> LENGTH: 24
<212> TYPE: RNA
<213> ORGANISM: Artificial Sequence
<220> FEATURE:
<223> OTHER INFORMATION: Synthetic

<400> SEQUENCE: 339

-continued gaugcucaga cacagaagga acug 24

<210> SEQ ID NO 340
<211> LENGTH: 24
<212> TYPE: RNA
<213> ORGANISM: Artificial Sequence
<220> FEATURE:
<223> OTHER INFORMATION: Synthetic

<400> SEQUENCE: 340
augcucagac acagaaggga cugg 24

<210> SEQ ID NO 341
<211> LENGTH: 24
<212> TYPE: RNA
<213> ORGANISM: Artificial Sequence
<220> FEATURE:
<223> OTHER INFORMATION: Synthetic

<400> SEQUENCE: 341
agacacagaa gggacuguga ucgc 24

<210> SEQ ID NO 342
<211> LENGTH: 25
<212> TYPE: RNA
<213> ORGANISM: Artificial Sequence
<220> FEATURE:
<223> OTHER INFORMATION: Synthetic

<400> SEQUENCE: 342
gcauccucuu cauuugauua uggga 25

<210> SEQ ID NO 343
<211> LENGTH: 25
<212> TYPE: RNA
<213> ORGANISM: Artificial Sequence
<220> FEATURE:
<223> OTHER INFORMATION: Synthetic

<400> SEQUENCE: 343
cauccucuuc auuugauuga gggaa 25

<210> SEQ ID NO 344
<211> LENGTH: 25
<212> TYPE: RNA
<213> ORGANISM: Artificial Sequence
<220> FEATURE:
<223> OTHER INFORMATION: Synthetic

<400> SEQUENCE: 344
auccucuuca uuugauugua ggaag 25

<210> SEQ ID NO 345
<211> LENGTH: 25
<212> TYPE: RNA
<213> ORGANISM: Artificial Sequence
<220> FEATURE:
<223> OTHER INFORMATION: Synthetic

<400> SEQUENCE: 345
uccucuucau uugauuguga gaagc 25

<210> SEQ ID NO 346
<211> LENGTH: 25
<212> TYPE: RNA
<213> ORGANISM: Artificial Sequence
<220> FEATURE:
<223> OTHER INFORMATION: Synthetic

<400> SEQUENCE: 346
ccucuucauu ugauugugga aagcc 25

<210> SEQ ID NO 347
<211> LENGTH: 25
<212> TYPE: RNA
<213> ORGANISM: Artificial Sequence
<220> FEATURE:
<223> OTHER INFORMATION: Synthetic

<400> SEQUENCE: 347
cuucauuuga uugugggaaa ccuca 25

<210> SEQ ID NO 348
<211> LENGTH: 25
<212> TYPE: RNA
<213> ORGANISM: Artificial Sequence
<220> FEATURE:
<223> OTHER INFORMATION: Synthetic

<400> SEQUENCE: 348
uucauuugau ugugggaaga cucaa 25

<210> SEQ ID NO 349
<211> LENGTH: 25
<212> TYPE: RNA
<213> ORGANISM: Artificial Sequence
<220> FEATURE:
<223> OTHER INFORMATION: Synthetic

<400> SEQUENCE: 349
ucauuugauu gugggaagca ucaag 25

<210> SEQ ID NO 350
<211> LENGTH: 24
<212> TYPE: RNA
<213> ORGANISM: Artificial Sequence
<220> FEATURE:
<223> OTHER INFORMATION: Synthetic

<400> SEQUENCE: 350
cauuugauug ugggaagcca caag 24

<210> SEQ ID NO 351
<211> LENGTH: 24
<212> TYPE: RNA
<213> ORGANISM: Artificial Sequence
<220> FEATURE:
<223> OTHER INFORMATION: Synthetic

<400> SEQUENCE: 351
auuugauugu gggaagccua aagg 24

<210> SEQ ID NO 352
<211> LENGTH: 25
<212> TYPE: RNA
<213> ORGANISM: Artificial Sequence
<220> FEATURE:
<223> OTHER INFORMATION: Synthetic

<400> SEQUENCE: 352
gugggaagcc ucaaguggaa ccgaa 25

<210> SEQ ID NO 353
<211> LENGTH: 25
<212> TYPE: RNA
<213> ORGANISM: Artificial Sequence
<220> FEATURE:
<223> OTHER INFORMATION: Synthetic

<400> SEQUENCE: 353
aagaaauguc cuggaagcaa uguag 25

<210> SEQ ID NO 354
<211> LENGTH: 25
<212> TYPE: RNA
<213> ORGANISM: Artificial Sequence
<220> FEATURE:
<223> OTHER INFORMATION: Synthetic

<400> SEQUENCE: 354
agaaaugucc uggaagcaua guagg 25

<210> SEQ ID NO 355
<211> LENGTH: 25
<212> TYPE: RNA
<213> ORGANISM: Artificial Sequence
<220> FEATURE:
<223> OTHER INFORMATION: Synthetic

<400> SEQUENCE: 355
gaaauguccu ggaagcauua uaggg 25

<210> SEQ ID NO 356
<211> LENGTH: 25
<212> TYPE: RNA
<213> ORGANISM: Artificial Sequence
<220> FEATURE:
<223> OTHER INFORMATION: Synthetic

<400> SEQUENCE: 356
aauguccugg aagcauugua ggggg 25

<210> SEQ ID NO 357
<211> LENGTH: 25
<212> TYPE: RNA
<213> ORGANISM: Artificial Sequence
<220> FEATURE:
<223> OTHER INFORMATION: Synthetic

<400> SEQUENCE: 357
auguccugga agcauuguaa ggggg 25

<210> SEQ ID NO 358
<211> LENGTH: 24
<212> TYPE: RNA
<213> ORGANISM: Artificial Sequence
<220> FEATURE:
<223> OTHER INFORMATION: Synthetic

<400> SEQUENCE: 358
agaacaaggu uuggaaagca cuuc 24

<210> SEQ ID NO 359
<211> LENGTH: 24
<212> TYPE: RNA
<213> ORGANISM: Artificial Sequence
<220> FEATURE:
<223> OTHER INFORMATION: Synthetic

<400> SEQUENCE: 359
gaacaagguu uggaaagcaa uucg 24

<210> SEQ ID NO 360
<211> LENGTH: 24
<212> TYPE: RNA
<213> ORGANISM: Artificial Sequence
<220> FEATURE:
<223> OTHER INFORMATION: Synthetic

<400> SEQUENCE: 360
aacaagguuu ggaaagcaca ucug 24

<210> SEQ ID NO 361
<211> LENGTH: 24
<212> TYPE: RNA
<213> ORGANISM: Artificial Sequence
<220> FEATURE:
<223> OTHER INFORMATION: Synthetic

<400> SEQUENCE: 361
acaagguuug gaaagcacua cugg 24

<210> SEQ ID NO 362
<211> LENGTH: 25
<212> TYPE: RNA
<213> ORGANISM: Artificial Sequence
<220> FEATURE:
<223> OTHER INFORMATION: Synthetic

<400> SEQUENCE: 362
caagguuugg aaagcacuua ugugg 25

<210> SEQ ID NO 363
<211> LENGTH: 25
<212> TYPE: RNA
<213> ORGANISM: Artificial Sequence
<220> FEATURE:
<223> OTHER INFORMATION: Synthetic

<400> SEQUENCE: 363
aagguuugga aagcacuuca gugga 25

<210> SEQ ID NO 364
<211> LENGTH: 25
<212> TYPE: RNA
<213> ORGANISM: Artificial Sequence
<220> FEATURE:
<223> OTHER INFORMATION: Synthetic

<400> SEQUENCE: 364
agguuuggaa agcacuucua uggag 25

<210> SEQ ID NO 365
<211> LENGTH: 25
<212> TYPE: RNA
<213> ORGANISM: Artificial Sequence
<220> FEATURE:
<223> OTHER INFORMATION: Synthetic

<400> SEQUENCE: 365
uggaaagcac uucuguggaa gcacc 25

<210> SEQ ID NO 366

-continued

<211> LENGTH: 25
<212> TYPE: RNA
<213> ORGANISM: Artificial Sequence
<220> FEATURE:
<223> OTHER INFORMATION: Synthetic

<400> SEQUENCE: 366
guggaggcac cuuaauauca ccaga 25

<210> SEQ ID NO 367
<211> LENGTH: 24
<212> TYPE: RNA
<213> ORGANISM: Artificial Sequence
<220> FEATURE:
<223> OTHER INFORMATION: Synthetic

<400> SEQUENCE: 367
cuuaauaucc ccagagugga ugcg 24

<210> SEQ ID NO 368
<211> LENGTH: 25
<212> TYPE: RNA
<213> ORGANISM: Artificial Sequence
<220> FEATURE:
<223> OTHER INFORMATION: Synthetic

<400> SEQUENCE: 368
uaauaucccc agagugggua cugac 25

<210> SEQ ID NO 369
<211> LENGTH: 25
<212> TYPE: RNA
<213> ORGANISM: Artificial Sequence
<220> FEATURE:
<223> OTHER INFORMATION: Synthetic

<400> SEQUENCE: 369
agagugggug cugacugcua cucac 25

<210> SEQ ID NO 370
<211> LENGTH: 25
<212> TYPE: RNA
<213> ORGANISM: Artificial Sequence
<220> FEATURE:
<223> OTHER INFORMATION: Synthetic

<400> SEQUENCE: 370
caaggucauc cugggugcaa accaa 25

<210> SEQ ID NO 371
<211> LENGTH: 25
<212> TYPE: RNA
<213> ORGANISM: Artificial Sequence
<220> FEATURE:
<223> OTHER INFORMATION: Synthetic

<400> SEQUENCE: 371
ccugggugca caccaagaaa ugaac 25

<210> SEQ ID NO 372
<211> LENGTH: 25
<212> TYPE: RNA
<213> ORGANISM: Artificial Sequence
<220> FEATURE:
<223> OTHER INFORMATION: Synthetic

<400> SEQUENCE: 372
gugcacacca agaagugaaa cucga 25

<210> SEQ ID NO 373
<211> LENGTH: 24
<212> TYPE: RNA
<213> ORGANISM: Artificial Sequence
<220> FEATURE:
<223> OTHER INFORMATION: Synthetic

<400> SEQUENCE: 373
agcagauauu gccuugcuaa agca 24

<210> SEQ ID NO 374
<211> LENGTH: 25
<212> TYPE: RNA
<213> ORGANISM: Artificial Sequence
<220> FEATURE:
<223> OTHER INFORMATION: Synthetic

<400> SEQUENCE: 374
gcagauauug ccuugcuaaa gcuaa 25

<210> SEQ ID NO 375
<211> LENGTH: 25
<212> TYPE: RNA
<213> ORGANISM: Artificial Sequence
<220> FEATURE:
<223> OTHER INFORMATION: Synthetic

<400> SEQUENCE: 375
cagauauugc cuugcuaaaa cuaag 25

<210> SEQ ID NO 376
<211> LENGTH: 25
<212> TYPE: RNA
<213> ORGANISM: Artificial Sequence
<220> FEATURE:
<223> OTHER INFORMATION: Synthetic

<400> SEQUENCE: 376
agauauugcc uugcuaaaga uaagc 25

<210> SEQ ID NO 377
<211> LENGTH: 25
<212> TYPE: RNA
<213> ORGANISM: Artificial Sequence
<220> FEATURE:
<223> OTHER INFORMATION: Synthetic

<400> SEQUENCE: 377
gauauugccu ugcuaaagca aagca 25

<210> SEQ ID NO 378
<211> LENGTH: 25
<212> TYPE: RNA
<213> ORGANISM: Artificial Sequence
<220> FEATURE:
<223> OTHER INFORMATION: Synthetic

<400> SEQUENCE: 378
auauugccuu gcuaaagcua agcag 25

<210> SEQ ID NO 379
<211> LENGTH: 25
<212> TYPE: RNA

<213> ORGANISM: Artificial Sequence
<220> FEATURE:
<223> OTHER INFORMATION: Synthetic

<400> SEQUENCE: 379
uauugccuug cuaaagcuaa gcagg 25

<210> SEQ ID NO 380
<211> LENGTH: 25
<212> TYPE: RNA
<213> ORGANISM: Artificial Sequence
<220> FEATURE:
<223> OTHER INFORMATION: Synthetic

<400> SEQUENCE: 380
ucaucacuga caaaguaaua ccagc 25

<210> SEQ ID NO 381
<211> LENGTH: 24
<212> TYPE: RNA
<213> ORGANISM: Artificial Sequence
<220> FEATURE:
<223> OTHER INFORMATION: Synthetic

<400> SEQUENCE: 381
ggacugaaug uuacaucaca ggcg 24

<210> SEQ ID NO 382
<211> LENGTH: 25
<212> TYPE: RNA
<213> ORGANISM: Artificial Sequence
<220> FEATURE:
<223> OTHER INFORMATION: Synthetic

<400> SEQUENCE: 382
gacugaaugu uacaucacua gcugg 25

<210> SEQ ID NO 383
<211> LENGTH: 25
<212> TYPE: RNA
<213> ORGANISM: Artificial Sequence
<220> FEATURE:
<223> OTHER INFORMATION: Synthetic

<400> SEQUENCE: 383
acugaauguu acaucacuga cuggg 25

<210> SEQ ID NO 384
<211> LENGTH: 25
<212> TYPE: RNA
<213> ORGANISM: Artificial Sequence
<220> FEATURE:
<223> OTHER INFORMATION: Synthetic

<400> SEQUENCE: 384
cugaauguua caucacugga ugggg 25

<210> SEQ ID NO 385
<211> LENGTH: 25
<212> TYPE: RNA
<213> ORGANISM: Artificial Sequence
<220> FEATURE:
<223> OTHER INFORMATION: Synthetic

<400> SEQUENCE: 385
ugaauguuac aucacuggca gggga 25

<210> SEQ ID NO 386
<211> LENGTH: 25
<212> TYPE: RNA
<213> ORGANISM: Artificial Sequence
<220> FEATURE:
<223> OTHER INFORMATION: Synthetic

<400> SEQUENCE: 386
aauguuacau cacuggcuga ggaga 25

<210> SEQ ID NO 387
<211> LENGTH: 24
<212> TYPE: RNA
<213> ORGANISM: Artificial Sequence
<220> FEATURE:
<223> OTHER INFORMATION: Synthetic

<400> SEQUENCE: 387
gaaacccaag guaccuuuga gacg 24

<210> SEQ ID NO 388
<211> LENGTH: 36
<212> TYPE: RNA
<213> ORGANISM: Artificial Sequence
<220> FEATURE:
<223> OTHER INFORMATION: Synthetic

<400> SEQUENCE: 388
uccaccacug ucacaggaaa gcagccgaaa ggcugc 36

<210> SEQ ID NO 389
<211> LENGTH: 36
<212> TYPE: RNA
<213> ORGANISM: Artificial Sequence
<220> FEATURE:
<223> OTHER INFORMATION: Synthetic

<400> SEQUENCE: 389
ugguaaugga cagaguuaua gcagccgaaa ggcugc 36

<210> SEQ ID NO 390
<211> LENGTH: 36
<212> TYPE: RNA
<213> ORGANISM: Artificial Sequence
<220> FEATURE:
<223> OTHER INFORMATION: Synthetic

<400> SEQUENCE: 390
uacugcaacc ugacacgaua gcagccgaaa ggcugc 36

<210> SEQ ID NO 391
<211> LENGTH: 36
<212> TYPE: RNA
<213> ORGANISM: Artificial Sequence
<220> FEATURE:
<223> OTHER INFORMATION: Synthetic

<400> SEQUENCE: 391
agaacuugcc aagcuuggua gcagccgaaa ggcugc 36

<210> SEQ ID NO 392
<211> LENGTH: 36
<212> TYPE: RNA
<213> ORGANISM: Artificial Sequence
<220> FEATURE:

<223> OTHER INFORMATION: Synthetic

<400> SEQUENCE: 392
aacuugccaa gcuuggucaa gcagccgaaa ggcugc 36

<210> SEQ ID NO 393
<211> LENGTH: 36
<212> TYPE: RNA
<213> ORGANISM: Artificial Sequence
<220> FEATURE:
<223> OTHER INFORMATION: Synthetic

<400> SEQUENCE: 393
uugccaagcu uggucaucua gcagccgaaa ggcugc 36

<210> SEQ ID NO 394
<211> LENGTH: 36
<212> TYPE: RNA
<213> ORGANISM: Artificial Sequence
<220> FEATURE:
<223> OTHER INFORMATION: Synthetic

<400> SEQUENCE: 394
auggacagag uuaucgagga gcagccgaaa ggcugc 36

<210> SEQ ID NO 395
<211> LENGTH: 36
<212> TYPE: RNA
<213> ORGANISM: Artificial Sequence
<220> FEATURE:
<223> OTHER INFORMATION: Synthetic

<400> SEQUENCE: 395
uggacagagu uaucgaggca gcagccgaaa ggcugc 36

<210> SEQ ID NO 396
<211> LENGTH: 36
<212> TYPE: RNA
<213> ORGANISM: Artificial Sequence
<220> FEATURE:
<223> OTHER INFORMATION: Synthetic

<400> SEQUENCE: 396
uggucaucua ugauaccaca gcagccgaaa ggcugc 36

<210> SEQ ID NO 397
<211> LENGTH: 36
<212> TYPE: RNA
<213> ORGANISM: Artificial Sequence
<220> FEATURE:
<223> OTHER INFORMATION: Synthetic

<400> SEQUENCE: 397
uacugcagga auccagauua gcagccgaaa ggcugc 36

<210> SEQ ID NO 398
<211> LENGTH: 36
<212> TYPE: RNA
<213> ORGANISM: Artificial Sequence
<220> FEATURE:
<223> OTHER INFORMATION: Synthetic

<400> SEQUENCE: 398
agaaaugucc uggaagcaua gcagccgaaa ggcugc 36

<210> SEQ ID NO 399
<211> LENGTH: 36
<212> TYPE: RNA
<213> ORGANISM: Artificial Sequence
<220> FEATURE:
<223> OTHER INFORMATION: Synthetic

<400> SEQUENCE: 399
gacaacagaa uauuauccaa gcagccgaaa ggcugc 36

<210> SEQ ID NO 400
<211> LENGTH: 36
<212> TYPE: RNA
<213> ORGANISM: Artificial Sequence
<220> FEATURE:
<223> OTHER INFORMATION: Synthetic

<400> SEQUENCE: 400
auggacagag uuaucaagga gcagccgaaa ggcugc 36

<210> SEQ ID NO 401
<211> LENGTH: 36
<212> TYPE: RNA
<213> ORGANISM: Artificial Sequence
<220> FEATURE:
<223> OTHER INFORMATION: Synthetic

<400> SEQUENCE: 401
gacaacagaa uauuauccaa gcagccgaaa ggcugc 36

<210> SEQ ID NO 402
<211> LENGTH: 36
<212> TYPE: RNA
<213> ORGANISM: Artificial Sequence
<220> FEATURE:
<223> OTHER INFORMATION: Synthetic

<400> SEQUENCE: 402
auggacagag uuaucaagga gcagccgaaa ggcugc 36

<210> SEQ ID NO 403
<211> LENGTH: 36
<212> TYPE: RNA
<213> ORGANISM: Artificial Sequence
<220> FEATURE:
<223> OTHER INFORMATION: Synthetic

<400> SEQUENCE: 403
gacaacagaa uauuauccaa gcagccgaaa ggcugc 36

<210> SEQ ID NO 404
<211> LENGTH: 27
<212> TYPE: RNA
<213> ORGANISM: Artificial Sequence
<220> FEATURE:
<223> OTHER INFORMATION: Synthetic

<400> SEQUENCE: 404
uccuguacca cauggcuuug cucaggu 27

<210> SEQ ID NO 405
<211> LENGTH: 27
<212> TYPE: RNA
<213> ORGANISM: Artificial Sequence
<220> FEATURE:
<223> OTHER INFORMATION: Synthetic

<400> SEQUENCE: 405
caaucuugga ccacauggcu uugcuca 27

<210> SEQ ID NO 406
<211> LENGTH: 27
<212> TYPE: RNA
<213> ORGANISM: Artificial Sequence
<220> FEATURE:
<223> OTHER INFORMATION: Synthetic

<400> SEQUENCE: 406
guagcuaucc uggaccacau ggcuuug 27

<210> SEQ ID NO 407
<211> LENGTH: 27
<212> TYPE: RNA
<213> ORGANISM: Artificial Sequence
<220> FEATURE:
<223> OTHER INFORMATION: Synthetic

<400> SEQUENCE: 407
gguaguaauc cuggaccaca uggcuuu 27

<210> SEQ ID NO 408
<211> LENGTH: 27
<212> TYPE: RNA
<213> ORGANISM: Artificial Sequence
<220> FEATURE:
<223> OTHER INFORMATION: Synthetic

<400> SEQUENCE: 408
ugguaucaau ccuggaccac auggcuu 27

<210> SEQ ID NO 409
<211> LENGTH: 27
<212> TYPE: RNA
<213> ORGANISM: Artificial Sequence
<220> FEATURE:
<223> OTHER INFORMATION: Synthetic

<400> SEQUENCE: 409
augguugcaa uccuggacca cauggcu 27

<210> SEQ ID NO 410
<211> LENGTH: 27
<212> TYPE: RNA
<213> ORGANISM: Artificial Sequence
<220> FEATURE:
<223> OTHER INFORMATION: Synthetic

<400> SEQUENCE: 410
caugguagca auccuggacc acauggc 27

<210> SEQ ID NO 411
<211> LENGTH: 27
<212> TYPE: RNA
<213> ORGANISM: Artificial Sequence
<220> FEATURE:
<223> OTHER INFORMATION: Synthetic

<400> SEQUENCE: 411
ccauguuagc aauccuggac cacaugg 27

<210> SEQ ID NO 412
<211> LENGTH: 27

<212> TYPE: RNA
<213> ORGANISM: Artificial Sequence
<220> FEATURE:
<223> OTHER INFORMATION: Synthetic

<400> SEQUENCE: 412
accauuguag caauccugga ccacaug 27

<210> SEQ ID NO 413
<211> LENGTH: 27
<212> TYPE: RNA
<213> ORGANISM: Artificial Sequence
<220> FEATURE:
<223> OTHER INFORMATION: Synthetic

<400> SEQUENCE: 413
ugccuugaua acucugucca ucaccau 27

<210> SEQ ID NO 414
<211> LENGTH: 27
<212> TYPE: RNA
<213> ORGANISM: Artificial Sequence
<220> FEATURE:
<223> OTHER INFORMATION: Synthetic

<400> SEQUENCE: 414
aggucuuucc ugugacagug guggagu 27

<210> SEQ ID NO 415
<211> LENGTH: 27
<212> TYPE: RNA
<213> ORGANISM: Artificial Sequence
<220> FEATURE:
<223> OTHER INFORMATION: Synthetic

<400> SEQUENCE: 415
cagguucuuc cugugacagu gguggag 27

<210> SEQ ID NO 416
<211> LENGTH: 27
<212> TYPE: RNA
<213> ORGANISM: Artificial Sequence
<220> FEATURE:
<223> OTHER INFORMATION: Synthetic

<400> SEQUENCE: 416
gcuugucagg uccuuccugu gacagug 27

<210> SEQ ID NO 417
<211> LENGTH: 27
<212> TYPE: RNA
<213> ORGANISM: Artificial Sequence
<220> FEATURE:
<223> OTHER INFORMATION: Synthetic

<400> SEQUENCE: 417
augacuaagc uuggcagguc cuuccug 27

<210> SEQ ID NO 418
<211> LENGTH: 27
<212> TYPE: RNA
<213> ORGANISM: Artificial Sequence
<220> FEATURE:
<223> OTHER INFORMATION: Synthetic

<400> SEQUENCE: 418
gaugaucaag cuuggcaggu ccuuccu 27

<210> SEQ ID NO 419
<211> LENGTH: 27
<212> TYPE: RNA
<213> ORGANISM: Artificial Sequence
<220> FEATURE:
<223> OTHER INFORMATION: Synthetic

<400> SEQUENCE: 419
uagauuacca agcuuggcag guccuuc 27

<210> SEQ ID NO 420
<211> LENGTH: 27
<212> TYPE: RNA
<213> ORGANISM: Artificial Sequence
<220> FEATURE:
<223> OTHER INFORMATION: Synthetic

<400> SEQUENCE: 420
auagaugacc aagcuuggca gguccuu 27

<210> SEQ ID NO 421
<211> LENGTH: 27
<212> TYPE: RNA
<213> ORGANISM: Artificial Sequence
<220> FEATURE:
<223> OTHER INFORMATION: Synthetic

<400> SEQUENCE: 421
cauaguugac caagcuuggc agguccu 27

<210> SEQ ID NO 422
<211> LENGTH: 27
<212> TYPE: RNA
<213> ORGANISM: Artificial Sequence
<220> FEATURE:
<223> OTHER INFORMATION: Synthetic

<400> SEQUENCE: 422
ucauauauga ccaagcuugg cagaucc 27

<210> SEQ ID NO 423
<211> LENGTH: 27
<212> TYPE: RNA
<213> ORGANISM: Artificial Sequence
<220> FEATURE:
<223> OTHER INFORMATION: Synthetic

<400> SEQUENCE: 423
gucauugaug accaagcuug gcagguc 27

<210> SEQ ID NO 424
<211> LENGTH: 27
<212> TYPE: RNA
<213> ORGANISM: Artificial Sequence
<220> FEATURE:
<223> OTHER INFORMATION: Synthetic

<400> SEQUENCE: 424
auguguuguc auagaugacc aagcuug 27

<210> SEQ ID NO 425
<211> LENGTH: 27
<212> TYPE: RNA
<213> ORGANISM: Artificial Sequence
<220> FEATURE:
<223> OTHER INFORMATION: Synthetic

<400> SEQUENCE: 425
auguuuaugu ggugucauag augacca 27

<210> SEQ ID NO 426
<211> LENGTH: 27
<212> TYPE: RNA
<213> ORGANISM: Artificial Sequence
<220> FEATURE:
<223> OTHER INFORMATION: Synthetic

<400> SEQUENCE: 426
gccaguauuu ggguaguuuu cuguggu 27

<210> SEQ ID NO 427
<211> LENGTH: 27
<212> TYPE: RNA
<213> ORGANISM: Artificial Sequence
<220> FEATURE:
<223> OTHER INFORMATION: Synthetic

<400> SEQUENCE: 427
caagcuagca uuuggguagu uuucugu 27

<210> SEQ ID NO 428
<211> LENGTH: 27
<212> TYPE: RNA
<213> ORGANISM: Artificial Sequence
<220> FEATURE:
<223> OTHER INFORMATION: Synthetic

<400> SEQUENCE: 428
aucaauccag cauuugggua guuuucu 27

<210> SEQ ID NO 429
<211> LENGTH: 27
<212> TYPE: RNA
<213> ORGANISM: Artificial Sequence
<220> FEATURE:
<223> OTHER INFORMATION: Synthetic

<400> SEQUENCE: 429
uucauuauca agccagcauu uggguag 27

<210> SEQ ID NO 430
<211> LENGTH: 27
<212> TYPE: RNA
<213> ORGANISM: Artificial Sequence
<220> FEATURE:
<223> OTHER INFORMATION: Synthetic

<400> SEQUENCE: 430
guucaugauc aagccagcau uugggua 27

<210> SEQ ID NO 431
<211> LENGTH: 27
<212> TYPE: RNA
<213> ORGANISM: Artificial Sequence
<220> FEATURE:
<223> OTHER INFORMATION: Synthetic

<400> SEQUENCE: 431
agcauuugga uuccugcagu aguucau 27

<210> SEQ ID NO 432
<211> LENGTH: 27
<212> TYPE: RNA
<213> ORGANISM: Artificial Sequence
<220> FEATURE:
<223> OTHER INFORMATION: Synthetic

<400> SEQUENCE: 432
ccacaucauc uggauuccug caguagu 27

<210> SEQ ID NO 433
<211> LENGTH: 27
<212> TYPE: RNA
<213> ORGANISM: Artificial Sequence
<220> FEATURE:
<223> OTHER INFORMATION: Synthetic

<400> SEQUENCE: 433
gccacugcau cuggauuccu gcaguag 27

<210> SEQ ID NO 434
<211> LENGTH: 27
<212> TYPE: RNA
<213> ORGANISM: Artificial Sequence
<220> FEATURE:
<223> OTHER INFORMATION: Synthetic

<400> SEQUENCE: 434
cugccucagc aucuggauuc cugcagu 27

<210> SEQ ID NO 435
<211> LENGTH: 27
<212> TYPE: RNA
<213> ORGANISM: Artificial Sequence
<220> FEATURE:
<223> OTHER INFORMATION: Synthetic

<400> SEQUENCE: 435
gcgucugguu gcaguacucc caccuga 27

<210> SEQ ID NO 436
<211> LENGTH: 27
<212> TYPE: RNA
<213> ORGANISM: Artificial Sequence
<220> FEATURE:
<223> OTHER INFORMATION: Synthetic

<400> SEQUENCE: 436
gcaguuccuu cugcgucuga gcauugc 27

<210> SEQ ID NO 437
<211> LENGTH: 27
<212> TYPE: RNA
<213> ORGANISM: Artificial Sequence
<220> FEATURE:
<223> OTHER INFORMATION: Synthetic

<400> SEQUENCE: 437
uaggcuugga accggguaa cagucgg 27

<210> SEQ ID NO 438
<211> LENGTH: 27
<212> TYPE: RNA
<213> ORGANISM: Artificial Sequence
<220> FEATURE:
<223> OTHER INFORMATION: Synthetic

<400> SEQUENCE: 438
cuagguuugg aaccggggua acagucg 27

<210> SEQ ID NO 439
<211> LENGTH: 27
<212> TYPE: RNA
<213> ORGANISM: Artificial Sequence
<220> FEATURE:
<223> OTHER INFORMATION: Synthetic

<400> SEQUENCE: 439
ucuagucuug gaaccggggu aacaguc 27

<210> SEQ ID NO 440
<211> LENGTH: 27
<212> TYPE: RNA
<213> ORGANISM: Artificial Sequence
<220> FEATURE:
<223> OTHER INFORMATION: Synthetic

<400> SEQUENCE: 440
cucuaugcuu ggaaccgggg uaacagu 27

<210> SEQ ID NO 441
<211> LENGTH: 27
<212> TYPE: RNA
<213> ORGANISM: Artificial Sequence
<220> FEATURE:
<223> OTHER INFORMATION: Synthetic

<400> SEQUENCE: 441
ccucuuggcu uggaaccggg guaacag 27

<210> SEQ ID NO 442
<211> LENGTH: 27
<212> TYPE: RNA
<213> ORGANISM: Artificial Sequence
<220> FEATURE:
<223> OTHER INFORMATION: Synthetic

<400> SEQUENCE: 442
gccucuaggc uuggaaccgg gguaaca 27

<210> SEQ ID NO 443
<211> LENGTH: 27
<212> TYPE: RNA
<213> ORGANISM: Artificial Sequence
<220> FEATURE:
<223> OTHER INFORMATION: Synthetic

<400> SEQUENCE: 443
agccuuuagg cuuggaaccg ggguaac 27

<210> SEQ ID NO 444
<211> LENGTH: 27
<212> TYPE: RNA
<213> ORGANISM: Artificial Sequence
<220> FEATURE:
<223> OTHER INFORMATION: Synthetic

<400> SEQUENCE: 444
acucuuucca uuaccauggu agcacuc 27

<210> SEQ ID NO 445

<211> LENGTH: 27
<212> TYPE: RNA
<213> ORGANISM: Artificial Sequence
<220> FEATURE:
<223> OTHER INFORMATION: Synthetic

<400> SEQUENCE: 445
aacucugucc auuaccaugg uagcacu 27

<210> SEQ ID NO 446
<211> LENGTH: 27
<212> TYPE: RNA
<213> ORGANISM: Artificial Sequence
<220> FEATURE:
<223> OTHER INFORMATION: Synthetic

<400> SEQUENCE: 446
uaacuuuguc cauuaccaug guagcac 27

<210> SEQ ID NO 447
<211> LENGTH: 27
<212> TYPE: RNA
<213> ORGANISM: Artificial Sequence
<220> FEATURE:
<223> OTHER INFORMATION: Synthetic

<400> SEQUENCE: 447
auaacucugu ccauuaccau gguagca 27

<210> SEQ ID NO 448
<211> LENGTH: 27
<212> TYPE: RNA
<213> ORGANISM: Artificial Sequence
<220> FEATURE:
<223> OTHER INFORMATION: Synthetic

<400> SEQUENCE: 448
gauaauucug uccauuacca ugguagc 27

<210> SEQ ID NO 449
<211> LENGTH: 27
<212> TYPE: RNA
<213> ORGANISM: Artificial Sequence
<220> FEATURE:
<223> OTHER INFORMATION: Synthetic

<400> SEQUENCE: 449
cgauaucucu guccauuacc augguag 27

<210> SEQ ID NO 450
<211> LENGTH: 27
<212> TYPE: RNA
<213> ORGANISM: Artificial Sequence
<220> FEATURE:
<223> OTHER INFORMATION: Synthetic

<400> SEQUENCE: 450
ucgauuacuc uguccauuac cauggua 27

<210> SEQ ID NO 451
<211> LENGTH: 27
<212> TYPE: RNA
<213> ORGANISM: Artificial Sequence
<220> FEATURE:
<223> OTHER INFORMATION: Synthetic

<400> SEQUENCE: 451
cucgauaacu cuguccauua ccauggu 27

<210> SEQ ID NO 452
<211> LENGTH: 27
<212> TYPE: RNA
<213> ORGANISM: Artificial Sequence
<220> FEATURE:
<223> OTHER INFORMATION: Synthetic

<400> SEQUENCE: 452
ccucguuaac ucuguccauu accaugg 27

<210> SEQ ID NO 453
<211> LENGTH: 27
<212> TYPE: RNA
<213> ORGANISM: Artificial Sequence
<220> FEATURE:
<223> OTHER INFORMATION: Synthetic

<400> SEQUENCE: 453
gccucuauaa cucuguccau uaccaug 27

<210> SEQ ID NO 454
<211> LENGTH: 27
<212> TYPE: RNA
<213> ORGANISM: Artificial Sequence
<220> FEATURE:
<223> OTHER INFORMATION: Synthetic

<400> SEQUENCE: 454
ugccuugaua acucugucca uuaccau 27

<210> SEQ ID NO 455
<211> LENGTH: 27
<212> TYPE: RNA
<213> ORGANISM: Artificial Sequence
<220> FEATURE:
<223> OTHER INFORMATION: Synthetic

<400> SEQUENCE: 455
gugccucgau aacucugucc auuacca 27

<210> SEQ ID NO 456
<211> LENGTH: 27
<212> TYPE: RNA
<213> ORGANISM: Artificial Sequence
<220> FEATURE:
<223> OTHER INFORMATION: Synthetic

<400> SEQUENCE: 456
cugugucagu gguggaguau gugccuc 27

<210> SEQ ID NO 457
<211> LENGTH: 27
<212> TYPE: RNA
<213> ORGANISM: Artificial Sequence
<220> FEATURE:
<223> OTHER INFORMATION: Synthetic

<400> SEQUENCE: 457 gagugguggug ucauagauga ccaagcu 27

<210> SEQ ID NO 458
<211> LENGTH: 27
<212> TYPE: RNA

<213> ORGANISM: Artificial Sequence
<220> FEATURE:
<223> OTHER INFORMATION: Synthetic

<400> SEQUENCE: 458
augcgugugu ggugucauag augacca 27

<210> SEQ ID NO 459
<211> LENGTH: 27
<212> TYPE: RNA
<213> ORGANISM: Artificial Sequence
<220> FEATURE:
<223> OTHER INFORMATION: Synthetic

<400> SEQUENCE: 459
uaugcuagug uggugucaua gaugacc 27

<210> SEQ ID NO 460
<211> LENGTH: 27
<212> TYPE: RNA
<213> ORGANISM: Artificial Sequence
<220> FEATURE:
<223> OTHER INFORMATION: Synthetic

<400> SEQUENCE: 460
cuaugugagu guggugucau agaugac 27

<210> SEQ ID NO 461
<211> LENGTH: 27
<212> TYPE: RNA
<213> ORGANISM: Artificial Sequence
<220> FEATURE:
<223> OTHER INFORMATION: Synthetic

<400> SEQUENCE: 461
ccaguuacag ugguggagua ugugccu 27

<210> SEQ ID NO 462
<211> LENGTH: 27
<212> TYPE: RNA
<213> ORGANISM: Artificial Sequence
<220> FEATURE:
<223> OTHER INFORMATION: Synthetic

<400> SEQUENCE: 462
aucccucgua uaacaauaag gggcugc 27

<210> SEQ ID NO 463
<211> LENGTH: 27
<212> TYPE: RNA
<213> ORGANISM: Artificial Sequence
<220> FEATURE:
<223> OTHER INFORMATION: Synthetic

<400> SEQUENCE: 463
gauccuucgu auaacaauaa ggggcug 27

<210> SEQ ID NO 464
<211> LENGTH: 27
<212> TYPE: RNA
<213> ORGANISM: Artificial Sequence
<220> FEATURE:
<223> OTHER INFORMATION: Synthetic

<400> SEQUENCE: 464
guucauaagg agccucuagg cuuggaa 27

<210> SEQ ID NO 465
<211> LENGTH: 27
<212> TYPE: RNA
<213> ORGANISM: Artificial Sequence
<220> FEATURE:
<223> OTHER INFORMATION: Synthetic

<400> SEQUENCE: 465
guuggugcuu guucagaagg agccucu 27

<210> SEQ ID NO 466
<211> LENGTH: 27
<212> TYPE: RNA
<213> ORGANISM: Artificial Sequence
<220> FEATURE:
<223> OTHER INFORMATION: Synthetic

<400> SEQUENCE: 466
uauguuccuu gauaacucug uccauuu 27

<210> SEQ ID NO 467
<211> LENGTH: 27
<212> TYPE: RNA
<213> ORGANISM: Artificial Sequence
<220> FEATURE:
<223> OTHER INFORMATION: Synthetic

<400> SEQUENCE: 467
guaugugccu ugauaacucu guccauu 27

<210> SEQ ID NO 468
<211> LENGTH: 27
<212> TYPE: RNA
<213> ORGANISM: Artificial Sequence
<220> FEATURE:
<223> OTHER INFORMATION: Synthetic

<400> SEQUENCE: 468
aguauuugcc uugauaacuc uguccau 27

<210> SEQ ID NO 469
<211> LENGTH: 27
<212> TYPE: RNA
<213> ORGANISM: Artificial Sequence
<220> FEATURE:
<223> OTHER INFORMATION: Synthetic

<400> SEQUENCE: 469
aaguaugugc cuugauaacu cugucca 27

<210> SEQ ID NO 470
<211> LENGTH: 27
<212> TYPE: RNA
<213> ORGANISM: Artificial Sequence
<220> FEATURE:
<223> OTHER INFORMATION: Synthetic

<400> SEQUENCE: 470
gaaguuugug ccuugauaac ucugucc 27

<210> SEQ ID NO 471
<211> LENGTH: 27
<212> TYPE: RNA
<213> ORGANISM: Artificial Sequence
<220> FEATURE:

-continued

<223> OTHER INFORMATION: Synthetic

<400> SEQUENCE: 471
ugaaguaugu gccuugauaa cucuguc 27

<210> SEQ ID NO 472
<211> LENGTH: 27
<212> TYPE: RNA
<213> ORGANISM: Artificial Sequence
<220> FEATURE:
<223> OTHER INFORMATION: Synthetic

<400> SEQUENCE: 472
ucuuguucaa gccagcauuu ggguagu 27

<210> SEQ ID NO 473
<211> LENGTH: 27
<212> TYPE: RNA
<213> ORGANISM: Artificial Sequence
<220> FEATURE:
<223> OTHER INFORMATION: Synthetic

<400> SEQUENCE: 473
aguucuugau caagccagca uuugggu 27

<210> SEQ ID NO 474
<211> LENGTH: 27
<212> TYPE: RNA
<213> ORGANISM: Artificial Sequence
<220> FEATURE:
<223> OTHER INFORMATION: Synthetic

<400> SEQUENCE: 474
ucugguuuuc ggcaguaguu cuugauc 27

<210> SEQ ID NO 475
<211> LENGTH: 27
<212> TYPE: RNA
<213> ORGANISM: Artificial Sequence
<220> FEATURE:
<223> OTHER INFORMATION: Synthetic

<400> SEQUENCE: 475
aucuguauuu cggcaguagu ucuugau 27

<210> SEQ ID NO 476
<211> LENGTH: 27
<212> TYPE: RNA
<213> ORGANISM: Artificial Sequence
<220> FEATURE:
<223> OTHER INFORMATION: Synthetic

<400> SEQUENCE: 476
gaucuugauu ucggcaguag uucuuga 27

<210> SEQ ID NO 477
<211> LENGTH: 27
<212> TYPE: RNA
<213> ORGANISM: Artificial Sequence
<220> FEATURE:
<223> OTHER INFORMATION: Synthetic

<400> SEQUENCE: 477
aggauuugga uuucggcagu aguucuu 27

<210> SEQ ID NO 478
<211> LENGTH: 27
<212> TYPE: RNA
<213> ORGANISM: Artificial Sequence
<220> FEATURE:
<223> OTHER INFORMATION: Synthetic

<400> SEQUENCE: 478
cacaguaucu ggauuucggc aguaguu 27

<210> SEQ ID NO 479
<211> LENGTH: 27
<212> TYPE: RNA
<213> ORGANISM: Artificial Sequence
<220> FEATURE:
<223> OTHER INFORMATION: Synthetic

<400> SEQUENCE: 479
uguauuacac caaggggcug ccacagg 27

<210> SEQ ID NO 480
<211> LENGTH: 27
<212> TYPE: RNA
<213> ORGANISM: Artificial Sequence
<220> FEATURE:
<223> OTHER INFORMATION: Synthetic

<400> SEQUENCE: 480
uuguauaaca ccaaggggcu gccacag 27

<210> SEQ ID NO 481
<211> LENGTH: 27
<212> TYPE: RNA
<213> ORGANISM: Artificial Sequence
<220> FEATURE:
<223> OTHER INFORMATION: Synthetic

<400> SEQUENCE: 481
guuguuuaac accaaggggc ugccaca 27

<210> SEQ ID NO 482
<211> LENGTH: 27
<212> TYPE: RNA
<213> ORGANISM: Artificial Sequence
<220> FEATURE:
<223> OTHER INFORMATION: Synthetic

<400> SEQUENCE: 482
uguuguauaa caccaagggg cugccac 27

<210> SEQ ID NO 483
<211> LENGTH: 27
<212> TYPE: RNA
<213> ORGANISM: Artificial Sequence
<220> FEATURE:
<223> OTHER INFORMATION: Synthetic

<400> SEQUENCE: 483
cuguuuuaua acaccaaggg gcugcca 27

<210> SEQ ID NO 484
<211> LENGTH: 27
<212> TYPE: RNA
<213> ORGANISM: Artificial Sequence
<220> FEATURE:
<223> OTHER INFORMATION: Synthetic

<400> SEQUENCE: 484
ucuguuguau aacaccaagg ggcugcc 27

<210> SEQ ID NO 485
<211> LENGTH: 27
<212> TYPE: RNA
<213> ORGANISM: Artificial Sequence
<220> FEATURE:
<223> OTHER INFORMATION: Synthetic

<400> SEQUENCE: 485
aucuguugua uaacaccaag gggcugc 27

<210> SEQ ID NO 486
<211> LENGTH: 27
<212> TYPE: RNA
<213> ORGANISM: Artificial Sequence
<220> FEATURE:
<223> OTHER INFORMATION: Synthetic

<400> SEQUENCE: 486
gaucuuuugu auaacaccaa ggggcug 27

<210> SEQ ID NO 487
<211> LENGTH: 27
<212> TYPE: RNA
<213> ORGANISM: Artificial Sequence
<220> FEATURE:
<223> OTHER INFORMATION: Synthetic

<400> SEQUENCE: 487
ggaucuguug uauaacacca aggggcu 27

<210> SEQ ID NO 488
<211> LENGTH: 27
<212> TYPE: RNA
<213> ORGANISM: Artificial Sequence
<220> FEATURE:
<223> OTHER INFORMATION: Synthetic

<400> SEQUENCE: 488
cguguuaggu ugcaguacuc ccaccug 27

<210> SEQ ID NO 489
<211> LENGTH: 27
<212> TYPE: RNA
<213> ORGANISM: Artificial Sequence
<220> FEATURE:
<223> OTHER INFORMATION: Synthetic

<400> SEQUENCE: 489
ucgugucagg uugcaguacu cccaccu 27

<210> SEQ ID NO 490
<211> LENGTH: 27
<212> TYPE: RNA
<213> ORGANISM: Artificial Sequence
<220> FEATURE:
<223> OTHER INFORMATION: Synthetic

<400> SEQUENCE: 490
gcaucuuguc agguugcagu acuccca 27

<210> SEQ ID NO 491
<211> LENGTH: 27

<212> TYPE: RNA
<213> ORGANISM: Artificial Sequence
<220> FEATURE:
<223> OTHER INFORMATION: Synthetic

<400> SEQUENCE: 491
agcauugugu cagguugcag uacuccc 27

<210> SEQ ID NO 492
<211> LENGTH: 27
<212> TYPE: RNA
<213> ORGANISM: Artificial Sequence
<220> FEATURE:
<223> OTHER INFORMATION: Synthetic

<400> SEQUENCE: 492
ugagcuucgu gucagguugc aguacuc 27

<210> SEQ ID NO 493
<211> LENGTH: 27
<212> TYPE: RNA
<213> ORGANISM: Artificial Sequence
<220> FEATURE:
<223> OTHER INFORMATION: Synthetic

<400> SEQUENCE: 493
cugaguaucg ugucagguug caguacu 27

<210> SEQ ID NO 494
<211> LENGTH: 27
<212> TYPE: RNA
<213> ORGANISM: Artificial Sequence
<220> FEATURE:
<223> OTHER INFORMATION: Synthetic

<400> SEQUENCE: 494
ucugaucauc gugucagguu gcaguac 27

<210> SEQ ID NO 495
<211> LENGTH: 27
<212> TYPE: RNA
<213> ORGANISM: Artificial Sequence
<220> FEATURE:
<223> OTHER INFORMATION: Synthetic

<400> SEQUENCE: 495
aucugugcau cgugucaggu ugcagua 27

<210> SEQ ID NO 496
<211> LENGTH: 27
<212> TYPE: RNA
<213> ORGANISM: Artificial Sequence
<220> FEATURE:
<223> OTHER INFORMATION: Synthetic

<400> SEQUENCE: 496
caucuuagca ucgugucagg uugcagu 27

<210> SEQ ID NO 497
<211> LENGTH: 27
<212> TYPE: RNA
<213> ORGANISM: Artificial Sequence
<220> FEATURE:
<223> OTHER INFORMATION: Synthetic

<400> SEQUENCE: 497
ugcauuugag caucguguca gguugca 27

<210> SEQ ID NO 498
<211> LENGTH: 27
<212> TYPE: RNA
<213> ORGANISM: Artificial Sequence
<220> FEATURE:
<223> OTHER INFORMATION: Synthetic

<400> SEQUENCE: 498
ucugcuucug agcaucgugu cagguug 27

<210> SEQ ID NO 499
<211> LENGTH: 27
<212> TYPE: RNA
<213> ORGANISM: Artificial Sequence
<220> FEATURE:
<223> OTHER INFORMATION: Synthetic

<400> SEQUENCE: 499
uucuguaucu gagcaucgug ucagguu 27

<210> SEQ ID NO 500
<211> LENGTH: 27
<212> TYPE: RNA
<213> ORGANISM: Artificial Sequence
<220> FEATURE:
<223> OTHER INFORMATION: Synthetic

<400> SEQUENCE: 500
auucuucauc ugagcaucgu gucaggu 27

<210> SEQ ID NO 501
<211> LENGTH: 27
<212> TYPE: RNA
<213> ORGANISM: Artificial Sequence
<220> FEATURE:
<223> OTHER INFORMATION: Synthetic

<400> SEQUENCE: 501
cauucugcau cugagcaucg ugucagg 27

<210> SEQ ID NO 502
<211> LENGTH: 27
<212> TYPE: RNA
<213> ORGANISM: Artificial Sequence
<220> FEATURE:
<223> OTHER INFORMATION: Synthetic

<400> SEQUENCE: 502
ccauuuugca ucugagcauc gugucag 27

<210> SEQ ID NO 503
<211> LENGTH: 27
<212> TYPE: RNA
<213> ORGANISM: Artificial Sequence
<220> FEATURE:
<223> OTHER INFORMATION: Synthetic

<400> SEQUENCE: 503
uccauucugc aucugagcau cguguca 27

<210> SEQ ID NO 504
<211> LENGTH: 27
<212> TYPE: RNA
<213> ORGANISM: Artificial Sequence
<220> FEATURE:
<223> OTHER INFORMATION: Synthetic

<400> SEQUENCE: 504
guccauucug caucugagca ucguguc 27

<210> SEQ ID NO 505
<211> LENGTH: 27
<212> TYPE: RNA
<213> ORGANISM: Artificial Sequence
<220> FEATURE:
<223> OTHER INFORMATION: Synthetic

<400> SEQUENCE: 505
aacucugucc auaaugguag uagcagu 27

<210> SEQ ID NO 506
<211> LENGTH: 27
<212> TYPE: RNA
<213> ORGANISM: Artificial Sequence
<220> FEATURE:
<223> OTHER INFORMATION: Synthetic

<400> SEQUENCE: 506
uaacuuuguc cauaauggua guagcag 27

<210> SEQ ID NO 507
<211> LENGTH: 27
<212> TYPE: RNA
<213> ORGANISM: Artificial Sequence
<220> FEATURE:
<223> OTHER INFORMATION: Synthetic

<400> SEQUENCE: 507
guaacucugu ccauaauggu aguagca 27

<210> SEQ ID NO 508
<211> LENGTH: 27
<212> TYPE: RNA
<213> ORGANISM: Artificial Sequence
<220> FEATURE:
<223> OTHER INFORMATION: Synthetic

<400> SEQUENCE: 508
gguaauucug uccauaaugg uaguagc 27

<210> SEQ ID NO 509
<211> LENGTH: 27
<212> TYPE: RNA
<213> ORGANISM: Artificial Sequence
<220> FEATURE:
<223> OTHER INFORMATION: Synthetic

<400> SEQUENCE: 509
cgguaucucu guccauaaug guaguag 27

<210> SEQ ID NO 510
<211> LENGTH: 27
<212> TYPE: RNA
<213> ORGANISM: Artificial Sequence
<220> FEATURE:
<223> OTHER INFORMATION: Synthetic

<400> SEQUENCE: 510
ucgguuacuc uguccauaau gguagua 27

<210> SEQ ID NO 511
<211> LENGTH: 27
<212> TYPE: RNA
<213> ORGANISM: Artificial Sequence
<220> FEATURE:
<223> OTHER INFORMATION: Synthetic

<400> SEQUENCE: 511
cucgguaacu cuguccauaa ugguagu 27

<210> SEQ ID NO 512
<211> LENGTH: 27
<212> TYPE: RNA
<213> ORGANISM: Artificial Sequence
<220> FEATURE:
<223> OTHER INFORMATION: Synthetic

<400> SEQUENCE: 512
ccucguuaac ucuguccaua augguag 27

<210> SEQ ID NO 513
<211> LENGTH: 27
<212> TYPE: RNA
<213> ORGANISM: Artificial Sequence
<220> FEATURE:
<223> OTHER INFORMATION: Synthetic

<400> SEQUENCE: 513
gugacugugg uggaguaugu gccucgg 27

<210> SEQ ID NO 514
<211> LENGTH: 27
<212> TYPE: RNA
<213> ORGANISM: Artificial Sequence
<220> FEATURE:
<223> OTHER INFORMATION: Synthetic

<400> SEQUENCE: 514
aguucuuccu gugacagugg uggagua 27

<210> SEQ ID NO 515
<211> LENGTH: 27
<212> TYPE: RNA
<213> ORGANISM: Artificial Sequence
<220> FEATURE:
<223> OTHER INFORMATION: Synthetic

<400> SEQUENCE: 515
accaaucuug gcaaguucuu ccuguga 27

<210> SEQ ID NO 516
<211> LENGTH: 27
<212> TYPE: RNA
<213> ORGANISM: Artificial Sequence
<220> FEATURE:
<223> OTHER INFORMATION: Synthetic

<400> SEQUENCE: 516
gaccaugcuu ggcaaguucu uccugug 27

<210> SEQ ID NO 517
<211> LENGTH: 27
<212> TYPE: RNA
<213> ORGANISM: Artificial Sequence
<220> FEATURE:
<223> OTHER INFORMATION: Synthetic

<400> SEQUENCE: 517
ugaccuagcu uggcaaguuc uuccugu 27

<210> SEQ ID NO 518
<211> LENGTH: 27
<212> TYPE: RNA
<213> ORGANISM: Artificial Sequence
<220> FEATURE:
<223> OTHER INFORMATION: Synthetic

<400> SEQUENCE: 518
augacuaagc uuggcaaguu cuuccug 27

<210> SEQ ID NO 519
<211> LENGTH: 27
<212> TYPE: RNA
<213> ORGANISM: Artificial Sequence
<220> FEATURE:
<223> OTHER INFORMATION: Synthetic

<400> SEQUENCE: 519
gaugaucaag cuuggcaagu ucuuccu 27

<210> SEQ ID NO 520
<211> LENGTH: 27
<212> TYPE: RNA
<213> ORGANISM: Artificial Sequence
<220> FEATURE:
<223> OTHER INFORMATION: Synthetic

<400> SEQUENCE: 520
agauguccaa gcuuggcaag uucuucc 27

<210> SEQ ID NO 521
<211> LENGTH: 27
<212> TYPE: RNA
<213> ORGANISM: Artificial Sequence
<220> FEATURE:
<223> OTHER INFORMATION: Synthetic

<400> SEQUENCE: 521
uagauuacca agcuuggcaa guucuuc 27

<210> SEQ ID NO 522
<211> LENGTH: 27
<212> TYPE: RNA
<213> ORGANISM: Artificial Sequence
<220> FEATURE:
<223> OTHER INFORMATION: Synthetic

<400> SEQUENCE: 522
auagaugacc aagcuuggca aguucuu 27

<210> SEQ ID NO 523
<211> LENGTH: 27
<212> TYPE: RNA
<213> ORGANISM: Artificial Sequence
<220> FEATURE:
<223> OTHER INFORMATION: Synthetic

<400> SEQUENCE: 523
cauaguugac caagcuuggc aaguucu 27

<210> SEQ ID NO 524

<211> LENGTH: 27
<212> TYPE: RNA
<213> ORGANISM: Artificial Sequence
<220> FEATURE:
<223> OTHER INFORMATION: Synthetic

<400> SEQUENCE: 524
ucauauauga ccaagcuugg caaguuc 27

<210> SEQ ID NO 525
<211> LENGTH: 27
<212> TYPE: RNA
<213> ORGANISM: Artificial Sequence
<220> FEATURE:
<223> OTHER INFORMATION: Synthetic

<400> SEQUENCE: 525
gucauugaug accaagcuug gcaaguu 27

<210> SEQ ID NO 526
<211> LENGTH: 27
<212> TYPE: RNA
<213> ORGANISM: Artificial Sequence
<220> FEATURE:
<223> OTHER INFORMATION: Synthetic

<400> SEQUENCE: 526
ugucauagau gaccaagcuu ggcaagu 27

<210> SEQ ID NO 527
<211> LENGTH: 27
<212> TYPE: RNA
<213> ORGANISM: Artificial Sequence
<220> FEATURE:
<223> OTHER INFORMATION: Synthetic

<400> SEQUENCE: 527
gugucuuaga ugaccaagcu uggcaag 27

<210> SEQ ID NO 528
<211> LENGTH: 27
<212> TYPE: RNA
<213> ORGANISM: Artificial Sequence
<220> FEATURE:
<223> OTHER INFORMATION: Synthetic

<400> SEQUENCE: 528
gguguugugu cauagaugac caagcuu 27

<210> SEQ ID NO 529
<211> LENGTH: 27
<212> TYPE: RNA
<213> ORGANISM: Artificial Sequence
<220> FEATURE:
<223> OTHER INFORMATION: Synthetic

<400> SEQUENCE: 529
cugguuuggu gucauagaug accaagc 27

<210> SEQ ID NO 530
<211> LENGTH: 27
<212> TYPE: RNA
<213> ORGANISM: Artificial Sequence
<220> FEATURE:
<223> OTHER INFORMATION: Synthetic

<400> SEQUENCE: 530
gcuggugugg ugucauagau gaccaag 27

<210> SEQ ID NO 531
<211> LENGTH: 27
<212> TYPE: RNA
<213> ORGANISM: Artificial Sequence
<220> FEATURE:
<223> OTHER INFORMATION: Synthetic

<400> SEQUENCE: 531
augcuugugu ggugucauag augacca 27

<210> SEQ ID NO 532
<211> LENGTH: 27
<212> TYPE: RNA
<213> ORGANISM: Artificial Sequence
<220> FEATURE:
<223> OTHER INFORMATION: Synthetic

<400> SEQUENCE: 532
cuauguuggu guggugucau agaugac 27

<210> SEQ ID NO 533
<211> LENGTH: 27
<212> TYPE: RNA
<213> ORGANISM: Artificial Sequence
<220> FEATURE:
<223> OTHER INFORMATION: Synthetic

<400> SEQUENCE: 533
acuauucugg ugugguguca uagauga 27

<210> SEQ ID NO 534
<211> LENGTH: 27
<212> TYPE: RNA
<213> ORGANISM: Artificial Sequence
<220> FEATURE:
<223> OTHER INFORMATION: Synthetic

<400> SEQUENCE: 534
cgacuuugcu gguguggugu cauagau 27

<210> SEQ ID NO 535
<211> LENGTH: 27
<212> TYPE: RNA
<213> ORGANISM: Artificial Sequence
<220> FEATURE:
<223> OTHER INFORMATION: Synthetic

<400> SEQUENCE: 535
uuugguuagu uuucuggggu ccgacua 27

<210> SEQ ID NO 536
<211> LENGTH: 27
<212> TYPE: RNA
<213> ORGANISM: Artificial Sequence
<220> FEATURE:
<223> OTHER INFORMATION: Synthetic

<400> SEQUENCE: 536
auuuguguag uuuucugggg uccgacu 27

<210> SEQ ID NO 537
<211> LENGTH: 27
<212> TYPE: RNA

<213> ORGANISM: Artificial Sequence
<220> FEATURE:
<223> OTHER INFORMATION: Synthetic

<400> SEQUENCE: 537
ucaggucagc auuuggguag uuuucug 27

<210> SEQ ID NO 538
<211> LENGTH: 27
<212> TYPE: RNA
<213> ORGANISM: Artificial Sequence
<220> FEATURE:
<223> OTHER INFORMATION: Synthetic

<400> SEQUENCE: 538
uguaauacca agggcgaauc ucagcau 27

<210> SEQ ID NO 539
<211> LENGTH: 27
<212> TYPE: RNA
<213> ORGANISM: Artificial Sequence
<220> FEATURE:
<223> OTHER INFORMATION: Synthetic

<400> SEQUENCE: 539
guguaucacc aagggcgaau cucagca 27

<210> SEQ ID NO 540
<211> LENGTH: 27
<212> TYPE: RNA
<213> ORGANISM: Artificial Sequence
<220> FEATURE:
<223> OTHER INFORMATION: Synthetic

<400> SEQUENCE: 540
ugguguaaca ccaagggcga aucucag 27

<210> SEQ ID NO 541
<211> LENGTH: 27
<212> TYPE: RNA
<213> ORGANISM: Artificial Sequence
<220> FEATURE:
<223> OTHER INFORMATION: Synthetic

<400> SEQUENCE: 541
augguuuaac accaagggcg aaucuca 27

<210> SEQ ID NO 542
<211> LENGTH: 27
<212> TYPE: RNA
<213> ORGANISM: Artificial Sequence
<220> FEATURE:
<223> OTHER INFORMATION: Synthetic

<400> SEQUENCE: 542
uccauugugu aacaccaagg gcgaauc 27

<210> SEQ ID NO 543
<211> LENGTH: 27
<212> TYPE: RNA
<213> ORGANISM: Artificial Sequence
<220> FEATURE:
<223> OTHER INFORMATION: Synthetic

<400> SEQUENCE: 543
cuggguucca ugguguaaca ccaaggg 27

<210> SEQ ID NO 544
<211> LENGTH: 27
<212> TYPE: RNA
<213> ORGANISM: Artificial Sequence
<220> FEATURE:
<223> OTHER INFORMATION: Synthetic

<400> SEQUENCE: 544
acugguaucc augguguaac accaagg 27

<210> SEQ ID NO 545
<211> LENGTH: 27
<212> TYPE: RNA
<213> ORGANISM: Artificial Sequence
<220> FEATURE:
<223> OTHER INFORMATION: Synthetic

<400> SEQUENCE: 545
cacugugauc caugguguaa caccaag 27

<210> SEQ ID NO 546
<211> LENGTH: 27
<212> TYPE: RNA
<213> ORGANISM: Artificial Sequence
<220> FEATURE:
<223> OTHER INFORMATION: Synthetic

<400> SEQUENCE: 546
acacuuggau ccauggugua acaccaa 27

<210> SEQ ID NO 547
<211> LENGTH: 27
<212> TYPE: RNA
<213> ORGANISM: Artificial Sequence
<220> FEATURE:
<223> OTHER INFORMATION: Synthetic

<400> SEQUENCE: 547
ugacauuggg auccauggug uaacacc 27

<210> SEQ ID NO 548
<211> LENGTH: 27
<212> TYPE: RNA
<213> ORGANISM: Artificial Sequence
<220> FEATURE:
<223> OTHER INFORMATION: Synthetic

<400> SEQUENCE: 548
ugagauuugc aaggacacuu gauucug 27

<210> SEQ ID NO 549
<211> LENGTH: 27
<212> TYPE: RNA
<213> ORGANISM: Artificial Sequence
<220> FEATURE:
<223> OTHER INFORMATION: Synthetic

<400> SEQUENCE: 549
gugaguguug caaggacacu ugauucu 27

<210> SEQ ID NO 550
<211> LENGTH: 27
<212> TYPE: RNA
<213> ORGANISM: Artificial Sequence
<220> FEATURE:

<223> OTHER INFORMATION: Synthetic

<400> SEQUENCE: 550
cgugauaguu gcaaggacac uugauuc 27

<210> SEQ ID NO 551
<211> LENGTH: 27
<212> TYPE: RNA
<213> ORGANISM: Artificial Sequence
<220> FEATURE:
<223> OTHER INFORMATION: Synthetic

<400> SEQUENCE: 551
aaugauccuc gauaacucug uccauca 27

<210> SEQ ID NO 552
<211> LENGTH: 27
<212> TYPE: RNA
<213> ORGANISM: Artificial Sequence
<220> FEATURE:
<223> OTHER INFORMATION: Synthetic

<400> SEQUENCE: 552
gaaugugccu cgauaacucu guccauc 27

<210> SEQ ID NO 553
<211> LENGTH: 27
<212> TYPE: RNA
<213> ORGANISM: Artificial Sequence
<220> FEATURE:
<223> OTHER INFORMATION: Synthetic

<400> SEQUENCE: 553
uugucuucug augccagugu ggguguca 27

<210> SEQ ID NO 554
<211> LENGTH: 27
<212> TYPE: RNA
<213> ORGANISM: Artificial Sequence
<220> FEATURE:
<223> OTHER INFORMATION: Synthetic

<400> SEQUENCE: 554
auugguaucc augguauaac accaagg 27

<210> SEQ ID NO 555
<211> LENGTH: 27
<212> TYPE: RNA
<213> ORGANISM: Artificial Sequence
<220> FEATURE:
<223> OTHER INFORMATION: Synthetic

<400> SEQUENCE: 555
cauugugauc caugguauaa caccaag 27

<210> SEQ ID NO 556
<211> LENGTH: 27
<212> TYPE: RNA
<213> ORGANISM: Artificial Sequence
<220> FEATURE:
<223> OTHER INFORMATION: Synthetic

<400> SEQUENCE: 556
acauuuggau ccaugguaua acaccaa 27

<210> SEQ ID NO 557
<211> LENGTH: 27
<212> TYPE: RNA
<213> ORGANISM: Artificial Sequence
<220> FEATURE:
<223> OTHER INFORMATION: Synthetic

<400> SEQUENCE: 557
gacauuggga uccaugguau aacacca 27

<210> SEQ ID NO 558
<211> LENGTH: 27
<212> TYPE: RNA
<213> ORGANISM: Artificial Sequence
<220> FEATURE:
<223> OTHER INFORMATION: Synthetic

<400> SEQUENCE: 558
gucaguuugc aguacuccca ucugaca 27

<210> SEQ ID NO 559
<211> LENGTH: 27
<212> TYPE: RNA
<213> ORGANISM: Artificial Sequence
<220> FEATURE:
<223> OTHER INFORMATION: Synthetic

<400> SEQUENCE: 559
uguguuaggu ugcaguacuc ccaucug 27

<210> SEQ ID NO 560
<211> LENGTH: 27
<212> TYPE: RNA
<213> ORGANISM: Artificial Sequence
<220> FEATURE:
<223> OTHER INFORMATION: Synthetic

<400> SEQUENCE: 560
uugugucagg uugcaguacu cccaucu 27

<210> SEQ ID NO 561
<211> LENGTH: 27
<212> TYPE: RNA
<213> ORGANISM: Artificial Sequence
<220> FEATURE:
<223> OTHER INFORMATION: Synthetic

<400> SEQUENCE: 561
auuguuucag guugcaguac ucccauc 27

<210> SEQ ID NO 562
<211> LENGTH: 27
<212> TYPE: RNA
<213> ORGANISM: Artificial Sequence
<220> FEATURE:
<223> OTHER INFORMATION: Synthetic

<400> SEQUENCE: 562
cauuguguca gguugcagua cucccau 27

<210> SEQ ID NO 563
<211> LENGTH: 27
<212> TYPE: RNA
<213> ORGANISM: Artificial Sequence
<220> FEATURE:
<223> OTHER INFORMATION: Synthetic

<400> SEQUENCE: 563
cguuguugcu uguucagaaa cagccgu 27

<210> SEQ ID NO 564
<211> LENGTH: 27
<212> TYPE: RNA
<213> ORGANISM: Artificial Sequence
<220> FEATURE:
<223> OTHER INFORMATION: Synthetic

<400> SEQUENCE: 564
gcuccuuugg ugcuuguuca gaaacag 27

<210> SEQ ID NO 565
<211> LENGTH: 27
<212> TYPE: RNA
<213> ORGANISM: Artificial Sequence
<220> FEATURE:
<223> OTHER INFORMATION: Synthetic

<400> SEQUENCE: 565
uguccuuccu guaacagugg uggagaa 27

<210> SEQ ID NO 566
<211> LENGTH: 27
<212> TYPE: RNA
<213> ORGANISM: Artificial Sequence
<220> FEATURE:
<223> OTHER INFORMATION: Synthetic

<400> SEQUENCE: 566
augucuuucc uguaacagug guggaga 27

<210> SEQ ID NO 567
<211> LENGTH: 27
<212> TYPE: RNA
<213> ORGANISM: Artificial Sequence
<220> FEATURE:
<223> OTHER INFORMATION: Synthetic

<400> SEQUENCE: 567
cauguucuuc cuguaacagu gguggag 27

<210> SEQ ID NO 568
<211> LENGTH: 27
<212> TYPE: RNA
<213> ORGANISM: Artificial Sequence
<220> FEATURE:
<223> OTHER INFORMATION: Synthetic

<400> SEQUENCE: 568
gguucucuga ugccagugug gugucau 27

<210> SEQ ID NO 569
<211> LENGTH: 27
<212> TYPE: RNA
<213> ORGANISM: Artificial Sequence
<220> FEATURE:
<223> OTHER INFORMATION: Synthetic

<400> SEQUENCE: 569
ugguuuucug augccagugu gguguca 27

<210> SEQ ID NO 570
<211> LENGTH: 27

<212> TYPE: RNA
<213> ORGANISM: Artificial Sequence
<220> FEATURE:
<223> OTHER INFORMATION: Synthetic

<400> SEQUENCE: 570
caggcuacca uuuggguagu auucugu 27

<210> SEQ ID NO 571
<211> LENGTH: 27
<212> TYPE: RNA
<213> ORGANISM: Artificial Sequence
<220> FEATURE:
<223> OTHER INFORMATION: Synthetic

<400> SEQUENCE: 571
ucaggucacc auuuggguag uauucug 27

<210> SEQ ID NO 572
<211> LENGTH: 27
<212> TYPE: RNA
<213> ORGANISM: Artificial Sequence
<220> FEATURE:
<223> OTHER INFORMATION: Synthetic

<400> SEQUENCE: 572
gucaguccac cauuugggua guauucu 27

<210> SEQ ID NO 573
<211> LENGTH: 27
<212> TYPE: RNA
<213> ORGANISM: Artificial Sequence
<220> FEATURE:
<223> OTHER INFORMATION: Synthetic

<400> SEQUENCE: 573
uucaguuggu gcuucuucag aaggaag 27

<210> SEQ ID NO 574
<211> LENGTH: 27
<212> TYPE: RNA
<213> ORGANISM: Artificial Sequence
<220> FEATURE:
<223> OTHER INFORMATION: Synthetic

<400> SEQUENCE: 574
uuucauuugg ugcuucuuca gaaggaa 27

<210> SEQ ID NO 575
<211> LENGTH: 27
<212> TYPE: RNA
<213> ORGANISM: Artificial Sequence
<220> FEATURE:
<223> OTHER INFORMATION: Synthetic

<400> SEQUENCE: 575
uuuucuguug gugcuucuuc agaagga 27

<210> SEQ ID NO 576
<211> LENGTH: 27
<212> TYPE: RNA
<213> ORGANISM: Artificial Sequence
<220> FEATURE:
<223> OTHER INFORMATION: Synthetic

<400> SEQUENCE: 576
guuuuuaguu ggugcuucuu cagaagg 27

<210> SEQ ID NO 577
<211> LENGTH: 27
<212> TYPE: RNA
<213> ORGANISM: Artificial Sequence
<220> FEATURE:
<223> OTHER INFORMATION: Synthetic

<400> SEQUENCE: 577
uguuuucagu uggugcuucu ucagaag 27

<210> SEQ ID NO 578
<211> LENGTH: 27
<212> TYPE: RNA
<213> ORGANISM: Artificial Sequence
<220> FEATURE:
<223> OTHER INFORMATION: Synthetic

<400> SEQUENCE: 578
cuguuuucag uuggugcuuc uucagaa 27

<210> SEQ ID NO 579
<211> LENGTH: 27
<212> TYPE: RNA
<213> ORGANISM: Artificial Sequence
<220> FEATURE:
<223> OTHER INFORMATION: Synthetic

<400> SEQUENCE: 579
gcuguuuuca guuggugcuu cuucaga 27

<210> SEQ ID NO 580
<211> LENGTH: 27
<212> TYPE: RNA
<213> ORGANISM: Artificial Sequence
<220> FEATURE:
<223> OTHER INFORMATION: Synthetic

<400> SEQUENCE: 580
ugcuguuuuc aguuggugcu ucuucag 27

<210> SEQ ID NO 581
<211> LENGTH: 27
<212> TYPE: RNA
<213> ORGANISM: Artificial Sequence
<220> FEATURE:
<223> OTHER INFORMATION: Synthetic

<400> SEQUENCE: 581
gugcuuuuuu caguuggugc uucuuca 27

<210> SEQ ID NO 582
<211> LENGTH: 27
<212> TYPE: RNA
<213> ORGANISM: Artificial Sequence
<220> FEATURE:
<223> OTHER INFORMATION: Synthetic

<400> SEQUENCE: 582
agugcuguuu ucaguuggug cuucuuc 27

<210> SEQ ID NO 583
<211> LENGTH: 27
<212> TYPE: RNA
<213> ORGANISM: Artificial Sequence -continued
<220> FEATURE:
<223> OTHER INFORMATION: Synthetic

<400> SEQUENCE: 583
caguguuguu uucaguuggu gcuucuu 27

<210> SEQ ID NO 584
<211> LENGTH: 27
<212> TYPE: RNA
<213> ORGANISM: Artificial Sequence
<220> FEATURE:
<223> OTHER INFORMATION: Synthetic

<400> SEQUENCE: 584
ccaguucugu uuucaguugg ugcuucu 27

<210> SEQ ID NO 585
<211> LENGTH: 27
<212> TYPE: RNA
<213> ORGANISM: Artificial Sequence
<220> FEATURE:
<223> OTHER INFORMATION: Synthetic

<400> SEQUENCE: 585
gccucuauaa cucuguccau caccucg 27

<210> SEQ ID NO 586
<211> LENGTH: 27
<212> TYPE: RNA
<213> ORGANISM: Artificial Sequence
<220> FEATURE:
<223> OTHER INFORMATION: Synthetic

<400> SEQUENCE: 586
uguucuuccu gugauagugg uggagag 27

<210> SEQ ID NO 587
<211> LENGTH: 27
<212> TYPE: RNA
<213> ORGANISM: Artificial Sequence
<220> FEATURE:
<223> OTHER INFORMATION: Synthetic

<400> SEQUENCE: 587
auguuuuucc ugugauagug guggaga 27

<210> SEQ ID NO 588
<211> LENGTH: 27
<212> TYPE: RNA
<213> ORGANISM: Artificial Sequence
<220> FEATURE:
<223> OTHER INFORMATION: Synthetic

<400> SEQUENCE: 588
cauguucuuc cugugauagu gguggag 27

<210> SEQ ID NO 589
<211> LENGTH: 27
<212> TYPE: RNA
<213> ORGANISM: Artificial Sequence
<220> FEATURE:
<223> OTHER INFORMATION: Synthetic

<400> SEQUENCE: 589
acauguucuu ccugugauag uggugga 27

<210> SEQ ID NO 590
<211> LENGTH: 27
<212> TYPE: RNA
<213> ORGANISM: Artificial Sequence
<220> FEATURE:
<223> OTHER INFORMATION: Synthetic

<400> SEQUENCE: 590
gacauuuucu uccugugaua guggugg 27

<210> SEQ ID NO 591
<211> LENGTH: 27
<212> TYPE: RNA
<213> ORGANISM: Artificial Sequence
<220> FEATURE:
<223> OTHER INFORMATION: Synthetic

<400> SEQUENCE: 591
ugacauguuc uuccugugau aguggug 27

<210> SEQ ID NO 592
<211> LENGTH: 27
<212> TYPE: RNA
<213> ORGANISM: Artificial Sequence
<220> FEATURE:
<223> OTHER INFORMATION: Synthetic

<400> SEQUENCE: 592
cugacuuguu cuuccuguga uaguggu 27

<210> SEQ ID NO 593
<211> LENGTH: 27
<212> TYPE: RNA
<213> ORGANISM: Artificial Sequence
<220> FEATURE:
<223> OTHER INFORMATION: Synthetic

<400> SEQUENCE: 593
acugauaugu ucuuccugug auagugg 27

<210> SEQ ID NO 594
<211> LENGTH: 27
<212> TYPE: RNA
<213> ORGANISM: Artificial Sequence
<220> FEATURE:
<223> OTHER INFORMATION: Synthetic

<400> SEQUENCE: 594
gacugucaug uucuuccugu gauagug 27

<210> SEQ ID NO 595
<211> LENGTH: 27
<212> TYPE: RNA
<213> ORGANISM: Artificial Sequence
<220> FEATURE:
<223> OTHER INFORMATION: Synthetic

<400> SEQUENCE: 595
agacuuacau guucuuccug ugauagu 27

<210> SEQ ID NO 596
<211> LENGTH: 27
<212> TYPE: RNA
<213> ORGANISM: Artificial Sequence
<220> FEATURE:
<223> OTHER INFORMATION: Synthetic

<400> SEQUENCE: 596
aagacugaca uguucuuccu gugauag 27

<210> SEQ ID NO 597
<211> LENGTH: 27
<212> TYPE: RNA
<213> ORGANISM: Artificial Sequence
<220> FEATURE:
<223> OTHER INFORMATION: Synthetic

<400> SEQUENCE: 597
caagauugac auguucuucc ugugaua 27

<210> SEQ ID NO 598
<211> LENGTH: 27
<212> TYPE: RNA
<213> ORGANISM: Artificial Sequence
<220> FEATURE:
<223> OTHER INFORMATION: Synthetic

<400> SEQUENCE: 598
ccaagucuga cauguucuuc cugugau 27

<210> SEQ ID NO 599
<211> LENGTH: 27
<212> TYPE: RNA
<213> ORGANISM: Artificial Sequence
<220> FEATURE:
<223> OTHER INFORMATION: Synthetic

<400> SEQUENCE: 599
accaauacug acauguucuu ccuguga 27

<210> SEQ ID NO 600
<211> LENGTH: 27
<212> TYPE: RNA
<213> ORGANISM: Artificial Sequence
<220> FEATURE:
<223> OTHER INFORMATION: Synthetic

<400> SEQUENCE: 600
acgacuaaga cugacauguu cuuccug 27

<210> SEQ ID NO 601
<211> LENGTH: 27
<212> TYPE: RNA
<213> ORGANISM: Artificial Sequence
<220> FEATURE:
<223> OTHER INFORMATION: Synthetic

<400> SEQUENCE: 601
gacgaucaag acugacaugu ucuuccu 27

<210> SEQ ID NO 602
<211> LENGTH: 27
<212> TYPE: RNA
<213> ORGANISM: Artificial Sequence
<220> FEATURE:
<223> OTHER INFORMATION: Synthetic

<400> SEQUENCE: 602
agacguccaa gacugacaug uucuucc 27

<210> SEQ ID NO 603

<211> LENGTH: 27
<212> TYPE: RNA
<213> ORGANISM: Artificial Sequence
<220> FEATURE:
<223> OTHER INFORMATION: Synthetic

<400> SEQUENCE: 603
uagacuacca agacugacau guucuuc 27

<210> SEQ ID NO 604
<211> LENGTH: 27
<212> TYPE: RNA
<213> ORGANISM: Artificial Sequence
<220> FEATURE:
<223> OTHER INFORMATION: Synthetic

<400> SEQUENCE: 604
uaguauaaug ggauccuccg augccaa 27

<210> SEQ ID NO 605
<211> LENGTH: 27
<212> TYPE: RNA
<213> ORGANISM: Artificial Sequence
<220> FEATURE:
<223> OTHER INFORMATION: Synthetic

<400> SEQUENCE: 605
cugguuaggc cagcauuugg auaguau 27

<210> SEQ ID NO 606
<211> LENGTH: 27
<212> TYPE: RNA
<213> ORGANISM: Artificial Sequence
<220> FEATURE:
<223> OTHER INFORMATION: Synthetic

<400> SEQUENCE: 606
gcuuguucag aaggagccuc ugugcuu 27

<210> SEQ ID NO 607
<211> LENGTH: 27
<212> TYPE: RNA
<213> ORGANISM: Artificial Sequence
<220> FEATURE:
<223> OTHER INFORMATION: Synthetic

<400> SEQUENCE: 607
cucaguuggu gcuuguucag aaggagc 27

<210> SEQ ID NO 608
<211> LENGTH: 27
<212> TYPE: RNA
<213> ORGANISM: Artificial Sequence
<220> FEATURE:
<223> OTHER INFORMATION: Synthetic

<400> SEQUENCE: 608
ucucaugugg ugcuuguuca gaaggag 27

<210> SEQ ID NO 609
<211> LENGTH: 27
<212> TYPE: RNA
<213> ORGANISM: Artificial Sequence
<220> FEATURE:
<223> OTHER INFORMATION: Synthetic

<400> SEQUENCE: 609
uucucuggug gugcuuguuc agaagga 27

<210> SEQ ID NO 610
<211> LENGTH: 27
<212> TYPE: RNA
<213> ORGANISM: Artificial Sequence
<220> FEATURE:
<223> OTHER INFORMATION: Synthetic

<400> SEQUENCE: 610
uuucuuaggu ggugcuuguu cagaagg 27

<210> SEQ ID NO 611
<211> LENGTH: 27
<212> TYPE: RNA
<213> ORGANISM: Artificial Sequence
<220> FEATURE:
<223> OTHER INFORMATION: Synthetic

<400> SEQUENCE: 611
uuuucucagg uggugcuugu ucagaag 27

<210> SEQ ID NO 612
<211> LENGTH: 27
<212> TYPE: RNA
<213> ORGANISM: Artificial Sequence
<220> FEATURE:
<223> OTHER INFORMATION: Synthetic

<400> SEQUENCE: 612
cuuuuuucag guggugcuug uucagaa 27

<210> SEQ ID NO 613
<211> LENGTH: 27
<212> TYPE: RNA
<213> ORGANISM: Artificial Sequence
<220> FEATURE:
<223> OTHER INFORMATION: Synthetic

<400> SEQUENCE: 613
gcuuuucuca gguggugcuu guucaga 27

<210> SEQ ID NO 614
<211> LENGTH: 27
<212> TYPE: RNA
<213> ORGANISM: Artificial Sequence
<220> FEATURE:
<223> OTHER INFORMATION: Synthetic

<400> SEQUENCE: 614
ggcuuuucuc agguggugcu uguucag 27

<210> SEQ ID NO 615
<211> LENGTH: 27
<212> TYPE: RNA
<213> ORGANISM: Artificial Sequence
<220> FEATURE:
<223> OTHER INFORMATION: Synthetic

<400> SEQUENCE: 615
gggcuuuucu cagguggugc uuguuca 27

<210> SEQ ID NO 616
<211> LENGTH: 27
<212> TYPE: RNA

<213> ORGANISM: Artificial Sequence
<220> FEATURE:
<223> OTHER INFORMATION: Synthetic

<400> SEQUENCE: 616 cagggguuuuu cucagguggu gcuuguu 27

<210> SEQ ID NO 617
<211> LENGTH: 27
<212> TYPE: RNA
<213> ORGANISM: Artificial Sequence
<220> FEATURE:
<223> OTHER INFORMATION: Synthetic

<400> SEQUENCE: 617
acaggucuuu ucucaggugg ugcuugu 27

<210> SEQ ID NO 618
<211> LENGTH: 27
<212> TYPE: RNA
<213> ORGANISM: Artificial Sequence
<220> FEATURE:
<223> OTHER INFORMATION: Synthetic

<400> SEQUENCE: 618
cacagugcuu uucucaggug gugcuug 27

<210> SEQ ID NO 619
<211> LENGTH: 27
<212> TYPE: RNA
<213> ORGANISM: Artificial Sequence
<220> FEATURE:
<223> OTHER INFORMATION: Synthetic

<400> SEQUENCE: 619
uccuguacca cagggcuuuu cucaggu 27

<210> SEQ ID NO 620
<211> LENGTH: 27
<212> TYPE: RNA
<213> ORGANISM: Artificial Sequence
<220> FEATURE:
<223> OTHER INFORMATION: Synthetic

<400> SEQUENCE: 620
ugguaucaau ccuggaccac agggcuu 27

<210> SEQ ID NO 621
<211> LENGTH: 27
<212> TYPE: RNA
<213> ORGANISM: Artificial Sequence
<220> FEATURE:
<223> OTHER INFORMATION: Synthetic

<400> SEQUENCE: 621
ccauguuagc aauccuggac cacaggg 27

<210> SEQ ID NO 622
<211> LENGTH: 27
<212> TYPE: RNA
<213> ORGANISM: Artificial Sequence
<220> FEATURE:
<223> OTHER INFORMATION: Synthetic

<400> SEQUENCE: 622
gguccuuccu gugacagugg uggagga 27

<210> SEQ ID NO 623
<211> LENGTH: 27
<212> TYPE: RNA
<213> ORGANISM: Artificial Sequence
<220> FEATURE:
<223> OTHER INFORMATION: Synthetic

<400> SEQUENCE: 623
aggucuuucc ugugacagug guggagg 27

<210> SEQ ID NO 624
<211> LENGTH: 27
<212> TYPE: RNA
<213> ORGANISM: Artificial Sequence
<220> FEATURE:
<223> OTHER INFORMATION: Synthetic

<400> SEQUENCE: 624
aguguuguau cauagaugac caagauu 27

<210> SEQ ID NO 625
<211> LENGTH: 27
<212> TYPE: RNA
<213> ORGANISM: Artificial Sequence
<220> FEATURE:
<223> OTHER INFORMATION: Synthetic

<400> SEQUENCE: 625
caguguggua ucauagauga ccaagau 27

<210> SEQ ID NO 626
<211> LENGTH: 27
<212> TYPE: RNA
<213> ORGANISM: Artificial Sequence
<220> FEATURE:
<223> OTHER INFORMATION: Synthetic

<400> SEQUENCE: 626
ccaguuuggu aucauagaug accaaga 27

<210> SEQ ID NO 627
<211> LENGTH: 27
<212> TYPE: RNA
<213> ORGANISM: Artificial Sequence
<220> FEATURE:
<223> OTHER INFORMATION: Synthetic

<400> SEQUENCE: 627
gccagugugg uaucauagau gaccaag 27

<210> SEQ ID NO 628
<211> LENGTH: 27
<212> TYPE: RNA
<213> ORGANISM: Artificial Sequence
<220> FEATURE:
<223> OTHER INFORMATION: Synthetic

<400> SEQUENCE: 628
ugccauugug guaucauaga ugaccaa 27

<210> SEQ ID NO 629
<211> LENGTH: 27
<212> TYPE: RNA
<213> ORGANISM: Artificial Sequence
<220> FEATURE:

<223> OTHER INFORMATION: Synthetic

<400> SEQUENCE: 629
augccugugu gguaucauag augacca 27

<210> SEQ ID NO 630
<211> LENGTH: 27
<212> TYPE: RNA
<213> ORGANISM: Artificial Sequence
<220> FEATURE:
<223> OTHER INFORMATION: Synthetic

<400> SEQUENCE: 630
gaugcuagug ugguaucaua gaugacc 27

<210> SEQ ID NO 631
<211> LENGTH: 27
<212> TYPE: RNA
<213> ORGANISM: Artificial Sequence
<220> FEATURE:
<223> OTHER INFORMATION: Synthetic

<400> SEQUENCE: 631
ugaugucagu gugguaucau agaugac 27

<210> SEQ ID NO 632
<211> LENGTH: 27
<212> TYPE: RNA
<213> ORGANISM: Artificial Sequence
<220> FEATURE:
<223> OTHER INFORMATION: Synthetic

<400> SEQUENCE: 632
cugauuccag ugugguauca uagauga 27

<210> SEQ ID NO 633
<211> LENGTH: 27
<212> TYPE: RNA
<213> ORGANISM: Artificial Sequence
<220> FEATURE:
<223> OTHER INFORMATION: Synthetic

<400> SEQUENCE: 633
ucugaugcca gugugguauc auagaug 27

<210> SEQ ID NO 634
<211> LENGTH: 27
<212> TYPE: RNA
<213> ORGANISM: Artificial Sequence
<220> FEATURE:
<223> OTHER INFORMATION: Synthetic

<400> SEQUENCE: 634
cucuguugcc agugugguau cauagau 27

<210> SEQ ID NO 635
<211> LENGTH: 27
<212> TYPE: RNA
<213> ORGANISM: Artificial Sequence
<220> FEATURE:
<223> OTHER INFORMATION: Synthetic

<400> SEQUENCE: 635
guccuuugau gccagugugg uaucaua 27

<210> SEQ ID NO 636
<211> LENGTH: 27
<212> TYPE: RNA
<213> ORGANISM: Artificial Sequence
<220> FEATURE:
<223> OTHER INFORMATION: Synthetic

<400> SEQUENCE: 636
gggucuucug augccagugu gguauca 27

<210> SEQ ID NO 637
<211> LENGTH: 27
<212> TYPE: RNA
<213> ORGANISM: Artificial Sequence
<220> FEATURE:
<223> OTHER INFORMATION: Synthetic

<400> SEQUENCE: 637
uuugguuagu uuucuggggu ccucuga 27

<210> SEQ ID NO 638
<211> LENGTH: 27
<212> TYPE: RNA
<213> ORGANISM: Artificial Sequence
<220> FEATURE:
<223> OTHER INFORMATION: Synthetic

<400> SEQUENCE: 638
auuuguguag uuuucugggg uccucug 27

<210> SEQ ID NO 639
<211> LENGTH: 27
<212> TYPE: RNA
<213> ORGANISM: Artificial Sequence
<220> FEATURE:
<223> OTHER INFORMATION: Synthetic

<400> SEQUENCE: 639
gaaucuggau uccugcagua guucucg 27

<210> SEQ ID NO 640
<211> LENGTH: 27
<212> TYPE: RNA
<213> ORGANISM: Artificial Sequence
<220> FEATURE:
<223> OTHER INFORMATION: Synthetic

<400> SEQUENCE: 640
ccagauucug gauuccugca guaguuc 27

<210> SEQ ID NO 641
<211> LENGTH: 27
<212> TYPE: RNA
<213> ORGANISM: Artificial Sequence
<220> FEATURE:
<223> OTHER INFORMATION: Synthetic

<400> SEQUENCE: 641
ucccauaauc uggauuccug caguagu 27

<210> SEQ ID NO 642
<211> LENGTH: 27
<212> TYPE: RNA
<213> ORGANISM: Artificial Sequence
<220> FEATURE:
<223> OTHER INFORMATION: Synthetic

<400> SEQUENCE: 642
uucccugaau cuggauuccu gcaguag 27

<210> SEQ ID NO 643
<211> LENGTH: 27
<212> TYPE: RNA
<213> ORGANISM: Artificial Sequence
<220> FEATURE:
<223> OTHER INFORMATION: Synthetic

<400> SEQUENCE: 643
uuuccuagaa ucuggauucc ugcagua 27

<210> SEQ ID NO 644
<211> LENGTH: 27
<212> TYPE: RNA
<213> ORGANISM: Artificial Sequence
<220> FEATURE:
<223> OTHER INFORMATION: Synthetic

<400> SEQUENCE: 644
guuucucaga aucuggauuc cugcagu 27

<210> SEQ ID NO 645
<211> LENGTH: 27
<212> TYPE: RNA
<213> ORGANISM: Artificial Sequence
<220> FEATURE:
<223> OTHER INFORMATION: Synthetic

<400> SEQUENCE: 645
uguuuuccag aaucuggauu ccugcag 27

<210> SEQ ID NO 646
<211> LENGTH: 27
<212> TYPE: RNA
<213> ORGANISM: Artificial Sequence
<220> FEATURE:
<223> OTHER INFORMATION: Synthetic

<400> SEQUENCE: 646
gguuguuucc cagaaucugg auuccug 27

<210> SEQ ID NO 647
<211> LENGTH: 27
<212> TYPE: RNA
<213> ORGANISM: Artificial Sequence
<220> FEATURE:
<223> OTHER INFORMATION: Synthetic

<400> SEQUENCE: 647
uuguguaaca ccaggguugu uucccag 27

<210> SEQ ID NO 648
<211> LENGTH: 27
<212> TYPE: RNA
<213> ORGANISM: Artificial Sequence
<220> FEATURE:
<223> OTHER INFORMATION: Synthetic

<400> SEQUENCE: 648
guuguuuaac accaggguug uuuccca 27

<210> SEQ ID NO 649
<211> LENGTH: 27

<212> TYPE: RNA
<213> ORGANISM: Artificial Sequence
<220> FEATURE:
<223> OTHER INFORMATION: Synthetic

<400> SEQUENCE: 649
gauuguagua cucccaccuc acacacg 27

<210> SEQ ID NO 650
<211> LENGTH: 27
<212> TYPE: RNA
<213> ORGANISM: Artificial Sequence
<220> FEATURE:
<223> OTHER INFORMATION: Synthetic

<400> SEQUENCE: 650
agauuucagu acucccaccu cacacac 27

<210> SEQ ID NO 651
<211> LENGTH: 27
<212> TYPE: RNA
<213> ORGANISM: Artificial Sequence
<220> FEATURE:
<223> OTHER INFORMATION: Synthetic

<400> SEQUENCE: 651
ucagauugca guacucccac cucacac 27

<210> SEQ ID NO 652
<211> LENGTH: 27
<212> TYPE: RNA
<213> ORGANISM: Artificial Sequence
<220> FEATURE:
<223> OTHER INFORMATION: Synthetic

<400> SEQUENCE: 652
gucaguuugc aguacuccca ccucaca 27

<210> SEQ ID NO 653
<211> LENGTH: 27
<212> TYPE: RNA
<213> ORGANISM: Artificial Sequence
<220> FEATURE:
<223> OTHER INFORMATION: Synthetic

<400> SEQUENCE: 653
auucuuuuuc ugagcauugu gucagau 27

<210> SEQ ID NO 654
<211> LENGTH: 27
<212> TYPE: RNA
<213> ORGANISM: Artificial Sequence
<220> FEATURE:
<223> OTHER INFORMATION: Synthetic

<400> SEQUENCE: 654
gauucuguuu cugagcauug ugucaga 27

<210> SEQ ID NO 655
<211> LENGTH: 27
<212> TYPE: RNA
<213> ORGANISM: Artificial Sequence
<220> FEATURE:
<223> OTHER INFORMATION: Synthetic

<400> SEQUENCE: 655
ugauuuuguu ucugagcauu gugucag 27

<210> SEQ ID NO 656
<211> LENGTH: 27
<212> TYPE: RNA
<213> ORGANISM: Artificial Sequence
<220> FEATURE:
<223> OTHER INFORMATION: Synthetic

<400> SEQUENCE: 656
cugauucugu uucugagcau uguguca 27

<210> SEQ ID NO 657
<211> LENGTH: 27
<212> TYPE: RNA
<213> ORGANISM: Artificial Sequence
<220> FEATURE:
<223> OTHER INFORMATION: Synthetic

<400> SEQUENCE: 657
ccugauucug uuucugagca uugugucc 27

<210> SEQ ID NO 658
<211> LENGTH: 27
<212> TYPE: RNA
<213> ORGANISM: Artificial Sequence
<220> FEATURE:
<223> OTHER INFORMATION: Synthetic

<400> SEQUENCE: 658
accuguuucu guuucugagc auugugu 27

<210> SEQ ID NO 659
<211> LENGTH: 27
<212> TYPE: RNA
<213> ORGANISM: Artificial Sequence
<220> FEATURE:
<223> OTHER INFORMATION: Synthetic

<400> SEQUENCE: 659
caccuuauuc uguuucugag cauugug 27

<210> SEQ ID NO 660
<211> LENGTH: 27
<212> TYPE: RNA
<213> ORGANISM: Artificial Sequence
<220> FEATURE:
<223> OTHER INFORMATION: Synthetic

<400> SEQUENCE: 660
acaccugauu cuguuucuga gcauugu 27

<210> SEQ ID NO 661
<211> LENGTH: 27
<212> TYPE: RNA
<213> ORGANISM: Artificial Sequence
<220> FEATURE:
<223> OTHER INFORMATION: Synthetic

<400> SEQUENCE: 661
gacacuugau ucuguuucug agcauug 27

<210> SEQ ID NO 662
<211> LENGTH: 27
<212> TYPE: RNA
<213> ORGANISM: Artificial Sequence
<220> FEATURE:
<223> OTHER INFORMATION: Synthetic

<400> SEQUENCE: 662
ggacaucuga uucuguuucu gagcauu 27

<210> SEQ ID NO 663
<211> LENGTH: 27
<212> TYPE: RNA
<213> ORGANISM: Artificial Sequence
<220> FEATURE:
<223> OTHER INFORMATION: Synthetic

<400> SEQUENCE: 663
uaggauaccu gauucuguuu cugagca 27

<210> SEQ ID NO 664
<211> LENGTH: 27
<212> TYPE: RNA
<213> ORGANISM: Artificial Sequence
<220> FEATURE:
<223> OTHER INFORMATION: Synthetic

<400> SEQUENCE: 664
ucuaguacac cugauucugu uucugag 27

<210> SEQ ID NO 665
<211> LENGTH: 27
<212> TYPE: RNA
<213> ORGANISM: Artificial Sequence
<220> FEATURE:
<223> OTHER INFORMATION: Synthetic

<400> SEQUENCE: 665
cucuaugaca ccugauucug uuucuga 27

<210> SEQ ID NO 666
<211> LENGTH: 27
<212> TYPE: RNA
<213> ORGANISM: Artificial Sequence
<220> FEATURE:
<223> OTHER INFORMATION: Synthetic

<400> SEQUENCE: 666
ucucuuggac accugauucu guuucug 27

<210> SEQ ID NO 667
<211> LENGTH: 27
<212> TYPE: RNA
<213> ORGANISM: Artificial Sequence
<220> FEATURE:
<223> OTHER INFORMATION: Synthetic

<400> SEQUENCE: 667
gucucuagga caccugauuc uguuucu 27

<210> SEQ ID NO 668
<211> LENGTH: 27
<212> TYPE: RNA
<213> ORGANISM: Artificial Sequence
<220> FEATURE:
<223> OTHER INFORMATION: Synthetic

<400> SEQUENCE: 668
agucuuuagg acaccugauu cuguuuc 27

<210> SEQ ID NO 669
<211> LENGTH: 27
<212> TYPE: RNA
<213> ORGANISM: Artificial Sequence
<220> FEATURE:
<223> OTHER INFORMATION: Synthetic

<400> SEQUENCE: 669
ggaguuucua ggacaccuga uucuguu 27

<210> SEQ ID NO 670
<211> LENGTH: 27
<212> TYPE: RNA
<213> ORGANISM: Artificial Sequence
<220> FEATURE:
<223> OTHER INFORMATION: Synthetic

<400> SEQUENCE: 670
ugggauucuc uaggacaccu gauucug 27

<210> SEQ ID NO 671
<211> LENGTH: 27
<212> TYPE: RNA
<213> ORGANISM: Artificial Sequence
<220> FEATURE:
<223> OTHER INFORMATION: Synthetic

<400> SEQUENCE: 671
agugguaguc ucuaggacac cugauuc 27

<210> SEQ ID NO 672
<211> LENGTH: 27
<212> TYPE: RNA
<213> ORGANISM: Artificial Sequence
<220> FEATURE:
<223> OTHER INFORMATION: Synthetic

<400> SEQUENCE: 672
caacauuggg agucucuagg acaccug 27

<210> SEQ ID NO 673
<211> LENGTH: 27
<212> TYPE: RNA
<213> ORGANISM: Artificial Sequence
<220> FEATURE:
<223> OTHER INFORMATION: Synthetic

<400> SEQUENCE: 673
uggaauaaca gugggagucu cuaggac 27

<210> SEQ ID NO 674
<211> LENGTH: 27
<212> TYPE: RNA
<213> ORGANISM: Artificial Sequence
<220> FEATURE:
<223> OTHER INFORMATION: Synthetic

<400> SEQUENCE: 674
cuggaucaac agugggaguc ucuagga 27

<210> SEQ ID NO 675
<211> LENGTH: 27
<212> TYPE: RNA
<213> ORGANISM: Artificial Sequence
<220> FEATURE:
<223> OTHER INFORMATION: Synthetic

<400> SEQUENCE: 675
acugguacaa cagugggagu cucuagg 27

<210> SEQ ID NO 676
<211> LENGTH: 27
<212> TYPE: RNA
<213> ORGANISM: Artificial Sequence
<220> FEATURE:
<223> OTHER INFORMATION: Synthetic

<400> SEQUENCE: 676
aacuguaaca acagugggag ucucuag 27

<210> SEQ ID NO 677
<211> LENGTH: 27
<212> TYPE: RNA
<213> ORGANISM: Artificial Sequence
<220> FEATURE:
<223> OTHER INFORMATION: Synthetic

<400> SEQUENCE: 677
gaacuugaac aacaguggga gucucua 27

<210> SEQ ID NO 678
<211> LENGTH: 27
<212> TYPE: RNA
<213> ORGANISM: Artificial Sequence
<220> FEATURE:
<223> OTHER INFORMATION: Synthetic

<400> SEQUENCE: 678
ggaacuggaa caacaguggg agucucu 27

<210> SEQ ID NO 679
<211> LENGTH: 27
<212> TYPE: RNA
<213> ORGANISM: Artificial Sequence
<220> FEATURE:
<223> OTHER INFORMATION: Synthetic

<400> SEQUENCE: 679
caguuugugc ugcuucagaa ugagccu 27

<210> SEQ ID NO 680
<211> LENGTH: 27
<212> TYPE: RNA
<213> ORGANISM: Artificial Sequence
<220> FEATURE:
<223> OTHER INFORMATION: Synthetic

<400> SEQUENCE: 680
ucaguuggug cugcuucaga augagcc 27

<210> SEQ ID NO 681
<211> LENGTH: 27
<212> TYPE: RNA
<213> ORGANISM: Artificial Sequence
<220> FEATURE:
<223> OTHER INFORMATION: Synthetic

<400> SEQUENCE: 681
cucaguuggu gcugcuucag aaugagc 27

<210> SEQ ID NO 682

<211> LENGTH: 27
<212> TYPE: RNA
<213> ORGANISM: Artificial Sequence
<220> FEATURE:
<223> OTHER INFORMATION: Synthetic

<400> SEQUENCE: 682
gcucauuugg ugcugcuuca gaaugag 27

<210> SEQ ID NO 683
<211> LENGTH: 27
<212> TYPE: RNA
<213> ORGANISM: Artificial Sequence
<220> FEATURE:
<223> OTHER INFORMATION: Synthetic

<400> SEQUENCE: 683
ugcucuguug gugcugcuuc agaauga 27

<210> SEQ ID NO 684
<211> LENGTH: 27
<212> TYPE: RNA
<213> ORGANISM: Artificial Sequence
<220> FEATURE:
<223> OTHER INFORMATION: Synthetic

<400> SEQUENCE: 684
uugcuuaguu ggugcugcuu cagaaug 27

<210> SEQ ID NO 685
<211> LENGTH: 27
<212> TYPE: RNA
<213> ORGANISM: Artificial Sequence
<220> FEATURE:
<223> OTHER INFORMATION: Synthetic

<400> SEQUENCE: 685
uuugcucagu uggugcugcu ucagaau 27

<210> SEQ ID NO 686
<211> LENGTH: 27
<212> TYPE: RNA
<213> ORGANISM: Artificial Sequence
<220> FEATURE:
<223> OTHER INFORMATION: Synthetic

<400> SEQUENCE: 686
guuuguucag uuggugcugc uucagaa 27

<210> SEQ ID NO 687
<211> LENGTH: 27
<212> TYPE: RNA
<213> ORGANISM: Artificial Sequence
<220> FEATURE:
<223> OTHER INFORMATION: Synthetic

<400> SEQUENCE: 687 gguuucuca guuggugcug cuucaga 27

<210> SEQ ID NO 688
<211> LENGTH: 27
<212> TYPE: RNA
<213> ORGANISM: Artificial Sequence
<220> FEATURE:
<223> OTHER INFORMATION: Synthetic

<400> SEQUENCE: 688 gggguuugcuc aguuggugcu gcuucag 27

<210> SEQ ID NO 689
<211> LENGTH: 27
<212> TYPE: RNA
<213> ORGANISM: Artificial Sequence
<220> FEATURE:
<223> OTHER INFORMATION: Synthetic

<400> SEQUENCE: 689
gggguuugcu caguuggugc ugcuuca 27

<210> SEQ ID NO 690
<211> LENGTH: 27
<212> TYPE: RNA
<213> ORGANISM: Artificial Sequence
<220> FEATURE:
<223> OTHER INFORMATION: Synthetic

<400> SEQUENCE: 690
ucuggucauu accaugguag cacugcc 27

<210> SEQ ID NO 691
<211> LENGTH: 27
<212> TYPE: RNA
<213> ORGANISM: Artificial Sequence
<220> FEATURE:
<223> OTHER INFORMATION: Synthetic

<400> SEQUENCE: 691
cucuguccau uaccauggua gcacugc 27

<210> SEQ ID NO 692
<211> LENGTH: 27
<212> TYPE: RNA
<213> ORGANISM: Artificial Sequence
<220> FEATURE:
<223> OTHER INFORMATION: Synthetic

<400> SEQUENCE: 692
uuccuuugac aguggugggag aaugugc 27

<210> SEQ ID NO 693
<211> LENGTH: 27
<212> TYPE: RNA
<213> ORGANISM: Artificial Sequence
<220> FEATURE:
<223> OTHER INFORMATION: Synthetic

<400> SEQUENCE: 693
uugacuuguc cuuccuguga caguggu 27

<210> SEQ ID NO 694
<211> LENGTH: 27
<212> TYPE: RNA
<213> ORGANISM: Artificial Sequence
<220> FEATURE:
<223> OTHER INFORMATION: Synthetic

<400> SEQUENCE: 694
auugauaugu ccuuccugug acagugg 27

<210> SEQ ID NO 695
<211> LENGTH: 27
<212> TYPE: RNA

<213> ORGANISM: Artificial Sequence
<220> FEATURE:
<223> OTHER INFORMATION: Synthetic

<400> SEQUENCE: 695
gauugucaug uccuuccugu gacagug 27

<210> SEQ ID NO 696
<211> LENGTH: 27
<212> TYPE: RNA
<213> ORGANISM: Artificial Sequence
<220> FEATURE:
<223> OTHER INFORMATION: Synthetic

<400> SEQUENCE: 696
agauuuacau guccuuccug ugacagu 27

<210> SEQ ID NO 697
<211> LENGTH: 27
<212> TYPE: RNA
<213> ORGANISM: Artificial Sequence
<220> FEATURE:
<223> OTHER INFORMATION: Synthetic

<400> SEQUENCE: 697
aagauugaca uguccuuccu gugacag 27

<210> SEQ ID NO 698
<211> LENGTH: 27
<212> TYPE: RNA
<213> ORGANISM: Artificial Sequence
<220> FEATURE:
<223> OTHER INFORMATION: Synthetic

<400> SEQUENCE: 698
caagauugac auguccuucc ugugaca 27

<210> SEQ ID NO 699
<211> LENGTH: 27
<212> TYPE: RNA
<213> ORGANISM: Artificial Sequence
<220> FEATURE:
<223> OTHER INFORMATION: Synthetic

<400> SEQUENCE: 699
accaauauug acauguccuu ccuguga 27

<210> SEQ ID NO 700
<211> LENGTH: 27
<212> TYPE: RNA
<213> ORGANISM: Artificial Sequence
<220> FEATURE:
<223> OTHER INFORMATION: Synthetic

<400> SEQUENCE: 700
gaccaugauu gacauguccu uccugug 27

<210> SEQ ID NO 701
<211> LENGTH: 27
<212> TYPE: RNA
<213> ORGANISM: Artificial Sequence
<220> FEATURE:
<223> OTHER INFORMATION: Synthetic

<400> SEQUENCE: 701
ugaccuagau ugacaugucc uuccugu 27

<210> SEQ ID NO 702
<211> LENGTH: 27
<212> TYPE: RNA
<213> ORGANISM: Artificial Sequence
<220> FEATURE:
<223> OTHER INFORMATION: Synthetic

<400> SEQUENCE: 702
augacuaaga uugacauguc cuuccug 27

<210> SEQ ID NO 703
<211> LENGTH: 27
<212> TYPE: RNA
<213> ORGANISM: Artificial Sequence
<220> FEATURE:
<223> OTHER INFORMATION: Synthetic

<400> SEQUENCE: 703
gaugaucaag auugacaugu ccuuccu 27

<210> SEQ ID NO 704
<211> LENGTH: 27
<212> TYPE: RNA
<213> ORGANISM: Artificial Sequence
<220> FEATURE:
<223> OTHER INFORMATION: Synthetic

<400> SEQUENCE: 704
ggauguccaa gauugacaug uccuucc 27

<210> SEQ ID NO 705
<211> LENGTH: 27
<212> TYPE: RNA
<213> ORGANISM: Artificial Sequence
<220> FEATURE:
<223> OTHER INFORMATION: Synthetic

<400> SEQUENCE: 705
uggauuacca agauugacau guccuuc 27

<210> SEQ ID NO 706
<211> LENGTH: 27
<212> TYPE: RNA
<213> ORGANISM: Artificial Sequence
<220> FEATURE:
<223> OTHER INFORMATION: Synthetic

<400> SEQUENCE: 706
auggaugacc aagauugaca uguccuu 27

<210> SEQ ID NO 707
<211> LENGTH: 27
<212> TYPE: RNA
<213> ORGANISM: Artificial Sequence
<220> FEATURE:
<223> OTHER INFORMATION: Synthetic

<400> SEQUENCE: 707
caugguugac caagauugac auguccu 27

<210> SEQ ID NO 708
<211> LENGTH: 27
<212> TYPE: RNA
<213> ORGANISM: Artificial Sequence
<220> FEATURE:

<223> OTHER INFORMATION: Synthetic

<400> SEQUENCE: 708
ucauguauga ccaagauuga caugucc 27

<210> SEQ ID NO 709
<211> LENGTH: 27
<212> TYPE: RNA
<213> ORGANISM: Artificial Sequence
<220> FEATURE:
<223> OTHER INFORMATION: Synthetic

<400> SEQUENCE: 709
gucauugaug accaagauug acauguc 27

<210> SEQ ID NO 710
<211> LENGTH: 27
<212> TYPE: RNA
<213> ORGANISM: Artificial Sequence
<220> FEATURE:
<223> OTHER INFORMATION: Synthetic

<400> SEQUENCE: 710
ugucauggau gaccaagauu gacaugu 27

<210> SEQ ID NO 711
<211> LENGTH: 27
<212> TYPE: RNA
<213> ORGANISM: Artificial Sequence
<220> FEATURE:
<223> OTHER INFORMATION: Synthetic

<400> SEQUENCE: 711
gugucuugga ugaccaagau ugacaug 27

<210> SEQ ID NO 712
<211> LENGTH: 27
<212> TYPE: RNA
<213> ORGANISM: Artificial Sequence
<220> FEATURE:
<223> OTHER INFORMATION: Synthetic

<400> SEQUENCE: 712
gguguuaugg augaccaaga uugacau 27

<210> SEQ ID NO 713
<211> LENGTH: 27
<212> TYPE: RNA
<213> ORGANISM: Artificial Sequence
<220> FEATURE:
<223> OTHER INFORMATION: Synthetic

<400> SEQUENCE: 713
uggugucaug gaugaccaag auugaca 27

<210> SEQ ID NO 714
<211> LENGTH: 27
<212> TYPE: RNA
<213> ORGANISM: Artificial Sequence
<220> FEATURE:
<223> OTHER INFORMATION: Synthetic

<400> SEQUENCE: 714
gugguuucau ggaugaccaa gauugac 27

<210> SEQ ID NO 715
<211> LENGTH: 27
<212> TYPE: RNA
<213> ORGANISM: Artificial Sequence
<220> FEATURE:
<223> OTHER INFORMATION: Synthetic

<400> SEQUENCE: 715
uguggugcua uggaugacca agauuga 27

<210> SEQ ID NO 716
<211> LENGTH: 27
<212> TYPE: RNA
<213> ORGANISM: Artificial Sequence
<220> FEATURE:
<223> OTHER INFORMATION: Synthetic

<400> SEQUENCE: 716
guguguuguc auggaugacc aagauug 27

<210> SEQ ID NO 717
<211> LENGTH: 27
<212> TYPE: RNA
<213> ORGANISM: Artificial Sequence
<220> FEATURE:
<223> OTHER INFORMATION: Synthetic

<400> SEQUENCE: 717
ggauuucugc aguaguucau ugucagg 27

<210> SEQ ID NO 718
<211> LENGTH: 27
<212> TYPE: RNA
<213> ORGANISM: Artificial Sequence
<220> FEATURE:
<223> OTHER INFORMATION: Synthetic

<400> SEQUENCE: 718
uggauuccug caguaguuca uugucag 27

<210> SEQ ID NO 719
<211> LENGTH: 27
<212> TYPE: RNA
<213> ORGANISM: Artificial Sequence
<220> FEATURE:
<223> OTHER INFORMATION: Synthetic

<400> SEQUENCE: 719
cuggauuccu gcaguaguuc auuguca 27

<210> SEQ ID NO 720
<211> LENGTH: 27
<212> TYPE: RNA
<213> ORGANISM: Artificial Sequence
<220> FEATURE:
<223> OTHER INFORMATION: Synthetic

<400> SEQUENCE: 720
ucugguuucc ugcaguaguu cauuguc 27

<210> SEQ ID NO 721
<211> LENGTH: 27
<212> TYPE: RNA
<213> ORGANISM: Artificial Sequence
<220> FEATURE:
<223> OTHER INFORMATION: Synthetic

<400> SEQUENCE: 721
aucuguauuc cugcaguagu ucauugu 27

<210> SEQ ID NO 722
<211> LENGTH: 27
<212> TYPE: RNA
<213> ORGANISM: Artificial Sequence
<220> FEATURE:
<223> OTHER INFORMATION: Synthetic

<400> SEQUENCE: 722
caucuugauu ccugcaguag uucauug 27

<210> SEQ ID NO 723
<211> LENGTH: 27
<212> TYPE: RNA
<213> ORGANISM: Artificial Sequence
<220> FEATURE:
<223> OTHER INFORMATION: Synthetic

<400> SEQUENCE: 723
gcaucuggau uccugcagua guucauu 27

<210> SEQ ID NO 724
<211> LENGTH: 27
<212> TYPE: RNA
<213> ORGANISM: Artificial Sequence
<220> FEATURE:
<223> OTHER INFORMATION: Synthetic

<400> SEQUENCE: 724
aucgguaucu ggauuccugc aguaguu 27

<210> SEQ ID NO 725
<211> LENGTH: 27
<212> TYPE: RNA
<213> ORGANISM: Artificial Sequence
<220> FEATURE:
<223> OTHER INFORMATION: Synthetic

<400> SEQUENCE: 725
uccauuguaa aacaccaagg gccugua 27

<210> SEQ ID NO 726
<211> LENGTH: 27
<212> TYPE: RNA
<213> ORGANISM: Artificial Sequence
<220> FEATURE:
<223> OTHER INFORMATION: Synthetic

<400> SEQUENCE: 726
cuggguucca ugguaaaaca ccaaggg 27

<210> SEQ ID NO 727
<211> LENGTH: 27
<212> TYPE: RNA
<213> ORGANISM: Artificial Sequence
<220> FEATURE:
<223> OTHER INFORMATION: Synthetic

<400> SEQUENCE: 727
gcuggugucc augguaaaac accaagg 27

<210> SEQ ID NO 728
<211> LENGTH: 27

<212> TYPE: RNA
<213> ORGANISM: Artificial Sequence
<220> FEATURE:
<223> OTHER INFORMATION: Synthetic

<400> SEQUENCE: 728
ugcugugguc caugguaaaa caccaag 27

<210> SEQ ID NO 729
<211> LENGTH: 27
<212> TYPE: RNA
<213> ORGANISM: Artificial Sequence
<220> FEATURE:
<223> OTHER INFORMATION: Synthetic

<400> SEQUENCE: 729
augcuugggu ccaugguaaa acaccaa 27

<210> SEQ ID NO 730
<211> LENGTH: 27
<212> TYPE: RNA
<213> ORGANISM: Artificial Sequence
<220> FEATURE:
<223> OTHER INFORMATION: Synthetic

<400> SEQUENCE: 730
gaugcugggg uccaugguaa aacacca 27

<210> SEQ ID NO 731
<211> LENGTH: 27
<212> TYPE: RNA
<213> ORGANISM: Artificial Sequence
<220> FEATURE:
<223> OTHER INFORMATION: Synthetic

<400> SEQUENCE: 731
cugauucugg gguccauggu aaaacac 27

<210> SEQ ID NO 732
<211> LENGTH: 27
<212> TYPE: RNA
<213> ORGANISM: Artificial Sequence
<220> FEATURE:
<223> OTHER INFORMATION: Synthetic

<400> SEQUENCE: 732
gcaucucguc agguugcagu acuccca 27

<210> SEQ ID NO 733
<211> LENGTH: 27
<212> TYPE: RNA
<213> ORGANISM: Artificial Sequence
<220> FEATURE:
<223> OTHER INFORMATION: Synthetic

<400> SEQUENCE: 733
agcauugcgu cagguugcag uacuccc 27

<210> SEQ ID NO 734
<211> LENGTH: 27
<212> TYPE: RNA
<213> ORGANISM: Artificial Sequence
<220> FEATURE:
<223> OTHER INFORMATION: Synthetic

<400> SEQUENCE: 734
ugagcuucgc gucagguugc aguacuc 27

<210> SEQ ID NO 735
<211> LENGTH: 27
<212> TYPE: RNA
<213> ORGANISM: Artificial Sequence
<220> FEATURE:
<223> OTHER INFORMATION: Synthetic

<400> SEQUENCE: 735
cugaguaucg cgucagguug caguacu 27

<210> SEQ ID NO 736
<211> LENGTH: 27
<212> TYPE: RNA
<213> ORGANISM: Artificial Sequence
<220> FEATURE:
<223> OTHER INFORMATION: Synthetic

<400> SEQUENCE: 736
ugucuuagca ucgcgucagg uugcagu 27

<210> SEQ ID NO 737
<211> LENGTH: 27
<212> TYPE: RNA
<213> ORGANISM: Artificial Sequence
<220> FEATURE:
<223> OTHER INFORMATION: Synthetic

<400> SEQUENCE: 737
uucugugucu gagcaucgcg ucagguu 27

<210> SEQ ID NO 738
<211> LENGTH: 27
<212> TYPE: RNA
<213> ORGANISM: Artificial Sequence
<220> FEATURE:
<223> OTHER INFORMATION: Synthetic

<400> SEQUENCE: 738
cuucuuuguc ugagcaucgc gucaggu 27

<210> SEQ ID NO 739
<211> LENGTH: 27
<212> TYPE: RNA
<213> ORGANISM: Artificial Sequence
<220> FEATURE:
<223> OTHER INFORMATION: Synthetic

<400> SEQUENCE: 739
acaguuccuu cugugucuga gcaucgc 27

<210> SEQ ID NO 740
<211> LENGTH: 27
<212> TYPE: RNA
<213> ORGANISM: Artificial Sequence
<220> FEATURE:
<223> OTHER INFORMATION: Synthetic

<400> SEQUENCE: 740
cacagucccu ucugugucug agcaucg 27

<210> SEQ ID NO 741
<211> LENGTH: 27
<212> TYPE: RNA
<213> ORGANISM: Artificial Sequence
<220> FEATURE:
<223> OTHER INFORMATION: Synthetic

<400> SEQUENCE: 741
agcgaucaca gucccuucug ugucuga 27

<210> SEQ ID NO 742
<211> LENGTH: 27
<212> TYPE: RNA
<213> ORGANISM: Artificial Sequence
<220> FEATURE:
<223> OTHER INFORMATION: Synthetic

<400> SEQUENCE: 742
ucccauaauc aaaugaagag gaugcac 27

<210> SEQ ID NO 743
<211> LENGTH: 27
<212> TYPE: RNA
<213> ORGANISM: Artificial Sequence
<220> FEATURE:
<223> OTHER INFORMATION: Synthetic

<400> SEQUENCE: 743
uucccucaau caaaugaaga ggaugca 27

<210> SEQ ID NO 744
<211> LENGTH: 27
<212> TYPE: RNA
<213> ORGANISM: Artificial Sequence
<220> FEATURE:
<223> OTHER INFORMATION: Synthetic

<400> SEQUENCE: 744
cuuccuacaa ucaaaugaag aggaugc 27

<210> SEQ ID NO 745
<211> LENGTH: 27
<212> TYPE: RNA
<213> ORGANISM: Artificial Sequence
<220> FEATURE:
<223> OTHER INFORMATION: Synthetic

<400> SEQUENCE: 745
gcuucucaca aucaaaugaa gaggaug 27

<210> SEQ ID NO 746
<211> LENGTH: 27
<212> TYPE: RNA
<213> ORGANISM: Artificial Sequence
<220> FEATURE:
<223> OTHER INFORMATION: Synthetic

<400> SEQUENCE: 746
ggcuuuccac aaucaaauga agaggau 27

<210> SEQ ID NO 747
<211> LENGTH: 27
<212> TYPE: RNA
<213> ORGANISM: Artificial Sequence
<220> FEATURE:
<223> OTHER INFORMATION: Synthetic

<400> SEQUENCE: 747
ugagguuucc cacaaucaaa ugaagag 27

<210> SEQ ID NO 748
<211> LENGTH: 27
<212> TYPE: RNA
<213> ORGANISM: Artificial Sequence
<220> FEATURE:
<223> OTHER INFORMATION: Synthetic

<400> SEQUENCE: 748
uugagucuuc ccacaaucaa augaaga 27

<210> SEQ ID NO 749
<211> LENGTH: 27
<212> TYPE: RNA
<213> ORGANISM: Artificial Sequence
<220> FEATURE:
<223> OTHER INFORMATION: Synthetic

<400> SEQUENCE: 749
cuugaugcuu cccacaauca aaugaag 27

<210> SEQ ID NO 750
<211> LENGTH: 27
<212> TYPE: RNA
<213> ORGANISM: Artificial Sequence
<220> FEATURE:
<223> OTHER INFORMATION: Synthetic

<400> SEQUENCE: 750
acuuguggcu ucccacaauc aaaugaa 27

<210> SEQ ID NO 751
<211> LENGTH: 27
<212> TYPE: RNA
<213> ORGANISM: Artificial Sequence
<220> FEATURE:
<223> OTHER INFORMATION: Synthetic

<400> SEQUENCE: 751
cacuuuaggc uucccacaau caaauga 27

<210> SEQ ID NO 752
<211> LENGTH: 27
<212> TYPE: RNA
<213> ORGANISM: Artificial Sequence
<220> FEATURE:
<223> OTHER INFORMATION: Synthetic

<400> SEQUENCE: 752
uucgguucca cuugaggcuu cccacaa 27

<210> SEQ ID NO 753
<211> LENGTH: 27
<212> TYPE: RNA
<213> ORGANISM: Artificial Sequence
<220> FEATURE:
<223> OTHER INFORMATION: Synthetic

<400> SEQUENCE: 753
cuacauugcu uccaggacau uucuucg 27

<210> SEQ ID NO 754
<211> LENGTH: 27
<212> TYPE: RNA
<213> ORGANISM: Artificial Sequence
<220> FEATURE:
<223> OTHER INFORMATION: Synthetic

<400> SEQUENCE: 754
ccuacuaugc uuccaggaca uuucuuc 27

<210> SEQ ID NO 755
<211> LENGTH: 27
<212> TYPE: RNA
<213> ORGANISM: Artificial Sequence
<220> FEATURE:
<223> OTHER INFORMATION: Synthetic

<400> SEQUENCE: 755
cccuauaaug cuuccaggac auuucuu 27

<210> SEQ ID NO 756
<211> LENGTH: 27
<212> TYPE: RNA
<213> ORGANISM: Artificial Sequence
<220> FEATURE:
<223> OTHER INFORMATION: Synthetic

<400> SEQUENCE: 756
cccccuacaa ugcuuccagg acauuuc 27

<210> SEQ ID NO 757
<211> LENGTH: 27
<212> TYPE: RNA
<213> ORGANISM: Artificial Sequence
<220> FEATURE:
<223> OTHER INFORMATION: Synthetic

<400> SEQUENCE: 757
cccccuuaca augcuuccag gacauuu 27

<210> SEQ ID NO 758
<211> LENGTH: 27
<212> TYPE: RNA
<213> ORGANISM: Artificial Sequence
<220> FEATURE:
<223> OTHER INFORMATION: Synthetic

<400> SEQUENCE: 758
agaagugcuu uccaaaccuu guucuga 27

<210> SEQ ID NO 759
<211> LENGTH: 27
<212> TYPE: RNA
<213> ORGANISM: Artificial Sequence
<220> FEATURE:
<223> OTHER INFORMATION: Synthetic

<400> SEQUENCE: 759
cagaauugcu uuccaaaccu uguucug 27

<210> SEQ ID NO 760
<211> LENGTH: 27
<212> TYPE: RNA
<213> ORGANISM: Artificial Sequence
<220> FEATURE:
<223> OTHER INFORMATION: Synthetic

<400> SEQUENCE: 760
acagaugugc uuuccaaacc uuguucu 27

<210> SEQ ID NO 761

<211> LENGTH: 27
<212> TYPE: RNA
<213> ORGANISM: Artificial Sequence
<220> FEATURE:
<223> OTHER INFORMATION: Synthetic

<400> SEQUENCE: 761
cacaguagug cuuuccaaac cuuguuc 27

<210> SEQ ID NO 762
<211> LENGTH: 27
<212> TYPE: RNA
<213> ORGANISM: Artificial Sequence
<220> FEATURE:
<223> OTHER INFORMATION: Synthetic

<400> SEQUENCE: 762
ccacauaagu gcuuuccaaa ccuuguu 27

<210> SEQ ID NO 763
<211> LENGTH: 27
<212> TYPE: RNA
<213> ORGANISM: Artificial Sequence
<220> FEATURE:
<223> OTHER INFORMATION: Synthetic

<400> SEQUENCE: 763
uccacugaag ugcuuuccaa accuugu 27

<210> SEQ ID NO 764
<211> LENGTH: 27
<212> TYPE: RNA
<213> ORGANISM: Artificial Sequence
<220> FEATURE:
<223> OTHER INFORMATION: Synthetic

<400> SEQUENCE: 764
cuccauagaa gugcuuucca aaccuug 27

<210> SEQ ID NO 765
<211> LENGTH: 27
<212> TYPE: RNA
<213> ORGANISM: Artificial Sequence
<220> FEATURE:
<223> OTHER INFORMATION: Synthetic

<400> SEQUENCE: 765
ggugcuucca cagaagugcu uuccaaa 27

<210> SEQ ID NO 766
<211> LENGTH: 27
<212> TYPE: RNA
<213> ORGANISM: Artificial Sequence
<220> FEATURE:
<223> OTHER INFORMATION: Synthetic

<400> SEQUENCE: 766
ucuggugaua uuaaggugcc uccacag 27

<210> SEQ ID NO 767
<211> LENGTH: 27
<212> TYPE: RNA
<213> ORGANISM: Artificial Sequence
<220> FEATURE:
<223> OTHER INFORMATION: Synthetic

<400> SEQUENCE: 767
cagcauccac ucuggggaua uuaaggu 27

<210> SEQ ID NO 768
<211> LENGTH: 27
<212> TYPE: RNA
<213> ORGANISM: Artificial Sequence
<220> FEATURE:
<223> OTHER INFORMATION: Synthetic

<400> SEQUENCE: 768
gucaguaccc acucugggga uauuaag 27

<210> SEQ ID NO 769
<211> LENGTH: 27
<212> TYPE: RNA
<213> ORGANISM: Artificial Sequence
<220> FEATURE:
<223> OTHER INFORMATION: Synthetic

<400> SEQUENCE: 769
gugaguagca gucagcaccc acucugg 27

<210> SEQ ID NO 770
<211> LENGTH: 27
<212> TYPE: RNA
<213> ORGANISM: Artificial Sequence
<220> FEATURE:
<223> OTHER INFORMATION: Synthetic

<400> SEQUENCE: 770
uugguuugca cccaggauga ccuugua 27

<210> SEQ ID NO 771
<211> LENGTH: 27
<212> TYPE: RNA
<213> ORGANISM: Artificial Sequence
<220> FEATURE:
<223> OTHER INFORMATION: Synthetic

<400> SEQUENCE: 771
guucauuucu uggugugcac ccaggau 27

<210> SEQ ID NO 772
<211> LENGTH: 27
<212> TYPE: RNA
<213> ORGANISM: Artificial Sequence
<220> FEATURE:
<223> OTHER INFORMATION: Synthetic

<400> SEQUENCE: 772
ucgaguuuca cuucuuggug ugcaccc 27

<210> SEQ ID NO 773
<211> LENGTH: 27
<212> TYPE: RNA
<213> ORGANISM: Artificial Sequence
<220> FEATURE:
<223> OTHER INFORMATION: Synthetic

<400> SEQUENCE: 773
uagcuuuagc aaggcaauau cugcuug 27

<210> SEQ ID NO 774
<211> LENGTH: 27
<212> TYPE: RNA

<213> ORGANISM: Artificial Sequence
<220> FEATURE:
<223> OTHER INFORMATION: Synthetic

<400> SEQUENCE: 774
uuagcuuuag caaggcaaua ucugcuu 27

<210> SEQ ID NO 775
<211> LENGTH: 27
<212> TYPE: RNA
<213> ORGANISM: Artificial Sequence
<220> FEATURE:
<223> OTHER INFORMATION: Synthetic

<400> SEQUENCE: 775
cuuaguuuua gcaaggcaau aucugcu 27

<210> SEQ ID NO 776
<211> LENGTH: 27
<212> TYPE: RNA
<213> ORGANISM: Artificial Sequence
<220> FEATURE:
<223> OTHER INFORMATION: Synthetic

<400> SEQUENCE: 776
gcuuaucuuu agcaaggcaa uaucugc 27

<210> SEQ ID NO 777
<211> LENGTH: 27
<212> TYPE: RNA
<213> ORGANISM: Artificial Sequence
<220> FEATURE:
<223> OTHER INFORMATION: Synthetic

<400> SEQUENCE: 777
ugcuuugcuu uagcaaggca auaucug 27

<210> SEQ ID NO 778
<211> LENGTH: 27
<212> TYPE: RNA
<213> ORGANISM: Artificial Sequence
<220> FEATURE:
<223> OTHER INFORMATION: Synthetic

<400> SEQUENCE: 778
cugcuuagcu uuagcaaggc aauaucu 27

<210> SEQ ID NO 779
<211> LENGTH: 27
<212> TYPE: RNA
<213> ORGANISM: Artificial Sequence
<220> FEATURE:
<223> OTHER INFORMATION: Synthetic

<400> SEQUENCE: 779
ccugcuuagc uuuagcaagg caauauc 27

<210> SEQ ID NO 780
<211> LENGTH: 27
<212> TYPE: RNA
<213> ORGANISM: Artificial Sequence
<220> FEATURE:
<223> OTHER INFORMATION: Synthetic

<400> SEQUENCE: 780
gcugguauua cuuugucagu gaugacg 27

<210> SEQ ID NO 781
<211> LENGTH: 27
<212> TYPE: RNA
<213> ORGANISM: Artificial Sequence
<220> FEATURE:
<223> OTHER INFORMATION: Synthetic

<400> SEQUENCE: 781
cagccuguga uguaacauuc aguccug 27

<210> SEQ ID NO 782
<211> LENGTH: 27
<212> TYPE: RNA
<213> ORGANISM: Artificial Sequence
<220> FEATURE:
<223> OTHER INFORMATION: Synthetic

<400> SEQUENCE: 782
ccagcuagug auguaacauu caguccu 27

<210> SEQ ID NO 783
<211> LENGTH: 27
<212> TYPE: RNA
<213> ORGANISM: Artificial Sequence
<220> FEATURE:
<223> OTHER INFORMATION: Synthetic

<400> SEQUENCE: 783
cccagucagu gauguaacau ucagucc 27

<210> SEQ ID NO 784
<211> LENGTH: 27
<212> TYPE: RNA
<213> ORGANISM: Artificial Sequence
<220> FEATURE:
<223> OTHER INFORMATION: Synthetic

<400> SEQUENCE: 784
ccccauccag ugauguaaca uucaguc 27

<210> SEQ ID NO 785
<211> LENGTH: 27
<212> TYPE: RNA
<213> ORGANISM: Artificial Sequence
<220> FEATURE:
<223> OTHER INFORMATION: Synthetic

<400> SEQUENCE: 785
uccccugcca gugauguaac auucagu 27

<210> SEQ ID NO 786
<211> LENGTH: 27
<212> TYPE: RNA
<213> ORGANISM: Artificial Sequence
<220> FEATURE:
<223> OTHER INFORMATION: Synthetic

<400> SEQUENCE: 786
ucuccucagc cagugaugua acauuca 27

<210> SEQ ID NO 787
<211> LENGTH: 27
<212> TYPE: RNA
<213> ORGANISM: Artificial Sequence
<220> FEATURE:

<223> OTHER INFORMATION: Synthetic

<400> SEQUENCE: 787
cagucucaaa gguaccuugg guuucuc 27

<210> SEQ ID NO 788
<211> LENGTH: 22
<212> TYPE: RNA
<213> ORGANISM: Artificial Sequence
<220> FEATURE:
<223> OTHER INFORMATION: Synthetic

<400> SEQUENCE: 788
uuuccuguga caguggugga gg 22

<210> SEQ ID NO 789
<211> LENGTH: 22
<212> TYPE: RNA
<213> ORGANISM: Artificial Sequence
<220> FEATURE:
<223> OTHER INFORMATION: Synthetic

<400> SEQUENCE: 789
uauaacucug uccauuacca gg 22

<210> SEQ ID NO 790
<211> LENGTH: 22
<212> TYPE: RNA
<213> ORGANISM: Artificial Sequence
<220> FEATURE:
<223> OTHER INFORMATION: Synthetic

<400> SEQUENCE: 790
uaucguguca gguugcagua gg 22

<210> SEQ ID NO 791
<211> LENGTH: 22
<212> TYPE: RNA
<213> ORGANISM: Artificial Sequence
<220> FEATURE:
<223> OTHER INFORMATION: Synthetic

<400> SEQUENCE: 791
uaccaagcuu ggcaaguucu gg 22

<210> SEQ ID NO 792
<211> LENGTH: 22
<212> TYPE: RNA
<213> ORGANISM: Artificial Sequence
<220> FEATURE:
<223> OTHER INFORMATION: Synthetic

<400> SEQUENCE: 792
uugaccaagc uuggcaaguu gg 22

<210> SEQ ID NO 793
<211> LENGTH: 22
<212> TYPE: RNA
<213> ORGANISM: Artificial Sequence
<220> FEATURE:
<223> OTHER INFORMATION: Synthetic

<400> SEQUENCE: 793
uagaugacca agcuuggcaa gg 22

<210> SEQ ID NO 794
<211> LENGTH: 22
<212> TYPE: RNA
<213> ORGANISM: Artificial Sequence
<220> FEATURE:
<223> OTHER INFORMATION: Synthetic

<400> SEQUENCE: 794
uccucgauaa cucuguccau gg 22

<210> SEQ ID NO 795
<211> LENGTH: 22
<212> TYPE: RNA
<213> ORGANISM: Artificial Sequence
<220> FEATURE:
<223> OTHER INFORMATION: Synthetic

<400> SEQUENCE: 795
ugccucgaua acucugucca gg 22

<210> SEQ ID NO 796
<211> LENGTH: 22
<212> TYPE: RNA
<213> ORGANISM: Artificial Sequence
<220> FEATURE:
<223> OTHER INFORMATION: Synthetic

<400> SEQUENCE: 796
ugugguauca uagaugacca gg 22

<210> SEQ ID NO 797
<211> LENGTH: 22
<212> TYPE: RNA
<213> ORGANISM: Artificial Sequence
<220> FEATURE:
<223> OTHER INFORMATION: Synthetic

<400> SEQUENCE: 797
uaaucuggau uccugcagua gg 22

<210> SEQ ID NO 798
<211> LENGTH: 22
<212> TYPE: RNA
<213> ORGANISM: Artificial Sequence
<220> FEATURE:
<223> OTHER INFORMATION: Synthetic

<400> SEQUENCE: 798
uaugcuucca ggacauuucu gg 22

<210> SEQ ID NO 799
<211> LENGTH: 22
<212> TYPE: RNA
<213> ORGANISM: Artificial Sequence
<220> FEATURE:
<223> OTHER INFORMATION: Synthetic

<400> SEQUENCE: 799
uuggauaaua uucuguuguc gg 22

<210> SEQ ID NO 800
<211> LENGTH: 22
<212> TYPE: RNA
<213> ORGANISM: Artificial Sequence
<220> FEATURE:
<223> OTHER INFORMATION: Synthetic

<400> SEQUENCE: 800
uccuugauaa cucuguccau gg 22

<210> SEQ ID NO 801
<211> LENGTH: 22
<212> TYPE: RNA
<213> ORGANISM: Artificial Sequence
<220> FEATURE:
<223> OTHER INFORMATION: Synthetic

<400> SEQUENCE: 801
uuggauaaua uucuguuguc gg 22

<210> SEQ ID NO 802
<211> LENGTH: 22
<212> TYPE: RNA
<213> ORGANISM: Artificial Sequence
<220> FEATURE:
<223> OTHER INFORMATION: Synthetic

<400> SEQUENCE: 802
uccuugauaa cucuguccau gg 22

<210> SEQ ID NO 803
<211> LENGTH: 22
<212> TYPE: RNA
<213> ORGANISM: Artificial Sequence
<220> FEATURE:
<223> OTHER INFORMATION: Synthetic

<400> SEQUENCE: 803
uuggauaaua uucuguuguc gg 22

<210> SEQ ID NO 804
<211> LENGTH: 19
<212> TYPE: RNA
<213> ORGANISM: Artificial Sequence
<220> FEATURE:
<223> OTHER INFORMATION: Synthetic

<400> SEQUENCE: 804
cugagcaaag ccauguggu 19

<210> SEQ ID NO 805
<211> LENGTH: 19
<212> TYPE: RNA
<213> ORGANISM: Artificial Sequence
<220> FEATURE:
<223> OTHER INFORMATION: Synthetic

<400> SEQUENCE: 805
agcaaagcca uguggucca 19

<210> SEQ ID NO 806
<211> LENGTH: 19
<212> TYPE: RNA
<213> ORGANISM: Artificial Sequence
<220> FEATURE:
<223> OTHER INFORMATION: Synthetic

<400> SEQUENCE: 806
aagccaugug guccaggau 19

<210> SEQ ID NO 807
<211> LENGTH: 19

<212> TYPE: RNA
<213> ORGANISM: Artificial Sequence
<220> FEATURE:
<223> OTHER INFORMATION: Synthetic

<400> SEQUENCE: 807
agccaugugg uccaggauu 19

<210> SEQ ID NO 808
<211> LENGTH: 19
<212> TYPE: RNA
<213> ORGANISM: Artificial Sequence
<220> FEATURE:
<223> OTHER INFORMATION: Synthetic

<400> SEQUENCE: 808
gccauguggu ccaggauug 19

<210> SEQ ID NO 809
<211> LENGTH: 19
<212> TYPE: RNA
<213> ORGANISM: Artificial Sequence
<220> FEATURE:
<223> OTHER INFORMATION: Synthetic

<400> SEQUENCE: 809
ccaugugguc caggauugc 19

<210> SEQ ID NO 810
<211> LENGTH: 19
<212> TYPE: RNA
<213> ORGANISM: Artificial Sequence
<220> FEATURE:
<223> OTHER INFORMATION: Synthetic

<400> SEQUENCE: 810
cauguggucc aggauugcu 19

<210> SEQ ID NO 811
<211> LENGTH: 19
<212> TYPE: RNA
<213> ORGANISM: Artificial Sequence
<220> FEATURE:
<223> OTHER INFORMATION: Synthetic

<400> SEQUENCE: 811
augugaucca ggauugcua 19

<210> SEQ ID NO 812
<211> LENGTH: 19
<212> TYPE: RNA
<213> ORGANISM: Artificial Sequence
<220> FEATURE:
<223> OTHER INFORMATION: Synthetic

<400> SEQUENCE: 812
ugugguccag gauugcuac 19

<210> SEQ ID NO 813
<211> LENGTH: 19
<212> TYPE: RNA
<213> ORGANISM: Artificial Sequence
<220> FEATURE:
<223> OTHER INFORMATION: Synthetic

<400> SEQUENCE: 813
ggugauggac agaguuauc 19

<210> SEQ ID NO 814
<211> LENGTH: 19
<212> TYPE: RNA
<213> ORGANISM: Artificial Sequence
<220> FEATURE:
<223> OTHER INFORMATION: Synthetic

<400> SEQUENCE: 814
uccaccacug ucacaggaa 19

<210> SEQ ID NO 815
<211> LENGTH: 19
<212> TYPE: RNA
<213> ORGANISM: Artificial Sequence
<220> FEATURE:
<223> OTHER INFORMATION: Synthetic

<400> SEQUENCE: 815
ccaccacugu cacaggaag 19

<210> SEQ ID NO 816
<211> LENGTH: 19
<212> TYPE: RNA
<213> ORGANISM: Artificial Sequence
<220> FEATURE:
<223> OTHER INFORMATION: Synthetic

<400> SEQUENCE: 816
cugucacagg aaggaccug 19

<210> SEQ ID NO 817
<211> LENGTH: 19
<212> TYPE: RNA
<213> ORGANISM: Artificial Sequence
<220> FEATURE:
<223> OTHER INFORMATION: Synthetic

<400> SEQUENCE: 817
ggaaggaccu gccaagcuu 19

<210> SEQ ID NO 818
<211> LENGTH: 19
<212> TYPE: RNA
<213> ORGANISM: Artificial Sequence
<220> FEATURE:
<223> OTHER INFORMATION: Synthetic

<400> SEQUENCE: 818
gaaggaccug ccaagcuug 19

<210> SEQ ID NO 819
<211> LENGTH: 19
<212> TYPE: RNA
<213> ORGANISM: Artificial Sequence
<220> FEATURE:
<223> OTHER INFORMATION: Synthetic

<400> SEQUENCE: 819
aggaccugcc aagcuuggu 19

<210> SEQ ID NO 820
<211> LENGTH: 19
<212> TYPE: RNA
<213> ORGANISM: Artificial Sequence
<220> FEATURE:
<223> OTHER INFORMATION: Synthetic

<400> SEQUENCE: 820
ggaccugcca agcuugguc 19

<210> SEQ ID NO 821
<211> LENGTH: 19
<212> TYPE: RNA
<213> ORGANISM: Artificial Sequence
<220> FEATURE:
<223> OTHER INFORMATION: Synthetic

<400> SEQUENCE: 821
gaccugccaa gcuugguca 19

<210> SEQ ID NO 822
<211> LENGTH: 19
<212> TYPE: RNA
<213> ORGANISM: Artificial Sequence
<220> FEATURE:
<223> OTHER INFORMATION: Synthetic

<400> SEQUENCE: 822
accugccaag cuuggucau 19

<210> SEQ ID NO 823
<211> LENGTH: 19
<212> TYPE: RNA
<213> ORGANISM: Artificial Sequence
<220> FEATURE:
<223> OTHER INFORMATION: Synthetic

<400> SEQUENCE: 823
ccugccaagc uuggucauc 19

<210> SEQ ID NO 824
<211> LENGTH: 19
<212> TYPE: RNA
<213> ORGANISM: Artificial Sequence
<220> FEATURE:
<223> OTHER INFORMATION: Synthetic

<400> SEQUENCE: 824
agcuugguca ucuaugaca 19

<210> SEQ ID NO 825
<211> LENGTH: 19
<212> TYPE: RNA
<213> ORGANISM: Artificial Sequence
<220> FEATURE:
<223> OTHER INFORMATION: Synthetic

<400> SEQUENCE: 825
gucaucuaug acaccacau 19

<210> SEQ ID NO 826
<211> LENGTH: 19
<212> TYPE: RNA
<213> ORGANISM: Artificial Sequence
<220> FEATURE:
<223> OTHER INFORMATION: Synthetic

<400> SEQUENCE: 826
cacagaaaac uacccaaau 19

-continued

<210> SEQ ID NO 827
<211> LENGTH: 19
<212> TYPE: RNA
<213> ORGANISM: Artificial Sequence
<220> FEATURE:
<223> OTHER INFORMATION: Synthetic

<400> SEQUENCE: 827
agaaaacuac ccaaaugcu 19

<210> SEQ ID NO 828
<211> LENGTH: 19
<212> TYPE: RNA
<213> ORGANISM: Artificial Sequence
<220> FEATURE:
<223> OTHER INFORMATION: Synthetic

<400> SEQUENCE: 828
aaaacuaccc aaaugcugg 19

<210> SEQ ID NO 829
<211> LENGTH: 19
<212> TYPE: RNA
<213> ORGANISM: Artificial Sequence
<220> FEATURE:
<223> OTHER INFORMATION: Synthetic

<400> SEQUENCE: 829
acccaaaugc uggcuugau 19

<210> SEQ ID NO 830
<211> LENGTH: 19
<212> TYPE: RNA
<213> ORGANISM: Artificial Sequence
<220> FEATURE:
<223> OTHER INFORMATION: Synthetic

<400> SEQUENCE: 830
cccaaaugcu ggcuugauc 19

<210> SEQ ID NO 831
<211> LENGTH: 19
<212> TYPE: RNA
<213> ORGANISM: Artificial Sequence
<220> FEATURE:
<223> OTHER INFORMATION: Synthetic

<400> SEQUENCE: 831
gaacuacugc aggaaucca 19

<210> SEQ ID NO 832
<211> LENGTH: 19
<212> TYPE: RNA
<213> ORGANISM: Artificial Sequence
<220> FEATURE:
<223> OTHER INFORMATION: Synthetic

<400> SEQUENCE: 832
uacugcagga auccagaug 19

<210> SEQ ID NO 833
<211> LENGTH: 19
<212> TYPE: RNA
<213> ORGANISM: Artificial Sequence
<220> FEATURE:
<223> OTHER INFORMATION: Synthetic

<400> SEQUENCE: 833
acugcaggaa uccagaugc 19

<210> SEQ ID NO 834
<211> LENGTH: 19
<212> TYPE: RNA
<213> ORGANISM: Artificial Sequence
<220> FEATURE:
<223> OTHER INFORMATION: Synthetic

<400> SEQUENCE: 834
ugcaggaauc cagaugcug 19

<210> SEQ ID NO 835
<211> LENGTH: 19
<212> TYPE: RNA
<213> ORGANISM: Artificial Sequence
<220> FEATURE:
<223> OTHER INFORMATION: Synthetic

<400> SEQUENCE: 835
aggugggagu acugcaacc 19

<210> SEQ ID NO 836
<211> LENGTH: 19
<212> TYPE: RNA
<213> ORGANISM: Artificial Sequence
<220> FEATURE:
<223> OTHER INFORMATION: Synthetic

<400> SEQUENCE: 836
aaugcucaga cgcagaagg 19

<210> SEQ ID NO 837
<211> LENGTH: 19
<212> TYPE: RNA
<213> ORGANISM: Artificial Sequence
<220> FEATURE:
<223> OTHER INFORMATION: Synthetic

<400> SEQUENCE: 837
gacuguuacc ccgguucca 19

<210> SEQ ID NO 838
<211> LENGTH: 19
<212> TYPE: RNA
<213> ORGANISM: Artificial Sequence
<220> FEATURE:
<223> OTHER INFORMATION: Synthetic

<400> SEQUENCE: 838
acuguuaccc cgguuccaa 19

<210> SEQ ID NO 839
<211> LENGTH: 19
<212> TYPE: RNA
<213> ORGANISM: Artificial Sequence
<220> FEATURE:
<223> OTHER INFORMATION: Synthetic

<400> SEQUENCE: 839
cuguuacccc gguuccaag 19

<210> SEQ ID NO 840

<211> LENGTH: 19
<212> TYPE: RNA
<213> ORGANISM: Artificial Sequence
<220> FEATURE:
<223> OTHER INFORMATION: Synthetic

<400> SEQUENCE: 840
uguuaccccg guuccaagc 19

<210> SEQ ID NO 841
<211> LENGTH: 19
<212> TYPE: RNA
<213> ORGANISM: Artificial Sequence
<220> FEATURE:
<223> OTHER INFORMATION: Synthetic

<400> SEQUENCE: 841
guuaccccgg uuccaagcc 19

<210> SEQ ID NO 842
<211> LENGTH: 19
<212> TYPE: RNA
<213> ORGANISM: Artificial Sequence
<220> FEATURE:
<223> OTHER INFORMATION: Synthetic

<400> SEQUENCE: 842
uuaccccggu uccaagccu 19

<210> SEQ ID NO 843
<211> LENGTH: 19
<212> TYPE: RNA
<213> ORGANISM: Artificial Sequence
<220> FEATURE:
<223> OTHER INFORMATION: Synthetic

<400> SEQUENCE: 843
uaccccgguu ccaagccua 19

<210> SEQ ID NO 844
<211> LENGTH: 19
<212> TYPE: RNA
<213> ORGANISM: Artificial Sequence
<220> FEATURE:
<223> OTHER INFORMATION: Synthetic

<400> SEQUENCE: 844
gugcuaccau gguaaugga 19

<210> SEQ ID NO 845
<211> LENGTH: 19
<212> TYPE: RNA
<213> ORGANISM: Artificial Sequence
<220> FEATURE:
<223> OTHER INFORMATION: Synthetic

<400> SEQUENCE: 845
ugcuaccaug guaauggac 19

<210> SEQ ID NO 846
<211> LENGTH: 19
<212> TYPE: RNA
<213> ORGANISM: Artificial Sequence
<220> FEATURE:
<223> OTHER INFORMATION: Synthetic

<400> SEQUENCE: 846
gcuaccaugg uaauggaca 19

<210> SEQ ID NO 847
<211> LENGTH: 19
<212> TYPE: RNA
<213> ORGANISM: Artificial Sequence
<220> FEATURE:
<223> OTHER INFORMATION: Synthetic

<400> SEQUENCE: 847
cuaccauggu aauggacag 19

<210> SEQ ID NO 848
<211> LENGTH: 19
<212> TYPE: RNA
<213> ORGANISM: Artificial Sequence
<220> FEATURE:
<223> OTHER INFORMATION: Synthetic

<400> SEQUENCE: 848
uaccauggua auggacaga 19

<210> SEQ ID NO 849
<211> LENGTH: 19
<212> TYPE: RNA
<213> ORGANISM: Artificial Sequence
<220> FEATURE:
<223> OTHER INFORMATION: Synthetic

<400> SEQUENCE: 849
accaugguaa uggacagag 19

<210> SEQ ID NO 850
<211> LENGTH: 19
<212> TYPE: RNA
<213> ORGANISM: Artificial Sequence
<220> FEATURE:
<223> OTHER INFORMATION: Synthetic

<400> SEQUENCE: 850
ccaugguaau ggacagagu 19

<210> SEQ ID NO 851
<211> LENGTH: 19
<212> TYPE: RNA
<213> ORGANISM: Artificial Sequence
<220> FEATURE:
<223> OTHER INFORMATION: Synthetic

<400> SEQUENCE: 851
caugguaaug gacagaguu 19

<210> SEQ ID NO 852
<211> LENGTH: 19
<212> TYPE: RNA
<213> ORGANISM: Artificial Sequence
<220> FEATURE:
<223> OTHER INFORMATION: Synthetic

<400> SEQUENCE: 852
augguaaugg acagaguua 19

<210> SEQ ID NO 853
<211> LENGTH: 19
<212> TYPE: RNA

-continued

<213> ORGANISM: Artificial Sequence
<220> FEATURE:
<223> OTHER INFORMATION: Synthetic

<400> SEQUENCE: 853
ugguaaugga cagaguuau 19

<210> SEQ ID NO 854
<211> LENGTH: 19
<212> TYPE: RNA
<213> ORGANISM: Artificial Sequence
<220> FEATURE:
<223> OTHER INFORMATION: Synthetic

<400> SEQUENCE: 854
gguaauggac agaguuauc 19

<210> SEQ ID NO 855
<211> LENGTH: 19
<212> TYPE: RNA
<213> ORGANISM: Artificial Sequence
<220> FEATURE:
<223> OTHER INFORMATION: Synthetic

<400> SEQUENCE: 855
guaauggaca gaguuaucg 19

<210> SEQ ID NO 856
<211> LENGTH: 19
<212> TYPE: RNA
<213> ORGANISM: Artificial Sequence
<220> FEATURE:
<223> OTHER INFORMATION: Synthetic

<400> SEQUENCE: 856
ggcacauacu ccaccacug 19

<210> SEQ ID NO 857
<211> LENGTH: 19
<212> TYPE: RNA
<213> ORGANISM: Artificial Sequence
<220> FEATURE:
<223> OTHER INFORMATION: Synthetic

<400> SEQUENCE: 857
cuuggucauc uaugacacc 19

<210> SEQ ID NO 858
<211> LENGTH: 19
<212> TYPE: RNA
<213> ORGANISM: Artificial Sequence
<220> FEATURE:
<223> OTHER INFORMATION: Synthetic

<400> SEQUENCE: 858
gucaucuaug acaccacac 19

<210> SEQ ID NO 859
<211> LENGTH: 19
<212> TYPE: RNA
<213> ORGANISM: Artificial Sequence
<220> FEATURE:
<223> OTHER INFORMATION: Synthetic

<400> SEQUENCE: 859
ucaucuauga caccacacu 19

<210> SEQ ID NO 860
<211> LENGTH: 19
<212> TYPE: RNA
<213> ORGANISM: Artificial Sequence
<220> FEATURE:
<223> OTHER INFORMATION: Synthetic

<400> SEQUENCE: 860
caucuaugac accacacuc 19

<210> SEQ ID NO 861
<211> LENGTH: 19
<212> TYPE: RNA
<213> ORGANISM: Artificial Sequence
<220> FEATURE:
<223> OTHER INFORMATION: Synthetic

<400> SEQUENCE: 861
gcacauacuc caccacugu 19

<210> SEQ ID NO 862
<211> LENGTH: 19
<212> TYPE: RNA
<213> ORGANISM: Artificial Sequence
<220> FEATURE:
<223> OTHER INFORMATION: Synthetic

<400> SEQUENCE: 862
agccccuuau uguuauacg 19

<210> SEQ ID NO 863
<211> LENGTH: 19
<212> TYPE: RNA
<213> ORGANISM: Artificial Sequence
<220> FEATURE:
<223> OTHER INFORMATION: Synthetic

<400> SEQUENCE: 863
gccccuuauu guuauacga 19

<210> SEQ ID NO 864
<211> LENGTH: 19
<212> TYPE: RNA
<213> ORGANISM: Artificial Sequence
<220> FEATURE:
<223> OTHER INFORMATION: Synthetic

<400> SEQUENCE: 864
ccaagccuag aggcuccuu 19

<210> SEQ ID NO 865
<211> LENGTH: 19
<212> TYPE: RNA
<213> ORGANISM: Artificial Sequence
<220> FEATURE:
<223> OTHER INFORMATION: Synthetic

<400> SEQUENCE: 865
aggcuccuuc ugaacaagc 19

<210> SEQ ID NO 866
<211> LENGTH: 19
<212> TYPE: RNA
<213> ORGANISM: Artificial Sequence
<220> FEATURE:

<223> OTHER INFORMATION: Synthetic

<400> SEQUENCE: 866
auggacagag uuaucaagg 19

<210> SEQ ID NO 867
<211> LENGTH: 19
<212> TYPE: RNA
<213> ORGANISM: Artificial Sequence
<220> FEATURE:
<223> OTHER INFORMATION: Synthetic

<400> SEQUENCE: 867
uggacagagu uaucaaggc 19

<210> SEQ ID NO 868
<211> LENGTH: 19
<212> TYPE: RNA
<213> ORGANISM: Artificial Sequence
<220> FEATURE:
<223> OTHER INFORMATION: Synthetic

<400> SEQUENCE: 868
ggacagaguu aucaaggca 19

<210> SEQ ID NO 869
<211> LENGTH: 19
<212> TYPE: RNA
<213> ORGANISM: Artificial Sequence
<220> FEATURE:
<223> OTHER INFORMATION: Synthetic

<400> SEQUENCE: 869
gacagaguua ucaaggcac 19

<210> SEQ ID NO 870
<211> LENGTH: 19
<212> TYPE: RNA
<213> ORGANISM: Artificial Sequence
<220> FEATURE:
<223> OTHER INFORMATION: Synthetic

<400> SEQUENCE: 870
acagaguuau caaggcaca 19

<210> SEQ ID NO 871
<211> LENGTH: 19
<212> TYPE: RNA
<213> ORGANISM: Artificial Sequence
<220> FEATURE:
<223> OTHER INFORMATION: Synthetic

<400> SEQUENCE: 871
cagaguuauc aaggcacau 19

<210> SEQ ID NO 872
<211> LENGTH: 19
<212> TYPE: RNA
<213> ORGANISM: Artificial Sequence
<220> FEATURE:
<223> OTHER INFORMATION: Synthetic

<400> SEQUENCE: 872
uacccaaaug cuggcuuga 19

<210> SEQ ID NO 873
<211> LENGTH: 19
<212> TYPE: RNA
<213> ORGANISM: Artificial Sequence
<220> FEATURE:
<223> OTHER INFORMATION: Synthetic

<400> SEQUENCE: 873
ccaaaugcug gcuugauca 19

<210> SEQ ID NO 874
<211> LENGTH: 19
<212> TYPE: RNA
<213> ORGANISM: Artificial Sequence
<220> FEATURE:
<223> OTHER INFORMATION: Synthetic

<400> SEQUENCE: 874
ucaagaacua cugccgaaa 19

<210> SEQ ID NO 875
<211> LENGTH: 19
<212> TYPE: RNA
<213> ORGANISM: Artificial Sequence
<220> FEATURE:
<223> OTHER INFORMATION: Synthetic

<400> SEQUENCE: 875
caagaacuac ugccgaaau 19

<210> SEQ ID NO 876
<211> LENGTH: 19
<212> TYPE: RNA
<213> ORGANISM: Artificial Sequence
<220> FEATURE:
<223> OTHER INFORMATION: Synthetic

<400> SEQUENCE: 876
aagaacuacu gccgaaauc 19

<210> SEQ ID NO 877
<211> LENGTH: 19
<212> TYPE: RNA
<213> ORGANISM: Artificial Sequence
<220> FEATURE:
<223> OTHER INFORMATION: Synthetic

<400> SEQUENCE: 877
gaacuacugc cgaaaucca 19

<210> SEQ ID NO 878
<211> LENGTH: 19
<212> TYPE: RNA
<213> ORGANISM: Artificial Sequence
<220> FEATURE:
<223> OTHER INFORMATION: Synthetic

<400> SEQUENCE: 878
cuacugccga aauccagau 19

<210> SEQ ID NO 879
<211> LENGTH: 19
<212> TYPE: RNA
<213> ORGANISM: Artificial Sequence
<220> FEATURE:
<223> OTHER INFORMATION: Synthetic

<400> SEQUENCE: 879
uguggcagcc ccuuggugu 19

<210> SEQ ID NO 880
<211> LENGTH: 19
<212> TYPE: RNA
<213> ORGANISM: Artificial Sequence
<220> FEATURE:
<223> OTHER INFORMATION: Synthetic

<400> SEQUENCE: 880
guggcagccc cuugguguu 19

<210> SEQ ID NO 881
<211> LENGTH: 19
<212> TYPE: RNA
<213> ORGANISM: Artificial Sequence
<220> FEATURE:
<223> OTHER INFORMATION: Synthetic

<400> SEQUENCE: 881
uggcagcccc uugguguua 19

<210> SEQ ID NO 882
<211> LENGTH: 19
<212> TYPE: RNA
<213> ORGANISM: Artificial Sequence
<220> FEATURE:
<223> OTHER INFORMATION: Synthetic

<400> SEQUENCE: 882
ggcagccccu ugguguuau 19

<210> SEQ ID NO 883
<211> LENGTH: 19
<212> TYPE: RNA
<213> ORGANISM: Artificial Sequence
<220> FEATURE:
<223> OTHER INFORMATION: Synthetic

<400> SEQUENCE: 883
gcagccccuu gguguuaua 19

<210> SEQ ID NO 884
<211> LENGTH: 19
<212> TYPE: RNA
<213> ORGANISM: Artificial Sequence
<220> FEATURE:
<223> OTHER INFORMATION: Synthetic

<400> SEQUENCE: 884
cagccccuug guguuauac 19

<210> SEQ ID NO 885
<211> LENGTH: 19
<212> TYPE: RNA
<213> ORGANISM: Artificial Sequence
<220> FEATURE:
<223> OTHER INFORMATION: Synthetic

<400> SEQUENCE: 885
agccccuugg uguuauaca 19

<210> SEQ ID NO 886
<211> LENGTH: 19

<212> TYPE: RNA
<213> ORGANISM: Artificial Sequence
<220> FEATURE:
<223> OTHER INFORMATION: Synthetic

<400> SEQUENCE: 886
gccccuuggu guuauacaa 19

<210> SEQ ID NO 887
<211> LENGTH: 19
<212> TYPE: RNA
<213> ORGANISM: Artificial Sequence
<220> FEATURE:
<223> OTHER INFORMATION: Synthetic

<400> SEQUENCE: 887
ccccuuggug uuauacaac 19

<210> SEQ ID NO 888
<211> LENGTH: 19
<212> TYPE: RNA
<213> ORGANISM: Artificial Sequence
<220> FEATURE:
<223> OTHER INFORMATION: Synthetic

<400> SEQUENCE: 888
ggugggagua cugcaaccu 19

<210> SEQ ID NO 889
<211> LENGTH: 19
<212> TYPE: RNA
<213> ORGANISM: Artificial Sequence
<220> FEATURE:
<223> OTHER INFORMATION: Synthetic

<400> SEQUENCE: 889
gugggaguac ugcaaccug 19

<210> SEQ ID NO 890
<211> LENGTH: 19
<212> TYPE: RNA
<213> ORGANISM: Artificial Sequence
<220> FEATURE:
<223> OTHER INFORMATION: Synthetic

<400> SEQUENCE: 890
ggaguacugc aaccugaca 19

<210> SEQ ID NO 891
<211> LENGTH: 19
<212> TYPE: RNA
<213> ORGANISM: Artificial Sequence
<220> FEATURE:
<223> OTHER INFORMATION: Synthetic

<400> SEQUENCE: 891
gaguacugca accugacac 19

<210> SEQ ID NO 892
<211> LENGTH: 19
<212> TYPE: RNA
<213> ORGANISM: Artificial Sequence
<220> FEATURE:
<223> OTHER INFORMATION: Synthetic

<400> SEQUENCE: 892
guacugcaac cugacacga 19

<210> SEQ ID NO 893
<211> LENGTH: 19
<212> TYPE: RNA
<213> ORGANISM: Artificial Sequence
<220> FEATURE:
<223> OTHER INFORMATION: Synthetic

<400> SEQUENCE: 893
uacugcaacc ugacacgau 19

<210> SEQ ID NO 894
<211> LENGTH: 19
<212> TYPE: RNA
<213> ORGANISM: Artificial Sequence
<220> FEATURE:
<223> OTHER INFORMATION: Synthetic

<400> SEQUENCE: 894
acugcaaccu gacacgaug 19

<210> SEQ ID NO 895
<211> LENGTH: 19
<212> TYPE: RNA
<213> ORGANISM: Artificial Sequence
<220> FEATURE:
<223> OTHER INFORMATION: Synthetic

<400> SEQUENCE: 895
cugcaaccug acacgaugc 19

<210> SEQ ID NO 896
<211> LENGTH: 19
<212> TYPE: RNA
<213> ORGANISM: Artificial Sequence
<220> FEATURE:
<223> OTHER INFORMATION: Synthetic

<400> SEQUENCE: 896
ugcaaccuga cacgaugcu 19

<210> SEQ ID NO 897
<211> LENGTH: 19
<212> TYPE: RNA
<213> ORGANISM: Artificial Sequence
<220> FEATURE:
<223> OTHER INFORMATION: Synthetic

<400> SEQUENCE: 897
caaccugaca cgaugcuca 19

<210> SEQ ID NO 898
<211> LENGTH: 19
<212> TYPE: RNA
<213> ORGANISM: Artificial Sequence
<220> FEATURE:
<223> OTHER INFORMATION: Synthetic

<400> SEQUENCE: 898
accugacacg augcucaga 19

<210> SEQ ID NO 899
<211> LENGTH: 19
<212> TYPE: RNA
<213> ORGANISM: Artificial Sequence
<220> FEATURE:
<223> OTHER INFORMATION: Synthetic

<400> SEQUENCE: 899
ccugacacga ugcucagau 19

<210> SEQ ID NO 900
<211> LENGTH: 19
<212> TYPE: RNA
<213> ORGANISM: Artificial Sequence
<220> FEATURE:
<223> OTHER INFORMATION: Synthetic

<400> SEQUENCE: 900
cugacacgau gcucagaug 19

<210> SEQ ID NO 901
<211> LENGTH: 19
<212> TYPE: RNA
<213> ORGANISM: Artificial Sequence
<220> FEATURE:
<223> OTHER INFORMATION: Synthetic

<400> SEQUENCE: 901
ugacacgaug cucagaugc 19

<210> SEQ ID NO 902
<211> LENGTH: 19
<212> TYPE: RNA
<213> ORGANISM: Artificial Sequence
<220> FEATURE:
<223> OTHER INFORMATION: Synthetic

<400> SEQUENCE: 902
gacacgaugc ucagaugca 19

<210> SEQ ID NO 903
<211> LENGTH: 19
<212> TYPE: RNA
<213> ORGANISM: Artificial Sequence
<220> FEATURE:
<223> OTHER INFORMATION: Synthetic

<400> SEQUENCE: 903
acacgaugcu cagaugcag 19

<210> SEQ ID NO 904
<211> LENGTH: 19
<212> TYPE: RNA
<213> ORGANISM: Artificial Sequence
<220> FEATURE:
<223> OTHER INFORMATION: Synthetic

<400> SEQUENCE: 904
cacgaugcuc agaugcaga 19

<210> SEQ ID NO 905
<211> LENGTH: 19
<212> TYPE: RNA
<213> ORGANISM: Artificial Sequence
<220> FEATURE:
<223> OTHER INFORMATION: Synthetic

<400> SEQUENCE: 905
ugcuacuacc auuauggac 19

-continued

<210> SEQ ID NO 906
<211> LENGTH: 19
<212> TYPE: RNA
<213> ORGANISM: Artificial Sequence
<220> FEATURE:
<223> OTHER INFORMATION: Synthetic

<400> SEQUENCE: 906
gcuacuacca uuauggaca 19

<210> SEQ ID NO 907
<211> LENGTH: 19
<212> TYPE: RNA
<213> ORGANISM: Artificial Sequence
<220> FEATURE:
<223> OTHER INFORMATION: Synthetic

<400> SEQUENCE: 907
cuacuaccau uauggacag 19

<210> SEQ ID NO 908
<211> LENGTH: 19
<212> TYPE: RNA
<213> ORGANISM: Artificial Sequence
<220> FEATURE:
<223> OTHER INFORMATION: Synthetic

<400> SEQUENCE: 908
uacuaccauu auggacaga 19

<210> SEQ ID NO 909
<211> LENGTH: 19
<212> TYPE: RNA
<213> ORGANISM: Artificial Sequence
<220> FEATURE:
<223> OTHER INFORMATION: Synthetic

<400> SEQUENCE: 909
acuaccauua uggacagag 19

<210> SEQ ID NO 910
<211> LENGTH: 19
<212> TYPE: RNA
<213> ORGANISM: Artificial Sequence
<220> FEATURE:
<223> OTHER INFORMATION: Synthetic

<400> SEQUENCE: 910
cuaccauuau ggacagagu 19

<210> SEQ ID NO 911
<211> LENGTH: 19
<212> TYPE: RNA
<213> ORGANISM: Artificial Sequence
<220> FEATURE:
<223> OTHER INFORMATION: Synthetic

<400> SEQUENCE: 911
uaccauuaug gacagaguu 19

<210> SEQ ID NO 912
<211> LENGTH: 19
<212> TYPE: RNA
<213> ORGANISM: Artificial Sequence
<220> FEATURE:
<223> OTHER INFORMATION: Synthetic

<400> SEQUENCE: 912
accauuaugg acagaguua 19

<210> SEQ ID NO 913
<211> LENGTH: 19
<212> TYPE: RNA
<213> ORGANISM: Artificial Sequence
<220> FEATURE:
<223> OTHER INFORMATION: Synthetic

<400> SEQUENCE: 913
gaggcacaua cuccaccac 19

<210> SEQ ID NO 914
<211> LENGTH: 19
<212> TYPE: RNA
<213> ORGANISM: Artificial Sequence
<220> FEATURE:
<223> OTHER INFORMATION: Synthetic

<400> SEQUENCE: 914
cuccaccacu gucacagga 19

<210> SEQ ID NO 915
<211> LENGTH: 19
<212> TYPE: RNA
<213> ORGANISM: Artificial Sequence
<220> FEATURE:
<223> OTHER INFORMATION: Synthetic

<400> SEQUENCE: 915
acaggaagaa cuugccaag 19

<210> SEQ ID NO 916
<211> LENGTH: 19
<212> TYPE: RNA
<213> ORGANISM: Artificial Sequence
<220> FEATURE:
<223> OTHER INFORMATION: Synthetic

<400> SEQUENCE: 916
caggaagaac uugccaagc 19

<210> SEQ ID NO 917
<211> LENGTH: 19
<212> TYPE: RNA
<213> ORGANISM: Artificial Sequence
<220> FEATURE:
<223> OTHER INFORMATION: Synthetic

<400> SEQUENCE: 917
aggaagaacu ugccaagcu 19

<210> SEQ ID NO 918
<211> LENGTH: 19
<212> TYPE: RNA
<213> ORGANISM: Artificial Sequence
<220> FEATURE:
<223> OTHER INFORMATION: Synthetic

<400> SEQUENCE: 918
ggaagaacuu gccaagcuu 19

<210> SEQ ID NO 919

<211> LENGTH: 19
<212> TYPE: RNA
<213> ORGANISM: Artificial Sequence
<220> FEATURE:
<223> OTHER INFORMATION: Synthetic

<400> SEQUENCE: 919
gaagaacuug ccaagcuug 19

<210> SEQ ID NO 920
<211> LENGTH: 19
<212> TYPE: RNA
<213> ORGANISM: Artificial Sequence
<220> FEATURE:
<223> OTHER INFORMATION: Synthetic

<400> SEQUENCE: 920
aagaacuugc caagcuugg 19

<210> SEQ ID NO 921
<211> LENGTH: 19
<212> TYPE: RNA
<213> ORGANISM: Artificial Sequence
<220> FEATURE:
<223> OTHER INFORMATION: Synthetic

<400> SEQUENCE: 921
agaacuugcc aagcuuggu 19

<210> SEQ ID NO 922
<211> LENGTH: 19
<212> TYPE: RNA
<213> ORGANISM: Artificial Sequence
<220> FEATURE:
<223> OTHER INFORMATION: Synthetic

<400> SEQUENCE: 922
gaacuugcca agcuugguc 19

<210> SEQ ID NO 923
<211> LENGTH: 19
<212> TYPE: RNA
<213> ORGANISM: Artificial Sequence
<220> FEATURE:
<223> OTHER INFORMATION: Synthetic

<400> SEQUENCE: 923
aacuugccaa gcuugguca 19

<210> SEQ ID NO 924
<211> LENGTH: 19
<212> TYPE: RNA
<213> ORGANISM: Artificial Sequence
<220> FEATURE:
<223> OTHER INFORMATION: Synthetic

<400> SEQUENCE: 924
acuugccaag cuuggucau 19

<210> SEQ ID NO 925
<211> LENGTH: 19
<212> TYPE: RNA
<213> ORGANISM: Artificial Sequence
<220> FEATURE:
<223> OTHER INFORMATION: Synthetic

<400> SEQUENCE: 925
cuugccaagc uuggucauc 19

<210> SEQ ID NO 926
<211> LENGTH: 19
<212> TYPE: RNA
<213> ORGANISM: Artificial Sequence
<220> FEATURE:
<223> OTHER INFORMATION: Synthetic

<400> SEQUENCE: 926
uugccaagcu uggucaucu 19

<210> SEQ ID NO 927
<211> LENGTH: 19
<212> TYPE: RNA
<213> ORGANISM: Artificial Sequence
<220> FEATURE:
<223> OTHER INFORMATION: Synthetic

<400> SEQUENCE: 927
ugccaagcuu ggucaucua 19

<210> SEQ ID NO 928
<211> LENGTH: 19
<212> TYPE: RNA
<213> ORGANISM: Artificial Sequence
<220> FEATURE:
<223> OTHER INFORMATION: Synthetic

<400> SEQUENCE: 928
gcuuggucau cuaugacac 19

<210> SEQ ID NO 929
<211> LENGTH: 19
<212> TYPE: RNA
<213> ORGANISM: Artificial Sequence
<220> FEATURE:
<223> OTHER INFORMATION: Synthetic

<400> SEQUENCE: 929
uuggucaucu augacacca 19

<210> SEQ ID NO 930
<211> LENGTH: 19
<212> TYPE: RNA
<213> ORGANISM: Artificial Sequence
<220> FEATURE:
<223> OTHER INFORMATION: Synthetic

<400> SEQUENCE: 930
uggucaucua ugacaccac 19

<210> SEQ ID NO 931
<211> LENGTH: 19
<212> TYPE: RNA
<213> ORGANISM: Artificial Sequence
<220> FEATURE:
<223> OTHER INFORMATION: Synthetic

<400> SEQUENCE: 931
gucaucuaug acaccacac 19

<210> SEQ ID NO 932
<211> LENGTH: 19
<212> TYPE: RNA

<213> ORGANISM: Artificial Sequence
<220> FEATURE:
<223> OTHER INFORMATION: Synthetic

<400> SEQUENCE: 932
caucuaugac accacacca 19

<210> SEQ ID NO 933
<211> LENGTH: 19
<212> TYPE: RNA
<213> ORGANISM: Artificial Sequence
<220> FEATURE:
<223> OTHER INFORMATION: Synthetic

<400> SEQUENCE: 933
aucuaugaca ccacaccag 19

<210> SEQ ID NO 934
<211> LENGTH: 19
<212> TYPE: RNA
<213> ORGANISM: Artificial Sequence
<220> FEATURE:
<223> OTHER INFORMATION: Synthetic

<400> SEQUENCE: 934
cuaugacacc acaccagca 19

<210> SEQ ID NO 935
<211> LENGTH: 19
<212> TYPE: RNA
<213> ORGANISM: Artificial Sequence
<220> FEATURE:
<223> OTHER INFORMATION: Synthetic

<400> SEQUENCE: 935
gucggacccc agaaaacua 19

<210> SEQ ID NO 936
<211> LENGTH: 19
<212> TYPE: RNA
<213> ORGANISM: Artificial Sequence
<220> FEATURE:
<223> OTHER INFORMATION: Synthetic

<400> SEQUENCE: 936
ucggacccca gaaaacuac 19

<210> SEQ ID NO 937
<211> LENGTH: 19
<212> TYPE: RNA
<213> ORGANISM: Artificial Sequence
<220> FEATURE:
<223> OTHER INFORMATION: Synthetic

<400> SEQUENCE: 937
gaaaacuacc caaaugcug 19

<210> SEQ ID NO 938
<211> LENGTH: 19
<212> TYPE: RNA
<213> ORGANISM: Artificial Sequence
<220> FEATURE:
<223> OTHER INFORMATION: Synthetic

<400> SEQUENCE: 938
gcugagauuc gcccuuggu 19

<210> SEQ ID NO 939
<211> LENGTH: 19
<212> TYPE: RNA
<213> ORGANISM: Artificial Sequence
<220> FEATURE:
<223> OTHER INFORMATION: Synthetic

<400> SEQUENCE: 939
cugagauucg cccuuggug 19

<210> SEQ ID NO 940
<211> LENGTH: 19
<212> TYPE: RNA
<213> ORGANISM: Artificial Sequence
<220> FEATURE:
<223> OTHER INFORMATION: Synthetic

<400> SEQUENCE: 940
gagauucgcc cuugguguu 19

<210> SEQ ID NO 941
<211> LENGTH: 19
<212> TYPE: RNA
<213> ORGANISM: Artificial Sequence
<220> FEATURE:
<223> OTHER INFORMATION: Synthetic

<400> SEQUENCE: 941
agauucgccc uugguguua 19

<210> SEQ ID NO 942
<211> LENGTH: 19
<212> TYPE: RNA
<213> ORGANISM: Artificial Sequence
<220> FEATURE:
<223> OTHER INFORMATION: Synthetic

<400> SEQUENCE: 942
uucgcccuug guguuacac 19

<210> SEQ ID NO 943
<211> LENGTH: 19
<212> TYPE: RNA
<213> ORGANISM: Artificial Sequence
<220> FEATURE:
<223> OTHER INFORMATION: Synthetic

<400> SEQUENCE: 943
cuugguguua caccaugga 19

<210> SEQ ID NO 944
<211> LENGTH: 19
<212> TYPE: RNA
<213> ORGANISM: Artificial Sequence
<220> FEATURE:
<223> OTHER INFORMATION: Synthetic

<400> SEQUENCE: 944
uugguguuac accauggau 19

<210> SEQ ID NO 945
<211> LENGTH: 19
<212> TYPE: RNA
<213> ORGANISM: Artificial Sequence
<220> FEATURE:

<223> OTHER INFORMATION: Synthetic

<400> SEQUENCE: 945
ugguguuaca ccauggauc 19

<210> SEQ ID NO 946
<211> LENGTH: 19
<212> TYPE: RNA
<213> ORGANISM: Artificial Sequence
<220> FEATURE:
<223> OTHER INFORMATION: Synthetic

<400> SEQUENCE: 946
gguguuacac cauggaucc 19

<210> SEQ ID NO 947
<211> LENGTH: 19
<212> TYPE: RNA
<213> ORGANISM: Artificial Sequence
<220> FEATURE:
<223> OTHER INFORMATION: Synthetic

<400> SEQUENCE: 947
uguuacacca uggauccca 19

<210> SEQ ID NO 948
<211> LENGTH: 19
<212> TYPE: RNA
<213> ORGANISM: Artificial Sequence
<220> FEATURE:
<223> OTHER INFORMATION: Synthetic

<400> SEQUENCE: 948
gaaucaagug uccuugcaa 19

<210> SEQ ID NO 949
<211> LENGTH: 19
<212> TYPE: RNA
<213> ORGANISM: Artificial Sequence
<220> FEATURE:
<223> OTHER INFORMATION: Synthetic

<400> SEQUENCE: 949
aaucaagugu ccuugcaac 19

<210> SEQ ID NO 950
<211> LENGTH: 19
<212> TYPE: RNA
<213> ORGANISM: Artificial Sequence
<220> FEATURE:
<223> OTHER INFORMATION: Synthetic

<400> SEQUENCE: 950
aucaaguguc cuugcaacu 19

<210> SEQ ID NO 951
<211> LENGTH: 19
<212> TYPE: RNA
<213> ORGANISM: Artificial Sequence
<220> FEATURE:
<223> OTHER INFORMATION: Synthetic

<400> SEQUENCE: 951
auggacagag uuaucgagg 19

-continued

<210> SEQ ID NO 952
<211> LENGTH: 19
<212> TYPE: RNA
<213> ORGANISM: Artificial Sequence
<220> FEATURE:
<223> OTHER INFORMATION: Synthetic

<400> SEQUENCE: 952
uggacagagu uaucgaggc 19

<210> SEQ ID NO 953
<211> LENGTH: 19
<212> TYPE: RNA
<213> ORGANISM: Artificial Sequence
<220> FEATURE:
<223> OTHER INFORMATION: Synthetic

<400> SEQUENCE: 953
acaccacacu ggcaucaga 19

<210> SEQ ID NO 954
<211> LENGTH: 19
<212> TYPE: RNA
<213> ORGANISM: Artificial Sequence
<220> FEATURE:
<223> OTHER INFORMATION: Synthetic

<400> SEQUENCE: 954
uugguguuau accauggau 19

<210> SEQ ID NO 955
<211> LENGTH: 19
<212> TYPE: RNA
<213> ORGANISM: Artificial Sequence
<220> FEATURE:
<223> OTHER INFORMATION: Synthetic

<400> SEQUENCE: 955
ugguguuaua ccauggauc 19

<210> SEQ ID NO 956
<211> LENGTH: 19
<212> TYPE: RNA
<213> ORGANISM: Artificial Sequence
<220> FEATURE:
<223> OTHER INFORMATION: Synthetic

<400> SEQUENCE: 956
gguguuauac cauggaucc 19

<210> SEQ ID NO 957
<211> LENGTH: 19
<212> TYPE: RNA
<213> ORGANISM: Artificial Sequence
<220> FEATURE:
<223> OTHER INFORMATION: Synthetic

<400> SEQUENCE: 957
guguuauacc auggauccc 19

<210> SEQ ID NO 958
<211> LENGTH: 19
<212> TYPE: RNA
<213> ORGANISM: Artificial Sequence
<220> FEATURE:
<223> OTHER INFORMATION: Synthetic

<400> SEQUENCE: 958
ucagauggga guacugcaa 19

<210> SEQ ID NO 959
<211> LENGTH: 19
<212> TYPE: RNA
<213> ORGANISM: Artificial Sequence
<220> FEATURE:
<223> OTHER INFORMATION: Synthetic

<400> SEQUENCE: 959
gaugggagua cugcaaccu 19

<210> SEQ ID NO 960
<211> LENGTH: 19
<212> TYPE: RNA
<213> ORGANISM: Artificial Sequence
<220> FEATURE:
<223> OTHER INFORMATION: Synthetic

<400> SEQUENCE: 960
augggaguac ugcaaccug 19

<210> SEQ ID NO 961
<211> LENGTH: 19
<212> TYPE: RNA
<213> ORGANISM: Artificial Sequence
<220> FEATURE:
<223> OTHER INFORMATION: Synthetic

<400> SEQUENCE: 961
ugggaguacu gcaaccuga 19

<210> SEQ ID NO 962
<211> LENGTH: 19
<212> TYPE: RNA
<213> ORGANISM: Artificial Sequence
<220> FEATURE:
<223> OTHER INFORMATION: Synthetic

<400> SEQUENCE: 962
gggaguacug caaccugac 19

<210> SEQ ID NO 963
<211> LENGTH: 19
<212> TYPE: RNA
<213> ORGANISM: Artificial Sequence
<220> FEATURE:
<223> OTHER INFORMATION: Synthetic

<400> SEQUENCE: 963
ggcuguuucu gaacaagca 19

<210> SEQ ID NO 964
<211> LENGTH: 19
<212> TYPE: RNA
<213> ORGANISM: Artificial Sequence
<220> FEATURE:
<223> OTHER INFORMATION: Synthetic

<400> SEQUENCE: 964
guuucugaac aagcaccaa 19

<210> SEQ ID NO 965
<211> LENGTH: 19

<212> TYPE: RNA
<213> ORGANISM: Artificial Sequence
<220> FEATURE:
<223> OTHER INFORMATION: Synthetic

<400> SEQUENCE: 965
cuccaccacu guuacagga 19

<210> SEQ ID NO 966
<211> LENGTH: 19
<212> TYPE: RNA
<213> ORGANISM: Artificial Sequence
<220> FEATURE:
<223> OTHER INFORMATION: Synthetic

<400> SEQUENCE: 966
uccaccacug uuacaggaa 19

<210> SEQ ID NO 967
<211> LENGTH: 19
<212> TYPE: RNA
<213> ORGANISM: Artificial Sequence
<220> FEATURE:
<223> OTHER INFORMATION: Synthetic

<400> SEQUENCE: 967
ccaccacugu uacaggaag 19

<210> SEQ ID NO 968
<211> LENGTH: 19
<212> TYPE: RNA
<213> ORGANISM: Artificial Sequence
<220> FEATURE:
<223> OTHER INFORMATION: Synthetic

<400> SEQUENCE: 968
gacaccacac uggcaucag 19

<210> SEQ ID NO 969
<211> LENGTH: 19
<212> TYPE: RNA
<213> ORGANISM: Artificial Sequence
<220> FEATURE:
<223> OTHER INFORMATION: Synthetic

<400> SEQUENCE: 969
acaccacacu ggcaucaga 19

<210> SEQ ID NO 970
<211> LENGTH: 19
<212> TYPE: RNA
<213> ORGANISM: Artificial Sequence
<220> FEATURE:
<223> OTHER INFORMATION: Synthetic

<400> SEQUENCE: 970
agaauacuac ccaaauggu 19

<210> SEQ ID NO 971
<211> LENGTH: 19
<212> TYPE: RNA
<213> ORGANISM: Artificial Sequence
<220> FEATURE:
<223> OTHER INFORMATION: Synthetic

<400> SEQUENCE: 971
gaauacuacc caaauggug 19

<210> SEQ ID NO 972
<211> LENGTH: 19
<212> TYPE: RNA
<213> ORGANISM: Artificial Sequence
<220> FEATURE:
<223> OTHER INFORMATION: Synthetic

<400> SEQUENCE: 972
aauacuaccc aaauggugg 19

<210> SEQ ID NO 973
<211> LENGTH: 19
<212> TYPE: RNA
<213> ORGANISM: Artificial Sequence
<220> FEATURE:
<223> OTHER INFORMATION: Synthetic

<400> SEQUENCE: 973
uccuucugaa gaagcacca 19

<210> SEQ ID NO 974
<211> LENGTH: 19
<212> TYPE: RNA
<213> ORGANISM: Artificial Sequence
<220> FEATURE:
<223> OTHER INFORMATION: Synthetic

<400> SEQUENCE: 974
ccuucugaag aagcaccaa 19

<210> SEQ ID NO 975
<211> LENGTH: 19
<212> TYPE: RNA
<213> ORGANISM: Artificial Sequence
<220> FEATURE:
<223> OTHER INFORMATION: Synthetic

<400> SEQUENCE: 975
cuucugaaga agcaccaac 19

<210> SEQ ID NO 976
<211> LENGTH: 19
<212> TYPE: RNA
<213> ORGANISM: Artificial Sequence
<220> FEATURE:
<223> OTHER INFORMATION: Synthetic

<400> SEQUENCE: 976
uucugaagaa gcaccaacu 19

<210> SEQ ID NO 977
<211> LENGTH: 19
<212> TYPE: RNA
<213> ORGANISM: Artificial Sequence
<220> FEATURE:
<223> OTHER INFORMATION: Synthetic

<400> SEQUENCE: 977
ucugaagaag caccaacug 19

<210> SEQ ID NO 978
<211> LENGTH: 19
<212> TYPE: RNA
<213> ORGANISM: Artificial Sequence
<220> FEATURE:
<223> OTHER INFORMATION: Synthetic

<400> SEQUENCE: 978
cugaagaagc accaacuga 19

<210> SEQ ID NO 979
<211> LENGTH: 19
<212> TYPE: RNA
<213> ORGANISM: Artificial Sequence
<220> FEATURE:
<223> OTHER INFORMATION: Synthetic

<400> SEQUENCE: 979
ugaagaagca ccaacugaa 19

<210> SEQ ID NO 980
<211> LENGTH: 19
<212> TYPE: RNA
<213> ORGANISM: Artificial Sequence
<220> FEATURE:
<223> OTHER INFORMATION: Synthetic

<400> SEQUENCE: 980
gaagaagcac caacugaaa 19

<210> SEQ ID NO 981
<211> LENGTH: 19
<212> TYPE: RNA
<213> ORGANISM: Artificial Sequence
<220> FEATURE:
<223> OTHER INFORMATION: Synthetic

<400> SEQUENCE: 981
aagaagcacc aacugaaaa 19

<210> SEQ ID NO 982
<211> LENGTH: 19
<212> TYPE: RNA
<213> ORGANISM: Artificial Sequence
<220> FEATURE:
<223> OTHER INFORMATION: Synthetic

<400> SEQUENCE: 982
agaagcacca acugaaaac 19

<210> SEQ ID NO 983
<211> LENGTH: 19
<212> TYPE: RNA
<213> ORGANISM: Artificial Sequence
<220> FEATURE:
<223> OTHER INFORMATION: Synthetic

<400> SEQUENCE: 983
gaagcaccaa cugaaaaca 19

<210> SEQ ID NO 984
<211> LENGTH: 19
<212> TYPE: RNA
<213> ORGANISM: Artificial Sequence
<220> FEATURE:
<223> OTHER INFORMATION: Synthetic

<400> SEQUENCE: 984
aagcaccaac ugaaaacag 19

-continued

<210> SEQ ID NO 985
<211> LENGTH: 19
<212> TYPE: RNA
<213> ORGANISM: Artificial Sequence
<220> FEATURE:
<223> OTHER INFORMATION: Synthetic

<400> SEQUENCE: 985
aggugaugga cagaguuau 19

<210> SEQ ID NO 986
<211> LENGTH: 19
<212> TYPE: RNA
<213> ORGANISM: Artificial Sequence
<220> FEATURE:
<223> OTHER INFORMATION: Synthetic

<400> SEQUENCE: 986
cuccaccacu aucacagga 19

<210> SEQ ID NO 987
<211> LENGTH: 19
<212> TYPE: RNA
<213> ORGANISM: Artificial Sequence
<220> FEATURE:
<223> OTHER INFORMATION: Synthetic

<400> SEQUENCE: 987
uccaccacua ucacaggaa 19

<210> SEQ ID NO 988
<211> LENGTH: 19
<212> TYPE: RNA
<213> ORGANISM: Artificial Sequence
<220> FEATURE:
<223> OTHER INFORMATION: Synthetic

<400> SEQUENCE: 988
ccaccacuau cacaggaag 19

<210> SEQ ID NO 989
<211> LENGTH: 19
<212> TYPE: RNA
<213> ORGANISM: Artificial Sequence
<220> FEATURE:
<223> OTHER INFORMATION: Synthetic

<400> SEQUENCE: 989
caccacuauc acaggaaga 19

<210> SEQ ID NO 990
<211> LENGTH: 19
<212> TYPE: RNA
<213> ORGANISM: Artificial Sequence
<220> FEATURE:
<223> OTHER INFORMATION: Synthetic

<400> SEQUENCE: 990
accacuauca caggaagaa 19

<210> SEQ ID NO 991
<211> LENGTH: 19
<212> TYPE: RNA
<213> ORGANISM: Artificial Sequence
<220> FEATURE:
<223> OTHER INFORMATION: Synthetic

<400> SEQUENCE: 991
ccacuaucac aggaagaac 19

<210> SEQ ID NO 992
<211> LENGTH: 19
<212> TYPE: RNA
<213> ORGANISM: Artificial Sequence
<220> FEATURE:
<223> OTHER INFORMATION: Synthetic

<400> SEQUENCE: 992
cacuaucaca ggaagaaca 19

<210> SEQ ID NO 993
<211> LENGTH: 19
<212> TYPE: RNA
<213> ORGANISM: Artificial Sequence
<220> FEATURE:
<223> OTHER INFORMATION: Synthetic

<400> SEQUENCE: 993
acuaucacag gaagaacau 19

<210> SEQ ID NO 994
<211> LENGTH: 19
<212> TYPE: RNA
<213> ORGANISM: Artificial Sequence
<220> FEATURE:
<223> OTHER INFORMATION: Synthetic

<400> SEQUENCE: 994
cuaucacagg aagaacaug 19

<210> SEQ ID NO 995
<211> LENGTH: 19
<212> TYPE: RNA
<213> ORGANISM: Artificial Sequence
<220> FEATURE:
<223> OTHER INFORMATION: Synthetic

<400> SEQUENCE: 995
uaucacagga agaacaugu 19

<210> SEQ ID NO 996
<211> LENGTH: 19
<212> TYPE: RNA
<213> ORGANISM: Artificial Sequence
<220> FEATURE:
<223> OTHER INFORMATION: Synthetic

<400> SEQUENCE: 996
aucacaggaa gaacauguc 19

<210> SEQ ID NO 997
<211> LENGTH: 19
<212> TYPE: RNA
<213> ORGANISM: Artificial Sequence
<220> FEATURE:
<223> OTHER INFORMATION: Synthetic

<400> SEQUENCE: 997
ucacaggaag aacauguca 19

<210> SEQ ID NO 998

<211> LENGTH: 19
<212> TYPE: RNA
<213> ORGANISM: Artificial Sequence
<220> FEATURE:
<223> OTHER INFORMATION: Synthetic

<400> SEQUENCE: 998
cacaggaaga acaugucag 19

<210> SEQ ID NO 999
<211> LENGTH: 19
<212> TYPE: RNA
<213> ORGANISM: Artificial Sequence
<220> FEATURE:
<223> OTHER INFORMATION: Synthetic

<400> SEQUENCE: 999
acaggaagaa caugucagu 19

<210> SEQ ID NO 1000
<211> LENGTH: 19
<212> TYPE: RNA
<213> ORGANISM: Artificial Sequence
<220> FEATURE:
<223> OTHER INFORMATION: Synthetic

<400> SEQUENCE: 1000
ggaagaacau gucagucuu 19

<210> SEQ ID NO 1001
<211> LENGTH: 19
<212> TYPE: RNA
<213> ORGANISM: Artificial Sequence
<220> FEATURE:
<223> OTHER INFORMATION: Synthetic

<400> SEQUENCE: 1001
gaagaacaug ucagucuug 19

<210> SEQ ID NO 1002
<211> LENGTH: 19
<212> TYPE: RNA
<213> ORGANISM: Artificial Sequence
<220> FEATURE:
<223> OTHER INFORMATION: Synthetic

<400> SEQUENCE: 1002
aagaacaugu cagucuugg 19

<210> SEQ ID NO 1003
<211> LENGTH: 19
<212> TYPE: RNA
<213> ORGANISM: Artificial Sequence
<220> FEATURE:
<223> OTHER INFORMATION: Synthetic

<400> SEQUENCE: 1003
agaacauguc agucuuggu 19

<210> SEQ ID NO 1004
<211> LENGTH: 19
<212> TYPE: RNA
<213> ORGANISM: Artificial Sequence
<220> FEATURE:
<223> OTHER INFORMATION: Synthetic

<400> SEQUENCE: 1004
ggcaucggag gaucccauu 19

<210> SEQ ID NO 1005
<211> LENGTH: 19
<212> TYPE: RNA
<213> ORGANISM: Artificial Sequence
<220> FEATURE:
<223> OTHER INFORMATION: Synthetic

<400> SEQUENCE: 1005
acuauccaaa ugcuggccu 19

<210> SEQ ID NO 1006
<211> LENGTH: 19
<212> TYPE: RNA
<213> ORGANISM: Artificial Sequence
<220> FEATURE:
<223> OTHER INFORMATION: Synthetic

<400> SEQUENCE: 1006
gcacagaggc uccuucuga 19

<210> SEQ ID NO 1007
<211> LENGTH: 19
<212> TYPE: RNA
<213> ORGANISM: Artificial Sequence
<220> FEATURE:
<223> OTHER INFORMATION: Synthetic

<400> SEQUENCE: 1007
uccuucugaa caagcacca 19

<210> SEQ ID NO 1008
<211> LENGTH: 19
<212> TYPE: RNA
<213> ORGANISM: Artificial Sequence
<220> FEATURE:
<223> OTHER INFORMATION: Synthetic

<400> SEQUENCE: 1008
ccuucugaac aagcaccac 19

<210> SEQ ID NO 1009
<211> LENGTH: 19
<212> TYPE: RNA
<213> ORGANISM: Artificial Sequence
<220> FEATURE:
<223> OTHER INFORMATION: Synthetic

<400> SEQUENCE: 1009
cuucugaaca agcaccacc 19

<210> SEQ ID NO 1010
<211> LENGTH: 19
<212> TYPE: RNA
<213> ORGANISM: Artificial Sequence
<220> FEATURE:
<223> OTHER INFORMATION: Synthetic

<400> SEQUENCE: 1010
uucugaacaa gcaccaccu 19

<210> SEQ ID NO 1011
<211> LENGTH: 19
<212> TYPE: RNA

-continued

<213> ORGANISM: Artificial Sequence
<220> FEATURE:
<223> OTHER INFORMATION: Synthetic

<400> SEQUENCE: 1011
ucugaacaag caccaccug 19

<210> SEQ ID NO 1012
<211> LENGTH: 19
<212> TYPE: RNA
<213> ORGANISM: Artificial Sequence
<220> FEATURE:
<223> OTHER INFORMATION: Synthetic

<400> SEQUENCE: 1012
cugaacaagc accaccuga 19

<210> SEQ ID NO 1013
<211> LENGTH: 19
<212> TYPE: RNA
<213> ORGANISM: Artificial Sequence
<220> FEATURE:
<223> OTHER INFORMATION: Synthetic

<400> SEQUENCE: 1013
ugaacaagca ccaccugag 19

<210> SEQ ID NO 1014
<211> LENGTH: 19
<212> TYPE: RNA
<213> ORGANISM: Artificial Sequence
<220> FEATURE:
<223> OTHER INFORMATION: Synthetic

<400> SEQUENCE: 1014
gaacaagcac caccugaga 19

<210> SEQ ID NO 1015
<211> LENGTH: 19
<212> TYPE: RNA
<213> ORGANISM: Artificial Sequence
<220> FEATURE:
<223> OTHER INFORMATION: Synthetic

<400> SEQUENCE: 1015
aacaagcacc accugagaa 19

<210> SEQ ID NO 1016
<211> LENGTH: 19
<212> TYPE: RNA
<213> ORGANISM: Artificial Sequence
<220> FEATURE:
<223> OTHER INFORMATION: Synthetic

<400> SEQUENCE: 1016
caagcaccac cugagaaaa 19

<210> SEQ ID NO 1017
<211> LENGTH: 19
<212> TYPE: RNA
<213> ORGANISM: Artificial Sequence
<220> FEATURE:
<223> OTHER INFORMATION: Synthetic

<400> SEQUENCE: 1017
aagcaccacc ugagaaaag 19

-continued

<210> SEQ ID NO 1018
<211> LENGTH: 19
<212> TYPE: RNA
<213> ORGANISM: Artificial Sequence
<220> FEATURE:
<223> OTHER INFORMATION: Synthetic

<400> SEQUENCE: 1018
agcaccaccu gagaaaagc 19

<210> SEQ ID NO 1019
<211> LENGTH: 19
<212> TYPE: RNA
<213> ORGANISM: Artificial Sequence
<220> FEATURE:
<223> OTHER INFORMATION: Synthetic

<400> SEQUENCE: 1019
cugagaaaag cccuguggu 19

<210> SEQ ID NO 1020
<211> LENGTH: 19
<212> TYPE: RNA
<213> ORGANISM: Artificial Sequence
<220> FEATURE:
<223> OTHER INFORMATION: Synthetic

<400> SEQUENCE: 1020
gcccuguggu ccaggauug 19

<210> SEQ ID NO 1021
<211> LENGTH: 19
<212> TYPE: RNA
<213> ORGANISM: Artificial Sequence
<220> FEATURE:
<223> OTHER INFORMATION: Synthetic

<400> SEQUENCE: 1021
cuguggucca ggauugcua 19

<210> SEQ ID NO 1022
<211> LENGTH: 19
<212> TYPE: RNA
<213> ORGANISM: Artificial Sequence
<220> FEATURE:
<223> OTHER INFORMATION: Synthetic

<400> SEQUENCE: 1022
cuccaccacu gucacagga 19

<210> SEQ ID NO 1023
<211> LENGTH: 19
<212> TYPE: RNA
<213> ORGANISM: Artificial Sequence
<220> FEATURE:
<223> OTHER INFORMATION: Synthetic

<400> SEQUENCE: 1023
uccaccacug ucacaggaa 19

<210> SEQ ID NO 1024
<211> LENGTH: 19
<212> TYPE: RNA
<213> ORGANISM: Artificial Sequence
<220> FEATURE:

<223> OTHER INFORMATION: Synthetic

<400> SEQUENCE: 1024
ucuuggucau cuaugauac 19

<210> SEQ ID NO 1025
<211> LENGTH: 19
<212> TYPE: RNA
<213> ORGANISM: Artificial Sequence
<220> FEATURE:
<223> OTHER INFORMATION: Synthetic

<400> SEQUENCE: 1025
cuuggucauc uaugauacc 19

<210> SEQ ID NO 1026
<211> LENGTH: 19
<212> TYPE: RNA
<213> ORGANISM: Artificial Sequence
<220> FEATURE:
<223> OTHER INFORMATION: Synthetic

<400> SEQUENCE: 1026
uuggucaucu augauacca 19

<210> SEQ ID NO 1027
<211> LENGTH: 19
<212> TYPE: RNA
<213> ORGANISM: Artificial Sequence
<220> FEATURE:
<223> OTHER INFORMATION: Synthetic

<400> SEQUENCE: 1027
uggucaucua ugauaccac 19

<210> SEQ ID NO 1028
<211> LENGTH: 19
<212> TYPE: RNA
<213> ORGANISM: Artificial Sequence
<220> FEATURE:
<223> OTHER INFORMATION: Synthetic

<400> SEQUENCE: 1028
ggucaucuau gauaccaca 19

<210> SEQ ID NO 1029
<211> LENGTH: 19
<212> TYPE: RNA
<213> ORGANISM: Artificial Sequence
<220> FEATURE:
<223> OTHER INFORMATION: Synthetic

<400> SEQUENCE: 1029
gucaucuaug auaccacac 19

<210> SEQ ID NO 1030
<211> LENGTH: 19
<212> TYPE: RNA
<213> ORGANISM: Artificial Sequence
<220> FEATURE:
<223> OTHER INFORMATION: Synthetic

<400> SEQUENCE: 1030
ucaucuauga uaccacacu 19

<210> SEQ ID NO 1031
<211> LENGTH: 19
<212> TYPE: RNA
<213> ORGANISM: Artificial Sequence
<220> FEATURE:
<223> OTHER INFORMATION: Synthetic

<400> SEQUENCE: 1031
caucuaugau accacacug 19

<210> SEQ ID NO 1032
<211> LENGTH: 19
<212> TYPE: RNA
<213> ORGANISM: Artificial Sequence
<220> FEATURE:
<223> OTHER INFORMATION: Synthetic

<400> SEQUENCE: 1032
aucuaugaua ccacacugg 19

<210> SEQ ID NO 1033
<211> LENGTH: 19
<212> TYPE: RNA
<213> ORGANISM: Artificial Sequence
<220> FEATURE:
<223> OTHER INFORMATION: Synthetic

<400> SEQUENCE: 1033
ucuaugauac cacacuggc 19

<210> SEQ ID NO 1034
<211> LENGTH: 19
<212> TYPE: RNA
<213> ORGANISM: Artificial Sequence
<220> FEATURE:
<223> OTHER INFORMATION: Synthetic

<400> SEQUENCE: 1034
cuaugauacc acacuggca 19

<210> SEQ ID NO 1035
<211> LENGTH: 19
<212> TYPE: RNA
<213> ORGANISM: Artificial Sequence
<220> FEATURE:
<223> OTHER INFORMATION: Synthetic

<400> SEQUENCE: 1035
ugauaccaca cuggcauca 19

<210> SEQ ID NO 1036
<211> LENGTH: 19
<212> TYPE: RNA
<213> ORGANISM: Artificial Sequence
<220> FEATURE:
<223> OTHER INFORMATION: Synthetic

<400> SEQUENCE: 1036
auaccacacu ggcaucaga 19

<210> SEQ ID NO 1037
<211> LENGTH: 19
<212> TYPE: RNA
<213> ORGANISM: Artificial Sequence
<220> FEATURE:
<223> OTHER INFORMATION: Synthetic

<400> SEQUENCE: 1037
agaggacccc agaaaacua 19

<210> SEQ ID NO 1038
<211> LENGTH: 19
<212> TYPE: RNA
<213> ORGANISM: Artificial Sequence
<220> FEATURE:
<223> OTHER INFORMATION: Synthetic

<400> SEQUENCE: 1038
gaggacccca gaaaacuac 19

<210> SEQ ID NO 1039
<211> LENGTH: 19
<212> TYPE: RNA
<213> ORGANISM: Artificial Sequence
<220> FEATURE:
<223> OTHER INFORMATION: Synthetic

<400> SEQUENCE: 1039
agaacuacug caggaaucc 19

<210> SEQ ID NO 1040
<211> LENGTH: 19
<212> TYPE: RNA
<213> ORGANISM: Artificial Sequence
<220> FEATURE:
<223> OTHER INFORMATION: Synthetic

<400> SEQUENCE: 1040
acuacugcag gaauccaga 19

<210> SEQ ID NO 1041
<211> LENGTH: 19
<212> TYPE: RNA
<213> ORGANISM: Artificial Sequence
<220> FEATURE:
<223> OTHER INFORMATION: Synthetic

<400> SEQUENCE: 1041
uacugcagga auccagauu 19

<210> SEQ ID NO 1042
<211> LENGTH: 19
<212> TYPE: RNA
<213> ORGANISM: Artificial Sequence
<220> FEATURE:
<223> OTHER INFORMATION: Synthetic

<400> SEQUENCE: 1042
acugcaggaa uccagauuc 19

<210> SEQ ID NO 1043
<211> LENGTH: 19
<212> TYPE: RNA
<213> ORGANISM: Artificial Sequence
<220> FEATURE:
<223> OTHER INFORMATION: Synthetic

<400> SEQUENCE: 1043
cugcaggaau ccagauucu 19

<210> SEQ ID NO 1044
<211> LENGTH: 19

<212> TYPE: RNA
<213> ORGANISM: Artificial Sequence
<220> FEATURE:
<223> OTHER INFORMATION: Synthetic

<400> SEQUENCE: 1044
ugcaggaauc cagauucug 19

<210> SEQ ID NO 1045
<211> LENGTH: 19
<212> TYPE: RNA
<213> ORGANISM: Artificial Sequence
<220> FEATURE:
<223> OTHER INFORMATION: Synthetic

<400> SEQUENCE: 1045
gcaggaaucc agauucugg 19

<210> SEQ ID NO 1046
<211> LENGTH: 19
<212> TYPE: RNA
<213> ORGANISM: Artificial Sequence
<220> FEATURE:
<223> OTHER INFORMATION: Synthetic

<400> SEQUENCE: 1046
ggaauccaga uucugggaa 19

<210> SEQ ID NO 1047
<211> LENGTH: 19
<212> TYPE: RNA
<213> ORGANISM: Artificial Sequence
<220> FEATURE:
<223> OTHER INFORMATION: Synthetic

<400> SEQUENCE: 1047
gggaaacaac ccugguguu 19

<210> SEQ ID NO 1048
<211> LENGTH: 19
<212> TYPE: RNA
<213> ORGANISM: Artificial Sequence
<220> FEATURE:
<223> OTHER INFORMATION: Synthetic

<400> SEQUENCE: 1048
ggaaacaacc cugguguua 19

<210> SEQ ID NO 1049
<211> LENGTH: 19
<212> TYPE: RNA
<213> ORGANISM: Artificial Sequence
<220> FEATURE:
<223> OTHER INFORMATION: Synthetic

<400> SEQUENCE: 1049
ugugugaggu gggaguacu 19

<210> SEQ ID NO 1050
<211> LENGTH: 19
<212> TYPE: RNA
<213> ORGANISM: Artificial Sequence
<220> FEATURE:
<223> OTHER INFORMATION: Synthetic

<400> SEQUENCE: 1050
gugugaggug ggaguacug 19

<210> SEQ ID NO 1051
<211> LENGTH: 19
<212> TYPE: RNA
<213> ORGANISM: Artificial Sequence
<220> FEATURE:
<223> OTHER INFORMATION: Synthetic

<400> SEQUENCE: 1051
gugagguggg aguacugca 19

<210> SEQ ID NO 1052
<211> LENGTH: 19
<212> TYPE: RNA
<213> ORGANISM: Artificial Sequence
<220> FEATURE:
<223> OTHER INFORMATION: Synthetic

<400> SEQUENCE: 1052
ugagguggga guacugcaa 19

<210> SEQ ID NO 1053
<211> LENGTH: 19
<212> TYPE: RNA
<213> ORGANISM: Artificial Sequence
<220> FEATURE:
<223> OTHER INFORMATION: Synthetic

<400> SEQUENCE: 1053
cugacacaau gcucagaaa 19

<210> SEQ ID NO 1054
<211> LENGTH: 19
<212> TYPE: RNA
<213> ORGANISM: Artificial Sequence
<220> FEATURE:
<223> OTHER INFORMATION: Synthetic

<400> SEQUENCE: 1054
ugacacaaug cucagaaac 19

<210> SEQ ID NO 1055
<211> LENGTH: 19
<212> TYPE: RNA
<213> ORGANISM: Artificial Sequence
<220> FEATURE:
<223> OTHER INFORMATION: Synthetic

<400> SEQUENCE: 1055
gacacaaugc ucagaaaca 19

<210> SEQ ID NO 1056
<211> LENGTH: 19
<212> TYPE: RNA
<213> ORGANISM: Artificial Sequence
<220> FEATURE:
<223> OTHER INFORMATION: Synthetic

<400> SEQUENCE: 1056
acacaaugcu cagaaacag 19

<210> SEQ ID NO 1057
<211> LENGTH: 19
<212> TYPE: RNA
<213> ORGANISM: Artificial Sequence
<220> FEATURE:
<223> OTHER INFORMATION: Synthetic

<400> SEQUENCE: 1057
cacaaugcuc agaaacaga 19

<210> SEQ ID NO 1058
<211> LENGTH: 19
<212> TYPE: RNA
<213> ORGANISM: Artificial Sequence
<220> FEATURE:
<223> OTHER INFORMATION: Synthetic

<400> SEQUENCE: 1058
acaaugcuca gaaacagaa 19

<210> SEQ ID NO 1059
<211> LENGTH: 19
<212> TYPE: RNA
<213> ORGANISM: Artificial Sequence
<220> FEATURE:
<223> OTHER INFORMATION: Synthetic

<400> SEQUENCE: 1059
caaugcucag aaacagaau 19

<210> SEQ ID NO 1060
<211> LENGTH: 19
<212> TYPE: RNA
<213> ORGANISM: Artificial Sequence
<220> FEATURE:
<223> OTHER INFORMATION: Synthetic

<400> SEQUENCE: 1060
aaugcucaga aacagaauc 19

<210> SEQ ID NO 1061
<211> LENGTH: 19
<212> TYPE: RNA
<213> ORGANISM: Artificial Sequence
<220> FEATURE:
<223> OTHER INFORMATION: Synthetic

<400> SEQUENCE: 1061
augcucagaa acagaauca 19

<210> SEQ ID NO 1062
<211> LENGTH: 19
<212> TYPE: RNA
<213> ORGANISM: Artificial Sequence
<220> FEATURE:
<223> OTHER INFORMATION: Synthetic

<400> SEQUENCE: 1062
ugcucagaaa cagaaucag 19

<210> SEQ ID NO 1063
<211> LENGTH: 19
<212> TYPE: RNA
<213> ORGANISM: Artificial Sequence
<220> FEATURE:
<223> OTHER INFORMATION: Synthetic

<400> SEQUENCE: 1063
cucagaaaca gaaucaggu 19

<210> SEQ ID NO 1064
<211> LENGTH: 19
<212> TYPE: RNA
<213> ORGANISM: Artificial Sequence
<220> FEATURE:
<223> OTHER INFORMATION: Synthetic

<400> SEQUENCE: 1064
cagaaacaga aucaggugu 19

<210> SEQ ID NO 1065
<211> LENGTH: 19
<212> TYPE: RNA
<213> ORGANISM: Artificial Sequence
<220> FEATURE:
<223> OTHER INFORMATION: Synthetic

<400> SEQUENCE: 1065
agaaacagaa ucagguguc 19

<210> SEQ ID NO 1066
<211> LENGTH: 19
<212> TYPE: RNA
<213> ORGANISM: Artificial Sequence
<220> FEATURE:
<223> OTHER INFORMATION: Synthetic

<400> SEQUENCE: 1066
gaaacagaau caggugucc 19

<210> SEQ ID NO 1067
<211> LENGTH: 19
<212> TYPE: RNA
<213> ORGANISM: Artificial Sequence
<220> FEATURE:
<223> OTHER INFORMATION: Synthetic

<400> SEQUENCE: 1067
aaacagaauc agguguccu 19

<210> SEQ ID NO 1068
<211> LENGTH: 19
<212> TYPE: RNA
<213> ORGANISM: Artificial Sequence
<220> FEATURE:
<223> OTHER INFORMATION: Synthetic

<400> SEQUENCE: 1068
aacagaauca gguguccua 19

<210> SEQ ID NO 1069
<211> LENGTH: 19
<212> TYPE: RNA
<213> ORGANISM: Artificial Sequence
<220> FEATURE:
<223> OTHER INFORMATION: Synthetic

<400> SEQUENCE: 1069
cagaaucagg uguccuaga 19

<210> SEQ ID NO 1070
<211> LENGTH: 19
<212> TYPE: RNA
<213> ORGANISM: Artificial Sequence
<220> FEATURE:
<223> OTHER INFORMATION: Synthetic

<400> SEQUENCE: 1070
gaaucaggug uccuagaga 19

<210> SEQ ID NO 1071
<211> LENGTH: 19
<212> TYPE: RNA
<213> ORGANISM: Artificial Sequence
<220> FEATURE:
<223> OTHER INFORMATION: Synthetic

<400> SEQUENCE: 1071
aucagguguc cuagagacu 19

<210> SEQ ID NO 1072
<211> LENGTH: 19
<212> TYPE: RNA
<213> ORGANISM: Artificial Sequence
<220> FEATURE:
<223> OTHER INFORMATION: Synthetic

<400> SEQUENCE: 1072
gguguccuag agacuccca 19

<210> SEQ ID NO 1073
<211> LENGTH: 19
<212> TYPE: RNA
<213> ORGANISM: Artificial Sequence
<220> FEATURE:
<223> OTHER INFORMATION: Synthetic

<400> SEQUENCE: 1073
ccuagagacu cccacuguu 19

<210> SEQ ID NO 1074
<211> LENGTH: 19
<212> TYPE: RNA
<213> ORGANISM: Artificial Sequence
<220> FEATURE:
<223> OTHER INFORMATION: Synthetic

<400> SEQUENCE: 1074
cuagagacuc ccacuguug 19

<210> SEQ ID NO 1075
<211> LENGTH: 19
<212> TYPE: RNA
<213> ORGANISM: Artificial Sequence
<220> FEATURE:
<223> OTHER INFORMATION: Synthetic

<400> SEQUENCE: 1075
uagagacucc cacuguugu 19

<210> SEQ ID NO 1076
<211> LENGTH: 19
<212> TYPE: RNA
<213> ORGANISM: Artificial Sequence
<220> FEATURE:
<223> OTHER INFORMATION: Synthetic

<400> SEQUENCE: 1076
agagacuccc acuguuguu 19

<210> SEQ ID NO 1077

<211> LENGTH: 19
<212> TYPE: RNA
<213> ORGANISM: Artificial Sequence
<220> FEATURE:
<223> OTHER INFORMATION: Synthetic

<400> SEQUENCE: 1077
gagacuccca cuguuguuc 19

<210> SEQ ID NO 1078
<211> LENGTH: 19
<212> TYPE: RNA
<213> ORGANISM: Artificial Sequence
<220> FEATURE:
<223> OTHER INFORMATION: Synthetic

<400> SEQUENCE: 1078
agacucccac uguuguucc 19

<210> SEQ ID NO 1079
<211> LENGTH: 19
<212> TYPE: RNA
<213> ORGANISM: Artificial Sequence
<220> FEATURE:
<223> OTHER INFORMATION: Synthetic

<400> SEQUENCE: 1079
gcucauucug aagcagcac 19

<210> SEQ ID NO 1080
<211> LENGTH: 19
<212> TYPE: RNA
<213> ORGANISM: Artificial Sequence
<220> FEATURE:
<223> OTHER INFORMATION: Synthetic

<400> SEQUENCE: 1080
cucauucuga agcagcacc 19

<210> SEQ ID NO 1081
<211> LENGTH: 19
<212> TYPE: RNA
<213> ORGANISM: Artificial Sequence
<220> FEATURE:
<223> OTHER INFORMATION: Synthetic

<400> SEQUENCE: 1081
ucauucugaa gcagcacca 19

<210> SEQ ID NO 1082
<211> LENGTH: 19
<212> TYPE: RNA
<213> ORGANISM: Artificial Sequence
<220> FEATURE:
<223> OTHER INFORMATION: Synthetic

<400> SEQUENCE: 1082
cauucugaag cagcaccaa 19

<210> SEQ ID NO 1083
<211> LENGTH: 19
<212> TYPE: RNA
<213> ORGANISM: Artificial Sequence
<220> FEATURE:
<223> OTHER INFORMATION: Synthetic

<400> SEQUENCE: 1083
auucugaagc agcaccaac 19

<210> SEQ ID NO 1084
<211> LENGTH: 19
<212> TYPE: RNA
<213> ORGANISM: Artificial Sequence
<220> FEATURE:
<223> OTHER INFORMATION: Synthetic

<400> SEQUENCE: 1084
uucugaagca gcaccaacu 19

<210> SEQ ID NO 1085
<211> LENGTH: 19
<212> TYPE: RNA
<213> ORGANISM: Artificial Sequence
<220> FEATURE:
<223> OTHER INFORMATION: Synthetic

<400> SEQUENCE: 1085
ucugaagcag caccaacug 19

<210> SEQ ID NO 1086
<211> LENGTH: 19
<212> TYPE: RNA
<213> ORGANISM: Artificial Sequence
<220> FEATURE:
<223> OTHER INFORMATION: Synthetic

<400> SEQUENCE: 1086
cugaagcagc accaacuga 19

<210> SEQ ID NO 1087
<211> LENGTH: 19
<212> TYPE: RNA
<213> ORGANISM: Artificial Sequence
<220> FEATURE:
<223> OTHER INFORMATION: Synthetic

<400> SEQUENCE: 1087
ugaagcagca ccaacugag 19

<210> SEQ ID NO 1088
<211> LENGTH: 19
<212> TYPE: RNA
<213> ORGANISM: Artificial Sequence
<220> FEATURE:
<223> OTHER INFORMATION: Synthetic

<400> SEQUENCE: 1088
gaagcagcac caacugagc 19

<210> SEQ ID NO 1089
<211> LENGTH: 19
<212> TYPE: RNA
<213> ORGANISM: Artificial Sequence
<220> FEATURE:
<223> OTHER INFORMATION: Synthetic

<400> SEQUENCE: 1089
aagcagcacc aacugagca 19

<210> SEQ ID NO 1090
<211> LENGTH: 19
<212> TYPE: RNA

<213> ORGANISM: Artificial Sequence
<220> FEATURE:
<223> OTHER INFORMATION: Synthetic

<400> SEQUENCE: 1090
cagugcuacc augguaaug 19

<210> SEQ ID NO 1091
<211> LENGTH: 19
<212> TYPE: RNA
<213> ORGANISM: Artificial Sequence
<220> FEATURE:
<223> OTHER INFORMATION: Synthetic

<400> SEQUENCE: 1091
agugcuacca ugguaaugg 19

<210> SEQ ID NO 1092
<211> LENGTH: 19
<212> TYPE: RNA
<213> ORGANISM: Artificial Sequence
<220> FEATURE:
<223> OTHER INFORMATION: Synthetic

<400> SEQUENCE: 1092
acauucucca ccacuguca 19

<210> SEQ ID NO 1093
<211> LENGTH: 19
<212> TYPE: RNA
<213> ORGANISM: Artificial Sequence
<220> FEATURE:
<223> OTHER INFORMATION: Synthetic

<400> SEQUENCE: 1093
cacugucaca ggaaggaca 19

<210> SEQ ID NO 1094
<211> LENGTH: 19
<212> TYPE: RNA
<213> ORGANISM: Artificial Sequence
<220> FEATURE:
<223> OTHER INFORMATION: Synthetic

<400> SEQUENCE: 1094
acugucacag gaaggacau 19

<210> SEQ ID NO 1095
<211> LENGTH: 19
<212> TYPE: RNA
<213> ORGANISM: Artificial Sequence
<220> FEATURE:
<223> OTHER INFORMATION: Synthetic

<400> SEQUENCE: 1095
cugucacagg aaggacaug 19

<210> SEQ ID NO 1096
<211> LENGTH: 19
<212> TYPE: RNA
<213> ORGANISM: Artificial Sequence
<220> FEATURE:
<223> OTHER INFORMATION: Synthetic

<400> SEQUENCE: 1096
ugucacagga aggacaugu 19

<210> SEQ ID NO 1097
<211> LENGTH: 19
<212> TYPE: RNA
<213> ORGANISM: Artificial Sequence
<220> FEATURE:
<223> OTHER INFORMATION: Synthetic

<400> SEQUENCE: 1097
gucacaggaa ggacauguc 19

<210> SEQ ID NO 1098
<211> LENGTH: 19
<212> TYPE: RNA
<213> ORGANISM: Artificial Sequence
<220> FEATURE:
<223> OTHER INFORMATION: Synthetic

<400> SEQUENCE: 1098
ucacaggaag gacauguca 19

<210> SEQ ID NO 1099
<211> LENGTH: 19
<212> TYPE: RNA
<213> ORGANISM: Artificial Sequence
<220> FEATURE:
<223> OTHER INFORMATION: Synthetic

<400> SEQUENCE: 1099
acaggaagga caugucaau 19

<210> SEQ ID NO 1100
<211> LENGTH: 19
<212> TYPE: RNA
<213> ORGANISM: Artificial Sequence
<220> FEATURE:
<223> OTHER INFORMATION: Synthetic

<400> SEQUENCE: 1100
caggaaggac augucaauc 19

<210> SEQ ID NO 1101
<211> LENGTH: 19
<212> TYPE: RNA
<213> ORGANISM: Artificial Sequence
<220> FEATURE:
<223> OTHER INFORMATION: Synthetic

<400> SEQUENCE: 1101
aggaaggaca ugucaaucu 19

<210> SEQ ID NO 1102
<211> LENGTH: 19
<212> TYPE: RNA
<213> ORGANISM: Artificial Sequence
<220> FEATURE:
<223> OTHER INFORMATION: Synthetic

<400> SEQUENCE: 1102
ggaaggacau gucaaucuu 19

<210> SEQ ID NO 1103
<211> LENGTH: 19
<212> TYPE: RNA
<213> ORGANISM: Artificial Sequence
<220> FEATURE:

<223> OTHER INFORMATION: Synthetic

<400> SEQUENCE: 1103
gaaggacaug ucaaucuug 19

<210> SEQ ID NO 1104
<211> LENGTH: 19
<212> TYPE: RNA
<213> ORGANISM: Artificial Sequence
<220> FEATURE:
<223> OTHER INFORMATION: Synthetic

<400> SEQUENCE: 1104
aaggacaugu caaucuugg 19

<210> SEQ ID NO 1105
<211> LENGTH: 19
<212> TYPE: RNA
<213> ORGANISM: Artificial Sequence
<220> FEATURE:
<223> OTHER INFORMATION: Synthetic

<400> SEQUENCE: 1105
aggacauguc aaucuuggu 19

<210> SEQ ID NO 1106
<211> LENGTH: 19
<212> TYPE: RNA
<213> ORGANISM: Artificial Sequence
<220> FEATURE:
<223> OTHER INFORMATION: Synthetic

<400> SEQUENCE: 1106
ggacauguca aucuugguc 19

<210> SEQ ID NO 1107
<211> LENGTH: 19
<212> TYPE: RNA
<213> ORGANISM: Artificial Sequence
<220> FEATURE:
<223> OTHER INFORMATION: Synthetic

<400> SEQUENCE: 1107
gacaugucaa ucuugguca 19

<210> SEQ ID NO 1108
<211> LENGTH: 19
<212> TYPE: RNA
<213> ORGANISM: Artificial Sequence
<220> FEATURE:
<223> OTHER INFORMATION: Synthetic

<400> SEQUENCE: 1108
acaugucaau cuuggucau 19

<210> SEQ ID NO 1109
<211> LENGTH: 19
<212> TYPE: RNA
<213> ORGANISM: Artificial Sequence
<220> FEATURE:
<223> OTHER INFORMATION: Synthetic

<400> SEQUENCE: 1109
caugucaauc uuggucauc 19

-continued

<210> SEQ ID NO 1110
<211> LENGTH: 19
<212> TYPE: RNA
<213> ORGANISM: Artificial Sequence
<220> FEATURE:
<223> OTHER INFORMATION: Synthetic

<400> SEQUENCE: 1110
augucaaucu uggucaucc 19

<210> SEQ ID NO 1111
<211> LENGTH: 19
<212> TYPE: RNA
<213> ORGANISM: Artificial Sequence
<220> FEATURE:
<223> OTHER INFORMATION: Synthetic

<400> SEQUENCE: 1111
ugucaaucuu ggucaucca 19

<210> SEQ ID NO 1112
<211> LENGTH: 19
<212> TYPE: RNA
<213> ORGANISM: Artificial Sequence
<220> FEATURE:
<223> OTHER INFORMATION: Synthetic

<400> SEQUENCE: 1112
gucaaucuug gucauccau 19

<210> SEQ ID NO 1113
<211> LENGTH: 19
<212> TYPE: RNA
<213> ORGANISM: Artificial Sequence
<220> FEATURE:
<223> OTHER INFORMATION: Synthetic

<400> SEQUENCE: 1113
ucaaucuugg ucauccaug 19

<210> SEQ ID NO 1114
<211> LENGTH: 19
<212> TYPE: RNA
<213> ORGANISM: Artificial Sequence
<220> FEATURE:
<223> OTHER INFORMATION: Synthetic

<400> SEQUENCE: 1114
caaucuuggu cauccauga 19

<210> SEQ ID NO 1115
<211> LENGTH: 19
<212> TYPE: RNA
<213> ORGANISM: Artificial Sequence
<220> FEATURE:
<223> OTHER INFORMATION: Synthetic

<400> SEQUENCE: 1115
aaucuugguc auccaugac 19

<210> SEQ ID NO 1116
<211> LENGTH: 19
<212> TYPE: RNA
<213> ORGANISM: Artificial Sequence
<220> FEATURE:
<223> OTHER INFORMATION: Synthetic

<400> SEQUENCE: 1116
aucuugguca uccaugaca 19

<210> SEQ ID NO 1117
<211> LENGTH: 19
<212> TYPE: RNA
<213> ORGANISM: Artificial Sequence
<220> FEATURE:
<223> OTHER INFORMATION: Synthetic

<400> SEQUENCE: 1117
ugacaaugaa cuacugcag 19

<210> SEQ ID NO 1118
<211> LENGTH: 19
<212> TYPE: RNA
<213> ORGANISM: Artificial Sequence
<220> FEATURE:
<223> OTHER INFORMATION: Synthetic

<400> SEQUENCE: 1118
gacaaugaac uacugcagg 19

<210> SEQ ID NO 1119
<211> LENGTH: 19
<212> TYPE: RNA
<213> ORGANISM: Artificial Sequence
<220> FEATURE:
<223> OTHER INFORMATION: Synthetic

<400> SEQUENCE: 1119
acaaugaacu acugcagga 19

<210> SEQ ID NO 1120
<211> LENGTH: 19
<212> TYPE: RNA
<213> ORGANISM: Artificial Sequence
<220> FEATURE:
<223> OTHER INFORMATION: Synthetic

<400> SEQUENCE: 1120
caaugaacua cugcaggaa 19

<210> SEQ ID NO 1121
<211> LENGTH: 19
<212> TYPE: RNA
<213> ORGANISM: Artificial Sequence
<220> FEATURE:
<223> OTHER INFORMATION: Synthetic

<400> SEQUENCE: 1121
aaugaacuac ugcaggaau 19

<210> SEQ ID NO 1122
<211> LENGTH: 19
<212> TYPE: RNA
<213> ORGANISM: Artificial Sequence
<220> FEATURE:
<223> OTHER INFORMATION: Synthetic

<400> SEQUENCE: 1122
augaacuacu gcaggaauc 19

<210> SEQ ID NO 1123
<211> LENGTH: 19

<212> TYPE: RNA
<213> ORGANISM: Artificial Sequence
<220> FEATURE:
<223> OTHER INFORMATION: Synthetic

<400> SEQUENCE: 1123
ugaacuacug caggaaucc 19

<210> SEQ ID NO 1124
<211> LENGTH: 19
<212> TYPE: RNA
<213> ORGANISM: Artificial Sequence
<220> FEATURE:
<223> OTHER INFORMATION: Synthetic

<400> SEQUENCE: 1124
cuacugcagg aauccagau 19

<210> SEQ ID NO 1125
<211> LENGTH: 19
<212> TYPE: RNA
<213> ORGANISM: Artificial Sequence
<220> FEATURE:
<223> OTHER INFORMATION: Synthetic

<400> SEQUENCE: 1125
caggcccuug guguuuuac 19

<210> SEQ ID NO 1126
<211> LENGTH: 19
<212> TYPE: RNA
<213> ORGANISM: Artificial Sequence
<220> FEATURE:
<223> OTHER INFORMATION: Synthetic

<400> SEQUENCE: 1126
cuugguguuu uaccaugga 19

<210> SEQ ID NO 1127
<211> LENGTH: 19
<212> TYPE: RNA
<213> ORGANISM: Artificial Sequence
<220> FEATURE:
<223> OTHER INFORMATION: Synthetic

<400> SEQUENCE: 1127
uugguguuuu accauggac 19

<210> SEQ ID NO 1128
<211> LENGTH: 19
<212> TYPE: RNA
<213> ORGANISM: Artificial Sequence
<220> FEATURE:
<223> OTHER INFORMATION: Synthetic

<400> SEQUENCE: 1128
ugguguuuua ccauggacc 19

<210> SEQ ID NO 1129
<211> LENGTH: 19
<212> TYPE: RNA
<213> ORGANISM: Artificial Sequence
<220> FEATURE:
<223> OTHER INFORMATION: Synthetic

<400> SEQUENCE: 1129
gguguuuuac cauggaccc 19

<210> SEQ ID NO 1130
<211> LENGTH: 19
<212> TYPE: RNA
<213> ORGANISM: Artificial Sequence
<220> FEATURE:
<223> OTHER INFORMATION: Synthetic

<400> SEQUENCE: 1130
guguuuuacc auggacccc 19

<210> SEQ ID NO 1131
<211> LENGTH: 19
<212> TYPE: RNA
<213> ORGANISM: Artificial Sequence
<220> FEATURE:
<223> OTHER INFORMATION: Synthetic

<400> SEQUENCE: 1131
guuuuaccau ggaccccag 19

<210> SEQ ID NO 1132
<211> LENGTH: 19
<212> TYPE: RNA
<213> ORGANISM: Artificial Sequence
<220> FEATURE:
<223> OTHER INFORMATION: Synthetic

<400> SEQUENCE: 1132
ggaguacugc aaccugacg 19

<210> SEQ ID NO 1133
<211> LENGTH: 19
<212> TYPE: RNA
<213> ORGANISM: Artificial Sequence
<220> FEATURE:
<223> OTHER INFORMATION: Synthetic

<400> SEQUENCE: 1133
gaguacugca accugacgc 19

<210> SEQ ID NO 1134
<211> LENGTH: 19
<212> TYPE: RNA
<213> ORGANISM: Artificial Sequence
<220> FEATURE:
<223> OTHER INFORMATION: Synthetic

<400> SEQUENCE: 1134
guacugcaac cugacgcga 19

<210> SEQ ID NO 1135
<211> LENGTH: 19
<212> TYPE: RNA
<213> ORGANISM: Artificial Sequence
<220> FEATURE:
<223> OTHER INFORMATION: Synthetic

<400> SEQUENCE: 1135
uacugcaacc ugacgcgau 19

<210> SEQ ID NO 1136
<211> LENGTH: 19
<212> TYPE: RNA
<213> ORGANISM: Artificial Sequence
<220> FEATURE:
<223> OTHER INFORMATION: Synthetic

<400> SEQUENCE: 1136
ugcaaccuga cgcgaugcu 19

<210> SEQ ID NO 1137
<211> LENGTH: 19
<212> TYPE: RNA
<213> ORGANISM: Artificial Sequence
<220> FEATURE:
<223> OTHER INFORMATION: Synthetic

<400> SEQUENCE: 1137
ccugacgcga ugcucagac 19

<210> SEQ ID NO 1138
<211> LENGTH: 19
<212> TYPE: RNA
<213> ORGANISM: Artificial Sequence
<220> FEATURE:
<223> OTHER INFORMATION: Synthetic

<400> SEQUENCE: 1138
cugacgcgau gcucagaca 19

<210> SEQ ID NO 1139
<211> LENGTH: 19
<212> TYPE: RNA
<213> ORGANISM: Artificial Sequence
<220> FEATURE:
<223> OTHER INFORMATION: Synthetic

<400> SEQUENCE: 1139
gaugcucaga cacagaagg 19

<210> SEQ ID NO 1140
<211> LENGTH: 19
<212> TYPE: RNA
<213> ORGANISM: Artificial Sequence
<220> FEATURE:
<223> OTHER INFORMATION: Synthetic

<400> SEQUENCE: 1140
augcucagac acagaaggg 19

<210> SEQ ID NO 1141
<211> LENGTH: 19
<212> TYPE: RNA
<213> ORGANISM: Artificial Sequence
<220> FEATURE:
<223> OTHER INFORMATION: Synthetic

<400> SEQUENCE: 1141
agacacagaa gggacugug 19

<210> SEQ ID NO 1142
<211> LENGTH: 19
<212> TYPE: RNA
<213> ORGANISM: Artificial Sequence
<220> FEATURE:
<223> OTHER INFORMATION: Synthetic

<400> SEQUENCE: 1142
gcauccucuu cauuugauu 19

<210> SEQ ID NO 1143
<211> LENGTH: 19
<212> TYPE: RNA
<213> ORGANISM: Artificial Sequence
<220> FEATURE:
<223> OTHER INFORMATION: Synthetic

<400> SEQUENCE: 1143
cauccucuuc auuugauug 19

<210> SEQ ID NO 1144
<211> LENGTH: 19
<212> TYPE: RNA
<213> ORGANISM: Artificial Sequence
<220> FEATURE:
<223> OTHER INFORMATION: Synthetic

<400> SEQUENCE: 1144
auccucuuca uuugauugu 19

<210> SEQ ID NO 1145
<211> LENGTH: 19
<212> TYPE: RNA
<213> ORGANISM: Artificial Sequence
<220> FEATURE:
<223> OTHER INFORMATION: Synthetic

<400> SEQUENCE: 1145
uccucuucau uugauugug 19

<210> SEQ ID NO 1146
<211> LENGTH: 19
<212> TYPE: RNA
<213> ORGANISM: Artificial Sequence
<220> FEATURE:
<223> OTHER INFORMATION: Synthetic

<400> SEQUENCE: 1146
ccucuucauu ugauugugg 19

<210> SEQ ID NO 1147
<211> LENGTH: 19
<212> TYPE: RNA
<213> ORGANISM: Artificial Sequence
<220> FEATURE:
<223> OTHER INFORMATION: Synthetic

<400> SEQUENCE: 1147
cuucauuuga uugugggaa 19

<210> SEQ ID NO 1148
<211> LENGTH: 19
<212> TYPE: RNA
<213> ORGANISM: Artificial Sequence
<220> FEATURE:
<223> OTHER INFORMATION: Synthetic

<400> SEQUENCE: 1148
uucauuugau ugugggaag 19

<210> SEQ ID NO 1149
<211> LENGTH: 19
<212> TYPE: RNA
<213> ORGANISM: Artificial Sequence
<220> FEATURE:
<223> OTHER INFORMATION: Synthetic

<400> SEQUENCE: 1149
ucauuugauu gugggaagc 19

<210> SEQ ID NO 1150
<211> LENGTH: 19
<212> TYPE: RNA
<213> ORGANISM: Artificial Sequence
<220> FEATURE:
<223> OTHER INFORMATION: Synthetic

<400> SEQUENCE: 1150
cauuugauug ugggaagcc 19

<210> SEQ ID NO 1151
<211> LENGTH: 19
<212> TYPE: RNA
<213> ORGANISM: Artificial Sequence
<220> FEATURE:
<223> OTHER INFORMATION: Synthetic

<400> SEQUENCE: 1151
auuugauugu gggaagccu 19

<210> SEQ ID NO 1152
<211> LENGTH: 19
<212> TYPE: RNA
<213> ORGANISM: Artificial Sequence
<220> FEATURE:
<223> OTHER INFORMATION: Synthetic

<400> SEQUENCE: 1152
gugggaagcc ucaagugga 19

<210> SEQ ID NO 1153
<211> LENGTH: 19
<212> TYPE: RNA
<213> ORGANISM: Artificial Sequence
<220> FEATURE:
<223> OTHER INFORMATION: Synthetic

<400> SEQUENCE: 1153
aagaaauguc cuggaagca 19

<210> SEQ ID NO 1154
<211> LENGTH: 19
<212> TYPE: RNA
<213> ORGANISM: Artificial Sequence
<220> FEATURE:
<223> OTHER INFORMATION: Synthetic

<400> SEQUENCE: 1154
agaaaugucc uggaagcau 19

<210> SEQ ID NO 1155
<211> LENGTH: 19
<212> TYPE: RNA
<213> ORGANISM: Artificial Sequence
<220> FEATURE:
<223> OTHER INFORMATION: Synthetic

<400> SEQUENCE: 1155
gaaauguccu ggaagcauu 19

<210> SEQ ID NO 1156

<211> LENGTH: 19
<212> TYPE: RNA
<213> ORGANISM: Artificial Sequence
<220> FEATURE:
<223> OTHER INFORMATION: Synthetic

<400> SEQUENCE: 1156
aauguccugg aagcauugu 19

<210> SEQ ID NO 1157
<211> LENGTH: 19
<212> TYPE: RNA
<213> ORGANISM: Artificial Sequence
<220> FEATURE:
<223> OTHER INFORMATION: Synthetic

<400> SEQUENCE: 1157
auguccugga agcauugua 19

<210> SEQ ID NO 1158
<211> LENGTH: 19
<212> TYPE: RNA
<213> ORGANISM: Artificial Sequence
<220> FEATURE:
<223> OTHER INFORMATION: Synthetic

<400> SEQUENCE: 1158
agaacaaggu uuggaaagc 19

<210> SEQ ID NO 1159
<211> LENGTH: 19
<212> TYPE: RNA
<213> ORGANISM: Artificial Sequence
<220> FEATURE:
<223> OTHER INFORMATION: Synthetic

<400> SEQUENCE: 1159
gaacaagguu uggaaagca 19

<210> SEQ ID NO 1160
<211> LENGTH: 19
<212> TYPE: RNA
<213> ORGANISM: Artificial Sequence
<220> FEATURE:
<223> OTHER INFORMATION: Synthetic

<400> SEQUENCE: 1160
aacaagguuu ggaaagcac 19

<210> SEQ ID NO 1161
<211> LENGTH: 19
<212> TYPE: RNA
<213> ORGANISM: Artificial Sequence
<220> FEATURE:
<223> OTHER INFORMATION: Synthetic

<400> SEQUENCE: 1161
acaagguuug gaaagcacu 19

<210> SEQ ID NO 1162
<211> LENGTH: 19
<212> TYPE: RNA
<213> ORGANISM: Artificial Sequence
<220> FEATURE:
<223> OTHER INFORMATION: Synthetic

<400> SEQUENCE: 1162 caaagguuugg aaagcacuu 19

<210> SEQ ID NO 1163
<211> LENGTH: 19
<212> TYPE: RNA
<213> ORGANISM: Artificial Sequence
<220> FEATURE:
<223> OTHER INFORMATION: Synthetic

<400> SEQUENCE: 1163
aagguuugga aagcacuuc 19

<210> SEQ ID NO 1164
<211> LENGTH: 19
<212> TYPE: RNA
<213> ORGANISM: Artificial Sequence
<220> FEATURE:
<223> OTHER INFORMATION: Synthetic

<400> SEQUENCE: 1164
agguuuggaa agcacuucu 19

<210> SEQ ID NO 1165
<211> LENGTH: 19
<212> TYPE: RNA
<213> ORGANISM: Artificial Sequence
<220> FEATURE:
<223> OTHER INFORMATION: Synthetic

<400> SEQUENCE: 1165
uggaaagcac uucugugga 19

<210> SEQ ID NO 1166
<211> LENGTH: 19
<212> TYPE: RNA
<213> ORGANISM: Artificial Sequence
<220> FEATURE:
<223> OTHER INFORMATION: Synthetic

<400> SEQUENCE: 1166
guggaggcac cuuaauauc 19

<210> SEQ ID NO 1167
<211> LENGTH: 19
<212> TYPE: RNA
<213> ORGANISM: Artificial Sequence
<220> FEATURE:
<223> OTHER INFORMATION: Synthetic

<400> SEQUENCE: 1167
cuuaauaucc ccagagugg 19

<210> SEQ ID NO 1168
<211> LENGTH: 19
<212> TYPE: RNA
<213> ORGANISM: Artificial Sequence
<220> FEATURE:
<223> OTHER INFORMATION: Synthetic

<400> SEQUENCE: 1168
uaauaucccc agagugggu 19

<210> SEQ ID NO 1169
<211> LENGTH: 19
<212> TYPE: RNA

<213> ORGANISM: Artificial Sequence
<220> FEATURE:
<223> OTHER INFORMATION: Synthetic

<400> SEQUENCE: 1169
agagugggug cugacugcu 19

<210> SEQ ID NO 1170
<211> LENGTH: 19
<212> TYPE: RNA
<213> ORGANISM: Artificial Sequence
<220> FEATURE:
<223> OTHER INFORMATION: Synthetic

<400> SEQUENCE: 1170
caaggucauc cugggugca 19

<210> SEQ ID NO 1171
<211> LENGTH: 19
<212> TYPE: RNA
<213> ORGANISM: Artificial Sequence
<220> FEATURE:
<223> OTHER INFORMATION: Synthetic

<400> SEQUENCE: 1171
ccugggugca caccaagaa 19

<210> SEQ ID NO 1172
<211> LENGTH: 19
<212> TYPE: RNA
<213> ORGANISM: Artificial Sequence
<220> FEATURE:
<223> OTHER INFORMATION: Synthetic

<400> SEQUENCE: 1172
gugcacacca agaagugaa 19

<210> SEQ ID NO 1173
<211> LENGTH: 19
<212> TYPE: RNA
<213> ORGANISM: Artificial Sequence
<220> FEATURE:
<223> OTHER INFORMATION: Synthetic

<400> SEQUENCE: 1173
agcagauauu gccuugcua 19

<210> SEQ ID NO 1174
<211> LENGTH: 19
<212> TYPE: RNA
<213> ORGANISM: Artificial Sequence
<220> FEATURE:
<223> OTHER INFORMATION: Synthetic

<400> SEQUENCE: 1174
gcagauauug ccuugcuaa 19

<210> SEQ ID NO 1175
<211> LENGTH: 19
<212> TYPE: RNA
<213> ORGANISM: Artificial Sequence
<220> FEATURE:
<223> OTHER INFORMATION: Synthetic

<400> SEQUENCE: 1175
cagauauugc cuugcuaaa 19

<210> SEQ ID NO 1176
<211> LENGTH: 19
<212> TYPE: RNA
<213> ORGANISM: Artificial Sequence
<220> FEATURE:
<223> OTHER INFORMATION: Synthetic

<400> SEQUENCE: 1176
agauauugcc uugcuaaag 19

<210> SEQ ID NO 1177
<211> LENGTH: 19
<212> TYPE: RNA
<213> ORGANISM: Artificial Sequence
<220> FEATURE:
<223> OTHER INFORMATION: Synthetic

<400> SEQUENCE: 1177
gauauugccu ugcuaaagc 19

<210> SEQ ID NO 1178
<211> LENGTH: 19
<212> TYPE: RNA
<213> ORGANISM: Artificial Sequence
<220> FEATURE:
<223> OTHER INFORMATION: Synthetic

<400> SEQUENCE: 1178
auauugccuu gcuaaagcu 19

<210> SEQ ID NO 1179
<211> LENGTH: 19
<212> TYPE: RNA
<213> ORGANISM: Artificial Sequence
<220> FEATURE:
<223> OTHER INFORMATION: Synthetic

<400> SEQUENCE: 1179
uauugccuug cuaaagcua 19

<210> SEQ ID NO 1180
<211> LENGTH: 19
<212> TYPE: RNA
<213> ORGANISM: Artificial Sequence
<220> FEATURE:
<223> OTHER INFORMATION: Synthetic

<400> SEQUENCE: 1180
ucaucacuga caaaguaau 19

<210> SEQ ID NO 1181
<211> LENGTH: 19
<212> TYPE: RNA
<213> ORGANISM: Artificial Sequence
<220> FEATURE:
<223> OTHER INFORMATION: Synthetic

<400> SEQUENCE: 1181
ggacugaaug uuacaucac 19

<210> SEQ ID NO 1182
<211> LENGTH: 19
<212> TYPE: RNA
<213> ORGANISM: Artificial Sequence
<220> FEATURE:

<223> OTHER INFORMATION: Synthetic

<400> SEQUENCE: 1182
gacugaaugu uacaucacu 19

<210> SEQ ID NO 1183
<211> LENGTH: 19
<212> TYPE: RNA
<213> ORGANISM: Artificial Sequence
<220> FEATURE:
<223> OTHER INFORMATION: Synthetic

<400> SEQUENCE: 1183
acugaauguu acaucacug 19

<210> SEQ ID NO 1184
<211> LENGTH: 19
<212> TYPE: RNA
<213> ORGANISM: Artificial Sequence
<220> FEATURE:
<223> OTHER INFORMATION: Synthetic

<400> SEQUENCE: 1184
cugaauguua caucacugg 19

<210> SEQ ID NO 1185
<211> LENGTH: 19
<212> TYPE: RNA
<213> ORGANISM: Artificial Sequence
<220> FEATURE:
<223> OTHER INFORMATION: Synthetic

<400> SEQUENCE: 1185
ugaauguuac aucacuggc 19

<210> SEQ ID NO 1186
<211> LENGTH: 19
<212> TYPE: RNA
<213> ORGANISM: Artificial Sequence
<220> FEATURE:
<223> OTHER INFORMATION: Synthetic

<400> SEQUENCE: 1186
aauguuacau cacuggcug 19

<210> SEQ ID NO 1187
<211> LENGTH: 19
<212> TYPE: RNA
<213> ORGANISM: Artificial Sequence
<220> FEATURE:
<223> OTHER INFORMATION: Synthetic

<400> SEQUENCE: 1187
gaaacccaag guaccuuug 19

<210> SEQ ID NO 1188
<211> LENGTH: 36
<212> TYPE: RNA
<213> ORGANISM: Artificial Sequence
<220> FEATURE:
<223> OTHER INFORMATION: Synthetic

<400> SEQUENCE: 1188
gacaacagaa uauuauccaa gcagccgaaa ggcugc 36

<210> SEQ ID NO 1189
<211> LENGTH: 22
<212> TYPE: RNA
<213> ORGANISM: Artificial Sequence
<220> FEATURE:
<223> OTHER INFORMATION: Synthetic

<400> SEQUENCE: 1189
uuggauaaua uucuguuguc gg 22

<210> SEQ ID NO 1190
<211> LENGTH: 19
<212> TYPE: RNA
<213> ORGANISM: Artificial Sequence
<220> FEATURE:
<223> OTHER INFORMATION: Synthetic

<400> SEQUENCE: 1190
gacaacagaa uauuaucca 19

<210> SEQ ID NO 1191
<211> LENGTH: 24
<212> TYPE: RNA
<213> ORGANISM: Artificial Sequence
<220> FEATURE:
<223> OTHER INFORMATION: Synthetic

<400> SEQUENCE: 1191
cguuaaucgc guauaauacg cgua 24

<210> SEQ ID NO 1192
<211> LENGTH: 27
<212> TYPE: RNA
<213> ORGANISM: Artificial Sequence
<220> FEATURE:
<223> OTHER INFORMATION: Synthetic

<400> SEQUENCE: 1192
auacgcguau uauacgcgau uaacgac 27

<210> SEQ ID NO 1193
<211> LENGTH: 25
<212> TYPE: RNA
<213> ORGANISM: Artificial Sequence
<220> FEATURE:
<223> OTHER INFORMATION: Synthetic

<400> SEQUENCE: 1193
cauauugcgc guauagucgc guuag 25

<210> SEQ ID NO 1194
<211> LENGTH: 27
<212> TYPE: RNA
<213> ORGANISM: Artificial Sequence
<220> FEATURE:
<223> OTHER INFORMATION: Synthetic

<400> SEQUENCE: 1194
cuaacgcgac uauacgcgca auauggu 27

<210> SEQ ID NO 1195
<211> LENGTH: 24
<212> TYPE: RNA
<213> ORGANISM: Artificial Sequence
<220> FEATURE:
<223> OTHER INFORMATION: Synthetic -continued

<400> SEQUENCE: 1195
ggcgcguaua gucgcgcgua uagc 24

<210> SEQ ID NO 1196
<211> LENGTH: 27
<212> TYPE: RNA
<213> ORGANISM: Artificial Sequence
<220> FEATURE:
<223> OTHER INFORMATION: Synthetic

<400> SEQUENCE: 1196
gacuauacgc gcgacuauac gcgccuc 27

<210> SEQ ID NO 1197
<211> LENGTH: 16
<212> TYPE: RNA
<213> ORGANISM: Artificial Sequence
<220> FEATURE:
<223> OTHER INFORMATION: Synthetic

<400> SEQUENCE: 1197
gcagccgaaa ggcugc 16